(12) United States Patent
Fogelman et al.

(10) Patent No.: US 8,148,328 B2
(45) Date of Patent: Apr. 3, 2012

(54) SALICYLANILIDES ENHANCE ORAL DELIVERY OF THERAPEUTIC PEPTIDES

(75) Inventors: Alan M. Fogelman, Beverly Hills, CA (US); Mohamad Navab, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 473 days.

(21) Appl. No.: 11/835,338

(22) Filed: Aug. 7, 2007

(65) Prior Publication Data
US 2009/0163408 A1    Jun. 25, 2009

Related U.S. Application Data

(60) Provisional application No. 60/836,501, filed on Aug. 8, 2006, provisional application No. 60/868,845, filed on Dec. 6, 2006.

(51) Int. Cl.
*A61K 38/16* (2006.01)
*A61K 38/03* (2006.01)

(52) U.S. Cl. .......... 514/12; 514/2; 514/18; 514/17; 514/16; 514/15; 514/14; 514/13; 514/788; 424/9.1

(58) Field of Classification Search .......... 514/2, 12, 514/18, 17, 15, 16, 13, 14, 788; 424/9.1
See application file for complete search history.

(56) References Cited

U.S. PATENT DOCUMENTS

| 4,093,812 | A | 6/1978 | Rainer |
| 5,275,805 | A | 1/1994 | Nabi et al. |
| 5,770,576 | A | 6/1998 | Morozov et al. |
| 6,596,544 | B1 | 7/2003 | Fogelman et al. |
| 6,664,230 | B1 | 12/2003 | Fogelman et al. |
| 6,869,568 | B2 | 3/2005 | Fogelman et al. |
| 6,930,085 | B2 | 8/2005 | Fogelman et al. |
| 6,933,279 | B2 | 8/2005 | Fogelman et al. |
| 7,049,283 | B2 | 5/2006 | Ault et al. |
| 7,144,862 | B2 | 12/2006 | Fogelman et al. |
| 7,148,197 | B2 | 12/2006 | Fogelman et al. |
| 7,166,578 | B2 | 1/2007 | Fogelman et al. |
| 7,199,102 | B2 | 4/2007 | Fogelman et al. |
| 7,250,304 | B2 | 7/2007 | Fogelman et al. |
| 7,531,514 | B2 | 5/2009 | Fogelman et al. |
| 7,579,319 | B2 | 8/2009 | Fogelman |
| 7,638,494 | B2 | 12/2009 | Fogelman et al. |
| 7,723,045 | B2 | 5/2010 | Fogelman et al. |
| 7,723,303 | B2 | 5/2010 | Fogelman et al. |
| 2002/0065255 | A1 | 5/2002 | Bay et al. |
| 2002/0123459 | A1 | 9/2002 | Ault et al. |
| 2003/0191057 | A1 | 10/2003 | Fogelman et al. |
| 2003/0203842 | A1 | 10/2003 | Dasseux et al. |
| 2004/0106825 | A1 | 6/2004 | Bay et al. |
| 2004/0120990 | A1 | 6/2004 | Cushman et al. |
| 2005/0163727 | A1 | 7/2005 | Doyle et al. |
| 2005/0164950 | A1 | 7/2005 | Fogelman et al. |
| 2006/0078622 | A1 | 4/2006 | Majuru et al. |
| 2006/0078623 | A1 | 4/2006 | Dhoot et al. |
| 2006/0173067 | A1 | 8/2006 | Fogelman et al. |
| 2006/0205669 | A1 | 9/2006 | Fogelman et al. |
| 2006/0257450 | A1 | 11/2006 | Mudumba et al. |
| 2006/0258698 | A1 | 11/2006 | Mudumba et al. |
| 2006/0258839 | A1 | 11/2006 | Fogelman et al. |
| 2006/0263306 | A1 | 11/2006 | Pan et al. |
| 2006/0276339 | A1 | 12/2006 | Windsor et al. |
| 2007/0004794 | A1 | 1/2007 | Olesen et al. |
| 2007/0053849 | A1 | 3/2007 | Doyle et al. |
| 2007/0060527 | A1 | 3/2007 | Fogelman et al. |
| 2007/0110685 | A1 | 5/2007 | Auspitz et al. |
| 2007/0254839 | A1 | 11/2007 | Fogelman et al. |
| 2008/0026021 | A1 | 1/2008 | Sagel et al. |
| 2008/0081023 | A1 | 4/2008 | Deckner et al. |
| 2008/0095821 | A1 | 4/2008 | Fogelman et al. |
| 2008/0096814 | A1 | 4/2008 | Fogelman et al. |
| 2008/0096815 | A1 | 4/2008 | Fogelman et al. |
| 2008/0096816 | A1 | 4/2008 | Fogelman et al. |
| 2008/0199535 | A1 | 8/2008 | Taylor et al. |
| 2008/0248126 | A1 | 10/2008 | Cheng et al. |
| 2008/0286210 | A1 | 11/2008 | He et al. |
| 2008/0293639 | A1 | 11/2008 | Fogelman et al. |
| 2009/0005434 | A1 | 1/2009 | Olesen et al. |
| 2009/0016990 | A1 | 1/2009 | Alberte et al. |
| 2009/0163408 | A1 | 6/2009 | Fogelman et al. |
| 2009/0286741 | A1 | 11/2009 | Fogelman et al. |
| 2011/0183889 | A1 | 7/2011 | Fogelman et al. |

FOREIGN PATENT DOCUMENTS

| CN | 1522149 A | 8/2004 |
| CN | 1658893 A | 8/2005 |
| WO | WO 01/75168 | 10/2001 |
| WO | WO 01/75170 | 10/2001 |
| WO | WO 02/02128 | 1/2002 |
| WO | WO 02/15923 | 2/2002 |
| WO | WO 03/086326 | 10/2003 |
| WO | WO 2004/006906 | 1/2004 |
| WO | WO 2004/034977 | 4/2004 |
| WO | WO 2005/016280 | 2/2005 |
| WO | WO 2006/020652 | 2/2006 |
| WO | WO 2006/034056 | 3/2006 |

(Continued)

OTHER PUBLICATIONS

U.S. Appl. No. 60/968,815, filed Aug. 29, 2007, Fogelman et al.
International Search Report and Written Opinion dated Oct. 1, 2008 issued in PCT/US07/17551 (W02008/021088).
PCT International Preliminary Report on Patentability and Written Opinion dated Feb. 19, 2009 issued in PCT/US2007/17551 (WO/2008/021088).
PCT International Search Report dated Apr. 14, 2009 issued in PCT/US2008/074624 (WO/2009/032749).
PCT International Preliminary Report on Patentability and Written Opinion dated Apr. 14, 2009 issued in PCT/US2008/074624 (WO/2009/032749).

(Continued)

*Primary Examiner* — Chih-Min Kam
(74) *Attorney, Agent, or Firm* — Tom Hunter; Weaver Austin Villeneuve & Sampson LLP

(57) ABSTRACT

This invention pertains to the surprising discovery that salicylanilides, e.g., niclosamide and/or niclosamide analogues when orally administered in conjunction with a peptide pharmaceutical (e.g., a class A amphipathic helical peptide as described herein) significantly increases the bioavailability of that peptide. Methods of peptide delivery using such "delivery agents" and pharmaceutical formulations are provided.

23 Claims, 31 Drawing Sheets

FOREIGN PATENT DOCUMENTS

| | | |
|---|---|---|
| WO | WO 2006/063132 | 6/2006 |
| WO | WO 2006/118805 | 11/2006 |
| WO | WO 2007/095126 | 8/2007 |
| WO | WO 2008/021088 | 2/2008 |
| WO | PCT/US2008/074624 | 8/2008 |
| WO | WO 2009/032749 | 3/2009 |
| WO | WO 2009/073725 | 6/2009 |

OTHER PUBLICATIONS

Chang el al., (2006) "Pharmacokinetics of Anti-SARS-CoV Agent Niciosamide and its Analogs in Rats", *Journal of Food and Drug Analysis*, 14(4):329-333.

Chinese First Office Action dated Jun. 23, 2011 issued in CN 200780037605.6.

A

B

C

D

E

F

G

Nicolsamid Sodium Salt No. BP-2000

No. BP-3000

No. BP-3001

No. BP-3002

No. BP-3003

No. BP-4000

No. BP-4001

4-chloro-*N*-(2-chloro-4-nitrophenyl)-
2-hydroxybenzamide 3-chloro-*N*-(2-chloro-4-nitrophenyl)-
2-hydroxybenzamide 2-chloro-*N*-(2-chloro-4-nitrophenyl)-
6-hydroxybenzamide 5-chloro-*N*-(2-chloro-4-nitrophenyl)-
2-hydroxybenzamide 3-chloro-*N*-(3-chloro-4-nitrophenyl)-
2-hydroxybenzamide 4-chloro-*N*-(3-chloro-4-nitrophenyl)-
2-hydroxybenzamide 2-chloro-*N*-(3-chloro-4-nitrophenyl)-
6-hydroxybenzamide 5-chloro-*N*-(2-chloro-3-nitrophenyl)-
2-hydroxybenzamide 5-chloro-*N*-(2-chloro-6-nitrophenyl)-
2-hydroxybenzamide 5-chloro-*N*-(2-chloro-5-nitrophenyl)-
2-hydroxybenzamide 3-chloro-*N*-(2-chloro-4-nitrophenyl)-
5-hydroxybenzamide 3-chloro-*N*-(2-chloro-4-nitrophenyl)-
4-hydroxybenzamide 3-chloro-*N*-(2-chloro-4-nitrophenyl)-
2-hydroxybenzamide Niclosamide in Water     Niclosamide + L-4F in Water

SALICYLANILIDES ENHANCE ORAL DELIVERY OF THERAPEUTIC PEPTIDES

CROSS-REFERENCE TO RELATED APPLICATIONS

This application claims priority to and benefit of U.S. Ser. No. 60/836,501, filed on Aug. 8, 2006, and U.S. Ser. No. 60/868,845, filed on Dec. 6, 2006, both of which are incorporated herein by reference in their entirety for all purposes.

STATEMENT AS TO RIGHTS TO INVENTIONS MADE UNDER FEDERALLY SPONSORED RESEARCH AND DEVELOPMENT

This work was supported, in part, by USPHS Grant 2 P01 HL-030568. The government of the United States of America may possess certain rights in this invention.

FIELD OF THE INVENTION

The present invention relates to oral peptide pharmaceuticals where the active compounds include a plurality of amino acids and at least one peptide bond in their molecular structures, and to methods of enhancing bioavailability of such peptide compounds when administered orally.

BACKGROUND OF THE INVENTION

Numerous human hormones, neurotransmitters, or therapeutic antibodies are peptides or comprise peptides as a substantial part of their molecular structures. Therapeutically effective amounts of such biologically relevant peptides may be administered to patients in a variety of ways. Oral delivery of pharmacologically active agents is generally the delivery route of choice since it is convenient, self administration is relatively easy and generally painless, resulting in greater patient compliance as compared to other modes of delivery.

Biological, chemical and physical barriers such as varying pH in the gastrointestinal tract, powerful digestive enzymes in the stomach and intestine, and active agent impermeable gastrointestinal membranes, however, often makes the effective delivery of peptide pharmaceuticals problematic. For example, the oral delivery of calcitonins, has proven difficult due, at least in part, to the insufficient stability of calcitonin in the gastrointestinal tract as well as the inability of calcitonin to be readily transported through the intestinal walls into the blood stream.

Consequently, peptide pharmaceuticals used in the prior art frequently have been administered by injection or by nasal administration. Insulin is one example of a peptide pharmaceutical frequently administered by injection. Injection and nasal administration, however, are significantly less convenient than, and involve more patient discomfort than, oral administration. Often this inconvenience or discomfort results in substantial patient noncompliance with a treatment regimen. Thus, there is a need in the art for more effective and reproducible oral administration of peptide pharmaceuticals like insulin, calcitonin and others discussed in more detail herein.

SUMMARY OF THE INVENTION

This invention pertains to the surprising discovery that salicylanilides, e.g., niclosamide and/or niclosamide analogues when orally administered in conjunction with a peptide pharmaceutical (e.g., a class A amphipathic helical peptide as described herein) significantly increase the bioavailability of that peptide. Methods of peptide delivery using such "delivery agents" and pharmaceutical formulations are provided.

Thus, in certain embodiments, compositions (e.g., pharmaceutical formulations) are provided that comprise a therapeutic agent (e.g., a therapeutic peptide) in combination with a salicylanilide (e.g., niclosamide and/or a niclosamide analogue). In certain embodiments the salicylanilide comprises niclosamide or niclosamide analogue such as 2'5-dichloro-4'-nitrosalicylanilide, 5-chloro-salicyl-(2-chloro-4-nitro) anilide 2-aminoethanol salt, 5-chloro-salicyl-(2-chloro-4-nitro) anilide piperazine salt, and 5-chloro-salicyl-(2-chloro-4-nitro) anilide monohydrate. In certain embodiments the niclosamide analogue is a compound in FIGS. 2, 3, 4, 5, 6, 7, and/or Table 1. In various embodiments the peptide ranges in length from 3 amino acids to 300 amino acids, preferably from about 5 to about 200 amino acids, more preferably from about 5, 10, 15, 18, 20, 25, or amino acids to about 200, 150, 100, 90, 70, or 50 amino acids. In various embodiments the peptide comprises an amphipathic helix. In certain embodiments the peptide is an ApoJ peptide, ApoA-I, ApoA-I milano, or 18A. In certain embodiments the peptide comprises a class A amphipathic helix. In various embodiments the peptide consists of all "L" amino acids, or one or more "D" amino acids, or all "D" amino acids. In certain embodiments the peptide is a D or L peptide whose sequence is shown in any of Tables 2-11 and/or SEQ ID Nos:1-989. In certain embodiments the peptide comprises a protecting group at the amino and/or carboxyl terminus. In certain embodiments the protecting group is a protecting group selected from the group consisting of acetyl, amide, and 3 to 20 carbon alkyl groups, Fmoc, Tboc, 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridine-sulphenyl (Npys), 1-(4,4-dimentyl-2,6-diaxocyclohexy-lidene)ethyl (Dde), 2,6-dichlorobenzyl (2,6-DiCl-Bzl), 2-chlorobenzyloxycarbonyl (2-Cl—Z),2-bromobenzyloxycarbonyl (2-Br—Z), Benzyloxymethyl (Bom), t-butoxycarbonyl (Boc), cyclohexyloxy (cHxO),t-butoxymethyl (Bum), t-butoxy (tBuO), t-Butyl (tBu), Acetyl (Ac), and Trifluoroacetyl (TFA). In certain embodiments the amino protecting group is a protecting group selected from the group consisting of acetyl, propeonyl, and a 3 to 20 carbon alkyl and/or the carboxyl said second protecting group is an amide. In certain embodiments the salyclanalide (e.g., niclosamide or niclosamide analogue) and the therapeutic peptide are intermixed. In certain embodiments the salicylanilide (e.g. niclosamide or niclosamide analogue) and the therapeutic peptide are combined (e.g., under acidic conditions) to form an adduct. In certain embodiments the composition is a unit dosage formulation. In certain embodiments the peptide and the salicylanilide are segregated from each other. In certain embodiments the composition is formulated so that the niclosamide or niclosamide analogue is released or solubilized before the peptide.

In certain embodiments said salicylanilide is niclosamide or a niclosamide analogue; and the peptide is a D or L peptide comprising the amino acid sequence DWFKAFYDKVAEK-FKEAF (SEQ ID NO:5) or the amino acid sequence FAEK-FKEAVKDYFAKFWD (SEQ ID NO:104). In certain embodiments the peptide comprises a carboxyl terminal protecting group (e.g., an amide) and/or an amino terminal protecting group (e.g., acetyl). In certain embodiments the niclosamide or niclosamide analogue is niclosamide. In certain embodiments the niclosamide forms an adduct with the peptide.

In various embodiments methods are provided for enhancing the in vivo activity of a therapeutic peptide orally administered to a mammal (e.g., a human or a non-human mammal). The methods typically involve orally administering the peptide in conjunction with an amount of niclosamide or a niclosamide analogue sufficient to enhance the in vivo activity of the peptide. In various embodiments the peptide ranges in length from 3 amino acids to 300 amino acids, preferably from about 5 to about 200 amino acids, more preferably from about 5, 10, 15, 18, 20, 25, or 30 amino acids to about 200, 150, 100, 90, 70, or 50 amino acids. In various embodiments the peptide comprises an amphipathic helix. In certain embodiments the peptide is an ApoJ peptide, ApoA-I, ApoA-I milano (Apolipoprotein M), or 18A. In certain embodiments the peptide comprises a class A amphipathic helix. In various embodiments the peptide consists of all "L" amino acids, or one or more "D" amino acids, or all "D" amino acids. In certain embodiments the peptide is a D or L peptide whose sequence is shown in any of Tables 2-11 and/or SEQ ID Nos:1-989. In certain embodiments the peptide is a D or L peptide comprising the amino acid sequence DWFKAFYDKVAEKFKEAF (SEQ ID NO:5) or the amino acid sequence FAEKFKEAVKDYFAKFWD (SEQ ID NO:104). In certain embodiments the peptide comprises a carboxyl terminal protecting group (e.g., an amide) and/or an amino terminal protecting group (e.g., acetyl). In various embodiments the peptide used in this method are protected with a carboxyl and/or an amino protecting group as described herein (e.g., a protecting group selected from the group consisting of acetyl, amide, and 3 to 20 carbon alkyl groups, Fmoc, Tboc, 9-fluorenacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl—Z),2-bromobenzyloxycarbonyl (2-Br—Z), Benzyloxymethyl (Bom), t-butoxycarbonyl (Boc), cyclohexyloxy (cHxO),t-butoxymethyl (Bum), t-butoxy (tBuO), t-Butyl (tBu), Acetyl (Ac), and Trifluoroacetyl (TFA)). In various embodiments the niclosamide or niclosamide analogue is administered before administration of said peptide. In various embodiments the niclosamide or niclosamide analogue is administered at the same time as said peptide. In certain embodiments the niclosamide or niclosamide analogue is combined with the peptide to form an adduct. In certain embodiments the niclosamide analogue is a compound in FIGS. 2, 3, 4, 5, 6, 7, and/or Table 1.

In another embodiment pharmaceutical formulations are provided. The formulations typically comprise an orally administered pharmacologically active agent (e.g., a therapeutic peptide); and a salicylanilide (e.g., niclosamide and/or a niclosamide analogue). In certain embodiments the pharmacologically active agent is a therapeutic peptide and the peptide and the salicylanilide form an adduct. In certain embodiments the pharmaceutically active agent is not a non-peptide antiproliferative agent and/or not a non-peptide anti-cancer drug. In certain embodiments the pharmaceutically active agent is a peptide antiproliferative agent. In certain embodiments the formulation comprises a therapeutic amphipathic helical peptide; and niclosamide and/or a niclosamide analogue, where the niclosamide and/or niclosamide analogue in the formulation shows substantially greater solubility in an aqueous solution than the niclosamide and/or niclosamide analogue in an aqueous solution absent the amphipathic helical peptide. In certain embodiments the peptide is selected from the group consisting of ApoJ, ApoA-I, ApoA-I milano, or 18A. In certain embodiments the peptide forms a class A amphipathic helix. In certain embodiments the peptide consists of all "L" amino acids, or at least one "D" amino acid, or all "D" amino acids. In various embodiments the peptide consists of all "L" amino acids, or one or more "D" amino acids, or all "D" amino acids. In certain embodiments the peptide is a D or L peptide whose sequence is shown in any of Tables 2-11 and/or SEQ ID Nos:1-989. In certain embodiments the peptide is a D or L peptide comprising the amino acid sequence DWFKAFYDKVAEKFKEAF (SEQ ID NO:5) or the amino acid sequence FAEKFKEAVKDYFAKFWD (SEQ ID NO:104). In certain embodiments the peptide comprises a carboxyl terminal protecting group (e.g., an amide) and/or an amino terminal protecting group (e.g., acetyl). In various embodiments the peptides used in this method are protected with a carboxyl and/or an amino protecting group as described herein (e.g., a protecting group selected from the group consisting of acetyl, amide, and 3 to 20 carbon alkyl groups, Fmoc, Tboc, 9-fluorenacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl—Z),2-bromobenzyloxycarbonyl (2-Br—Z), Benzyloxymethyl (Bom), t-butoxycarbonyl (Boc), cyclohexyloxy (cHxO),t-butoxymethyl (Bum), t-butoxy (tBuO), t-Butyl (tBu), Acetyl (Ac), and Trifluoroacetyl (TFA)). In various embodiments the niclosamide or niclosamide analogue is administered before administration of said peptide. In various embodiments the niclosamide or niclosamide analogue is administered at the same time as said peptide. In certain embodiments the niclosamide or niclosamide analogue is combined with the peptide to form an adduct. In certain embodiments the niclosamide or niclosamide analogue is a compound in FIGS. 2, 3, 4, 5, 6, 7, and/or Table 1.

Also provided are methods of mitigating one or more symptoms of a pathology characterized by an inflammatory response in a mammal (e.g., a human, a non-human primate, a feline, an equine, a porcine, a bovine, a rodent, etc.). The methods typically involve orally administering to the mammal an amphipathic helical peptide that mitigates one or more symptoms of atherosclerosis or other pathology characterized by an inflammatory response in conjunction with niclosamide or a niclosamide analogue, whereby the oral delivery provides in vivo activity of the peptide to mitigate one or more symptoms of the pathology. In certain embodiments the niclosamide or niclosamide analogue is administered before the peptide, or administered simultaneously with peptide. In certain embodiments the niclosamide or niclosamide analogue and the peptide are administered as a single formulation. In certain embodiments the niclosamide or niclosamide analogue and the peptide are combined to form an adduct prior to administration. In certain embodiments the niclosamide or niclosamide analogue is selected from the group consisting of 2'5-dichloro-4'-nitrosalicylanilide, 5-chlorosalicyl-(2-chloro-4-nitro) anilide 2-aminoethanol salt, 5-chloro-salicyl-(2-chloro-4-nitro) anilide piperazine salt, and 5-chloro-salicyl-(2-chloro-4-nitro) anilide monohydrate. In certain embodiments the niclosamide or niclosamide analogue is a compound in FIGS. 2, 3, 4, 5, 6, 7, and/or Table 1. In certain embodiments the niclosamide or niclosamide analogue and/or the peptide are administered as a unit dosage formulation. In certain embodiments the niclosamide or niclosamide analogue and the peptide are administered as a unit dosage formulation formulated so that the niclosamide or niclosamide analogue is released or solubilized simultaneously with, or before the peptide. In certain embodiments the pathology is selected from the group consisting of atherosclerosis, rheumatoid arthritis, lupus erythematous, polyarteritis nodosa, osteoporosis, Altzheimer's disease, multiple sclerosis, chronic obstructive pulmonary disease, asthma, diabetes, and a viral illnesses. In various embodiments the peptide ranges in length from 3 amino acids to 300 amino acids, preferably from about 5 to about 200 amino acids, more preferably from about 5, 10, 15, 18, 20, 25, or 30 amino acids to about 200, 150, 100, 90, 70, or 50 amino acids. In various embodiments the peptide comprises an amphipathic helix. In certain embodiments the peptide is an ApoJ peptide, ApoA-I, ApoA-I milano (Apolipoprotein M), or 18A. In certain embodiments the peptide comprises a class A amphipathic helix. In various embodiments the peptide consists of all "L" amino acids, or one or more "D" amino acids, or all "D" amino acids. In certain embodiments the peptide is a D or L peptide whose sequence is shown in any of Tables 2-11 and/or SEQ ID Nos:1-989. In certain embodiments the peptide is a D or L peptide comprising the amino acid sequence DWFKAFYDKVAEKFKEAF (SEQ ID NO:5) or the amino acid sequence FAEKFKEAVKDYFAKFWD (SEQ ID NO:104). In certain embodiments the peptide comprises a carboxyl terminal protecting group (e.g., an amide) and/or an amino terminal protecting group (e.g., acetyl). In various embodiments the peptide used in this method are protected with a carboxyl and/or an amino protecting group as described herein (e.g., a protecting group selected from the group consisting of acetyl, amide, and 3 to 20 carbon alkyl groups, Fmoc, Tboc, 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-C1-Z),2-bromobenzyloxycarbonyl (2-Br—Z), Benzyloxymethyl (Bom), t-butoxycarbonyl (Boc), cyclohexyloxy (cHxO),t-butoxymethyl (Bum), t-butoxy (tBuO), t-Butyl (tBu), Acetyl (Ac), and Trifluoroacetyl (TFA)).

In various embodiments kits are provided. In certain embodiments the kits comprise a container containing a salicylanilide and a therapeutic peptide. The salicylanilide and the peptide can be in separate containers or combined in a single container. In certain embodiments the salicylanilide and the peptide are combined to form an adduct. In various embodiments the salicylanilide is niclosamide or a niclosamide analogue as described herein. In certain embodiments the peptide is a therapeutic peptide as described herein (e.g., ApoJ, ApoA-I, ApoA-I milano, and 18A, D-4F, L-4F, retro D-4F, retro L-4F, etc.).

In certain embodiments this invention also contemplates formulations and methods where the salicylanilide (e.g., niclosamide and/or a niclosamide analogue) is replaced or used in combination with any one or more of the other "delivery agents" described herein (e.g., N-(5-chlorosalicyloyl)-8-aminocaprylic acid (5-CNAC), N-(10-[2-hydroxybenzoyl] aminodecanoic acid (SNAD), and N-(8-[2-hydroxybenzoyl] amino)caprylic acid (SNAC) and various salts thereof (e.g., disodium salts), any one or more of the delivery agents disclosed in U.S. Pat. No. 5,866,536, U.S. Pat. No. 5,773,647, and WO 00/059863, and the like).

In certain embodiments this invention excludes formulations and/or methods utilizing any one or more of the delivery agents disclosed in U.S. Pat. No. 5,866,536, U.S. Pat. No. 5,773,647, WO 00/059863.

In certain embodiments niclosamide analogs used in the methods and compositions described herein include, but are not limited to those defined by Formula I, where substituents $R^1$, $R^2$, $R^5$, $R^6$, $R^7$, $R^8$, $R^9$, $R^{10}$, $R^{11}$ and $R^{12}$ are as described herein. In certain embodiments these substituents do not comprise one or more of the following moieties: carboxylic acid, and/or alkyl carboxylates, and/or hydroxamic acid and/or alkyl hydroxamates, and/or sulfonic acid and/or alkyl sulfones, and/or phosphoric acid and/or alkyl phosphates, and/or tetrazole.

DEFINITIONS

The phrase "enhancing the in vivo activity" or "enhancing the apparent activity" when referring to the agents described herein indicates that the agents, when administered in conjunction with an orally delivered pharmaceutical produce a greater biological response in the organism than the same dosage orally administered without the agent. Without being bound to a particular theory, the in vivo activity can be enhanced by any of a number of mechanisms including, but not limited to increased absorption, decreased degradation, a combination of increased absorption and decreased degradation, enhanced active transport, and the like.

The terms "coadministration" or "administration in conjunction with" when used in reference to the use of a delivery agent (e.g., niclosamide, niclosamide analogue or other delivery agent described herein) in conjunction with an orally administered pharmaceutical (e.g., a therapeutic peptide such as L-4F) indicates that the delivery agent and the orally administered pharmaceutical are administered so that there is at least some chronological overlap in the activity of the delivery agent and administration of the pharmaceutical such that the delivery agent enhances in vivo activity (e.g., via increased uptake and/or bioavailability) of the pharmaceutical. In sequential administration there may even be some substantial delay (e.g., minutes or even hours) between administration of the delivery agent and the pharmaceutical as long as the delivery agent is present in a manner that enhances in vivo activity of the pharmaceutical.

The term mammal includes essentially any mammal including, but not limited to dogs, cats, sheep, cattle, horses, goats, mice, rabbits, hamsters, pigs, monkeys and other non-human primates, and humans. Thus, veterinary as well as medical applications of this invention are contemplated.

The term "oral bioavailability" refers to the bioavailablity (e.g., plasma concentration) of an active agent when administered orally (e.g., in an oral formulation).

The term "L form peptide" refers to a peptide comprising all L form amino acids.

The term "D form peptide" refers to a peptide comprising at least one D amino acid. In certain embodiments at least half, and preferably all of the amino acids are D amino acids.

The term "treat" when used with reference to treating, e.g., a pathology or disease refers to the mitigation and/or elimination of one or more symptoms of that pathology or disease, and/or a reduction in the rate of onset or severity of one or more symptoms of that pathology or disease, and/or the prevention of that pathology or disease.

The terms "isolated", "purified", or "biologically pure" when referring to an isolated polypeptide refer to material that is substantially or essentially free from components that normally accompany it as found in its native state. With respect to nucleic acids and/or polypeptides the term can refer to nucleic acids or polypeptides that are no longer flanked by the sequences typically flanking them in nature. Chemically synthesized polypeptides are "isolated" because they are not found in a native state (e.g., in blood, serum, etc.). In certain embodiments, the term "isolated" indicates that the polypeptide is not found in nature.

The terms "polypeptide", "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers. Where the amino acid sequence of a peptide is provided the description of that peptide includes L peptides, D peptides, inverse peptides, retro peptides, and retroinverse peptides.

The term "an amphipathic helical peptide" refers to a peptide comprising at least one amphipathic helix (amphipathic helical domain). Certain amphipathic helical peptides of this invention can comprise two or more (e.g., 3, 4, 5, etc.) amphipathic helices.

The term "class A amphipathic helix" refers to a protein structure that forms an α-helix producing a segregation of a polar and nonpolar faces with the positively charged residues residing at the polar-nonpolar interface and the negatively charged residues residing at the center of the polar face (see, e.g., Segrest et al. (1990) Proteins: Structure, Function, and Genetics 8: 103-117).

"Apolipoprotein J" (apo J) is known by a variety of names including clusterin, TRPM2, GP80, and SP 40 (see, e.g., Fritz (1995) Pp 112 In: Clusterin: Role in Vertebrate Development, Function, and Adaptation (Harmony JAK Ed.), R. G. Landes, Georgetown, Tex.). It was first described as a heterodimeric glycoprotein and a component of the secreted proteins of cultured rat Sertoli cells (see, e.g., Kissinger et al. (1982) Biol. Reprod.; 27: 233240). The translated product is a single-chain precursor protein that undergoes intracellular cleavage into a disulfide-linked 34 kDa α subunit and a 47 kDa β subunit (see, e.g., Collard and Griswold (1987) Biochem., 26: 3297-3303). It has been associated with cellular injury, lipid transport, apoptosis and it may be involved in clearance of cellular debris caused by cell injury or death. Clusterin has been shown to bind to a variety of molecules with high affinity including lipids, peptides, and proteins and the hydrophobic probe 1-anilino-8-naphthalenesulfonate (Bailey et al. (2001) Biochem., 40: 11828-11840).

The class G amphipathic helix is found in globular proteins, and thus, the name class G. The feature of this class of amphipathic helix is that it possesses a random distribution of positively charged and negatively charged residues on the polar face with a narrow nonpolar face. Because of the narrow nonpolar face this class does not readily associate with phospholipid (see, e.g., Segrest et al. (1990) Proteins: Structure, Function, and Genetics. 8: 103-117; Erratum (1991) Proteins: Structure, Function and Genetics, 9: 79). Several exchangeable apolipoproteins possess similar but not identical characteristics to the G amphipathic helix. Similar to the class G amphipathic helix, this other class possesses a random distribution of positively and negatively charged residues on the polar face. However, in contrast to the class G amphipathic helix which has a narrow nonpolar face, this class has a wide nonpolar face that allows this class to readily bind phospholipid and the class is termed G* to differentiate it from the G class of amphipathic helix (see, e.g., Segrest et al. (1992) J. Lipid Res., 33: 141-166; Anantharamaiah et al. (1993) Pp. 109-142 In: The Amphipathic Helix, Epand, R. M. Ed CRC Press, Boca Raton, Fla.). Computer programs to identify and classify amphipathic helical domains have been described by Jones et al. (1992) J. Lipid Res. 33: 287-296) and include, but are not limited to the helical wheel program (WHEEL or WHEEL/SNORKEL), helical net program (HELNET, HELNET/SNORKEL, HELNET/Angle), program for addition of helical wheels (COMBO or COMBO/SNORKEL), program for addition of helical nets (COMNET, COMNET/SNORKEL, COMBO/SELECT, COMBO/NET), consensus wheel program (CONSENSUS, CONSENSUS/SNORKEL), and the like.

The term "ameliorating" when used with respect to "ameliorating one or more symptoms of atherosclerosis" refers to a reduction, prevention, or elimination of one or more symptoms characteristic of atherosclerosis and/or associated pathologies. Such a reduction includes, but is not limited to a reduction or elimination of oxidized phospholipids, a reduction in atherosclerotic plaque formation and rupture, a reduction in clinical events such as heart attack, angina, or stroke, a decrease in hypertension, a decrease in inflammatory protein biosynthesis, reduction in plasma cholesterol, and the like.

The term "enantiomeric amino acids" refers to amino acids that can exist in at least two forms that are nonsuperimposable mirror images of each other. Most amino acids (except glycine) are enantiomeric and exist in a so-called L-form (L amino acid) or D-form (D amino acid). Most naturally occurring amino acids are "L" amino acids. The terms "D amino acid" and "L amino acid" are used to refer to absolute configuration of the amino acid, rather than a particular direction of rotation of plane-polarized light. The usage herein is consistent with standard usage by those of skill in the art. Amino acids are designated herein using standard 1-letter or three-letter codes, e.g., as designated in Standard ST.25 in the Handbook On Industrial Property Information and Documentation.

The term "protecting group" refers to a chemical group that, when attached to a functional group in an amino acid (e.g., a side chain, an alpha amino group, an alpha carboxyl group, etc.) blocks or masks the properties of that functional group. In certain embodiments amino-terminal protecting groups include, but are not limited to acetyl, or amino groups. Other amino-terminal protecting groups include, but are not limited to alkyl chains as in fatty acids, propeonyl, formyl and others. In certain embodiments, preferred carboxyl terminal protecting groups include, but are not limited to, groups that form amides or esters.

The phrase "protect a phospholipid from oxidation by an oxidizing agent" refers to the ability of a compound to reduce the rate of oxidation of a phospholipid (or the amount of oxidized phospholipid produced) when that phospholipid is contacted with an oxidizing agent (e.g., hydrogen peroxide, 13-(S)—HPODE, 15-(S)—HPETE, HPODE, HPETE, HODE, HETE, etc.).

The terms "low density lipoprotein" or "LDL" is defined in accordance with common usage of those of skill in the art. Generally, LDL refers to the lipid-protein complex which when isolated by ultracentrifugation is found in the density range d=1.019 to d=1.063.

The terms "high density lipoprotein" or "HDL" is defined in accordance with common usage of those of skill in the art. Generally "HDL" refers to a lipid-protein complex which when isolated by ultracentrifugation is found in the density range of d=1.063 to d=1.21.

The term "Group I HDL" refers to a high density lipoprotein or components thereof (e.g., apo A-I, paraoxonase, platelet activating factor acetylhydrolase, etc.) that reduce oxidized lipids (e.g., in low density lipoproteins) or that protect oxidized lipids from oxidation by oxidizing agents.

The term "Group II HDL" refers to an HDL that offers reduced activity or no activity in protecting lipids from oxidation or in repairing (e.g., reducing) oxidized lipids.

The term "HDL component" refers to a component (e.g., molecules) that comprises a high density lipoprotein (HDL). Assays for HDL that protect lipids from oxidation or that repair (e.g., reduce oxidized lipids) also include assays for components of HDL (e.g., apo A-I, paraoxonase, platelet activating factor acetylhydrolase, etc.) that display such activity.

The terms "human apo A-I peptide" or "human apo A-I protein" can refer to a full-length human apo A-I peptide or to a fragment or domain thereof comprising a class A amphipathic helix.

A "monocytic reaction" as used herein refers to monocyte activity characteristic of the "inflammatory response" associated with atherosclerotic plaque formation. The monocytic reaction is characterized by monocyte adhesion to cells of the vascular wall (e.g., cells of the vascular endothelium), and/or chemotaxis into the subendothelial space, and/or differentiation of monocytes into macrophages.

The following abbreviations may be used herein: PAPC: L-α-1-palmitoyl-2-arachidonoyl-sn-glycero-3-phosphocholine; POVPC: 1-palmitoyl-2-(5-oxovaleryl)-sn-glycero-3-phosphocholine; PGPC: 1-palmitoyl-2-glutaryl-sn-glycero-3-phosphocholine; PEIPC: 1-palmitoyl-2-(5,6-epoxyisoprostane $E_2$)-sn-glycero-3-phosphocholine; ChCl8: 2: cholesteryl linoleate; ChCl8:2-OOH: cholesteryl linoleate hydroperoxide; DMPC: 1,2-ditetradecanoyl-rac-glycerol-3-phosphocholine; PON: paraoxonase; HPF: Standardized high power field; PAPC: L-α-1-palmitoyl-2-arachidonoyl-sn-glycero-3-phosphocholine; BL/6: C57BL/6J; C3H:C3H/HeJ.

The term "conservative substitution" is used in reference to proteins or peptides to reflect amino acid substitutions that do not substantially alter the activity (specificity (e.g., for lipoproteins)) or binding affinity (e.g., for lipids or lipoproteins)) of the molecule. Typically conservative amino acid substitutions involve substitution one amino acid for another amino acid with similar chemical properties (e.g., charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. With respect to the peptides of this invention sequence identity is determined over the full length of the peptide.

One example of algorithm that is suitable for determining percent sequence identity and sequence similarity is the BLAST algorithm, which is described in Altschul et al. (1990) *J. Mol. Biol.* 215: 403-410. Software for performing BLAST analyses is publicly available through the National Center for Biotechnology Information (www.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul (1993) *Proc. Natl. Acad. Sci. USA*, 90: 5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

The phrases "adjacent to each other in a helical wheel diagram of a peptide" or "contiguous in a helical wheel diagram of a peptide" when referring to residues in a helical peptide indicates that in the helical wheel representation the residues appear adjacent or contiguous even though they may not be adjacent or contiguous in the linear peptide.

As used herein, the terms "alkyl" and the prefix "alk-" are inclusive of both straight chain and branched chain groups and of cyclic groups, i.e., cycloalkyl. Cyclic groups can be monocyclic or polycyclic and preferably have from 3 to 6 ring carbon atoms, inclusive. Illustrative cyclic groups include cyclopropyl, cyclobutyl, cyclopentyl, and cyclohexyl groups. The $C_{1-10}$ alkyl group can be substituted or unsubstituted. Illustrative substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, carboxyalkyl, and carboxyl groups. $C_{1-10}$ alkyls include, but are not limited to, methyl, ethyl, n-propyl, isopropyl, cyclopropyl, cyclopropylmethyl, cyclopropylethyl, n-butyl, iso-butyl, sec-butyl, tert-butyl, cyclobutyl, cyclobutylmethyl, cyclobutylethyl, n-pentyl, cyclopentyl, cyclopentylmethyl, cyclopentylethyl, 1-methylbutyl, 2-methylbutyl, 3-methylbutyl, 2,2-dimethylpropyl, 1-ethylpropyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-timethylpropyl, 1-ethyl-1-methylpropyl, 1-ethyl-2-methylpropyl, cyclohexyl, and the like.

A "$C_{2-10}$ alkenyl" refers to a branched or unbranched hydrocarbon group containing one or more double bonds and having from 2 to 10 carbon atoms. A $C_{2-10}$ alkenyl can optionally include monocyclic or polycyclic rings, in which each ring has from three to six members. The $C_{2-10}$ alkenyl group can be substituted or unsubstituted. Illustrative substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, carboxyalkyl, and carboxyl groups. $C_{2-10}$ alkenyls include, but are not limited to, vinyl; allyl; 2-cyclopropyl-1-ethenyl; 1-propenyl; 1-butenyl; 2-butenyl; 3-butenyl; 2-methyl-1-propenyl; 2-methyl-2-propenyl; 1-pentenyl; 2-pentenyl; 3-pentenyl; 4-pentenyl; 3-methyl-1-butenyl; 3-methyl-2-butenyl; 3-methyl-3-butenyl; 2-methyl-1-butenyl; 2-methyl-2-butenyl; 2-methyl-3-butenyl; 2-ethyl-2-propenyl; 1-methyl-1-butenyl; 1-methyl-2-butenyl; 1-methyl-3-butenyl; 2-methyl-2-pentenyl; 3-methyl-2-pentenyl; 4-methyl-2-pentenyl; 2-methyl-3-pentenyl; 3-methyl-3-pentenyl; 4-methyl-3-pentenyl; 2-methyl-4-pentenyl; 3-methyl-4-pentenyl; 1,2-dimethyl-1-propenyl; 1,2-dimethyl-1-butenyl; 1,3-dimethyl-1-butenyl; 1,2-dimethyl-2-butenyl; 1,1-dimethyl-2-butenyl; 2,3-dimethyl-2-butenyl; 2,3-dimethyl-3-butenyl; 1,3-dimethyl-3-butenyl; 1,1-dimethyl-3-butenyl; 2,2-dimethyl-3-butenyl; and the like.

A "$C_{2-10}$ alkynyl" refers to a branched or unbranched hydrocarbon group containing one or more triple bonds and having from 2 to 10 carbon atoms. A $C_{2-10}$ alkynyl can optionally include monocyclic, bicyclic, or tricyclic rings, in which each ring has five or six members. The $C_{2-10}$ alkynyl group can be substituted or unsubstituted. Illustrative substituents include alkoxy, aryloxy, sulfhydryl, alkylthio, arylthio, halide, hydroxy, fluoroalkyl, perfluoralkyl, amino, aminoalkyl, disubstituted amino, quaternary amino, hydroxyalkyl, carboxyalkyl, and carboxyl groups. $C_{2-10}$ alkynyls include, but are not limited to, ethynyl, 1-propynyl, 2-propynyl, 1-butynyl, 2-butynyl, 3-butenyl, 1-pentynyl, 2-pentynyl, 3-pentynyl, 4-pentynyl, 5-hexene-1-ynyl, 2-hexynyl, 3-hexynyl, 4-hexynyl, 5-hexynyl; 1-methyl-2-propynyl; 1-methyl-2-butenyl; 1-methyl-3-butynyl; 2-methyl-3-butynyl; 1,2-dimethyl-3-butynyl; 2,2-dimethyl-3-butynyl; 1-methyl-2-pentynyl; 2-methyl-3-pentynyl; 1-methyl-4-pentynyl; 2-methyl-4-pentynyl, 3-methyl-4-pentynyl, and the like.

A "$C_{2-6}$ heterocyclyl" refers to a stable 5- to 7-membered monocyclic or 7- to 14-membered bicyclic heterocyclic ring that is saturated, partially unsaturated or unsaturated (aromatic), and that consists of 2 to 6 carbon atoms and 1, 2, 3 or 4 heteroatoms independently selected from the group consisting of N, O, and S and including any bicyclic group in which any of the above-defined heterocyclic rings is fused to a benzene ring. The heterocyclyl group can be substituted or unsubstituted. Illustrative substituents include, but are not limited to alkoxy, aryloxy, sulfhydryl, alkylthio, arylthio, halide, hydroxy, fluoroalkyl, perfluoralkyl, amino, aminoalkyl, disubstituted amino, quaternary amino, hydroxyalkyl, carboxyalkyl, and carboxyl groups. The nitrogen and sulfur heteroatoms can optionally be oxidized. The heterocyclic ring can be covalently attached via any heteroatom or carbon atom that results in a stable structure, e.g., an imidazolinyl ring can be linked at either of the ring-carbon atom positions or at the nitrogen atom. A nitrogen atom in the heterocycle can optionally be quaternized. In certain embodiments, when the total number of S and O atoms in the heterocycle exceeds 1, then these heteroatoms are not adjacent to one another. Heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidole, pyridothiazole, pyridinyl, pyridyl, pyrimidinyl, pyrrolidinyl, pyrrolinyl, pyrrolyl, quinolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. In certain embodiments, 5 to 6 membered heterocycles include, but are not limited to, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, tetrazolyl, and the like.

A "$C_{6-12}$ aryl" refers to an aromatic group having a ring system comprised of carbon atoms with conjugated electrons (e.g., phenyl). The aryl group typically has from 6 to 12 carbon atoms. Aryl groups can optionally include monocyclic, bicyclic, or tricyclic rings, in which each ring has five or six members. The aryl group can be substituted or unsubstituted. Illustrative substituents include, but are not limited to, alkyl, hydroxy, alkoxy, aryloxy, sulfhydryl, alkylthio, arylthio, halide, fluoroalkyl, carboxyl, hydroxyalkyl, carboxyalkyl, amino, aminoalkyl, monosubstituted amino, disubstituted amino, quaternary amino groups, and the like.

A "$C_{7-14}$ alkaryl" refers to an alkyl substituted by an aryl group (e.g., benzyl, phenethyl, or 3,4-dichlorophenethyl) having from 7 to 14 carbon atoms.

A "$C_{3-10}$ alkheterocyclyl" refers to an alkyl substituted heterocyclic group having from 3 to 10 carbon atoms in addition to one or more heteroatoms (e.g., 3-furanylmethyl, 2-furanylmethyl, 3-tetrahydrofuranylmethyl, 2-tetrahydrofuranylmethyl, and the like).

A "$C_{1-10}$ heteroalkyl" refers to a branched or unbranched alkyl, alkenyl, or alkynyl group having from 1 to 10 carbon atoms in addition to one or more heteroatoms, where one or more methylenes ($CH_2$) or methines (CH) are replaced by nitrogen, oxygen, sulfur, carbonyl, thiocarbonyl, phosphoryl, or sulfonyl. Heteroalkyls include, but are not limited to, tertiary amines, secondary amines, ethers, thioethers, amides, thioamides, carbamates, thiocarbamates, phosphoramidates, sulfonamides, and disulfides. A heteroalkyl can optionally include monocyclic, bicyclic, or tricyclic rings, in which each ring has three to six members. The heteroalkyl group can be substituted or unsubstituted. Illustrative substituents include, but are not limited to alkoxy, aryloxy, sulfhydryl, allylthio, arylthio, halide, hydroxyl, fluoroalkyl, perfluoralkyl, amino, amino alkyl, disubstituted amino, quaternary amino, hydroxyalkyl, hydroxyalkyl, carboxyalkyl, and carboxyl groups.

The term "acyl" refers to a chemical moiety with the formula R—C(O)—, where R is selected from $C_{1-10}$ alkyl, $C_{1-10}$ alkenyl, $C_{1-10}$ alkynyl, $C_{2-6}$ heterocyclyl, $C_{6-12}$ aryl, $C_{7-14}$ alkaryl, $C_{3-10}$ alkheterocyclyl, $C_{1-10}$ heteroalkyl, and the like.

A "halide" refers to meant bromine, chlorine, iodine, or fluorine.

DETAILED DESCRIPTION

Figure 1:
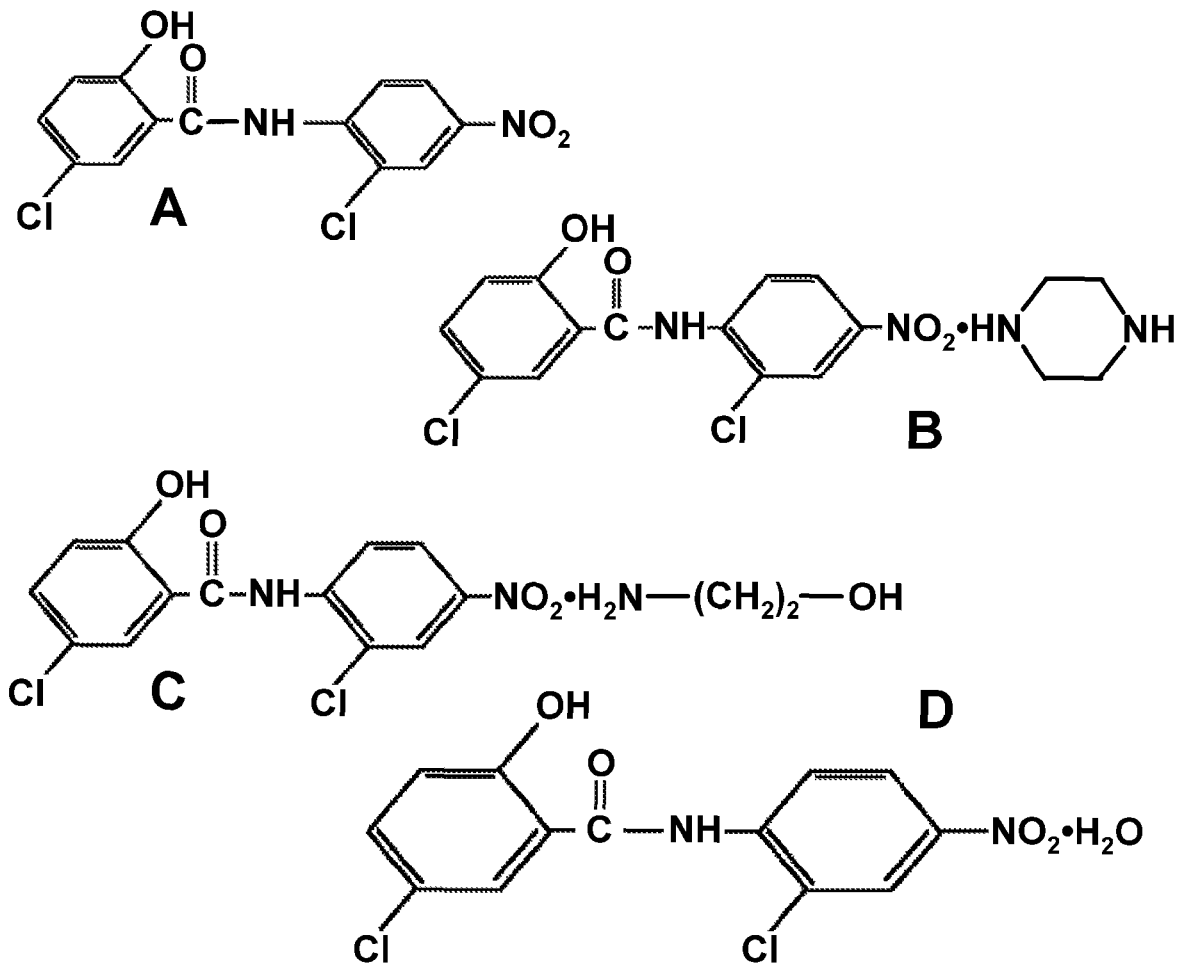
FIG. 1, panels A-D, shows various forms of niclosamide. A: 2'5-dichloro-4'-nitrosalicylanilide; B: 5-chloro-salicyl-(2-chloro-4-nitro) anilide 2-aminoethanol salt; C: 5-chloro-salicyl-(2-chloro-4-nitro) anilide piperazine salt; and D: 5-chloro-salicyl-(2-chloro-4-nitro)anilide monohydrate.

This invention pertains to the surprising discovery that salicylanilides, including, but not limited to niclosamide and/or niclosamide analogues when orally administered in conjunction with a pharmaceutical (e.g., a peptide pharmaceutical such as a helical peptide (e.g., a class A amphipathic helical peptide, a G* helical peptide, etc.) as described herein) significantly increases the bioavailability and/or apparent in vivo activity of that peptide. Moreover, the increase in bioavailability or apparent activity is sufficient so that peptide pharmaceuticals previously formulated as "D" amino acid isomers and protected at both termini to permit oral administration can readily be formulated utilizing all L form amino acids with optionally protected termini for oral administration. This significantly reduces the cost to manufacture such peptides and increases the predictability of the peptide's behavior in mammalian systems since the biological activity of L peptides is generally better characterized and understood.

Moreover, it was a surprising discovery that when salicylanilides, including, but not limited to niclosamide and/or niclosamide analogues, are combined (e.g., under acidic conditions) with peptide or protein therapeutics (e.g., amphipathic helical peptides, e.g., apolipoprotein A-I [apoA-I] or portions of apoA-I, or ApoJ, etc.) the salicylanilide and the peptide form an adduct that increases the apparent solubility of the bioactive agent(s) and/or the bioavailablity of the agent(s).

Thus, in certain embodiments, this invention contemplates methods of enhancing the uptake and in vivo activity of a peptide orally administered to a mammal by orally administering the peptide in conjunction with an amount of niclosamide or a niclosamide analogue sufficient to enhance in vivo activity (e.g., via enhanced uptake and/or bioavailability) of the peptide. To facilitate such methods, in certain embodiments, pharmaceutical formulations are contemplated that comprise both the peptide pharmaceutical(s) along with niclosamide and/or a niclosamide analogue. In certain embodiments the result of the reaction between the salicylanilide (e.g., niclosamide or niclosamides analogue) with the peptide or protein will be achieved by chemical synthesis prior to administration of the peptide/protein comprising the salicylanilide-derived adduct.

It was also a surprising discovery that the amphipathic helical peptides described herein can increase the solubility of niclosamide and/or niclosamide analogues in aqueous systems thereby enhancing/facilitating the incorporation of niclosamide in a pharmaceutical formulation. Thus, in certain embodiments, this invention contemplates pharmaceutical formulations comprising a combination of a therapeutic amphipathic helical peptide (e.g., D-4F, L-4F, L-5F, etc.) and niclosamide or a niclosamide analogue, wherein said niclosamide in the formulation shows substantially greater solubility in an aqueous solution than niclosamide in an aqueous solution absent the amphipathic helical peptide.

In certain embodiments, this invention also pertains to the surprising discovery that agents such as N-(5-chlorosalicyloyl)-8-aminocaprylic acid (5-CNAC), N-(10-[2-hydroxybenzoyl]aminodecanoic acid (SNAD), and N-(8-[2-hydroxybenzoyl]amino)caprylic acid (SNAC), and the like, can increase the oral bioavailability and/or apparent activity of L form peptides to therapeutically relevant levels. This permits the use of such L form peptides as orally delivered therapeutics where previously D form peptides were preferred. In certain preferred embodiments the L form peptides are the amphipathic helical peptides described herein (e.g., L-4F, L-5F, etc.).

In certain embodiments, when administered in conjunction niclosamide and/or niclosamide analogues as described herein (including, but not necessarily limited to those shown in Formula I and/or Table 1), L-form peptides, e.g., as described herein, do not even require amino or carboxyl terminal blocking/protecting groups. Peptides lacking such blocking groups can easily be synthesized using recombinant expression systems rather than chemical peptide synthesis methods. Bioreactors can thus readily be used to prepare such unprotected peptides at very low cost (as compared to chemically synthesized peptides).

In various embodiments formulations comprising one or more therapeutic peptides in combination with niclosamide and/or niclosamide analogues as described herein, are contemplated. The formulations are typically suitable for oral administration. In certain embodiments the formulations can provide for release of niclosamide and/or niclosamide analogues and/or permeability enhancer(s) before the peptide.

While niclosamide and niclosamide analogues and/or other "permeability" enhancers described herein are particularly useful for enhancing the oral bioavailability of L peptides as described herein, the uses of these agents is not so limited. Thus, in certain embodiments the use of such agents with protected L peptides and or protected or unprotected peptides comprising one or more D amino acid residues is also contemplated.

I. Salicylanilides to Enhance Pharmaceutical In Vivo Activity.

As indicated above, it is a surprising discovery that various salicylanilides including, but not limited to niclosamide and niclosamide analogues are effective to substantially increase the in vivo activity (e.g., bioavailability, bioactivity, etc.) of a pharmaceutical (e.g., a therapeutic peptide) orally administered to a mammal.

A) Niclosamide and Niclosamide Analogues

Niclosamide is a chloronitrophenol derivative (see compound A in FIG. 1) principally used against aquatic snails but also as an antiparasitic drug in human and veterinary medicine. Niclosamide is known by the IUPAC designation: 2'5-dichloro-4'-nitrosalicylanilide and by the CAS designation: CAS: 5-chloro-N-(2-chloro-4-nitrophenyl)-2-hydroxybenzamide.

Niclosamide is not very water soluble, 5-8 mg/L at 20° C., sparingly soluble in ether, ethanol and chloroform, and soluble in acetone; the ethanolamine salt dissolves in distilled water 180-280 mg/L at 20° C. It was a surprising discovery, however, that the inclusion of an amphipathic helical peptide, e.g., as described herein, significantly increases the solubility of niclosamide and facilitates the preparation of pharmaceutical formulations.

In tablets niclosamide undergoes a biodegradation in moist environments but niclosamide itself is stable in an aqueous solution for several months. The ethanolamine salt is stable to heat, hydrolyzed by concentrated acid or alkali, and stable in aquatic environments.

Niclosamide is readily available in a number of formulations. These include, but are not limited to, the ethanolamine salt (see compound C in FIG. 1) known by the IUPAC designation 5-chloro-salicyl-(2-chloro-4-nitro) anilide 2-aminoethanol salt or the CAS designation 5-chloro-N-(2-chloro-4-nitrophenyl)-2-hydroxybenzamide with 2-aminoethanol (1:1), the piperazine salt (see compound B in FIG. 1) known by the IUPAC designation 5-chloro-salicyl-(2-chloro-4-nitro) anilide piperazine salt or the CAS designation 5-chloro-N-(2-chloro-4-nitrophenyl)-2-hydroxybenzamide with piperazine (2:1), and niclosamide monohydrate (see compound D in FIG. 1) known by the IUPAC designation 5-chloro-salicyl-(2-chloro-4-nitro) anilide monohydrate or the CAS designation 5-chloro-N-(2-chloro-4-nitrophenyl)-2-hydroxybenzamide with monohydrate (1:1).

Niclosamide is commercially available in a number of formulations including, but not limited to BAYER 73®, BAYER 2353®, BAYER 25 648®, BAYLUSCID®, BAYLUSCIDE®, CESTOCID®, CLONITRALID, DICHLOSALE®, FENASAL®, HL 2447®, IOMESAN®, IOMEZAN®, LINTEX®, MANOSIL®, NASEMO®, NICLOSAMID®, PHENASAL®, TREDEMINE®, SULQUI®, VERMITID®, VERMITIN®, YOMESAN®, and the like.

This invention also contemplates the use of various niclosamide analogues to enhance the in vivo of orally administered pharmaceuticals (e.g., therapeutic peptides). Such analogues include, but are not limited to, compounds according to Formula I:

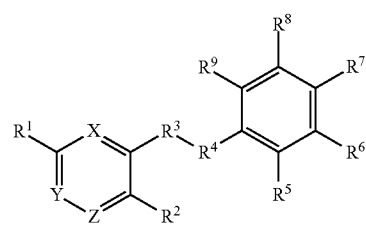

I where X is N or $CR^{10}$; Y is N or $CR^{11}$; Z is N or $CR^{12}$; and each of $R^1$, $R^2$, $R^5$, $R^6$, $R^7$, $R^8$, $R^9$, $R^{10}$, $R^{11}$ and $R^{12}$ is independently selected from H, halide (F, Cl, Br, or I), $NO_2$, OH, $OR^{13}$, $SR^{14}$, $NR^{15}R^{16}$, CN, $CF_3$, $C_{1-10}$ alkyl, $C_{2-10}$ alkenyl, $C_{2-10}$ alkynyl, $C_{2-6}$ heterocyclyl, $C_{6-12}$ aryl, $C_{7-14}$ alkaryl, $C_{3-10}$ alkheterocyclyl, $C_{1-10}$ heteroalkyl, or is described by one of the Formulas II-XIV:

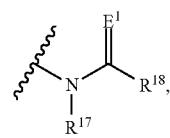

II

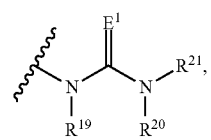

III

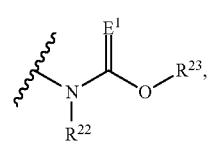

IV

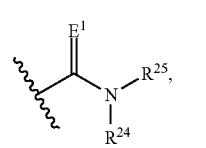

V

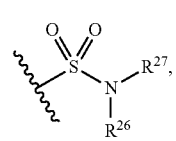

VI

-continued

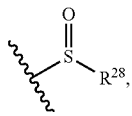
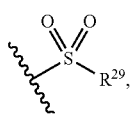
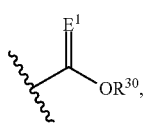
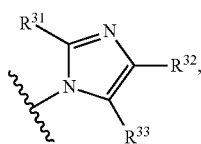
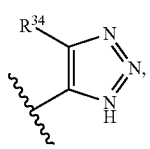
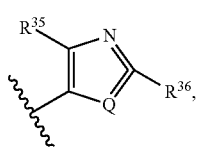
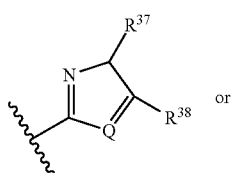
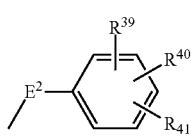

In compounds of formula I, $R^3$ and $R^4$ are independently selected from the group consisting of C=O, C=S, C=NR$^{42}$, NH, NR$^{43}$, CHOR$^{44}$, CH$_2$, and the like. Groups $R^2$ and $R^4$; X and $R^4$; $R^5$ and $R^3$; $R^9$ and $R^3$ may combine to form a six-membered ring, using connections described by one of the groups:

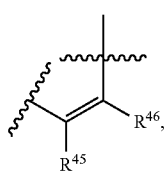

-continued

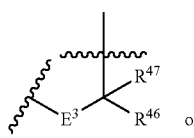
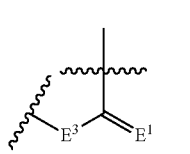

For compounds of formula I, each $E^1$ is independently O, S, or NR$^{42}$; each $E^2$ is independently CR$^{49}$R$^{50}$, O or S; each $E^3$ is independently CR$^{51}$R$^{52}$, O, S, or NR$^{53}$; each Q is, independently, O, S, or NR$^{54}$. $R^{13}$ and $R^{14}$ are each independently, acyl, C$_{1-10}$ alkyl, C$_{2-10}$ alkenyl, C$_{2-10}$ alkynyl, C$_{2-6}$ heterocyclyl, C$_{6-12}$ aryl, C$_{7-14}$ alkaryl, C$_{3-10}$ alkheterocyclyl, C$_{1-10}$ heteroalkyl; $R^{18}$, $R^{23}$, $R^{28}$, $R^{29}$, $R^{30}$, $R^{42}$, $R^{54}$ are each, independently, C$_{1-10}$ alkyl, C$_{2-10}$ alkenyl, C$_{2-10}$ alkynyl, C$_{2-6}$ heterocyclyl, C$_{6-12}$ aryl, C$_{7-14}$ alkaryl, C$_{3-10}$ alkheterocyclyl, C$_{1-10}$ heteroalkyl; $R^{15}$, $R^{16}$, $R^{17}$, $R^{19}$, $R^{20}$, $R^{21}$, $R^{22}$, $R^{24}$, $R^{25}$, $R^{26}$, $R^{27}$, $R^{43}$, $R^{44}$, $R^{45}$, $R^{46}$, $R^{47}$, $R^{48}$, $R^{51}$, $R^{52}$, and $R^{53}$ are each, independently, H, C$_{1-10}$ alkyl, C$_{2-10}$ alkenyl, C$_{2-10}$ alkynyl, C$_{2-6}$ heterocyclyl, C$_{6-12}$ aryl, C$_{7-14}$ alkaryl, C$_{3-10}$ alkheterocyclyl, C$_{1-10}$ heteroalkyl; $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{49}$, and $R^{50}$ are each, independently, H, halide, NO$_2$, CN, CF$_3$, C$_{1-10}$ alkyl, C$_{2-10}$ alkenyl, C$_{2-10}$ alkynyl, C$_{2-6}$ heterocyclyl, C$_{6-12}$ aryl, C$_{7-14}$ alkaryl, C$_{3-10}$ alkheterocyclyl, or C$_{1-10}$ heteroalkyl.

In certain embodiments, compounds of formula I are further described by any of formulas XVIII-XXI:

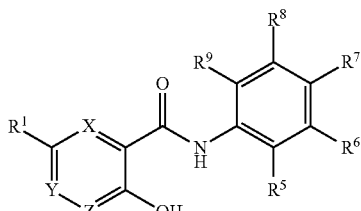
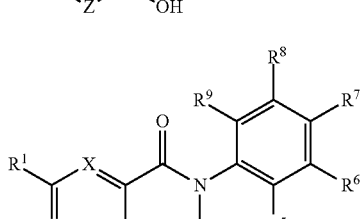
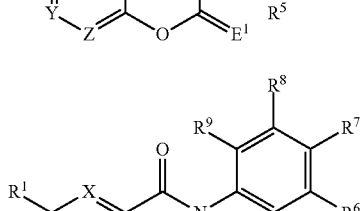
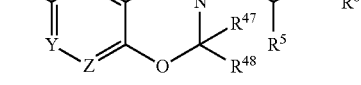

-continued

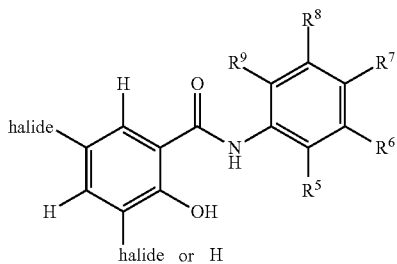

XXI where X, Y, Z, E¹, R¹, R⁵, R⁶, R⁷, R⁸, R⁹, R⁴⁷, and R⁴⁸ are as defined above.

In certain embodiments compounds include compounds described by Formula XXII:

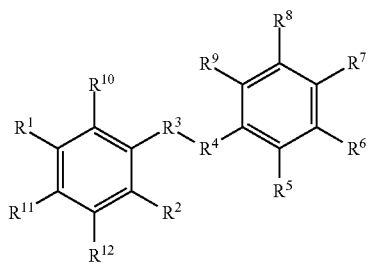

XXII where $R^1$, $R^2$, $R^5$, $R^6$, $R^7$, $R^8$, $R^9$, $R^{10}$, $R^{11}$ and $R^{12}$ are independently selected from the group consisting of H, halide, NO₂, CF₃, OH, acyl, CN, C₁-C₁₀ alkyl (preferably C₁-C₃ alkyl), C₁-C₁₀ heteroalkyl (preferably C₁-C₃ heteroalkyl); and wherein $R^3$ and $R^4$ are as defined above. In certain embodiments, $R^3$ is C═O, while $R^4$ is NH or $R^3$ is NH while $R^4$ is C═O. In these and certain other embodiments, only two of $R^1$, $R^2$, $R^{10}$, $R^{11}$, and $R^{12}$ are present, and one is H or OH, while the other is halogen (e.g., Cl, Br, or F).

In these and certain other embodiments, only two of $R^5$, $R^6$, $R^7$, $R^8$, and $R^9$ are present and these are NO₂ and halogen (e.g., Cl, Br, or F).

Figure 4:
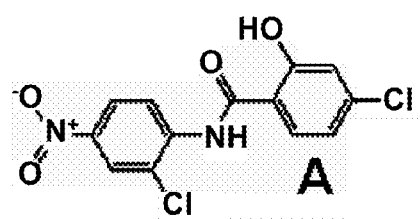
FIG. 4 illustrates niclosamide analogues in which one halogen group is relocated within the same ring (see, e.g., compounds A-D) or both halogen groups are relocated within the same ring (see, e.g., compounds E-G).
Figure 4:
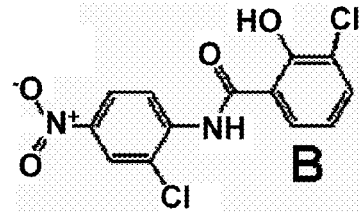
Figure 4:
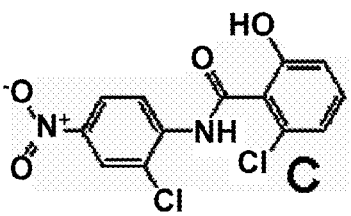
Figure 4:
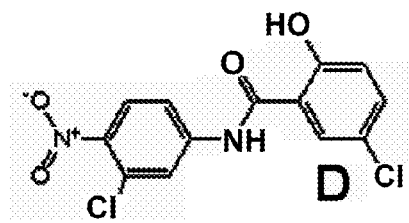
Figure 4:
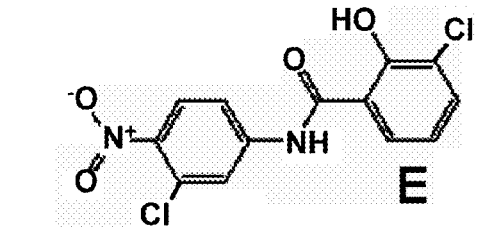
Figure 4:
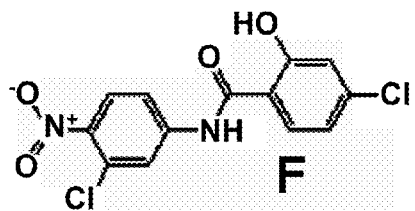
Figure 4:
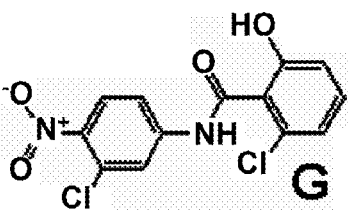
Figure 5:
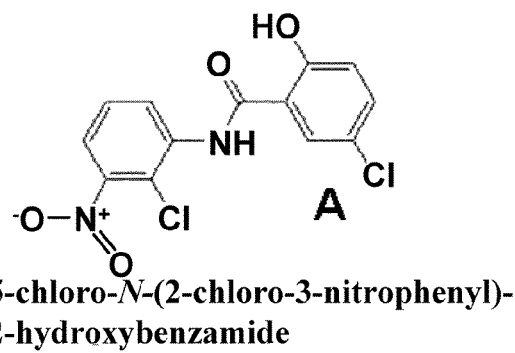
FIG. 5 illustrates niclosamides in which the nitro group is relocated within the same ring (see, e.g., compounds A-C) and niclosamide analogues where the hydroxyl group is relocated within the same ring (see, e.g., compounds D-F).
Figure 5:
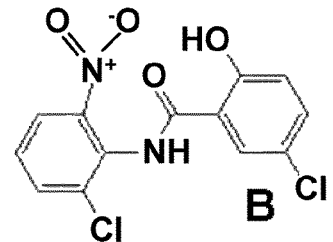
Figure 5:
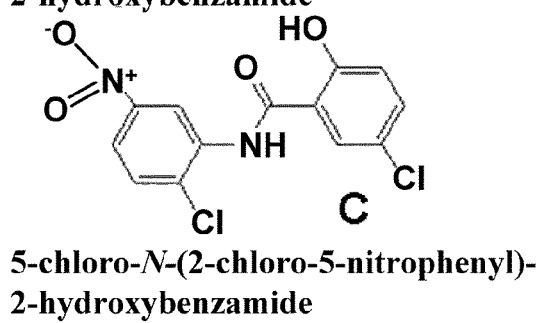
Figure 5:
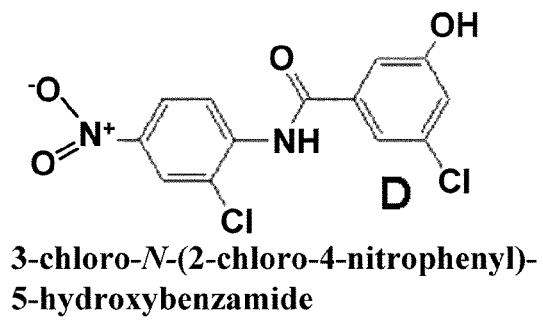
Figure 5:
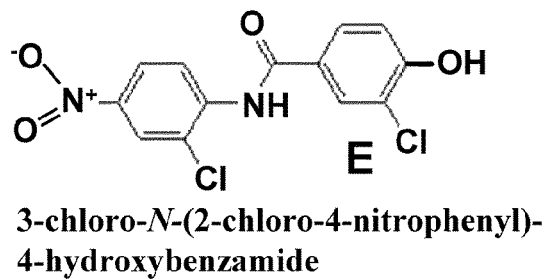
Figure 5:
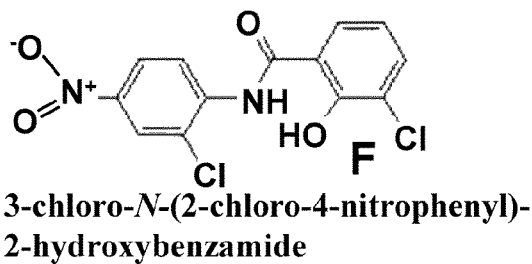
Figure 6:
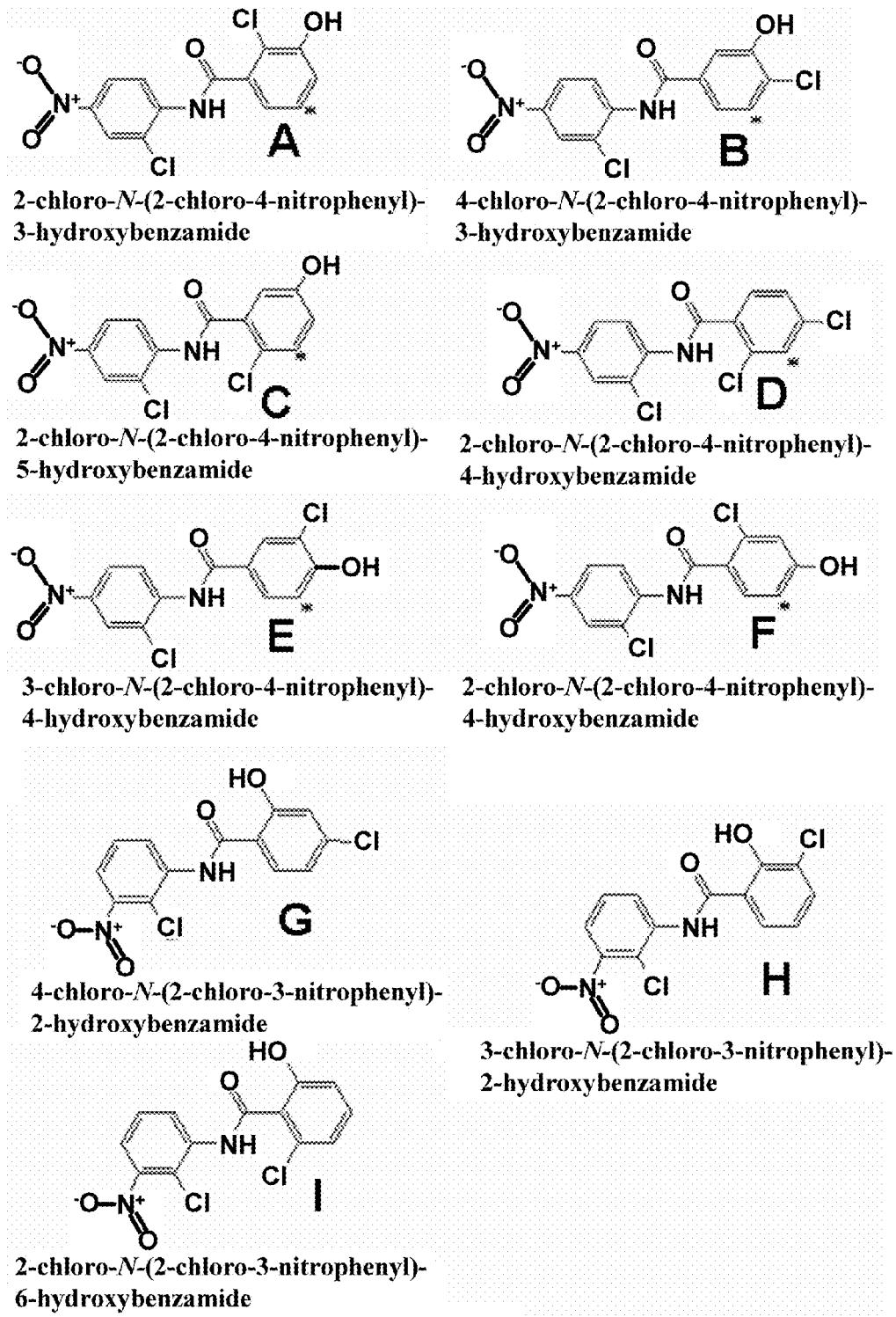
FIG. 6 illustrates niclosamide analogues where both halogen and hydroxy and/or nitro groups are relocated while keeping the substituents within the aromatic ring (see, e.g., compounds A-F) and niclosamide analogues having a nitro- and a hydroxyl group relocation (see, e.g., compounds G-I).
Figure 7:
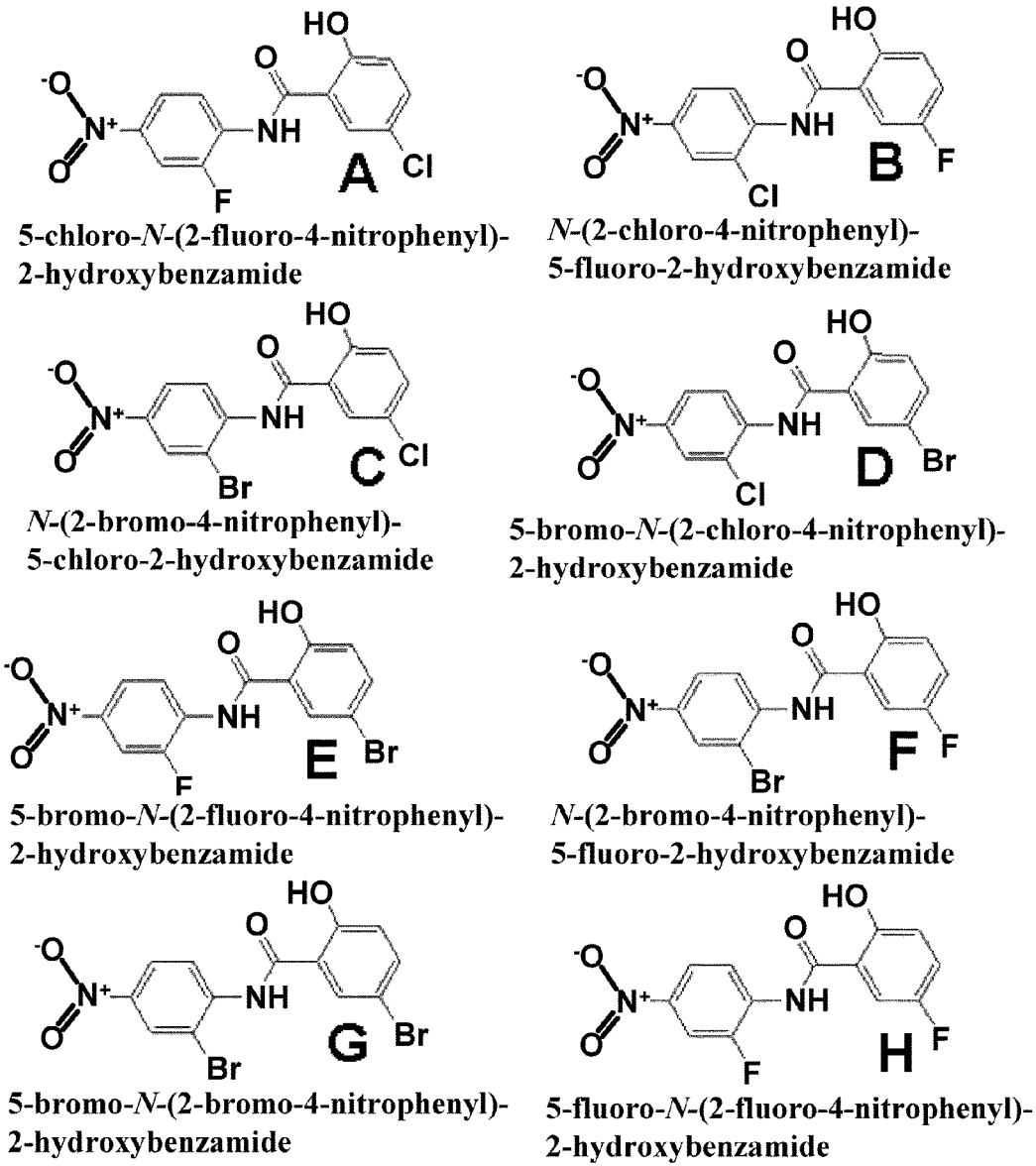
FIG. 7 illustrates niclosamide analogues comprising a single halogen exchange (see, e.g., compounds A-D), niclosamide analogues comprising a double halogen exchange (see, e.g., compounds E-F), niclosamide analogues comprising an exchange of Cl— to Br— (see, e.g., compound G), and niclosamide analogs comprising an exchange of Cl— to F— (see, e.g., compound H).

In certain embodiments niclosamide analogues include, but are not limited to niclosamide analogues in which one halogen group is relocated within the same ring (see, e.g., compounds A-D in FIG. 4) or both halogen groups are relocated within the same ring (see, e.g., compounds E-G in FIG. 4), niclosamides in which the nitro group is relocated within the same ring (see, e.g., compounds A-C in FIG. 5), niclosamide analogues where the hydroxyl group is relocated within the same ring (see, e.g., compounds D-F in FIG. 5), niclosamide analogues where both halogen and hydroxy and/or nitro groups are relocated while keeping the substituents within the aromatic ring (see, e.g., compounds A-F in FIG. 6), compounds like A-F in FIG. 6, except having except (3-chloro-4-nitrophenyl) in place of (2-chloro-4-nitrophenyl), niclosamide analogues having a nitro- and a hydroxyl group relocation (see, e.g., compounds G-I in FIG. 6), niclosamide analogues comprising a single halogen exchange (see, e.g., compounds A-D in FIG. 7), niclosamide analogues comprising a double halogen exchange (see, e.g., compounds E-F in FIG. 7), niclosamide analogs comprising an exchange of Cl— to Br— (see, e.g., compound G in FIG. 7), niclosamide analogs comprising an exchange of Cl— to F— (see, e.g., compound H in FIG. 7), and the like.

In certain embodiments the niclosamide analogues include, but are not limited to compounds according to Formula XXIII:

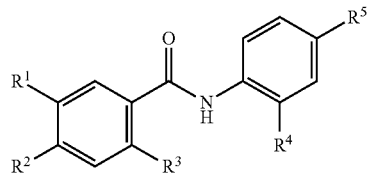

XXIII where $R^1$, $R^2$, $R^3$, $R^4$, and $R^5$, are independently present or absent, and when present are independently selected from the group consisting of Cl, Br, alkyl, methyl, hydroxyalkyl, and the like. These analogues are meant to be illustrative and not limiting. Using the teaching provided herein, other suitable niclosamide analogs will be recognized by one of skill in the art.

In certain embodiments the salicylanilides include, but are not limited to salicylanilides shown in Table 1.

TABLE 1

Illustrative salicylanilides.

| Cmpd | Salicylanilide | Parent Acid | Parent Amine |
|---|---|---|---|
| BP 1001 | ![salicylanilide structure with O₂N, Cl, HO, Cl substituents] | ![parent acid structure with HO, HO, Cl substituents] | ![parent amine structure with O₂N, NH₂, Cl substituents] |

TABLE 1-continued

Illustrative salicylanilides.

| Cmpd | Salicylanilide | Parent Acid | Parent Amine |
|---|---|---|---|
| BP 1002 | | | |
| BP 1003 | | | |
| BP 1004 | | | |
| BP 1005 | | | |
| BP 1006 | | | |
| BP 1007 | | | |
| BP 1008 | | | |

TABLE 1-continued

Illustrative salicylanilides.

| Cmpd | Salicylanilide | Parent Acid | Parent Amine |
|---|---|---|---|
| BP 1009 | | | |
| BP 1010 | | | |
| BP 1011 | | | |
| BP 1012 | | | |
| BP 1013 | | | |
| BP 1014 | | | |
| BP 1015 | | | |

TABLE 1-continued

Illustrative salicylanilides.

| Cmpd | Salicylanilide | Parent Acid | Parent Amine |
|---|---|---|---|
| BP 1016 | | | |
| BP 1017 | | | |
| BP 1018 | | | |
| BP 1019 | | | |
| BP 1020 | | | |
| BP 1021 | | | |
| BP 1022 | | | |

TABLE 1-continued

Illustrative salicylanilides.

| Cmpd | Salicylanilide | Parent Acid | Parent Amine |
|---|---|---|---|
| BP 1023 | | | |
| BP 1024 | | | |
| BP 1025 | | | |
| BP 1026 | | | |
| BP 1027 | | | |
| BP 1028 | | | |
| BP 1029 | | | |

TABLE 1-continued

Illustrative salicylanilides.

| Cmpd | Salicylanilide | Parent Acid | Parent Amine |
|---|---|---|---|
| BP 1030 | | | |
| BP 1031 | | | |
| BP 1032 | | | |
| BP 1033 | | | |
| BP 1034 | | | |
| BP 1035 | | | |
| BP 1036 | | | |

TABLE 1-continued
Illustrative salicylanilides.
| Cmpd | Salicylanilide | Parent Acid | Parent Amine |
|---|---|---|---|
| BP 1037 | 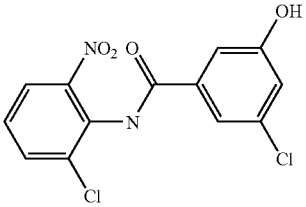 | 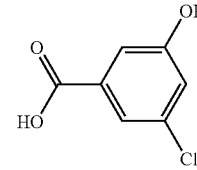 | 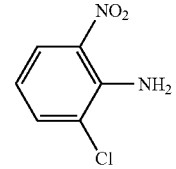 |
| BP 1038 | 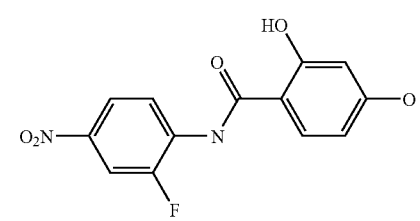 | 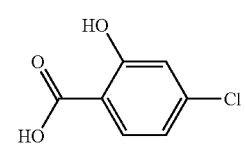 | 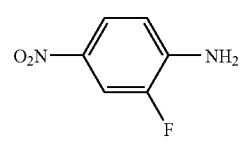 |
| BP 1039 | 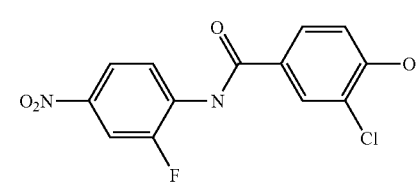 | 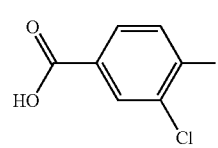 | 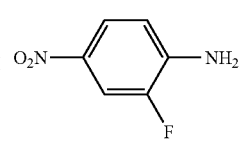 |
| BP 1040 | 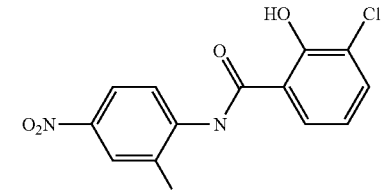 | 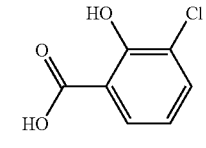 | 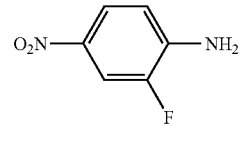 |
| BP 1041 | 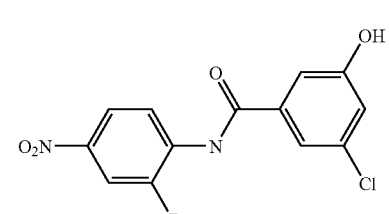 | 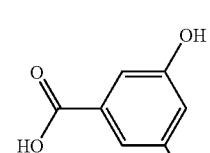 | 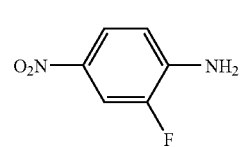 |
| BP 1042 | 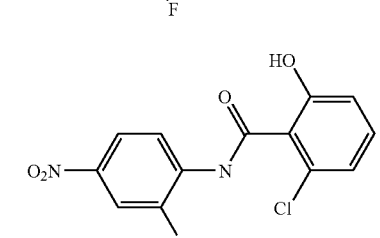 | 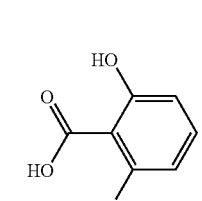 | 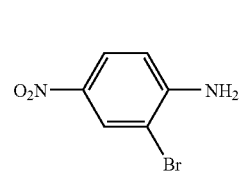 |
| BP 1043 | 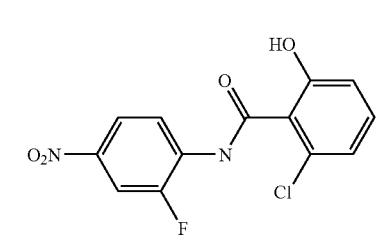 | 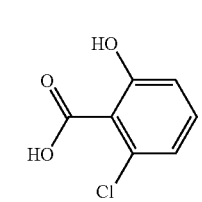 | 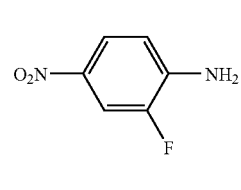 |

TABLE 1-continued
Illustrative salicylanilides.
| Cmpd | Salicylanilide | Parent Acid | Parent Amine |
|---|---|---|---|
| BP 1044 | 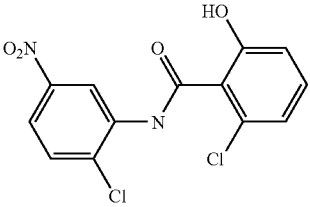 | 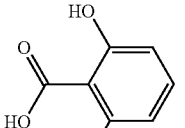 | 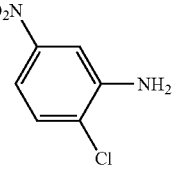 |
| BP 1045 | 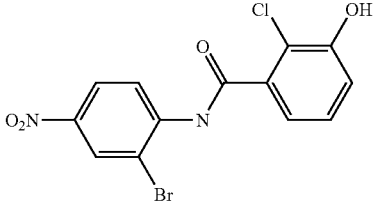 | 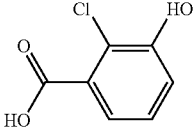 | 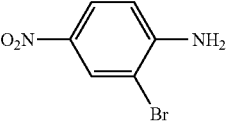 |
| BP 1046 | 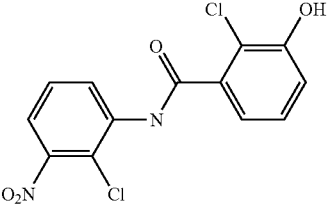 | 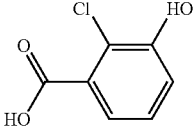 | 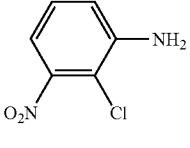 |
| BP 1047 | 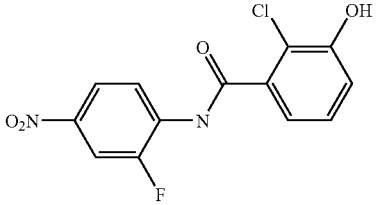 | 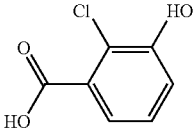 | 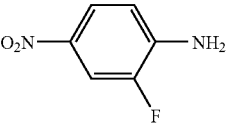 |
| BP 1048 | 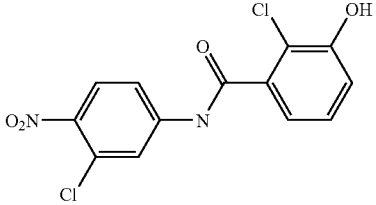 | 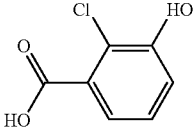 | 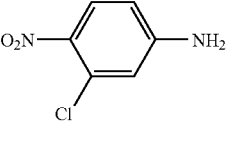 |
| BP 1049 | 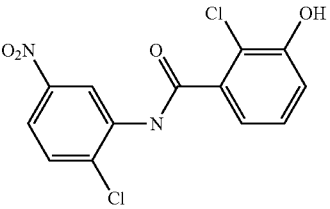 | 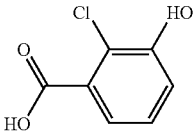 | 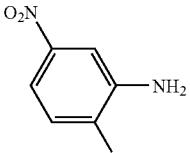 |
| BP 1050 | 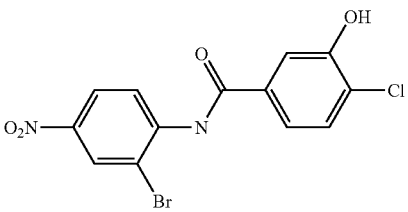 | 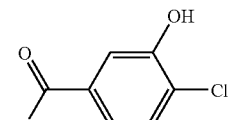 | 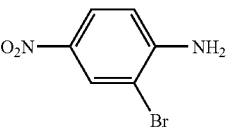 |

TABLE 1-continued

Illustrative salicylanilides.

| Cmpd | Salicylanilide | Parent Acid | Parent Amine |
|---|---|---|---|
| BP 1051 | | | |
| BP 1052 | | | |
| BP 1053 | | | |
| BP 1055 | | | |
| BP 1056 | | | |
| BP 1057 | | | |
| BP 1058 | | | |

TABLE 1-continued

Illustrative salicylanilides.

| Cmpd | Salicylanilide | Parent Acid | Parent Amine |
| --- | --- | --- | --- |
| BP 1059 | | | |
| BP 1061 | | | |
| BP 1063 | | | |
| BP 1064 | | | |
| BP 1065 | | | |
| BP 1067 | | | |
| BP 1068 | | | |

TABLE 1-continued

Illustrative salicylanilides.

| Cmpd | Salicylanilide | Parent Acid | Parent Amine |
|---|---|---|---|
| BP 1069 | [structure] | [structure] | [structure] |
| BP 1070 | [structure] | [structure] | [structure] |
| BP 1071 | [structure] | [structure] | [structure] |
| BP 1072 | [structure] | [structure] | [structure] |
| BP 1073 | [structure] | [structure] | [structure] |

B) Other Salicylanilides

Figure 2:
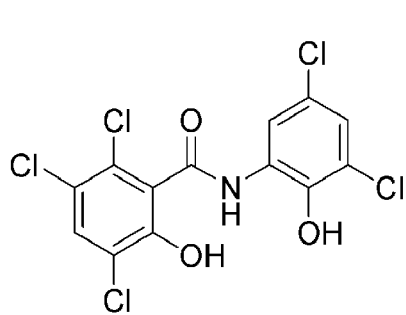
FIG. 2 illustrates various niclosamide analogues. A: Oxyclozanide (3,3',5,5',6-pentachloro-2'-hydroxy salicylanilide; 2,3,5-trichloro-N-(3,5-dichloro-2-hydroxyphenyl)-6-hydroxybenzamide); B: Closantel (5'-Chloro-alpha4-(p-chlorophenyl)-alpha4-cyano-3,5-diiodo-2',4'-salicyloxylidide; N-[5-Choloro-4-[(4-Chlorophenyl) Cyanomethyl]-2-Methylphenyl]-2-Hydroxy-3-5-Diiodobenzamide); C: Rafoxanide (also known as Disalan; Flukanide; N-(3-chloro-4-(4-chlorophenoxy)phenyl)-2-hydroxy-3,5-diiodobenzamide; 3'-Chloro-4'-(p-chlorophenoxy)-3,5-diiodosalicylanilide); D: Flusalan (3,5-Dibromo-2-hydroxy-N-(3-trifluoromethyl-phenyl)-benzamide); E: Tribromsalan (3,5-Dibromo-N-(4-bromo-phenyl)-2-hydroxy-benzamide); F: Resorantel (N-(4-Bromo-phenyl)-2,6-dihydroxy-benzamide); G: Clioxanide (Acetic acid 2-(4-chloro-phenylcarbamoyl)-4,6-diiodo-phenyl ester).
Figure 2:
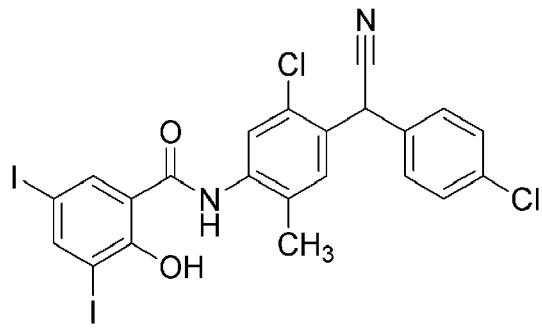
Figure 2:
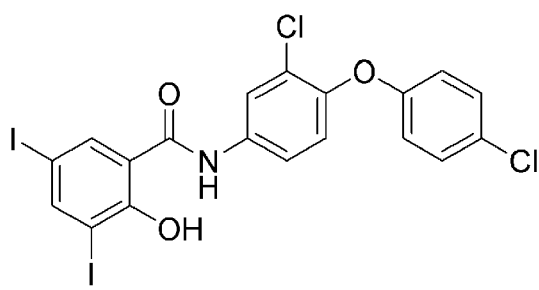
Figure 2:
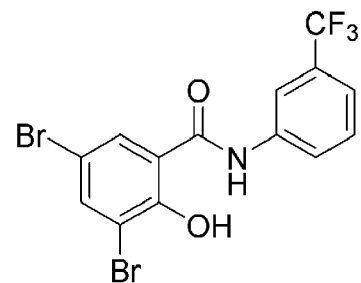
Figure 2:
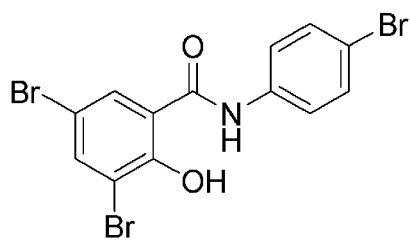
Figure 2:
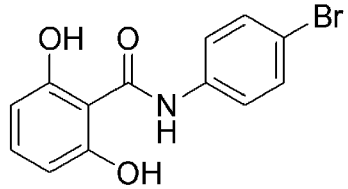
Figure 2:
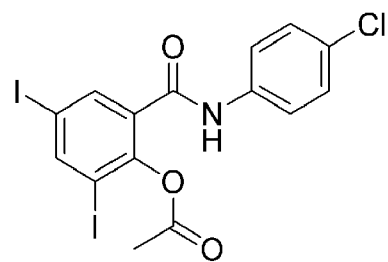
Figure 3:
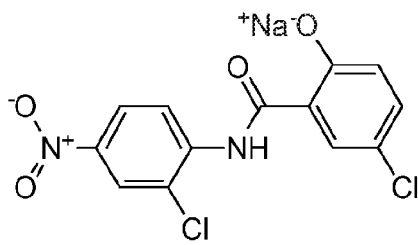
FIG. 3 illustrates various niclosamide analogues and salts thereof.
Figure 3:
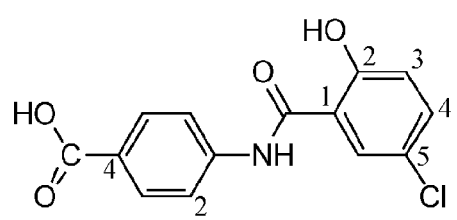
Figure 3:
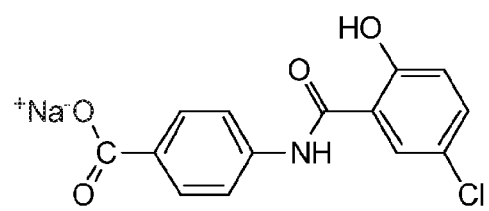
Figure 3:
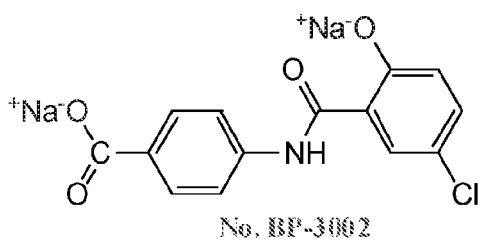
Figure 3:
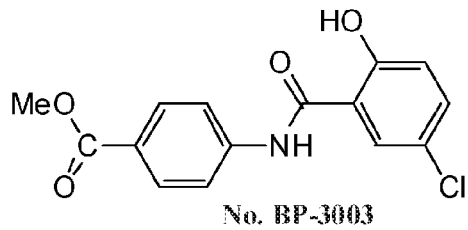
Figure 3:
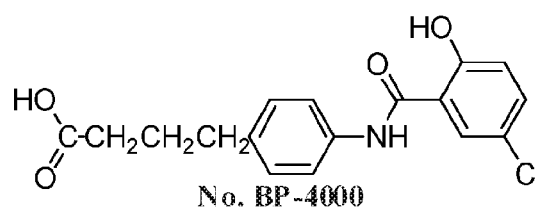
Figure 3:
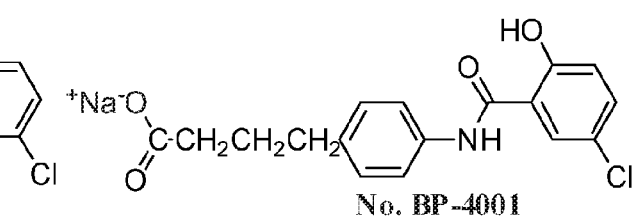

Without being bound by a particular theory, it is believed that a number of other salicylanilides can act in a manner similar to niclosamide to enhance in vivo activity of orally administered pharmaceuticals (e.g., therapeutic peptides). Illustrative salicylanilides include, but are not limited to Closantel (CAS #: 57808-65-8, see, e.g., FIG. 2, compound A), Oxyclozanide (CAS #: 2277-92-1, see, e.g., FIG. 2, compound B), Rafoxanide (CAS #: 22662-39-1, see, e.g., FIG. 2, compound C), Flusalan (CAS #: 4776-06-1, see, e.g., FIG. 2, compound D), Tribromsalan (CAS #: 87-10-5, see, e.g., FIG. 2, compound E), Resorantel (CAS #: 20788-07-2, see, e.g., FIG. 2, compound F), Clioxanide (CAS #: 14437-41-3, see, e.g., FIG. 2, compound G) Other suitable salicylanilides include Brotianide (CAS #: 23233-88-7), 4'-chloro-3-nitrosalicylanilide, 4'-chloro-5-nitrosalicylanilide, 2'-chloro-5'-methoxy-3-nitrosalicylanilide, 2'-methoxy-3,4'-dinitrosalicylanilide, 2',4'-dimethyl-3-nitrosalicylanilide, 4',5-dibromo-3-nitrosalicylanilide, 2'-chloro-3,4'-dinitrosalicylanilide, 2'-ethyl-3-nitrosalicylanilide, 2'-bromo-3-nitrosalicylanilide, and the like. In certain embodiments the salicylanilides include one or more of the compounds shown in FIG. 3.

It is noted that these salicylanilides are intended to be illustrative and not limiting. Methods of making salicylanilides are well known to those of skill in the art (see, e.g., PCT/US2003/022026 (WO 2004/006906) which is herein incorporated by reference for all purposes).

C) Identifying Effective Salicylanilides.

Using the teaching provided herein, other suitable salicylanilides can readily be identified using only routine experimentation. Various salicylanilides can be purchased from commercial vendors (e.g., Sigma Chemical, Aldrich, etc.) and then screened for their ability to enhance the apparent in vivo activity of an orally administered pharmaceutical (e.g., a peptide such as L-4F). Such screening methods can include for example, administering the salicylanilide in question in conjunction with L-4F (SEQ ID NO:5) to an apoE null mouse with appropriate controls and evaluating HDL-containing blood fractions for their ability to inhibit monocyte chemotactic activity induced by a standard control human LDL in cultures of human aortic endothelial cells. Salicylanilides that, when administered with L-4F produce more protective HDL than L-4F alone are compounds that enhance the in vivo activity (apparent activity) of that peptide. Such assays are illustrated herein in Example 1.

II. Other Delivery Agents.

Without being bound to a particular theory, in view of the niclosamide data presented herein, it is also believed that number of other delivery agents are also capable of enhancing the in vivo activity (apparent activity) of therapeutic orally administered pharmaceuticals, including, but not limited to amphipathic helical peptides (e.g., ApoA-I, ApoA-I milano, 4F, D18A, etc.) such that the L form of the peptide achieves therapeutically relevant levels of bioavailability when administered with the delivery agent(s).

Such delivery agents include, but are not limited to agents such N-(5-chlorosalicyloyl)-8-aminocaprylic acid (5-CNAC), N-(10-[2-hydroxybenzoyl]aminodecanoic acid (SNAD), and N-(8-[2-hydroxybenzoyl]amino)caprylic acid (SNAC) and various salts (e.g., disodium salts) thereof. In certain embodiments such delivery agents include any one or more of the modified amino acids disclosed in aforementioned U.S. Pat. No. 5,866,536 or any one of the modified amino acids described in U.S. Pat. No. 5,773,647, which are incorporated herein by reference. Also included are various salts of such agents including, but not limited to the disodium salts described in WO 00/059863 which is incorporated herein by reference.

In certain embodiments the delivery agents comprise a compound selected from the group consisting of 4-[4-{N-(4-bromobenzoyl)aminophenyl]}butyric acid, 4-{4-N-(2-iodobenzoyl)aminophenyl]}butyric acid, 3-(4-(2,5-dimethoxybenzoyl)aminophenyl)propionic acid, 4-{n-[4-(3-iodobenzoyl)aminophenyl]}butyric acid, 4-(o-anisoyl) aminophenylacetic acid, 3-[4-(2,4-dimethoxybenzoyl) aminophenyl]prioionic acid, 4-{4-[N-(4-iodobenzoyl)] aminophenyl}butyric acid, 3-4-(2,3-dimethoxybenzoyl) aminophenyl]pripionic acid, 4-{N-2[N-2-bromobenzoyl)] aminophenyl}butyric acid, 4-{N-2[N-3-bromobenzoyl] aminophenyl}butyric acid, 4-{4-[N-(4-bromobenzoyl) aminophenyl]}butyric acid, 4-{N-[4-(2-methoxy-4-nitrobenzoyl)aminophenyl]}butyric acid, 4-(4-(2,3-dimethoxybenzoyl)aminophenyl)butyric acid, 4-[4-N-(4-methoxy-3-nitrobenzoyl)aminophenyl]butyric acid, and the like.

III. Therapeutic Peptides.

This invention pertains to the use of salicylanilides (e.g., niclosamide) as well as other delivery agents to facilitate/permit the oral delivery of therapeutic peptides even when the peptides are L-form peptides and/or are unprotected. A therapeutic peptide is a peptide that is used to mitigate one or more symptoms of a disease or pathology.

A wide variety of therapeutic peptides are known to those of skill in the art and can be use in the formulations and methods of this invention. Such peptides include, for example, growth hormone (e.g., isolated and/or human, porcine, or bovine growth hormones), natural, synthetic, or recombinant growth hormone releasing hormones (GHRH), interferons (e.g., alpha, beta, and gamma interferon), interleukins (e.g., interleukin-1, interleukin, 2, etc.), natural, synthetic or recombinant insulin (e.g., porcine, bovine, human insulins), insulin-like growth factor-1 (IGF-1), insulin-like growth factor-2 (IGF2, somatostatin), heparin, heparinoids, dermatans, chondroitins, calcitonin (e.g., natural, synthetic, or recombinant salmon, procine, eel, chicken, and human calcitonin), antigens (e.g., influenza antigen, hepatitis A, B, C antigen, HPV antigen, etc), antibodies (polyclonal and monoclonal) (e.g., HERCEPTIN®, RITUXAN®, AVASTIN®, ERBITUX®, etc.), oxytocin, leutinizing-hormone-releasing hormone (LHRH), follicle stimulating hormone (FSH); glucocerebrosidase, thrombopoietin; filgrastim; prostaglandins; vasopressin; cromolyn sodium (e.g., sodium or disodium chromoglycate), vancomycin, desferrioxamine (DFO); parathyroid hormone (PTH) including its fragments, antimicrobials (e.g., anti-bacterial agents, including anti-fungal agents, etc.), and the like. In addition, the therapeutic peptides include analogs, fragments, mimetics or modified derivatives of these compounds (e.g., polyethylene glycol (PEG)-modified derivatives, glycosylated derivatives, etc.), or any combination thereof.

In certain preferred embodiments, the therapeutic peptides are peptides that ameliorate one or more symptoms of a pathology associated with an inflammatory response (e.g., atherosclerosis). Such peptides include, but are not limited to ApoA-I (natural, synthetic, recombinant), ApoA-I milano, (natural, synthetic, recombinant), apolipoprotein M, 18A, and related peptides (see, e.g., U.S. Pat. No. 4,643,988, U.S. Pat. No. 6,037,323, and PCT Publication WO 97/36927 all of which are incorporated herein by reference).

In certain particularly preferred embodiments, the therapeutic peptides used in the methods and formulations described herein include one or more of the peptides described below.

A) Class A Amphipathic Helical Peptides.

In certain embodiments, the peptides for use in the method of this invention include class A amphipathic helical peptides, e.g., as described in U.S. Pat. No. 6,664,230, and PCT Publications WO 02/15923 and WO 2004/034977. It was discovered that peptides comprising a class A amphipathic helix ("class A peptides"), in addition to being capable of mitigating one or more symptoms of atherosclerosis are also useful in the treatment of one or more of the other indications described herein.

Class A peptides are characterized by formation of an α-helix that produces a segregation of polar and non-polar residues thereby forming a polar and a nonpolar face with the positively charged residues residing at the polar-nonpolar interface and the negatively charged residues residing at the center of the polar face (see, e.g., Anantharamaiah (1986) *Meth. Enzymol.*, 128: 626-668). It is noted that the fourth exon of apo A-I, when folded into 3.667 residues/turn produces a class A amphipathic helical structure.

One class A peptide, designated 18A (see, e.g., Anantharamaiah (1986) *Meth. Enzymol.*, 128: 626-668) was modified as described herein to produce peptides orally administrable and highly effective at inhibiting or preventing one or more symptoms of atherosclerosis and/or other indications described herein. Without being bound by a particular theory, it is believed that the peptides of this invention may act in vivo by picking up/sequestering seeding molecule(s) that mitigate oxidation of LDL.

We determined that increasing the number of Phe residues on the hydrophobic face of 18A would theoretically increase lipid affinity as determined by the computation described by Palgunachari et al. (1996) *Arteriosclerosis, Thrombosis, & Vascular Biol.* 16: 328-338. Theoretically, a systematic substitution of residues in the nonpolar face of 18A with Phe could yield six peptides. Peptides with an additional 2, 3 and 4 Phe would have theoretical lipid affinity (λ) values of 13, 14 and 15 units, respectively. However, the λ values jumped four units if the additional Phe were increased from 4 to 5 (to 19λ units). Increasing to 6 or 7 Phe would produce a less dramatic increase (to 20 and 21λ units, respectively).

A number of these class A peptides were made including, the peptide designated 4F (L-4F), D-4F, 5F (L-5F), and D-5F, and the like. Various class A peptides inhibited lesion development in atherosclerosis-susceptible mice. In addition, the peptides show varying, but significant degrees of efficacy in mitigating one or more symptoms of the various pathologies described herein. A number of such peptides are illustrated in Table 2.

TABLE 2

Illustrative class A amphipathic helical peptides for use in this invention.

| Peptide Name | Amino Acid Sequence | SEQ ID NO. |
|---|---|---|
| 18A | D-W-L-K-A-F-Y-D-K-V-A-E-K-L-K-E-A-F | 1 |
| 2F | Ac-D-W-L-K-A-F-Y-D-K-V-A-E-K-L-K-E-A-F-NH$_2$ | 2 |
| 3F | Ac-D-W-F-K-A-F-Y-D-K-V-A-E-K-L-K-E-A-F-NH$_2$ | 3 |
| 3F14 | Ac-D-W-L-K-A-F-Y-D-K-V-A-E-K-F-K-E-A-F-NH$_2$ | 4 |
| 4F | Ac-D-W-F-K-A-F-Y-D-K-V-A-E-K-F-K-E-A-F-NH$_2$ | 5 |
| 5F | Ac-D-W-L-K-A-F-Y-D-K-V-F-E-K-F-K-E-F-F-NH$_2$ | 6 |
| 6F | Ac-D-W-L-K-A-F-Y-D-K-F-F-E-K-F-K-E-F-F-NH$_2$ | 7 |
| 7F | Ac-D-W-F-K-A-F-Y-D-K-F-F-E-K-F-K-E-F-F-NH$_2$ | 8 |
|  | Ac-D-W-L-K-A-F-Y-D-K-V-A-E-K-F-K-E-F-F-NH$_2$ | 9 |
|  | Ac-D-W-L-K-A-F-Y-D-K-V-F-E-K-F-K-E-A-F-NH$_2$ | 10 |
|  | Ac-D-W-L-K-A-F-Y-D-K-V-F-E-K-L-K-E-F-F-NH$_2$ | 11 |
|  | Ac-D-W-L-K-A-F-Y-D-K-V-A-E-K-F-K-E-F-F-NH$_2$ | 12 |
|  | Ac-D-W-L-K-A-F-Y-D-K-V-F-E-K-F-K-E-F-F-NH$_2$ | 13 |
|  | Ac-E-W-L-K-L-F-Y-E-K-V-L-E-K-F-K-E-A-F-NH$_2$ | 14 |
|  | Ac-E-W-L-K-A-F-Y-D-K-V-A-E-K-F-K-E-A-F-NH$_2$ | 15 |
|  | Ac-E-W-L-K-A-F-Y-D-K-V-A-E-K-L-K-E-F-F-NH$_2$ | 16 |
|  | Ac-E-W-L-K-A-F-Y-D-K-V-F-E-K-F-K-E-A-F-NH$_2$ | 17 |
|  | Ac-E-W-L-K-A-F-Y-D-K-V-F-E-K-L-K-E-F-F-NH$_2$ | 18 |
|  | Ac-E-W-L-K-A-F-Y-D-K-V-A-E-K-F-K-E-F-F-NH$_2$ | 19 |
|  | Ac-E-W-L-K-A-F-Y-D-K-V-F-E-K-F-K-E-F-F-NH$_2$ | 20 |
|  | Ac-A-F-Y-D-K-V-A-E-K-L-K-E-A-F-NH$_2$ | 21 |
|  | Ac-A-F-Y-D-K-V-A-E-K-F-K-E-A-F-NH$_2$ | 22 |
|  | Ac-A-F-Y-D-K-V-A-E-K-F-K-E-A-F-NH$_2$ | 23 |
|  | Ac-A-F-Y-D-K-F-F-E-K-F-K-E-F-F-NH$_2$ | 24 |
|  | Ac-A-F-Y-D-K-F-F-E-K-F-K-E-F-F-NH$_2$ | 25 |
|  | Ac-A-F-Y-D-K-V-A-E-K-F-K-E-A-F-NH$_2$ | 26 |
|  | Ac-A-F-Y-D-K-V-A-E-K-L-K-E-F-F-NH$_2$ | 27 |
|  | Ac-A-F-Y-D-K-V-F-E-K-F-K-E-A-F-NH$_2$ | 28 |
|  | Ac-A-F-Y-D-K-V-F-E-K-L-K-E-F-F-NH$_2$ | 29 |
|  | Ac-A-F-Y-D-K-V-A-E-K-F-K-E-F-F-NH$_2$ | 30 |
|  | Ac-K-A-F-Y-D-K-V-F-E-K-F-K-E-F-NH$_2$ | 31 |
|  | Ac-L-F-Y-E-K-V-L-E-K-F-K-E-A-F-NH$_2$ | 32 |
|  | Ac-A-F-Y-D-K-V-A-E-K-F-K-E-A-F-NH$_2$ | 33 |
|  | Ac-A-F-Y-D-K-V-A-E-K-L-K-E-F-F-NH$_2$ | 34 |
|  | Ac-A-F-Y-D-K-V-F-E-K-F-K-E-A-F-NH$_2$ | 35 |
|  | Ac-A-F-Y-D-K-V-F-E-K-L-K-E-F-F-NH$_2$ | 36 |
|  | Ac-A-F-Y-D-K-V-A-E-K-F-K-E-F-F-NH$_2$ | 37 |
|  | Ac-A-F-Y-D-K-V-F-E-K-F-K-E-F-F-NH$_2$ | 38 |
|  | Ac-D-W-L-K-A-L-Y-D-K-V-A-E-K-L-K-E-A-L-NH$_2$ | 39 |
|  | Ac-D-W-F-K-A-F-Y-E-K-V-A-E-K-L-K-E-F-F-NH$_2$ | 40 |
|  | Ac-D-W-F-K-A-F-Y-E-K-F-F-E-K-F-K-E-F-F-NH$_2$ | 41 |
|  | Ac-E-W-L-K-A-L-Y-E-K-V-A-E-K-L-K-E-A-L-NH$_2$ | 42 |
|  | Ac-E-W-L-K-A-F-Y-E-K-V-A-E-K-L-K-E-A-F-NH$_2$ | 43 |
|  | Ac-E-W-F-K-A-F-Y-E-K-V-A-E-K-L-K-E-F-F-NH$_2$ | 44 |
|  | Ac-E-W-L-K-A-F-Y-E-K-V-F-E-K-F-K-E-F-F-NH$_2$ | 45 |
|  | Ac-E-W-L-K-A-F-Y-E-K-F-F-E-K-F-K-E-F-F-NH$_2$ | 46 |
|  | Ac-E-W-F-K-A-F-Y-E-K-F-F-E-K-F-K-E-F-F-NH$_2$ | 47 |
|  | Ac-D-F-L-K-A-W-Y-D-K-V-A-E-K-L-K-E-A-W-NH$_2$ | 48 |
|  | Ac-E-F-L-K-A-W-Y-E-K-V-A-E-K-L-K-E-A-W-NH$_2$ | 49 |
|  | Ac-D-F-W-K-A-W-Y-D-K-V-A-E-K-L-K-E-W-W-NH$_2$ | 50 |
|  | Ac-E-F-W-K-A-W-Y-E-K-V-A-E-K-L-K-E-W-W-NH$_2$ | 51 |
|  | Ac-D-K-L-K-A-F-Y-D-K-V-F-E-W-A-K-E-A-F-NH$_2$ | 52 |
|  | Ac-D-K-W-K-A-V-Y-D-K-F-A-E-A-F-K-E-F-L-NH$_2$ | 53 |
|  | Ac-E-K-L-K-A-F-Y-E-K-V-F-E-W-A-K-E-A-F-NH$_2$ | 54 |
|  | Ac-E-K-W-K-A-V-Y-E-K-F-A-E-A-F-K-E-F-L-NH$_2$ | 55 |
|  | Ac-D-W-L-K-A-F-V-D-K-F-A-E-K-F-K-E-A-Y-NH$_2$ | 56 |
|  | Ac-E-K-W-K-A-V-Y-E-K-F-A-E-A-F-K-E-F-L-NH$_2$ | 57 |
|  | Ac-D-W-L-K-A-F-V-Y-D-K-V-F-K-L-K-E-F-F-NH$_2$ | 58 |
|  | Ac-E-W-L-K-A-F-V-Y-E-K-V-F-K-L-K-E-F-F-NH$_2$ | 59 |
|  | Ac-D-W-L-R-A-F-Y-D-K-V-A-E-K-L-K-E-A-F-NH$_2$ | 60 |
|  | Ac-E-W-L-R-A-F-Y-E-K-V-A-E-K-L-K-E-A-F-NH$_2$ | 61 |
|  | Ac-D-W-L-K-A-F-Y-D-R-V-A-E-K-L-K-E-A-F-NH$_2$ | 62 |
|  | Ac-E-W-L-K-A-F-Y-E-R-V-A-E-K-L-K-E-A-F-NH$_2$ | 63 |
|  | Ac-D-W-L-K-A-F-Y-D-K-V-A-E-R-L-K-E-A-F-NH$_2$ | 64 |
|  | Ac-E-W-L-K-A-F-Y-E-K-V-A-E-R-L-K-E-A-F-NH$_2$ | 65 |
|  | Ac-D-W-L-K-A-F-Y-D-K-V-A-E-K-L-R-E-A-F-NH$_2$ | 66 |

TABLE 2-continued

Illustrative class A amphipathic helical peptides for use in this invention.

| Peptide Name Amino Acid Sequence | SEQ ID NO. |
|---|---|
| Ac-E-W-L-K-A-F-Y-E-K-V-A-E-K-L-R-E-A-F-NH₂ | 67 |
| Ac-D-W-L-K-A-F-Y-D-R-V-A-E-R-L-K-E-A-F-NH₂ | 68 |
| Ac-E-W-L-K-A-F-Y-E-R-V-A-E-R-L-K-E-A-F-NH₂ | 69 |
| Ac-D-W-L-R-A-F-Y-D-K-V-A-E-K-L-R-E-A-F-NH₂ | 70 |
| Ac-E-W-L-R-A-F-Y-E-K-V-A-E-K-L-R-E-A-F-NH₂ | 71 |
| Ac-D-W-L-R-A-F-Y-D-R-V-A-E-K-L-K-E-A-F-NH₂ | 72 |
| Ac-E-W-L-R-A-F-Y-E-R-V-A-E-K-L-K-E-A-F-NH₂ | 73 |
| Ac-D-W-L-K-A-F-Y-D-K-V-A-E-R-L-R-E-A-F-NH₂ | 74 |
| Ac-E-W-L-K-A-F-Y-E-K-V-A-E-R-L-R-E-A-F-NH₂ | 75 |
| Ac-D-W-L-R-A-F-Y-D-K-V-A-E-R-L-K-E-A-F-NH₂ | 76 |
| Ac-E-W-L-R-A-F-Y-E-K-V-A-E-R-L-K-E-A-F-NH2 | 77 |
| D-W-L-K-A-F-Y-D-K-V-A-E-K-L-K-E-A-F-<u>P</u>-D-W-L-K-A-F-Y-D-K-V-A-E-K-L-K-E-A-F | 78 |
| D-W-L-K-A-F-Y-D-K-V-A-E-K-L-K-E-F-F-<u>P</u>-D-W-L-K-A-F-Y-D-K-V-A-E-K-L-K-E-F-F | 79 |
| D-W-F-K-A-F-Y-D-K-V-A-E-K-L-K-E-A-F-<u>P</u>-D-W-F-K-A-F-Y-D-K-V-A-E-K-L-K-E-A-F | 80 |
| D-K-L-K-A-F-Y-D-K-V-F-E-W-A-K-E-A-F-<u>P</u>-D-K-L-K-A-F-Y-D-K-V-F-E-W-L-K-E-A-F | 81 |
| D-K-W-K-A-V-Y-D-K-F-A-E-A-F-K-E-F-L-<u>P</u>-D-K-W-K-A-V-Y-D-K-F-A-E-A-F-K-E-F-L | 82 |
| D-W-F-K-A-F-Y-D-K-V-A-E-K-F-K-E-A-F-<u>P</u>-D-W-F-K-A-F-Y-D-K-V-A-E-K-F-K-E-A-F | 83 |
| D-W-L-K-A-F-V-Y-D-K-V-F-K-L-K-E-F-F-<u>P</u>-D-W-L-K-A-F-V-Y-D-K-V-F-K-L-K-E-F-F | 84 |
| D-W-L-K-A-F-Y-D-K-F-A-E-K-F-K-E-F-F-<u>P</u>-D-W-L-K-A-F-Y-D-K-F-A-E-K-F-K-E-F-F | 85 |
| Ac-E-W-F-K-A-F-Y-E-K-V-A-E-K-F-K-E-A-F-NH₂ | 86 |
| Ac-D-W-F-K-A-F-Y-D-K-V-A-E-K-F-NH₂ | 87 |
| Ac-F-K-A-F-Y-D-K-V-A-E-K-F-K-E-NH₂ | 88 |
| Ac-F-K-A-F-Y-E-K-V-A-E-K-F-K-E-NH₂ | 89 |
| NMA-F-K-A-F-Y-D-K-V-A-E-K-F-K-E-NH₂ | 90 |
| NMA-F-K-A-F-Y-E-K-V-A-E-K-F-K-E-NH₂ | 91 |
| NMA-D-W-F-K-A-F-Y-D-K-V-A-E-K-F-K-E-A-F-NH₂ | 92 |
| NMA-E-W-F-K-A-F-Y-E-K-V-A-E-K-F-K-E-A-F-NH₂ | 93 |
| NMA-A-F-Y-D-K-V-A-E-K-F-K-E-A-F-NH₂ | 94 |
| NMA-D-W-F-K-A-F-Y-D-K-V-A-E-K-F-NH₂ | 95 |
| Ac-D-W-L-K-A-F-Y-D-K-V-F-E-K-F-K-E-F-NH₂ | 96 |
| NMA-D-W-L-K-A-F-Y-D-K-V-F-E-K-F-K-E-F-NH₂ | |
| Ac-E-W-L-K-A-F-Y-E-K-V-F-E-K-F-K-E-F-NH₂ | 97 |
| NMA-E-W-L-K-A-F-Y-E-K-V-F-E-K-F-K-E-F-NH₂ | |
| Ac-A-F-Y-D-K-V-F-E-K-F-K-E-F-F-NH₂ | 98 |
| NMA-A-F-Y-D-K-V-F-E-K-F-K-E-F-F-NH₂ | |
| Ac-A-F-Y-E-K-V-F-E-K-F-K-E-F-F-NH₂ | 99 |
| NMA-A-F-Y-E-K-V-F-E-K-F-K-E-F-F-NH₂ | |
| Ac-D-W-L-K-A-F-Y-D-K-V-F-E-K-F-NH₂ | 100 |
| NMA-D-W-L-K-A-F-Y-D-K-V-F-E-K-F-NH₂ | |
| Ac-E-W-L-K-A-F-Y-E-K-V-F-E-K-F-NH₂ | 101 |
| NMA-E-W-L-K-A-F-Y-E-K-V-F-E-K-F-NH₂ | |
| Ac-L-K-A-F-Y-D-K-V-F-E-K-F-K-E-NH₂ | 102 |
| NMA-L-K-A-F-Y-D-K-V-F-E-K-F-K-E-NH₂ | |
| Ac-L-K-A-F-Y-E-K-V-F-E-K-F-K-E-NH₂ | 103 |
| NMA-L-K-A-F-Y-E-K-V-F-E-K-F-K-E-NH₂ | |

[1]Linkers are underlined.
NMA is N-Methyl Anthranilyl.

NMA is N-Methyl Anthranilyl.

In certain preferred embodiments, the peptides include variations of 4F ((SEQ ID NO:5 in Table 2), also known as L-4F, where all residues are L form amino acids) or D-4F where one or more residues are D form amino acids). In any of the peptides described herein, the C-terminus, and/or N-terminus, and/or internal residues can be blocked with one or more blocking groups as described herein. Also, with respect to any of the peptides disclosed herein this invention contemplates L-form peptides as well as D form peptides, retro-sequences, inverse-sequences, and retro-inverse sequences.

In addition, while various peptides of Table 2, are illustrated with an acetyl group or an N-methylanthranilyl group protecting the amino terminus and an amide group protecting the carboxyl terminus, any of these protecting groups may be eliminated and/or substituted with another protecting group as described herein. In particularly preferred embodiments, the peptides comprise one or more D-form amino acids as described herein. In certain embodiments, every amino acid (e.g., every enantiomeric amino acid) of the peptides of Table 2 is a D-form amino acid.

It is also noted that Table 2 is not fully inclusive. Using the teachings provided herein, other suitable class A amphipathic helical peptides can routinely be produced (e.g., by conservative or semi-conservative substitutions (e.g., D replaced by E), extensions, deletions, and the like). Thus, for example, one embodiment utilizes truncations of any one or more of peptides shown herein (e.g., peptides identified by SEQ ID Nos:2-20 and 39—in Table 2). Thus, for example, SEQ ID NO:21 illustrates a peptide comprising 14 amino acids from the C-terminus of 18A comprising one or more D amino acids, while SEQ ID NOS:22-38 illustrate other truncations.

Longer peptides are also suitable. Such longer peptides may entirely form a class A amphipathic helix, or the class A amphipathic helix (helices) can form one or more domains of the peptide. In addition, this invention contemplates multimeric versions of the peptides (e.g., concatamers). Thus, for example, the peptides illustrated herein can be coupled together (directly or through a linker (e.g., a carbon linker, or one or more amino acids) with one or more intervening amino acids). Illustrative polymeric peptides include 18A-Pro-18A and the peptides of SEQ ID NOs:78-85, in certain embodiments comprising one or more D amino acids, more preferably with every amino acid a D amino acid as described herein and/or having one or both termini protected.

It will also be appreciated in addition to the D-form and L-form peptide sequences expressly illustrated herein, this invention also contemplates retro and retro-inverso forms of each of these peptides. In retro forms, the direction of the sequence is reversed. In inverse forms, the chirality of the constituent amino acids is reversed (i.e., L form amino acids become D form amino acids and D form amino acids become L form amino acids). In the retro-inverso form, both the order and the chirality of the amino acids is reversed. Thus, for example, a retro form of the 4F peptide (DWFKAFYDK-VAEKFKEAF, SEQ ID NO:5), where the amino terminus is at the aspartate (D) and the carboxyl terminus is at the phenylalanine (F), has the same sequence, but the amino terminus is at the phenylalanine and the carboxy terminus is at the aspartate (i.e., FAEKFKEAVKDYFAKFWD, SEQ ID NO:104). Where the 4F peptide comprises all L amino acids, the retro-inverso form will have the sequence shown above (SEQ ID NO:104) and comprise all D form amino acids. As illustrated in the helical wheel diagrams shown in related application U.S. Ser. No. 11/407,390 and PCT/US2006/014389, which are incorporated herein by reference, 4F and retroinverso (Rev-4F) are mirror images of each other with identical segregation of the polar and nonpolar faces with the positively charged residues residing at the polar-nonpolar interface and the negatively charged residues residing at the center of the polar face. These mirror images of the same polymer of amino acids are identical in terms of the segregation of the polar and nonpolar faces with the positively charged residues residing at the polar-nonpolar interface and the negatively charged residues residing at the center of the polar face. Thus, 4F and Rev-4F are enantiomers of each other. For a discussion of retro- and retro-inverso peptides see, e.g., Chorev and Goodman, (1995) *TibTech*, 13: 439-445.

Where reference is made to a sequence and orientation is not expressly indicated, the sequence can be viewed as representing the amino acid sequence in the amino to carboxyl orientation, the retro form (i.e., the amino acid sequence in the carboxyl to amino orientation), the retro form where L amino acids are replaced with D amino acids or D amino acids are replaced with L amino acids, and the retro-inverso form where both the order is reversed and the amino acid chirality is reversed.

B) Class A Amphipathic Helical Peptide Mimetics of apoA-I Having Aromatic or Aliphatic Residues in the Non-Polar Face In certain embodiments, this invention also provides modified class A amphipathic helix peptides. Certain preferred . peptides incorporate one or more aromatic residues at the center of the nonpolar face, e.g., $3F^{C\pi}$, (as present in 4F), or with one or more aliphatic residues at the center of the nonpolar face, e.g., $3F^{I\pi}$, see, e.g., Table 3. Without being bound to a particular theory, we believe the central aromatic residues on the nonpolar face of the peptide $3F^{C\pi}$, due to the presence of π electrons at the center of the nonpolar face, allow water molecules to penetrate near the hydrophobic lipid alkyl chains of the peptide-lipid complex, which in turn would enable the entry of reactive oxygen species (such as lipid hydroperoxides) shielding them from the cell surface. Similarly, we also believe the peptides with aliphatic residues at the center of the nonpolar face, e.g., $3F^{I\pi}$, will act similarly but not quite as effectively as $3F^{C\pi}$.

Preferred peptides will convert pro-inflammatory HDL to anti-inflammatory HDL or make anti-inflammatory HDL more anti-inflammatory, and/or decrease LDL-induced monocyte chemotactic activity generated by artery wall cells equal to or greater than D-4F or other peptides shown in Table 2.

TABLE 3

Examples of certain preferred peptides.

| Name | Sequence | SEQ ID NO |
|---|---|---|
| ($3F^{C\pi}$) | Ac-DKWKAVYDKFAEAFKEFL-NH$_2$ | 105 |
| ($3F^{I\pi}$) | Ac-DKLKAFYDKVFEWAKEAF-NH$_2$ | 106 |

C) Other Class A and Some Class Y Amphipathic Helical Peptides.

In certain embodiments this invention also contemplates class a amphipathic helical peptides that have an amino acid composition identical to one or more of the class a amphipathic helical peptides described above. Thus, for example, in certain embodiments this invention contemplates peptides having an amino acid composition identical to 4F. Thus, in certain embodiments, this invention includes peptides that comprise 18 amino acids, where the 18 amino acids consist of 3 alanines (A), 2 aspartates (D), 2 glutamates (E), 4 phenylalanines (F), 4 lysines (K), 1 valine (V), 1 tryptophan (W), and 1 tyrosine (Y); and where the peptide forms a class A amphipathic helix; and protects a phospholipid against oxidation by an oxidizing agent. In various embodiments, the peptides comprise least one "D" amino acid residue; and in certain embodiments, the peptides comprise all "D: form amino acid residues. A variety of such peptides are illustrated in Table 4. Reverse (retro-), inverse, retro-inverso-, and circularly permuted forms of these peptides are also contemplated.

TABLE 4

Illustrative 18 amino acid length class A amphipathic helical peptides with the amino acid composition 3 alanines (A), 2 aspartates (D), 2 glutamates (E), 4 phenylalanines (F), 4 lysines (K), 1 valine (V), 1 tryptophan (W), and 1 tyrosine (Y).

| Name | Sequence | SEQ ID NO |
|---|---|---|
| [Switch D-E]-4F analogs | | |
| [Switch D-E]-1-4F | Ac-EWFKAFYEKVADKFKDAF-NH$_2$ | 107 |
| [Switch D-E]-2-4F | Ac-EWFKAFYDKVADKFKEAF-NH$_2$ | 108 |

TABLE 4-continued

Illustrative 18 amino acid length class A amphipathic helical peptides with the amino acid composition 3 alanines (A), 2 aspartates (D), 2 glutamates (E), 4 phenylalanines (F), 4 lysines (K), 1 valine (V), 1 tryptophan (W), and 1 tyrosine (Y).

| Name | Sequence | SEQ ID NO |
|---|---|---|
| [Switch D-E]-3-4F | Ac-DWFKAFYEKVADKFKEAF-NH₂ | 109 |
| [Switch D-E]-4-4F | Ac-DWFKAFYEKVAEKFKDAF-NH₂ | 110 |
| [W-2, F-3 positions reversed] | | |
| 4F-2 | Ac-DFWKAFYDKVAEKFKEAF-NH₂ | 111 |
| [Switch D-E]-1-4F-2 | Ac-EFWKAFYEKVADKFKDAF-NH₂ | 112 |
| [Switch D-E]-2-4F-2 | Ac-EFWKAFYDKVADKFKEAF-NH₂ | 113 |
| [Switch D-E]-3-4F-2 | Ac-DFWKAFYEKVADKFKEAF-NH₂ | 114 |
| [Switch D-E]-4-4F-2 | Ac-DFWKAFYEKVAEKFKDAF-NH₂ | 115 |
| [F-6 and Y-7 positions switched] | | |
| 4F-3 | Ac-DWFKAYFDKVAEKFKEAF-NH₂ | 116 |
| [Switch D-E]-1-4F-5 | Ac-EWFKAYFEKVADKFKDAF-NH₂ | 117 |
| [Switch D-E]-2-4F-5 | Ac-EWFKAYFDKVADKFKEAF-NH₂ | 118 |
| [Switch D-E]-3-4F-5 | Ac-DWFKAYFEKVADKFKEAF-NH₂ | 119 |
| [Switch D-E]-4-4F-5 | Ac-DWFKAYFEKVAEKFKDAF-NH₂ | 120 |
| [Y-7 and 10V positions switched] | | |
| 4F-4 | Ac-DWFKAFVDKYAEKFKEAF-NH₂ | 121 |
| [Switch D-E]-1-4F-4 | Ac-EWFKAFVEKYADKFKDAF-NH₂ | 122 |
| [Switch D-E]-2-4F-4 | Ac-EWFKAFVDKYADKFKEAF-NH₂ | 123 |
| [Switch D-E]-3-4F-4 | Ac-DWFKAFVEKYADKFKEAF-NH₂ | 124 |
| [Switch D-E]-4-4F | Ac-DWFKAFVEKYAEKFKDAF-NH₂ | 125 |
| [V-10 and A-11 switched] | | |
| 4-F-5 | Ac-DWFKAFYDKAVEKFKEAF-NH₂ | 126 |
| [Switch D-E]-1-4F-5 | Ac-EWFKAFYEKAVDKFKDAF-NH₂ | 127 |
| [Switch D-E]-2-4F-5 | Ac-EWFKAFYDKAVDKFKEAF-NH₂ | 128 |
| [Switch D-E]-3-4F-5 | Ac-DWFKAFYEKAVDKFKEAF-NH₂ | 129 |
| [Switch D-E]-4-4F-5 | Ac-DWFKAFYEKAVEKFKDAF-NH₂ | 130 |
| [A-11 and F-14 switched] | | |
| 4F-6 | Ac-DWFKAFYDKVFEKAKEAF-NH₂ | 131 |
| [Switch D-E]-1-4F-6 | Ac-EWFKAFYEKVFDKAKDAF-NH₂ | 132 |
| [Switch D-E]-2-4F-6 | Ac-EWFKAFYDKVFDKAKEAF-NH₂ | 133 |
| [Switch D-E]-3-4F-6 | Ac-DWFKAFYEKVFDKAKEAF-NH₂ | 134 |
| [Switch D-E]-4-4F-6 | Ac-DWFKAFYEKVFEKAKDAF-NH₂ | 135 |
| [F-14 and A-17 switched] | | |
| 4F-7 | Ac-DWFKAFYDKVAEKAKEFF-NH₂ | 136 |
| [Switch D-E]-1-4F-7 | Ac-EWFKAFYEKVADKAKDFF-NH₂ | 137 |
| [Switch D-E]-2-4F-7 | Ac-EWFKAFYDKVADKAKEFF-NH₂ | 138 |
| [Switch D-E]-3-4F-7 | Ac-DWFKAFYEKVADKAKEFF-NH₂ | 139 |
| [Switch D-E]-4-4F-7 | Ac-DWFKAFYEKVAEKAKDFF-NH₂ | 140 |
| [A-17 and F-18 switched] | | |
| 4F-8 | Ac-DWFKAFYDKVAEKFKEFA-NH₂ | 141 |
| [Switch D-E]-1-4F-8 | Ac-EWFKAFYEKVADKFKDFA-NH₂ | 142 |
| [Switch D-E]-2-4F-8 | Ac-EWFKAFYDKVADKFKEFA-NH₂ | 143 |
| [Switch D-E]-3-4F-8 | Ac-DWFKAFYEKVADKFKEFA-NH₂ | 144 |
| [Switch D-E]-4-4F-8 | Ac-DWFKAFYEKVAEKFKDFA-NH₂ | 145 |
| [W-2 and A-17 switched] | | |
| 4F-9 | Ac-DAFKAFYDKVAEKFKEWF-NH₂ | 146 |
| [Switch D-E]-1-4F-9 | Ac-EAFKAFYEKVADKFKDWF-NH₂ | 147 |
| [Switch D-E]-2-4F-9 | Ac-EAFKAFYDKVADKFKEWF-NH₂ | 148 |
| [Switch D-E]-3-4F-9 | Ac-DAFKAFYEKVADKFKEWF-NH₂ | 149 |
| [Switch D-E]-4-4F-9 | Ac-DAFKAFYEKVAEKFKDWF-NH₂ | 150 |
| [W-2 and A-11 switched] | | |
| 4F-10 | Ac-DAFKAFYDKWEKFKEAF-NH₂ | 151 |
| [Switch D-E]-1-4F-10 | Ac-EAFKAFYEKVWDKFKDAF-NH₂ | 152 |
| [Switch D-E]-2-4F-10 | Ac-EAFKAFYDKVWDKFKEAF-NH₂ | 153 |
| [Switch D-E]-3-4F-10 | Ac-DAFKAFYEKVWDKFKEAF-NH₂ | 154 |
| [Switch D-E]-4-4F-10 | Ac-DAFKAFYEKVWEKFKDAF-NH₂ | 155 |
| [W-2 and Y-7 switched] | | |
| 4F-11 | Ac-DYFKAFWDKVAEKFKEAF-NH₂ | 156 |
| [Switch D-E]-1-4F-11 | Ac-EYFKAFWEKVADKFKDAF-NH₂ | 157 |
| [Switch D-E]-2-4F-11 | Ac-EYFKAFWDKVADKFKEAF-NH₂ | 158 |
| [Switch D-E]-3-4F-11 | Ac-DYFKAFWEKVADKFKEAF-NH₂ | 159 |
| [Switch D-E]-4-4F-11 | Ac-DYFKAFWEKVAEKFKDAF-NH₂ | 160 |

TABLE 4-continued

Illustrative 18 amino acid length class A amphipathic helical peptides with the amino acid composition 3 alanines (A), 2 aspartates (D), 2 glutamates (E), 4 phenylalanines (F), 4 lysines (K), 1 valine (V), 1 tryptophan (W), and 1 tyrosine (Y).

| Name | Sequence | SEQ ID NO |
|---|---|---|
| [F-3 and A-17 switched] | | |
| 4F-12 | Ac-DWAKAFYDKVAEKFKEFF-NH$_2$ | 161 |
| [Switch D-E]-1-4F-12 | Ac-EWAKAFYEKVADKFKDFF-NH$_2$ | 162 |
| [Switch D-E]-2-4F-12 | Ac-EWAKAFYDKVADKFKEFF-NH$_2$ | 163 |
| [Switch D-E]-3-4F-12 | Ac-DWAKAFYEKVADKFKEFF-NH$_2$ | 164 |
| [Switch D-E]-4-4F-12 | Ac-DWAKAFYEKVAEKFKDFF-NH$_2$ | 165 |
| | | |
| [F-6 and A-17 switched] | | |
| 4F-13 | Ac-DWFKAAYDKVAEKFKEFF-NH$_2$ | 166 |
| [Switch D-E]-1-4F-13 | Ac-EWFKAAYEKVADKFKDFF-NH$_2$ | 167 |
| [Switch D-E]-2-4F-13 | Ac-EWFKAAYDKVADKFKEFF-NH$_2$ | 168 |
| [Switch D-E]-3-4F-13 | Ac-DWFKAAYEKVADKFKEFF-NH$_2$ | 169 |
| [Switch D-E]-4-4F-13 | Ac-DWFKAAYEKVAEKFKDFF-NH$_2$ | 170 |
| | | |
| [Y-7 and A-17 switched] | | |
| 4F-14 | Ac-DWFKAFADKVAEKFKEYF-NH$_2$ | 171 |
| [Switch D-E]-1-4F-14 | Ac-EWFKAFAEKVADKFKDYF-NH$_2$ | 172 |
| [Switch D-E]-2-4F-14 | Ac-EWFKAFADKVADKFKEYF-NH$_2$ | 173 |
| [Switch D-E]-3-4F-14 | Ac-DWFKAFAEKVADKFKEYF-NH$_2$ | 174 |
| [Switch D-E]-4-4F | Ac-DWFKAFAEKVAEKFKDYF-NH$_2$ | 175 |
| | | |
| [V-10 and A-17 switched] | | |
| 4F-15 | Ac-DWFKAFYDKAAEKFKEVF-NH$_2$ | 176 |
| [Switch D-E]-1-4F-15 | Ac-EWFKAFYEKAADKFKDVF-NH$_2$ | 177 |
| [Switch D-E]-2-4F-15 | Ac-EWFKAFYDKAADKFKEVF-NH$_2$ | 178 |
| [Switch D-E]-3-4F-15 | Ac-DWFKAFYEKAADKFKEVF-NH$_2$ | 179 |
| [Switch D-E]-4-4F-15 | Ac-DWFKAFYEKAAEKFKDVF-NH$_2$ | 180 |
| | | |
| [F3 and Y-7 switched] | | |
| 4F-16 | Ac-DWYKAFFDKVAEKFKEAF-NH$_2$ | 181 |
| [Switch D-E]-1-4F-16 | Ac-EWYKAFFEKVADKFKDAF-NH$_2$ | 182 |
| [Switch D-E]-2-4F-16 | Ac-EWYKAFFDKVADKFKEAF-NH$_2$ | 183 |
| [Switch D-E]-3-4F-16 | Ac-DWYKAFFEKVADKFKEAF-NH$_2$ | 184 |
| [Switch D-E]-4-4F-16 | Ac-DWYKAFFEKVAEKFKDAF-NH$_2$ | 185 |
| | | |
| [F-3 and V-10 switched] | | |
| 4F-17 | Ac-DWVKAFYDKFAEKFKEAF-NH$_2$ | 186 |
| [Switch D-E]-1-4F-17 | Ac-EWVKAFYEKFADKFKDAF-NH$_2$ | 187 |
| [Switch D-E]-2-4F-17 | Ac-EWVKAFYDKFADKFKEAF-NH$_2$ | 188 |
| [Switch D-E]-3-4F-17 | Ac-DWVKAFYEKFADKFKEAF-NH$_2$ | 189 |
| [Switch D-E]-4-4F-17 | Ac-DWVKAFYEKFAEKFKDAF-NH$_2$ | 190 |
| | | |
| [Y-7 and F-14 switched] | | |
| 4F-18 | Ac-DWFKAFFDKVAEKYKEAF-NH$_2$ | 191 |
| [Switch D-E]-1-4F-18 | Ac-EWFKAFFEKVADKYKDAF-NH$_2$ | 192 |
| [Switch D-E]-2-4F-18 | Ac-EWFKAFFDKVADKYKEAF-NH$_2$ | 193 |
| [Switch D-E]-3-4F-18 | Ac-DWFKAFFEKVADKYKEAF-NH$_2$ | 194 |
| [Switch D-E]-3-4F-18 | Ac-DWFKAFFEKVADKYKEAF-NH$_2$ | 195 |
| | | |
| [Y-7 and F-18 switched] | | |
| 4F-19 | Ac-DWFKAFFDKVAEKFKEAY-NH$_2$ | 196 |
| [Switch D-E]-1-4F-19 | Ac-EWFKAFFEKVADKFKDAY-NH$_2$ | 197 |
| [Switch D-E]-2-4F-19 | Ac-EWFKAFFDKVADKFKEAY-NH$_2$ | 198 |
| [Switch D-E]-3-4F-19 | Ac-DWFKAFFEKVADKFKEAY-NH$_2$ | 199 |
| [Switch D-E]-4-4F-19 | Ac-DWFKAFFEKVAEKFKDAY-NH$_2$ | 200 |
| | | |
| [V-10 and F-18 switched] | | |
| 4F-20 | Ac-DWFKAFYDKFAEKFKEAV-NH$_2$ | 201 |
| [Switch D-E]-1-4F-20 | Ac-EWFKAFYEKFADKFKDAV-NH$_2$ | 202 |
| [Switch D-E]-2-4F-20 | Ac-EWFKAFYDKFADKFKEAV-NH$_2$ | 203 |
| [Switch D-E]-3-4F-20 | Ac-DWFKAFYEKFADKFKEAV-NH$_2$ | 204 |
| [Switch D-E]-4-4F-20 | Ac-DWFKAFYEKFAEKFKDAV-NH$_2$ | 205 |
| | | |
| [W-2 and K13 switched] | | |
| 4F-21 | Ac-DKFKAFYDKVAEKFWEAF-NH$_2$ | 206 |
| [Switch D-E]-1-4F-21 | Ac-EKFKAFYEKVADKFWDAF-NH$_2$ | 207 |
| [Switch D-E]-2-4F-21 | Ac-EKFKAFYDKVADKFWEAF-NH$_2$ | 208 |
| [Switch D-E]-3-4F-21 | Ac-DKFKAFYEKVADKFWEAF-NH$_2$ | 209 |
| [Switch D-E]-4-4F-21 | Ac-DKFKAFYEKVAEKFWDAF-NH$_2$ | 210 |

TABLE 4-continued

Illustrative 18 amino acid length class A amphipathic helical peptides with the amino acid composition 3 alanines (A), 2 aspartates (D), 2 glutamates (E), 4 phenylalanines (F), 4 lysines (K), 1 valine (V), 1 tryptophan (W), and 1 tyrosine (Y).

| Name | Sequence | SEQ ID NO |
|---|---|---|
| [W-3, F-13 and K-2 4F] | | |
| 4F-22 | Ac-DKWKAFYDKVAEKFFEAF-NH$_2$ | 211 |
| [Switch D-E]-1-4F-22 | Ac-EKWKAFYEKVADKFFDAF-NH$_2$ | 212 |
| [Switch D-E]-2-4F-22 | Ac-EKWKAFYDKVADKFFEAF-NH$_2$ | 213 |
| [Switch D-E]-3-4F-22 | Ac-DKWKAFYEKVADKFFEAF-NH$_2$ | 214 |
| [Switch D-E]-4-4F-22 | Ac-DKWKAFYEKVAEKFFDAF-NH$_2$ | 215 |
| | | |
| [K-2, W10, V-13] | | |
| 4F-23 | Ac-DKFKAFYDKWAEVFKEAF-NH$_2$ | 216 |
| | | |
| [Switch D-E]-4F analogs | | |
| [Switch D-E]-1-4F-23 | Ac-EKFKAFYEKWADVFKDAF-NH$_2$ | 217 |
| [Switch D-E]-2-4F-23 | Ac-EKFKAFYDKWADVFKEAF-NH$_2$ | 218 |
| [Switch D-E]-3-4F-23 | Ac-DKFKAFYEKWADVFKEAF-NH$_2$ | 219 |
| [Switch D-E]-4-4F-23 | Ac-DKFKAFYEKWAEVFKDAF-NH$_2$ | 220 |
| | | |
| [K-2, F-13, W-14 4F] | | |
| 4F-24 | Ac-DKFKAFYDKVAEFWKEAF-NH$_2$ | 221 |
| | | |
| [Switch D-E]-4F analogs | | |
| [Switch D-E]-1-4F-24 | Ac-EKFKAFYEKVADFWKDAF-NH$_2$ | 222 |
| [Switch D-E]-2-4F-24 | Ac-EKFKAFYDKVADFWKEAF-NH$_2$ | 223 |
| [Switch D-E]-3-4F-24 | Ac-DKFKAFYEKVADFWKEAF-NH$_2$ | 224 |
| [Switch D-E]-4-4F-24 | Ac-DKFKAFYEKVAEFWKDAF-NH$_2$ | 225 |
| | | |
| Reverse 4F analogs | | |
| Rev-4F | Ac-FAEKFKEAVKDYFAKFWD-NH$_2$ | 226 |
| [Switch D-E]-1-Rev-4F | Ac-FADKFKDAVKEYFAKFWE-NH$_2$ | 227 |
| [Switch D-E]-2-Rev-4F | Ac-FADKFKEAVKDYFAKFWE-NH$_2$ | 228 |
| [Switch D-E]-3-Rev-4F | Ac-FAEKFKDAVKEYFAKFWD-NH$_2$ | 229 |
| [Switch D-E]-4-Rev-4F | Ac-FAEKFKDAVKDYFAKFWE-NH$_2$ | 230 |
| | | |
| [A-2 and W-17 switched] | | |
| Rev-4F-1 | Ac-FWEKFKEAVKDYFAKFAD-NH$_2$ | 231 |
| [Switch D-E]-1-Rev-4F-1 | Ac-FWDKFKDAVKEYFAKFAE-NH$_2$ | 232 |
| [Switch D-E]-2-Rev-4F-1 | Ac-FADKFKEAVKDYFAKFWE-NH$_2$ | 233 |
| [Switch D-E]-3-Rev-4F-1 | Ac-FAEKFKDAVKEYFAKFWD-NH$_2$ | 234 |
| [Switch D-E]-4-Rev-4F-1 | Ac-FAEKFKDAVKDYFAKFWE-NH$_2$ | 235 |
| | | |
| [Switch A-2 and F-16] | | |
| Rev-4F-2 | Ac-FFEKFKEAVKDYFAKAWD-NH$_2$ | 236 |
| [Switch D-E]-1-Rev-4F-2 | Ac-FFDKFKDAVKEYFAKAWE-NH$_2$ | 237 |
| [Switch D-E]-2-Rev-4F-2 | Ac-FFDKFKEAVKDYFAKAWE-NH$_2$ | 238 |
| [Switch D-E]-3-Rev-4F-2 | Ac-FFEKFKDAVKEYFAKAWD-NH$_2$ | 239 |
| [Switch D-E]-4-Rev-4F-2 | Ac-FFEKFKDAVKDYFAKAWE-NH$_2$ | 240 |
| | | |
| [switch F-5 and A-8] | | |
| Rev-4F-3 | Ac-FAEKAKEFVKDYFAKFWD-NH$_2$ | 241 |
| [Switch D-E]-1-Rev-4F-3 | Ac-FADKAKDFVKEYFAKFWE-NH$_2$ | 242 |
| [Switch D-E]-2-Rev-4F-3 | Ac-FADKAKEFVKDYFAKFWE-NH$_2$ | 243 |
| [Switch D-E]-3-Rev-4F-3 | Ac-FAEKAKDFVKEYFAKFWD-NH$_2$ | 244 |
| [Switch D-E]-4-Rev-4F-3 | Ac-FAEKAKDFVKDYFAKFWE-NH$_2$ | 245 |
| | | |
| [Switch A-8 and V9] | | |
| Rev-4F-4 | Ac-FAEKFKEVAKDYFAKFWD-NH$_2$ | 246 |
| [Switch D-E]-1-Rev-4F-4 | Ac-FADKFKDVAKEYFAKFWE-NH$_2$ | 247 |
| [Switch D-E]-2-Rev-4F-4 | Ac-FADKFKEVAKDYFAKFWE-NH$_2$ | 248 |
| [Switch D-E]-3-Rev-4F-4 | Ac-FAEKFKDVAKEYFAKFWD-NH$_2$ | 249 |
| [Switch D-E]-4-Rev-4F-4 | Ac-FAEKFKDVAKDYFAKFWE-NH$_2$ | 250 |
| | | |
| [Switch V-9 to Y-12] | | |
| Rev-4F-5 | Ac-FAEKFKEAYKDVFAKFWD-NH$_2$ | 251 |
| [Switch D-E]-1-Rev-4F-5 | Ac-FADKFKDAYKEVFAKFWE-NH$_2$ | 252 |
| [Switch D-E]-2-Rev-4F-5 | Ac-FADKFKEAYKDVFAKFWE-NH$_2$ | 253 |
| [Switch D-E]-3-Rev-4F-5 | Ac-FAEKFKDAYKEVFAKFWD-NH$_2$ | 254 |
| [Switch D-E]-4-Rev-4F-5 | Ac-FAEKFKDAYKDVFAKFWE-NH$_2$ | 255 |
| | | |
| [Switch Y-12 and F-13] | | |
| Rev-4F-6 | Ac-FAEKFKEAVKDFYAKFWD-NH$_2$ | 256 |
| [Switch D-E]-1-Rev-4F-6 | Ac-FADKFKDAVKEFYAKFWE-NH$_2$ | 257 |

TABLE 4-continued

Illustrative 18 amino acid length class A amphipathic helical peptides with the amino acid composition 3 alanines (A), 2 aspartates (D), 2 glutamates (E), 4 phenylalanines (F), 4 lysines (K), 1 valine (V), 1 tryptophan (W), and 1 tyrosine (Y).

| Name | Sequence | SEQ ID NO |
|---|---|---|
| [Switch D-E]-2-Rev-4F-6 | Ac-FADKFKDAVKDFYAKFWE-NH$_2$ | 258 |
| [Switch D-E]-3-Rev-4F-6 | Ac-FAEKFKDAVKEFYAKFWD-NH$_2$ | 259 |
| [Switch D-E]-4-Rev-4F-6 | Ac-FAEKFKDAVKDFYAKFWE-NH$_2$ | 260 |
| [Switch K-6 and W-17] Rev-4F-7 | Ac-FAEKFWEAVKDYFAKFKD-NH$_2$ | 261 |
| [Switch D-E]-1-Rev-4F-7 | Ac-FADKFWDAVKEYFAKFKE-NH$_2$ | 262 |
| [Switch D-E]-2-Rev-4F-7 | Ac-FADKFWEAVKDYFAKFKE-NH$_2$ | 263 |
| [Switch D-E]-3-Rev-4F-7 | Ac-FAEKFWDAVKEYFAKFKD-NH$_2$ | 264 |
| [Switch D-E]-4-Rev-4F-7 | Ac-FAEKFWDAVKDYFAKFKE-NH$_2$ | 265 |
| [Switch F-1 and A-2] Rev-4F-8 | Ac-AFEKFKEAVKDYFAKFWD-NH$_2$ | 266 |
| [Switch D-E]-1-Rev-4F-8 | Ac-AFDKFKDAVKEYFAKFWE-NH$_2$ | 267 |
| [Switch D-E]-2-Rev-4F-8 | Ac-AFDKFKEAVKDYFAKFWE-NH$_2$ | 268 |
| [Switch D-E]-3-Rev-4F-8 | Ac-AFEKFKDAVKEYFAKFWD-NH$_2$ | 269 |
| [Switch D-E]-4-Rev-4F-8 | Ac-AFEKFKDAVKDYFAKFWE-NH$_2$ | 270 |
| [F-1 and V-9 are switched] Rev-F-9 | Ac-VAEKFKEAFKDYFAKFWD-NH$_2$ | 271 |
| [Switch D-E]-1-Rev-4F-9 | Ac-VADKFKDAFKEYFAKFWE-NH$_2$ | 272 |
| [Switch D-E]-2-Rev-4F-9 | Ac-VADKFKEAFKDYFAKFWE-NH$_2$ | 273 |
| [Switch D-E]-3-Rev-4F-9 | Ac-VAEKFKDAFKEYFAKFWD-NH$_2$ | 274 |
| [Switch D-E]-4-Rev-4F-9 | Ac-VAEKFKDAFKDYFAKFWE-NH$_2$ | 275 |
| [F-1 and Y-12 are switched] Rev-4F-10 | Ac-YAEKFKEAVKDFFAKFWD-NH$_2$ | 276 |
| [Switch D-E]-1-Rev-4F-10 | Ac-YADKFKDAVKEFFAKFWE-NH$_2$ | 277 |
| [Switch D-E]-2-Rev-4F-10 | Ac-YADKFKEAVKDFFAKFWE-NH$_2$ | 278 |
| [Switch D-E]-3-Rev-4F-10 | Ac-YAEKFKDAVKEFFAKFWD-NH$_2$ | 279 |
| [Switch D-E]-4-Rev-4F-10 | Ac-YAEKFKDAVKDFFAKFWE-NH$_2$ | 280 |
| [F-1 and A-8 are switched] Rev-4F-11 | Ac-AAEKFKEFVKDYFAKFWD-NH$_2$ | 281 |
| [Switch D-E]-1-Rev-4F-11 | Ac-AADKFKDFVKEYFAKFWE-NH$_2$ | 282 |
| [Switch D-E]-2-Rev-4F-11 | Ac-AADKFKEFVKDYFAKFWE-NH$_2$ | 283 |
| [Switch D-E]-3-Rev-4F-11 | Ac-AAEKFKDFVKEYFAKFWD-NH$_2$ | 284 |
| [Switch D-E]-4-Rev-4F-11 | Ac-AAEKFKDFVKDYFAKFWE-NH$_2$ | 285 |
| [A-2 and F-5 are switched] Rev-4F-12 | Ac-FFEKAKEAVKDYFAKFWD-NH$_2$ | 286 |
| [Switch D-E]-1-Rev-4F-12 | Ac-FFDKAKDAVKEYFAKFWE-NH$_2$ | 287 |
| [Switch D-E]-2-Rev-4F-12 | Ac-FFDKAKEAVKDYFAKFWE-NH$_2$ | 288 |
| [Switch D-E]-3-Rev-4F-12 | Ac-FFEKAKDAVKEYFAKFWD-NH$_2$ | 289 |
| [Switch D-E]-4-Rev-4F-12 | Ac-FFEKAKDAVKDYFAKFWE-NH$_2$ | 290 |
| [A-2 and Y12 are switched Rev-4F-13 | Ac-FYEKFKEAVKDAFAKFWD-NH$_2$ | 291 |
| [Switch D-E]-1-Rev-4F-13 | Ac-FYDKFKDAVKEAFAKFWE-NH$_2$ | 292 |
| [Switch D-E]-2-Rev-4F-13 | Ac-FYDKFKEAVKDAFAKFWE-NH$_2$ | 293 |
| [Switch D-E]-3-Rev-4F-13 | Ac-FYEKFKDAVKEAFAKFWD-NH$_2$ | 294 |
| [Switch D-E]-4-Rev-4F-13 | Ac-FYEKFKDAVKDAFAKFWE-NH$_2$ | 295 |
| [A-2 and V-9 are switched] Rev-4F-14 | Ac-FVEKFKEAAKDYFAKFWD-NH$_2$ | 296 |
| [Switch D-E]-1-Rev-4F-14 | Ac-FVDKFKDAAKEYFAKFWE-NH$_2$ | 297 |
| [Switch D-E]-2-Rev-4F-14 | Ac-FVDKFKEAAKDYFAKFWE-NH$_2$ | 298 |
| [Switch D-E]-3-Rev-4F-14 | Ac-FVEKFKDAAKEYFAKFWD-NH$_2$ | 299 |
| [Switch D-E]-4-Rev-4F-14 | Ac-FVEKFKDAAKDYFAKFWE-NH$_2$ | 300 |
| [F-5 and Y-12 are switched] Rev-4F-15 | Ac-FAEKYKEAVKDFFAKFWD-NH$_2$ | 301 |
| [Switch D-E]-1-Rev-4F-15 | Ac-FADKYKDAVKEFFAKFWE-NH$_2$ | 302 |
| [Switch D-E]-2-Rev-4F-15 | Ac-FADKYKEAVKDFFAKFWE-NH$_2$ | 303 |
| [Switch D-E]-3-Rev-4F-15 | Ac-FAEKYKDAVKEFFAKFWD-NH$_2$ | 304 |
| [Switch D-E]-4-Rev-4F-15 | Ac-FAEKYKDAVKDFFAKFWE-NH$_2$ | 305 |
| [F-5 and V-9 are switched] Rev-4F-16 | Ac-FAEKVKEAFKDYFAKFWD-NH$_2$ | 306 |
| [Switch D-E]-1-Rev-4F-16 | Ac-FADKVKDAFKEYFAKFWE-NH$_2$ | 307 |
| [Switch D-E]-2-Rev-4F-16 | Ac-FADKVKEAFKDYFAKFWE-NH$_2$ | 308 |

TABLE 4-continued

Illustrative 18 amino acid length class A amphipathic helical peptides with the amino acid composition 3 alanines (A), 2 aspartates (D), 2 glutamates (E), 4 phenylalanines (F), 4 lysines (K), 1 valine (V), 1 tryptophan (W), and 1 tyrosine (Y).

| Name | Sequence | SEQ ID NO |
|---|---|---|
| [Switch D-E]-3-Rev-4F-16 | Ac-FAEKVKDAFKEYFAKFWD-NH$_2$ | 309 |
| [Switch D-E]-4-Rev-4F-16 | Ac-FAEKVKDAFKDYFAKFWE-NH$_2$ | 310 |
| | | |
| [A-8 and Y-12 switched] Rev-4F-17 | Ac-FAEKFKEYVKDAFAKFWD-NH$_2$ | 311 |
| [Switch D-E]-1-Rev-4F-17 | Ac-FADKFKDYVKEAFAKFWE-NH$_2$ | 312 |
| [Switch D-E]-2-Rev-4F-17 | Ac-FADKFKEYVKDAFAKFWE-NH$_2$ | 313 |
| [Switch D-E]-3-Rev-4F-17 | Ac-FAEKFKDYVKEAFAKFWD-NH$_2$ | 314 |
| [Switch D-E]-4-Rev-4F-17 | Ac-FAEKFKDYVKDAFAKFWE-NH$_2$ | 315 |
| | | |
| [V-9 and F-13 are switched] Rev-4F-18 | Ac-FAEKFKEAFKDYVAKFWD-NH$_2$ | 316 |
| [Switch D-E]-1-Rev-4F-18 | Ac-FADKFKDAFKEYVAKFWE-NH$_2$ | 317 |
| [Switch D-E]-2-Rev-4F-18 | Ac-FADKFKEAFKDYVAKFWE-NH$_2$ | 318 |
| [Switch D-E]-3-Rev-4F-18 | Ac-FAEKFKDAFKEYVAKFWD-NH$_2$ | 319 |
| [Switch D-E]-4-Rev-4F-18 | Ac-FAEKFKDAFKEYVAKFWE-NH$_2$ | 320 |
| | | |
| [V-9 and F-16 switched] Rev-4F-19 | Ac-FAEKFKEAFKDYFAKVWD-NH$_2$ | 321 |
| [Switch D-E]-1-Rev-4F-19 | Ac-FADKFKDAFKEYFAKVWE-NH$_2$ | 322 |
| [Switch D-E]-2-Rev-4F-19 | Ac-FADKFKEAFKDYFAKVWE-NH$_2$ | 323 |
| [Switch D-E]-3-Rev-4F-19 | Ac-FAEKFKDAFKEYFAKVWD-NH$_2$ | 324 |
| Switch D-E]-4-Rev-4F-19 | Ac-FAEKFKDAFKDYFAKVWE-NH$_2$ | 325 |
| | | |
| [Y-12 and F-16 are switched Rev-4F-20 | Ac-FAEKFKEAVKDFFAKYWD-NH$_2$ | 326 |
| [Switch D-E]-1-Rev-4F-20 | Ac-FADKFKDAVKEFFAKYWE-NH$_2$ | 327 |
| [Switch D-E]-2-Rev-4F-20 | Ac-FADKFKEAVKDFFAKYWE-NH$_2$ | 328 |
| [Switch D-E]-3-Rev-4F-20 | Ac-FAEKFKDAVKEFFAKYWD-NH$_2$ | 329 |
| [Switch D-E]-4-Rev-4F-20 | Ac-FAEKFKDAVKDFFAKYWE-NH$_2$ | 330 |
| | | |
| [W-1, F-6 and K-17 Rev 4F] Rev-4F-21 | Ac-WAEKFFEAVKDYFAKFKD-NH$_2$ | 331 |
| [Switch D-E]-1-Rev-4F-7 | Ac-WADKFFDAVKEYFAKFKE-NH$_2$ | 332 |
| [Switch D-E]-2-Rev-4F-7 | Ac-WADKFFEAVKDYFAKFKE-NH$_2$ | 333 |
| [Switch D-E]-3-Rev-4F-7 | Ac-WAEKFFDAVKEYFAKFKD-NH$_2$ | 334 |
| [Switch D-E]-4-Rev-4F-7 | Ac-WAEKFFDAVKDYFAKFKE-NH$_2$ | 335 |
| | | |
| [W-5, F-6 and K-17 Rev-4F] Rev-4F-22 | Ac-FAEKWFEAVKDYFAKFKD-NH$_2$ | 336 |
| [Switch D-E]-1-Rev-4F-22 | Ac-FADKWFDAVKEYFAKFKE-NH$_2$ | 337 |
| [Switch D-E]-2-Rev-4F-22 | Ac-FADKWFEAVKDYFAKFKE-NH$_2$ | 338 |
| [Switch D-E]-3-Rev-4F-22 | Ac-FAEKWFDAVKEYFAKFKD-NH$_2$ | 339 |
| [Switch D-E]-4-Rev-4F-22 | Ac-FAEKWFDAVKDYFAKFKE-NH$_2$ | 340 |
| | | |
| [V-6, W-9, K-17 Rev-4F] Rev-4F-23 | Ac-FAEKFVEAWKDYFAKFKD-NH$_2$ | 341 |
| [Switch D-E]-1-Rev-4F-23 | Ac-FADKFVDAWKEYFAKFKE-NH$_2$ | 342 |
| [Switch D-E]-2-Rev-4F-23 | Ac-FADKFVEAWKDYFAKFKE-NH$_2$ | 343 |
| [Switch D-E]-3-Rev-4F-23 | Ac-FAEKFVDAWKEYFAKFKD-NH$_2$ | 344 |
| [Switch D-E]-4-Rev-4F-23 | Ac-FAEKFVDAWKDYFAKFKE-NH$_2$ | 345 |
| | | |
| [Y-2, A-4, W-12, K-17 Rev-4F] Rev-4F-24 | Ac-FYEKFAEAVKDWFAKFKD-NH$_2$ | 346 |
| [Switch D-E]-1-Rev-4F-24 | Ac-FYDKFADAVKEWFAKFKE-NH$_2$ | 347 |
| [Switch D-E]-2-Rev-4F-24 | Ac-FYDKFAEAVKDWFAKFKE-NH$_2$ | 348 |
| [Switch D-E]-3-Rev-4F-24 | Ac-FYEKFADAVKEWFAKFKD-NH$_2$ | 349 |
| [Switch D-E]-4-Rev-4F-24 | Ac-FYEKFADAVKDWFAKFKE-NH$_2$ | 350 |

Based on helical wheel diagrams, it is possible to readily identify biologically active and useful peptides. Thus, for example, the following peptides have been accurately identified as active: 3F1; 3F2; 4F the inverse forms thereof, the reverse (retro) forms thereof and the retro-inverso forms thereof. Thus, in certain embodiments, this invention contemplates active agents comprising a peptide that is 18 amino acids in length and forms a class A amphipathic helix where the peptide has the amino acid composition 2 aspartates, 2 glutamates, 4 lysines, 1 tryptophan, 1 tyrosine, no more than one leucine, no more than 1 valine, no less than 1 and no more than 3 alanines, and with 3 to 6 amino acids from the group: phenylalanine, alpha-naphthalanine, beta-naphthalanine, histidine, and contains either 9 or 10 amino acids on the polar face in a helical wheel representation of the class A amphipathic helix including 4 amino acids with positive charge at neutral pH with two of the positively charged residues residing at the interface between the polar and non-polar faces and with two of the four positively charged residues on the polar face that are contiguous and on the non-polar face two of the amino acid residues from the group: phenylalanine, alpha-naphthalanine, beta-naphthalanine, histidine are also contiguous and if there are 4 or more amino acids from this group on the non-polar face there are also at least 2 residues from this group that are not contiguous.

In certain embodiments, this invention also contemplates certain class Y as well as class A amphipathic helical peptides. Class Y amphipathic helical peptides are known to those of skill in the art (see, e.g., Segrest et al. (1992) *J. Lipid Res.* 33: 141-166; Oram and Heinecke (2005) *Physiol Rev.* 85: 1343-1372, and the like). In various embodiments these peptides include, but are not limited to an 18 amino acid peptide that forms a class A amphipathic helix or a class Y amphipathic helix described by Formula XXIV (SEQ ID NO:351):

D X X K Y X X D K X Y D KX K D Y X          XXIV where the D's are independently Asp or Glu; the Ks are independently Lys or Arg; the Xs are independently Leu, norLeu, Val, Ile, Trp, Phe, Tyr, β-Nal, or α-Nal and all X residues are on the non-polar face (e.g., when viewed in a helical wheel diagram) except for one that can be on the polar face between two K residues; the Y's are independently Ala, His, Ser, Gln, Asn, or Thr non-polar face (e.g., when viewed in a helical wheel diagram) and the Y's are independently one Ala on the polar face, one His, one Ser, one Gln one Asn, or one Thr on the polar face (e.g., when viewed in a helical wheel diagram), where no more than two K are be contiguous (e.g., when viewed in a helical wheel diagram); and where no more than 3 D's are contiguous (e.g., when viewed in a helical wheel diagram) and the fourth D is be separated from the other D's by a Y. Illustrative peptides of this kind which include peptides with histidine, and/or alpha- and/or beta-napthalanine are shown in Table 5. Reverse (retro-), inverse, retro-inverso-, and circularly permuted forms of these peptides are also contemplated.

TABLE 5

Illustrates various class A and/or class Y peptide analogs with His incorporated into the sequence.

| Short name | Peptide sequence | SEQ ID NO |
|---|---|---|
| [A-5>H]4F | Ac-DWFKHFYDKVAEKFKEAF-NH$_2$ | 352 |
| [A-5>H, D-E switched]4F | Ac-EWFKHFYEKVADKFKDAF-NH$_2$ | 353 |
| [A-5>H, D-1>E]4F | Ac-EWFKHFYDKVAEKFKEAF-NH$_2$ | 354 |
| [A-5>H, D-8>E]4-F | Ac-DWFKHFYEKVAEKFKEAF-NH$_2$ | 355 |
| [A-5>H, E-12>D]4F | Ac-DWFKHFYDKVADKFKEAF-NH$_2$ | 356 |
| [A-5>H, E-16>D]4F | Ac-DWFKHFYDKVAEKFKDAF-NH$_2$ | 357 |
| [F-3>H, A-5>F]-4F | Ac-DWHKFFYDKVAEKFKEAF-NH$_2$ | 358 |
| [F-3>H, A-5>F, D-E switched]-4F | Ac-EWHKFFYEKVADKFKDAF-NH$_2$ | 359 |
| [F-3>H, A-5>F, D-1>E]-4F | Ac-EWHKFFYDKVAEKFKEAF-NH$_2$ | 360 |
| [F-3>H, A-5>F, D-8>E]-4F | Ac-DWHKFFYEKVAEKFKEAF-NH$_2$ | 361 |
| [F-3>H, A-5>F, E-12>D]-4F | Ac-DWHKFFYDKVADKFKEAF-NH$_2$ | 362 |
| [F-3>H, A-5>F, E-16>D]-4F | Ac-DWHKFFYDKVAEKFKDAF-NH$_2$ | 363 |
| [A-5>F, F-6>H]4F | Ac-DWFKFHYDKVAEKFKEAF-NH$_2$ | 364 |
| [A-5>F, F-6>H, D-E switched]4F | Ac-EWFKFHYEKVADKFKDAF-NH$_2$ | 365 |
| [[A-5>F, F-6>H, D-1>E]4F | Ac-EWFKFHYDKVAEKFKEAF-NH$_2$ | 366 |
| [A-5>F, F-6>H, D-8>E]4F | Ac-DWFKFHYEKVAEKFKEAF-NH$_2$ | 367 |
| [A-5>F, F-6>H, E-12>D]4F | Ac-DWFKFHYDKVADKFKEAF-NH$_2$ | 368 |
| [A-5>F, F-6>H, E-16>D]4F | Ac-DWFKFHYDKVAEKFKDAF-NH$_2$ | 369 |
| [A-5>V, V-10>H]4F | Ac-DWFKVFYDKHAEKFKEAF-NH$_2$ | 370 |
| [A-5>V, V-10>H, D-E switched]4F | Ac-EWFKVFYEKHADKFKDAF-NH$_2$ | 371 |
| [A-5>V, V-10>H, D-1>E]4F | Ac-EWFKVFYDKHAEKFKEAF-NH$_2$ | 372 |
| [A-5>V, V-10>H, D-8>E]4F | Ac-DWFKVFYEKHAEKFKEAF-NH$_2$ | 373 |
| [A-5>V, V-10>H, E-12>D]4F | Ac-DWFKVFYDKHADKFKEAF-NH$_2$ | 374 |
| [A-5>V, V-10>H, E16>D]4F | Ac-DWFKVFYDKHAEKFKDAF-NH$_2$ | 375 |

TABLE 5-continued

Illustrates various class A and/or class Y peptide analogs with His incorporated into the sequence.

| Short name | Peptide sequence | SEQ ID NO |
|---|---|---|
| [[A-17>H]4F | Ac-DWFKAFYDKVAEKFKEHF-NH$_2$ | 376 |
| [A-17>H, D-E switched]4F | Ac-EWFKAFYEKVADKFKDHF-NH$_2$ | 377 |
| [[A-17>H, D-1>E]4F | Ac-EWFKAFYDKVAEKFKEHF-NH$_2$ | 378 |
| [[A-17>H, D-8>E]4F | Ac-DWFKAFYEKVAEKFKEHF-NH$_2$ | 379 |
| [[A-17>H, E-12>D]4F | Ac-DWFKAFYDKVADKFKEHF-NH$_2$ | 380 |
| [[A-17>H, E16>D]4F | Ac-DWFKAFYDKVAEKFKDHF-NH$_2$ | 381 |
| [A-17>F, F-18>H]4F | Ac-DWFKAFYDKVAEKFKEFH-NH$_2$ | 382 |
| [A-17>F, F-18>H, D-E switched]4F | Ac-EWFKAFYEKVADKFKDFH-NH$_2$ | 383 |
| [A-17>F, F-18>H, D-1>E]-4F | Ac-EWFKAFYDKVAEKFKEFH-NH$_2$ | 384 |
| [A-17>F, F-18>H]4F | Ac-DWFKAFYDKVAEKFKEFH-NH$_2$ | 385 |
| [A-17>F, F-18>H, D-8>E]-4F | Ac-DWFKAFYEKVAEKFKEFH-NH$_2$ | 386 |
| [A-17>F, F-18>H, E-12>D]4F | Ac-DWFKAFYDKVAEKFKEFH-NH$_2$ | 387 |
| [A-17>F, F-18>H], E-16>D]-4F | Ac-DWFKAFYDKVAEKFKDFH-NH$_2$ | 388 |
| Rev-4F | Ac-FAEKFKEAVKDYFAKFWD-NH$_2$ | 389 |
| [A-2>H]Rev4F | Ac-FHEKFKEAVKDYFAKFWD-NH$_2$ | 390 |
| Rev-[A-2>H, D>E]-4F | Ac-FHEKFKEAVKEYFAKFWE-NH$_2$ | 391 |
| Rev-[A-2>H, E>D]4F | Ac-FHDKFKDAVKDYFAKFWD-NH$_2$ | 392 |
| [A-2>H, D-E switched]Rev-4F | Ac-FHDKFKDAVKEYFAKFWE-NH$_2$ | 393 |
| [A-2>H, E-3>D]Rev-4F | Ac-FHDKFKEAVKDYFAKFWD-NH$_2$ | 394 |
| [A-2>H, E-7>D]Rev-4F | Ac-FHEKFKDAVKDYFAKFWD-NH$_2$ | 395 |
| [A-2>H, D-11>E]Rev-4F | Ac-FHEKFKEAVKEYFAKFWD-NH$_2$ | 396 |
| [A-2>H, D-18>E]Rev-4F | Ac-FHEKFKEAVKDYFAKFWE-NH$_2$ | 397 |
| [F-1>H, A-2>F]Rev-4F | Ac-HFEKFKEAVKDYFAKFWD-NH$_2$ | 398 |
| [F-1>H, A-2>F, D-E switched]Rev 4F | Ac-HFDKFKDAVKEYFAKFWE-NH$_2$ | 399 |
| [F-1>H, A-2>F, D>E]Rev-4F | Ac-HFEKFKEAVKEYFAKFWE-NH$_2$ | 400 |
| [F-1>H, A-2>F, E-3>D]Rev-4F | Ac-HFDKFKEAVKDYFAKFWD-NH$_2$ | 401 |
| [F-1>H, A-2>F, E-7>D]Rev-4F | Ac-HFEKFKDAVKDYFAKFWD-NH$_2$ | 402 |
| [F-1>H, A-2>F, D-11 >E]Rev-4F | Ac-HFEKFKEAVKEYFAKFWD-NH$_2$ | 403 |
| [F-1>H, A-2>F, D-18>E]Rev-4F | Ac-HFEKFKEAVKDYFAKFWE-NH$_2$ | 404 |
| [A-2>F, F-5>H]Rev D-4F | Ac-FFEKHEAVKDYFAKFWD-NH$_2$ | 405 |
| [A-2>F, F-5>H, D-E switched]Rev D-4F | Ac-FFDKHKDAVKEYFAKFWE-NH$_2$ | 406 |
| [A-2>F, F-5>H, D>E]Rev D-4F | Ac-FFEKHKEAVKEYFAKFWE-NH$_2$ | 407 |
| [A-2>F, F-5>H, E>D]Rev D-4F | Ac-FFDKHKDAVKDYFAKFWD-NH$_2$ | 408 |
| [A-2>F, F-5>H, E-3>D]Rev D-4F | Ac-FFDKHKEAVKDYFAKFWD-NH$_2$ | 409 |
| [A-2>F, F-5>H, D-11>E]Rev D-4F | Ac-FFEKHKEAVKEYFAKFWD-NH$_2$ | 410 |
| [A-2>F, F-5>H, D-18>E]Rev D-4F | Ac-FFEKHKEAVKDYFAKFWE-NH$_2$ | 411 |

TABLE 5-continued

Illustrates various class A and/or class Y peptide analogs with His incorporated into the sequence.

| Short name | Peptide sequence | SEQ ID NO |
|---|---|---|
| [A-2>V, V-9>H]Rev D-4F | Ac-FVEKFKEAHKDYFAKFWD-NH$_2$ | 412 |
| [A-2>V, V-9>H, D-E switched]Rev D-4F | Ac-FVDKFKDAHKEYFAKFWE-NH$_2$ | 413 |
| [A-2>V, V-9>H, D>E]Rev D-4F | Ac-FVEKFKEAHKEYFAKFWE-NH$_2$ | 414 |
| [A-2>V, V-9>H, E>D]Rev D-4F | Ac-FVDKFKDAH**KDYFAKFWD-NH$_2$ | 415 |
| [A-2>V, V-9>H, E-3>D]Rev D-4F | Ac-FVDKFKEAHKDYFAKFWD-NH$_2$ | 416 |
| [A-2>V, V-9>H, E-7>D]Rev D-4F | Ac-FVEKFKDAH**KDYFAKFWD-NH$_2$ | 417 |
| [A-2>V, V-9>H, D-11>E]Rev D-4F | Ac-FVEKFKEAHKEYFAKFWD-NH$_2$ | 418 |
| [A-2>V, V-9>H, D-18>E]Rev D-4F | Ac-FVEKFKEAHKDYFAKFWE-NH$_2$ | 419 |
| [A-8>H]Rev-4F | Ac-FAEKFKEHVKDYFAKFWD-NH$_2$ | 420 |
| [A-8>H, D-E switched]Rev-4F | Ac-FADKFKDHVKEYFAKFWE-NH$_2$ | 421 |
| [A-8>H, D>E]Rev-4F | Ac-FAEKFKEHVKEYFAKFWE-NH$_2$ | 422 |
| [A-8>H, E>D]Rev-4F | Ac-FADKFKDHVKDYFAKFWD-NH$_2$ | 423 |
| [A-8>H, E-3>D]Rev-4F | Ac-FADKFKEHVKDYFAKFWD-NH$_2$ | 424 |
| [A-8>H, E-7>D]Rev-4F | Ac-FAEKFKDHVKDYFAKFWD-NH$_2$ | 425 |
| [A-8>H, D-11>E]Rev-4F | Ac-FAEKFKEHVKEYFAKFWD-NH$_2$ | 426 |
| [A-8>H, D-18>E]Rev-4F | Ac-FAEKFKEHVKDYFAKFWE-NH$_2$ | 427 |
| [A-8>F, F-13>H]Rev-4F | Ac-FAEKFKEFVKDYHAKFWD-NH$_2$ | 428 |
| [A-8>F, F-13>H, D-E switched]Rev-4F | Ac-FADKFKDFVKEYHAKFWE-NH$_2$ | 429 |
| [A-8>F, F-13>H, E-3>D]Rev-4F | Ac-FADKFKEFVKDYHAKFWD-NH$_2$ | 430 |
| [A-8>F, F-13>H, E-7>D]Rev-4F | Ac-FAEKFKDFVKDYHAKFWD-NH$_2$ | 431 |
| [A-8>F, F-13>H, E>D]Rev-4F | Ac-FADKFKDFVKDYHAKFWD-NH$_2$ | 432 |
| [A-8>F, F-13>H, D>E]Rev-4F | Ac-FAEKFKEFVKEYHAKFWE-NH$_2$ | 433 |
| [A-8>F, F-13>H, D-11>E]Rev-4F | Ac-FAEKFKEFVKEYHAKFWD-NH$_2$ | 434 |
| [A-8>F, F-13>H, D-18>E]Rev-4F | Ac-FAEKFKEFVKDYHAKFWE-NH$_2$ | 435 |
| [A-8>F, F16>H]Rev.-4F | Ac-FAEKFKEFVKDYFAKHWD-NH$_2$ | 436 |
| [A-8>F, F16>H, D-E switched]Rev.-4F | Ac-FADKFKDFVKEYFAKHWE-NH$_2$ | 437 |
| [A-8>F, F16>H, D>E]Rev.-4F | Ac-FAEKFKEFVKEYFAKHWE-NH$_2$ | 438 |
| [A-8>F, F16>H, E>D]Rev.-4F | Ac-FADKFKDFVKDYFAKHWD-NH$_2$ | 439 |
| [A-8>F, F16>H, E-3>D]Rev.-4F | Ac-FADKFKEFVKDYFAKHWD-NH$_2$ | 440 |
| [A-8>F, F16>H, E-7>D]Rev.-4F | Ac-FAEKFKDFVKDYFAKHWD-NH$_2$ | 441 |
| [A-8>F, F16>H, D-11>E]Rev.-4F | Ac-FAEKFKEFVKEYFAKHWD-NH$_2$ | 442 |
| [A-8>F, F16>H, D-18>E]Rev.-4F | Ac-FAEKFKEFVKDYFAKHWE-NH$_2$ | 443 |

Examples of class A 4F and Rev 4F analogs with beta-Nph. Similarly, alpha-Nph analogs can be designed. Similarly to the above analogs, His can be incorporated to Nph analogs. D>E analogs, E>D analogs and D-E switch analogs are additional possibilities similarly to the above described analogs.

| 4Nph | Ac-DWNphKANphYDKVAEKNphKEANph-NH$_2$ | 444 |
| [D-E switched]4Nph | Ac-EWNphKANphYEKVADKNphKDANph**-NH$_2$ | 445 |

TABLE 5-continued

Illustrates various class A and/or class Y peptide analogs with His incorporated into the sequence.

| Short name | Peptide sequence | SEQ ID NO |
|---|---|---|
| [D>E]4Nph | Ac-EWNphKANphYEKVAEKNphKEANph-NH$_2$ | 446 |
| [E>D]4Nph | Ac-DWNphKANphYDKVADKNphKDANph-NH$_2$ | 447 |
| [D-1>E]4Nph | Ac-EWNphKANnhYDKVAEKNphKEANph-NH$_2$ | 448 |
| [D-8>E]4Nph | Ac-DWNphKANphYEKVAEKNphKEANph-NH$_2$ | 449 |
| [E-12>D]4Nph | Ac-DWNphKANphYDKVADKNphKEANph-NH$_2$ | 450 |
| [E-16>D]4Nph | Ac-DWNphKANphYDKVAEKNphKDANph-NH$_2$ | 451 |

As decribed above for 4Nph, a minimum of 7 additional analogs for each of the analogs given below.

| [F-3, 6,>Nph]4F | Ac-DWNphKANphYDKVAEKFKEAF-NH$_2$ | 452 |
| [F-14, 18>Nph]4F | Ac-DWFKAFYDKVAEKNphKEANph-NH$_2$ | 453 |
| [[F-3>Nph]4F | Ac-DWNphKAFYDKVAEKFKEAF-NH$_2$ | 454 |
| [F-6>Nph]4F | Ac-DWFKANphYDKVAEKFKEAF-NH$_2$ | 455 |
| [F-14>Nph]4F | Ac-DWFKAFYDKVAEKNphKEAF-NH$_2$ | 456 |
| [F-18>Nph]4F | Ac-DWFKAFYDKVAEKFKEANph-NH$_2$ | 457 |

For each of the analog described below, a minimum of 7 additional analogs are possible as described above by switching D-E, D>E and E>D and single D or E analogs.

| Rev-4Nph | Ac-NphAEKNphKEAVKDYNphAKNphWD-NH$_2$ | 458 |
| [F-3, 6>Nph]Rev 4F | Ac-NphAEKNphKEAVKDYFAKFWD-NH$_2$ | 459 |
| [F-13, 16]Rev-4F | Ac-FAEKFKEAVKDYNphAKNphWD-NH$_2$ | 460 |
| [F-3>Nph]Rev-4F | Ac-NphAEKFKEAVKDYFAKFWD-NH$_2$ | 461 |
| [F-6>Nph]Rev-4F | Ac-FAEKNphKEAVKDYFAKFWD-NH$_2$ | 462 |
| [F-13>Nph]Rev-4F | Ac-FAEKFKEAVKDYNphAKFWD-NH$_2$ | 463 |
| [F-16>Nph]Rev-4F | Ac-FAEKFKEAVKDYFAKNphWD-NH$_2$ | 464 |

For the analogs described below, additional analogs are possible by incorporating His or alpha-Nph and beta-Nph

| Rev-[D>E]-4F | Ac-FAEKFKEAVKEYFAKFWE-NH$_2$ | 465 |
| Rev-[E>D]4F | Ac-FADKFKDAVKDYFAKFWD-NH$_2$ | 466 |
| Rev-R4-4F | Ac-FAERFREAVKDYFAKFWD-NH$_2$ | 467 |
| Rev-R6-4F | Ac-FAEKFREAVKDYFAKFWD-NH$_2$ | 468 |
| Rev-R10-4F | Ac-FAEKFKEAVRDYFAKFWD-NH$_2$ | 469 |
| Rev-R14-4F | Ac-FAEKFKEAVKDYFARFWD-NH$_2$ | 470 |
| Rev-[D>E]-4F | Ac-FAEKFKEAVKEYFAKFWE-NH$_2$ | 471 |
| Rev-[E>D]4F | Ac-FADKFKDAVKDYFAKFWD-NH$_2$ | 472 |
| Rev-R4-4F | Ac-FAERFREAVKDYFAKFWD-NH$_2$ | 473 |
| Rev-R6-4F | Ac-FAEKFREAVKDYFAKFWD-NH$_2$ | 474 |
| Rev-R10-4F | Ac-FAEKFKEAVRDYFAKFWD-NH$_2$ | 475 |
| Rev-R14-4F | Ac-FAEKFKEAVKDYFARFWD-NH$_2$ | 476 |

TABLE 5-continued

Illustrates various class A and/or class Y peptide analogs with His incorporated into the sequence.

| Short name | Peptide sequence | SEQ ID NO |
|---|---|---|
| Rev-[D>E]-4F | Ac-FAEKFKEAVKEYFAKFWE-NH$_2$ | 477 |
| Rev-[E>D]4F | Ac-FADKFKDAVKDYFAKFWD-NH$_2$ | 478 |
| Rev-R4-4F | Ac-FAERFREAVKDYFAKFWD-NH$_2$ | 479 |
| Rev-R6-4F | Ac-FAEKFREAVKDYFAKFWD-NH$_2$ | 480 |
| Rev-R10-4F | Ac-FAEKFKEAVRDYFAKFWD-NH$_2$ | 481 |
| Rev-R14-4F | Ac-FAEKFKEAVKDYFARFWD-NH$_2$ | 482 |
| Rev-R4-4F | Ac-FAERFREAVKDYFAKFWD-NH$_2$ | 483 |
| Rev-R6-4F | Ac-FAEKFREAVKDYFAKFWD-NH$_2$ | 484 |
| Rev-R10-4F | Ac-FAEKFKEAVRDYFAKFWD-NH$_2$ | 485 |
| Rev-R14-4F | Ac-FAEKFKEAVKDYFARFWD-NH$_2$ | 486 |
| Rev-[D>E]-4F | Ac-FAEKFKEAVKEYFAKFWE-NH$_2$ | 487 |
| Rev-[E>D]4F | Ac-FADKFKDAVKDYFAKFWD-NH$_2$ | 488 |
| Rev-R4-4F | Ac-FAERFREAVKDYFAKFWD-NH$_2$ | 489 |
| Rev-R6-4F | Ac-FAEKFREAVKDYFAKFWD-NH$_2$ | 490 |
| Rev-R10-4F | Ac-FAEKFKEAVRDYFAKFWD-NH$_2$ | 491 |
| Rev-R14-4F | Ac-FAEKFKEAVKDYFARFWD-NH$_2$ | 492 |

For each of the analogs below, additional H and Nph analogs are possible using the examples described above. Each analog can yield 7 analogs with the changes described in the examples give above.

| Short name | Peptide sequence | SEQ ID NO |
|---|---|---|
| Rev3F-2 | Ac-LFEKFAEAFKDYVAKWKD-NH$_2$ | 493 |
| RevR4-3F-2 | Ac-LFERFAEAFKDYVAKWKD-NH$_2$ | 494 |
| RevR10-3F2 | Ac-LFEKFAEAFRDYVAKWKD-NH$_2$ | 495 |
| RevR15-3F-2 | Ac-LFEKFAEAFKDYVARWKD-NH$_2$ | 496 |
| RevR17-3F-2 | Ac-LFEKFAEAFKDYVAKWRD-NH$_2$ | 497 |
| Rev[D>E]3F2 | Ac-LFEKFAEAFKEYVAKWKE-NH$_2$ | 498 |
| Rev[E>D]3F-2 | Ac-LFDKFADAFKDYVAKWKD-NH$_2$ | 499 |
| Rev-[E3>D]-3F-2 | Ac-LFDKFAEAFKDYVAKWKD-NH$_2$ | 500 |
| Rev-[E7>D]-3F-2 | Ac-LFEKFADAFKDYVAKWKD-NH$_2$ | 501 |
| Rev[D11>E]3F-2 | Ac-LFEKFAEAFKEYVAKWKD-NH$_2$ | 502 |
| Rev-[D18>E]3F-2 | Ac-LFEKFAEAFKDYVAKWKE-NH$_2$ | 503 |
| Rev3F-1 | Ac-FAEKAWEFVKDYFAKLKD-NH$_2$ | 504 |
| RevR4-3F-1 | Ac-FAERAWEFVKDYFAKLKD-NH$_2$ | 505 |
| RevR10-3F-1 | Ac-FAEKAWEFVKDYFAKLKD-NH$_2$ | 506 |
| RevR15-3F-1 | Ac-FAEKAWEFVKDYFAKLKD-NH$_2$ | 507 |
| RevR17-3F-1 | Ac-FAEKAWEFVKDYFAKLRD-NH$_2$ | 508 |
| Rev[D>E]3F-1 | Ac-FAEKAWEFVKEYFAKLKE-NH$_2$ | 509 |
| Rev[E>D}3F-1 | Ac-FADKAWDFVKDYFAKLKD-NH$_2$ | 510 |
| Rev[E3>D]-3F-1 | Ac-FADKAWEFVKDYFAKLKD-NH$_2$ | 511 |

TABLE 5-continued

Illustrates various class A and/or class Y peptide analogs with His incorporated into the sequence.

| Short name | Peptide sequence | SEQ ID NO |
|---|---|---|
| Rev[E7>D]3F-1 | Ac-FAEKAWDFVKDYFAKLKD-NH$_2$ | 512 |
| Rev-[D11>E]3F-1 | Ac-FAEKAWEFVKEYFAKLKD-NH$_2$ | 513 |
| Rev-[D18>E]3F-1 | Ac-FAEKAWEFVKDYFAKLKE-NH$_2$ | 514 |
| Rev-5F | Ac-FFEKFKEFVKDYFAKLWD-NH$_2$ | 515 |
| Rev-[D>E]5F | Ac-FFEKFKEFVKEYFAKLWE-NH$_2$ | 516 |
| Rev-[E>D]5F | Ac-FFDKFKDFVKDYFAKLWD-NH$_2$ | 517 |
| Rev-R4-5F | Ac-FFERFKEFVKDYFAKLWD-NH$_2$ | 518 |
| Rev-R6-5F | Ac-FFEKFREFVKDYFAKLWD-NH$_2$ | 519 |
| Rev-R10-5F | Ac-FFEKFKEFVRDYFAKLWD-NH$_2$ | 520 |
| Rev-R15-5F | Ac-FFEKFKEFVKDYFARLWD-NH$_2$ | 521 |
| Rev-[E3>D]-5F | Ac-FFDKFKEFVKDYFAKLWD-NH$_2$ | 522 |
| Rev-[E7>D]5F | Ac-FFEKFKDFVKDYFAKLWD-NH$_2$ | 523 |
| Rev-[D11>E]-5F | Ac-FFEKFKEFVKEYFAKLWD-NH$_2$ | 524 |
| Rev-[D18>E]-5F | Ac-FFEKFKEFVKDYFAKLWE-NH$_2$ | 525 |
| Rev-5F-2 | Ac-FLEKFKEFVKDYFAKFWD-NH$_2$ | 526 |
| Rev-[D>E]-5F-2 | Ac-FLEKFKEFVKEYFAKFWE-NH$_2$ | 527 |
| Rev-[E>D]-5F-2 | Ac-FLDKFKEFVKDYFAKFWD-NH$_2$ | 528 |
| Rev-[E3>D]-5F-2 | Ac-FLDKFKEFVKDYFAKFWD-NH$_2$ | 529 |
| Rev-[E7>D]-5F-2 | Ac-FLEKFKDFVKDYFAKFWD-NH$_2$ | 530 |
| Rev-[D11>E]-5F-2 | Ac-FLEKFKEFVKEYFAKFWD-NH$_2$ | 531 |
| Rev-[D18>E]-5F-2 | Ac-FLEKFKEFVKDYFAKFWE-NH$_2$ | 532 |
| Rev-R4-5F-2 | Ac-FLERFKEFVKDYFAKFWD-NH$_2$ | 533 |
| Rev-R6-5F-2 | Ac-FLEKFREFVKDYFAKFWD-NH$_2$ | 534 |
| RevR10-5F-2 | Ac-FLEKFKEFVRDYFAKFWD-NH$_2$ | 535 |
| Rev-R16-5F-2 | Ac-FLEKFKEFVKDYFARFWD-NH$_2$ | 536 |
| Rev-6F | Ac-FFEKFKEFFKDYFAKLWD-NH$_2$ | 537 |
| Rev-[D>E]-6F | Ac-FFEKFKEFFKEYFAKLWE-NH$_2$ | 538 |
| Rev-[E>D]-6F | Ac-FFDKFKDFFKDYFAKLWD-NH$_2$ | 539 |
| Rev-R4-6F | Ac-FFERFKEFFKDYFAKLWD-NH$_2$ | 540 |
| Rev-R6-6F | Ac-FFEKFREFFKDYFAKLWD-NH$_2$ | 541 |
| Rev-R10-6F | Ac-FFEKFKEFFRDYFAKLWD-NH$_2$ | 542 |
| Rev-R14-6F | Ac-FFERFKEFFKDYFARLWD-NH$_2$ | 543 |
| Rev-[E3>D]-6F | Ac-FFDKFKEFFKDYFAKLWD-NH$_2$ | 544 |
| Rev-[E7>D]-6F | Ac-FFEKFKDFFKDYFAKLWD-NH$_2$ | 545 |
| Rev-[D11>E]-6F | Ac-FFEKFKEFFKEYFAKLWD-NH$_2$ | 546 |
| Rev-[D18>E]-6F | Ac-FFEKFKEFFKDYFAKLWE-NH$_2$ | 547 |

TABLE 5-continued

Illustrates various class A and/or class Y peptide analogs with His incorporated into the sequence.

| Short name | Peptide sequence | SEQ ID NO |
|---|---|---|
| Rev-4F | Ac-FAEKFKEAVKDYFAKFWD-NH$_2$ | 548 |
| Rev-[D>E]-4F | Ac-FAEKFKEAVKEYFAKFWE-NH$_2$ | 549 |
| Rev-[E>D]4F | Ac-FADKFKDAVKDYFAKFWD-NH$_2$ | 550 |
| Rev-R4-4F | Ac-FAERFREAVKDYFAKFWD-NH$_2$ | 551 |
| Rev-R6-4F | Ac-FAEKFREAVKDYFAKFWD-NH$_2$ | 552 |
| Rev-R10-4F | Ac-FAEKFKEAVRDYFAKFWD-NH$_2$ | 553 |
| Rev-R14-4F | Ac-FAEKFKEAVKDYFARFWD-NH$_2$ | 554 |
| 4F-2 | Ac-DKWKAVYDKFAEAFKEFF-NH$_2$ | 555 |
| [D>E]-4F-2 | Ac-EKWKAVYEKFAEAFKEFF-NH$_2$ | 556 |
| [E>D]-4F-2 | Ac-DKWKAVYDKFADAFKDFF-NH$_2$ | 557 |
| R2-4F-2 | Ac-DRWKAVYDKFAEAFKEFF-NH$_2$ | 558 |
| R4-4F-2 | Ac-DKWRAVYDKFAEAFKEFF-NH$_2$ | 559 |
| R9-4F-2 | Ac-DKWKAVYDRFAEAFKEFF-NH$_2$ | 560 |
| R14-4F-2 | Ac-DKWKAVYDKFAEAFREFF-NH$_2$ | 561 |
| Rev4F-2 | Ac-FFEKFAEAFKDYVAKWKD-NH$_2$ | 562 |
| Rev-[D>E]-4F-2 | Ac-FFEKFAEAFKEYVAKWKE-NH$_2$ | 563 |
| Rev-[E>D]-3F-2 | Ac-FFDKFADAFKDYVAKWKD-NH$_2$ | 564 |
| Rev-R4-4F-2 | Ac-FFERFAEAFKDYVAKWKD-NH$_2$ | 565 |
| Rev-R10-4F-2 | Ac-FFERFAEAFRDYVAKWKD-NH$_2$ | 566 |
| Rev-R15-4F-2 | Ac-FFEKFAEAFKDYVARWKD-NH$_2$ | 567 |
| Rev-R17-4F-2 | Ac-FFERFAEAFKDYVAKWRD-NH$_2$ | 568 |
| Rev-[E3>D]-4F-2 | Ac-FFDKFAEAFKDYVAKWKD-NH$_2$ | 569 |
| Rev-[E7>D]-4F-2 | Ac-FFEKFADAFKDYVAKWKD-NH$_2$ | 570 |
| Rev-[D11>E]-4F-2 | Ac-FFERFAEAFKEYVAKWKD-NH$_2$ | 571 |
| Rev-[D18>E]-4F-2 | Ac-FFERFAEAFKDYVAKWKE-NH$_2$ | 572 |
| Rev-7F | Ac-FFEKFKEFFKDYFAKFWD-NH$_2$ | 573 |
| Rev-[E>D]-7F | Ac-FFDKFKDFFKDYFAKFWD-NH$_2$ | 574 |
| Rev-[D>E]-7F | Ac-FFEKFKEFFKEYFAKFWE-NH$_2$ | 575 |
| Rev-R4-7F | Ac-FFERFKEFFKDYFAKFWD-NH$_2$ | 576 |
| Rev-R6-7F | Ac-FFEKFREFFKDYFAKFWD-NH$_2$ | 577 |
| Rev-R10-7F | Ac-FFEKFKEFFRDYFAKFWD-NH$_2$ | 578 |
| Rev-R14-7F | Ac-FFEKFKEFFKDYFARFWD-NH$_2$ | 579 |
| Rev-[E3>D]-7F | Ac-FFDKFKEFFKDYFAKFWD-NH$_2$ | 580 |
| Rev-[E7>D]7F | Ac-FFEKFKDFFKDYFAKFWD-NH$_2$ | 581 |
| Rev-[D11>E]-7F | Ac-FFEKFKEFFKEYFAKFWD-NH$_2$ | 582 |
| Rev-[D18>E]-7F | Ac-FFEKFKEFFKDYFAKFWE-NH$_2$ | 583 |

It is also noted that any of the peptides described herein can comprise non-natural amino acids in addition to or instead of the corresponding natural amino acids identified herein. Such modifications include, but are not limited to acetylation, amidation, formylation, methylation, sulfation, and the like. Illustrative non-natural amino acids include, but are not limited to Ornithine, norleucine, norvaline, N-methylvaline, 6-N-methyllysine, N-methylisoleucine, N-methylglycine, sarcosine, inosine, allo-isoleucine, isodesmolysine, 4-hydroxyproline, 3-hydroxyproline, allo-hydroxylysine, hydroxylisine, N-ethylasparagine, N-ethylglycine, 2,3-diaminopropionic acid, 2,2'-diaminopropionic acid, desmosine, 2,4-diaminobutyric acid, 2-aminopimelic acid, 3-aminoisobutyric acid, 2-aminoisobutyric acid, 2-aminoheptanoic acid, 6-aminocaproic acid, 4-aminobutyric acid, 2-aminobutyric acid, beta-alanine, 3-aminoadipic acid, 2-aminoadipic acid, and the like. In certain embodiments andy one or more of the "natural" amino acids of the peptides described herein, can be substituted with the corresponding non-natural amino acid (e.g., as describe above).

In certain embodiments, this invention contemplates particularly the use of modified lysines. Such modifications include, but are not limited to, biotin modification of epsilon lysines and/or methylation of the epsilon lysines. Illustrative peptide comprising epsilon methylated lysines include, but are not limited to: Ac-D-W—F—K(eCH$_3$)$_2$-A-F—Y-D-K(eCH$_3$)$_2$—V-A-E-K(eCH$_3$)$_2$—F—K(eCH$_3$)$_2$-E-A-F—NH(CH$_3$)$_2$ (SEQ ID NO:635) and: Ac-DWFK(eCH$_3$)$_2$AFYDK(eCH$_3$)$_2$VAEK(eCH$_3$)$_2$FK(eCH$_3$)$_2$EAF-NH(CH$_3$) (SEQ ID NO:636). Other modified amino acids include but are not limited to ornithine analogs and homoaminoalanine analogs (instead of (CH$_2$)$_4$—NH$_2$ for Lys it can be —(CH$_2$)$_2$—NH$_2$ for Haa and —(CH$_2$)$_3$—NH$_2$ for Orn] and the like. It is noted that these modifications are illustrative and not intended to be limiting. Illustrative 4F analogues that possess modified amino acids are shown in Table 6.

TABLE 6

Illustrative 4F analogs that comprise modified amino acids.

| Peptide | SEQ ID NO |
|---|---|
| εN-Dimethyl-Lys derivative of 4F (εN-Dime): | |
| Ac-D-W-F-K(εN-Dime)-A-F-Y-D-K(εN-Dime)-V-A-E-K(εN-Dime)-F-K(εN-Dime)-E-A-F-NH$_2$ | 586 |
| Ac-D-W-F-K-(εN-Dime)-A-F-Y-D-K(εN-Dime)-V-A-E-K(εN-Dime)-F-K((εN-Dime)-E-A-F-NH-Me | 587 |
| Ac-D-W-F-K-(εN-Dime)-A-F-Y-D-K(εN-Dime)-V-A-E-K(εN-Dime)-F-K(εN-Dime)-E-A-F-N-(Me)$_2$ | 588 |
| εN-Diethyl-Lys derivatives of 4F (εN-Diet) | |
| Ac-D-W-F-K(εN-Diet)-A-F-Y-D-K(εN-Diet)-V-A-E-K(εN-Diet)-F-K(εN-Diet)-E-A-F-NH$_2$ | 589 |
| Ac-D-W-F-K(εN-Diet)-A-F-Y-D-K(εN-Diet)-V-A-E-K(εN-Diet)-F-K(εN-Diet)-E-A-F-NH-Et | 590 |
| Ac-D-W-F-K(εN-Diet)-A-F-Y-D-K(εN-Diet)-V-A-E-K(εN-Diet)-F-K(εN-Diet)-E-A-F-NH-(Et)$_2$ | 591 |
| εN-Monomethyl-Lys derivative of 4F (εN-Me) | |
| Ac-D-W-F-K(εN-Me)-A-F-Y-D-K(εN-Me)-V-A-E-K(εN-Me)-F-K(εN-Me)-E-A-F-NH$_2$ | 592 |
| Ac-D-W-F-K(εN-Me)-A-F-Y-D-K(εN-Me)-V-A-E-K(εN-Me)-F-K(εN-Me)-E-A-F-NH-Me | 593 |
| Ac-D-W-F-K(εN-Me)-A-F-Y-D-K(εN-Me)-V-A-E-K(εN-Me)-F-K(εN-Me)-E-A-F-N-(Me)$_2$ | 594 |
| εN-ethylLys derivative of 4F (εNEt) | |
| Ac-D-W-F-K(εN-Et)-A-F-Y-D-K(εN-Et)-V-A-E-K(εN-Et)-F-K(εN-Et)-E-A-F-NH$_2$ | 595 |
| Ac-D-W-F-K(εN-Et)-A-F-Y-D-K(εN-Et)-V-A-E-K(εN-Et)-F-K(εN-Et)-E-A-F-NH-Et | 596 |
| Ac-D-W-F-K(εN-Et)-A-F-Y-D-K(εN-Et)-V-A-E-K(εN-Et)-F-K(εN-Et)-E-A-F-NH-(Et)$_2$ | 597 |
| HomoLys analogs of 4F (hK) (—CH$_2$)$_5$—NH$_2$: | |
| Ac-D-W-F-hK-A-F-Y-D-hK-V-A-E-hK-F-hK-E-A-F-NH$_2$ | 598 |
| Ac-D-W-F-hK(εN-Dime)-A-F-Y-D-hK(εN-Dime)-V-A-E-hK(εN-Dime)-F-hK(εN-Dime)-E-A-F-NH$_2$ | 599 |

TABLE 6-continued

Illustrative 4F analogs that comprise modified amino acids.

| Peptide | SEQ ID NO |
|---|---|
| Ac-D-W-F-hK(εN-Dime)-A-F-Y-D-hK(εN-Dime)-V-A-E-hK(εN-Dime)-F-hK(εN-Dime)-E-A-F-N-(Me)$_2$ | 600 |
| Ac-D-W-F-hK(εN-Dime)-A-F-Y-D-hK(εN-Dime)-V-A-E-hK(εN-Dime)-F-hK(εN-Dime)-E-A-F-NH-Me | 601 |
| Ac-D-W-F-hK(εN-Diet)-A-F-Y-D-hK(εN-Diet)-V-A-E-hK(εN-Diet)-F-hK(εN-Diet)-E-A-F-NH-Et | 602 |
| Ac-D-W-F-hK(εN-Me)-A-F-Y-D-hK(εN-Me)-V-A-E-hK(εN-Me)-F-hK(εN-Me)-E-A-F-NH$_2$ | 603 |
| Ac-D-W-F-hK(εN-Me)-A-F-Y-D-hK(εN-Me)-V-A-E-hK(εN-Me)-F-hK(εN-Me)-E-A-F-NH-Me | 604 |
| Ac-D-W-F-hK(εN-Me)-A-F-Y-D-hK(εN-Me)-V-A-E-hK(εN-Me)-F-hK(εN-Me)-E-A-F-N-(Me)$_2$ | 605 |
| Ac-D-W-F-hK(εN-Et)-A-F-Y-D-hK(εN-Et)-V-A-E-hK(εN-Et)-F-hK(εN-Et)-E-A-F-NH$_2$ | 606 |
| Ac-D-W-F-hK(εN-Et)-A-F-Y-D-hK(εN-Et)-V-A-E-hK(εN-Et)-F-hK(εN-Et)-E-A-F-NH-Et | 607 |
| Ac-D-W-F-hK(εN-Et)-A-F-Y-D-hK(εN-Et)-V-A-E-hK(εN-Et)-F-hK(εN-Et)-E-A-F-NH-(Et)$_2$ | 608 |
| 4F analogs in which K is replaced O (O = Ornithine, —(CH$_2$)$_3$—NH$_2$): | 609 |
| Ac-D-W-F-O-A-F-Y-D-O-V-A-E-O-F-O-E-A-F-NH$_2$ | 610 |
| Ac-D-W-F-O(δN-Dime)-A-F-Y-D-O(δN-Dime)-V-A-E-O(δN-Dime)-F-O(δN-Dime)-E-A-F-NH$_2$ | 611 |
| Ac-D-W-F-O(δN-Dime)-A-F-Y-D-}(δN-Dime)-V-A-E-O(δN-Dime)-F-O(δN-Dime)-E-A-F-N-(Me)$_2$ | 612 |
| Ac-D-W-F-O(δN-Dime)-A-F-Y-D-O(δN-Dime)-V-A-E-O(δN-Dime)-F-O(δN-Dime)-E-A-F-NH-Me | 613 |
| Ac-D-W-F-O(δN-Diet)-A-F-Y-D-O(δN-Diet)-V-A-E-O(δN-Diet)-F-O(δN-Diet)-E-A-F-NH-Et | 614 |
| Ac-D-W-F-O(δN-Me)-A-F-Y-D-O(δN-Me)-V-A-E-O(δN-Me)-F-O(δN-Me)-E-A-F-NH$_2$ | 615 |
| Ac-D-W-F-O(δN-Me)-A-F-Y-D-O(δN-Me)-V-A-E-O(δN-Me)-F-O(δN-Me)-E-A-F-NH-Me | 616 |
| Ac-D-W-F-O(δN-Me)-A-F-Y-D-O(δN-Me)-V-A-E-O(δN-Me)-F-O(δN-Me)-E-A-F-N-(Me)$_2$ | 617 |
| Ac-D-W-F-O(δN-Et)-A-F-Y-D-O(δN-Et)-V-A-E-O(δN-Et)-F-O(δN-Et)-E-A-F-NH$_2$ | 618 |
| Ac-D-W-F-O(δN-Et)-A-F-Y-D-O(δN-Et)-V-A-E-O(δN-Et)-F-O(δN-Et)-E-A-F-NH-Et | 619 |
| Ac-D-W-F-O(δN-Et)-A-F-Y-D-O(δN-Et)-V-A-E-OdεN-Et)-F-O(δN-Et)-E-A-F-NH-(Et)$_2$ | 620 |

The peptides and modifications shown above are intended to be illustrative and not limiting.

D) Smaller Peptides.

It was also a surprising discovery that certain small peptides consisting of a minimum of three amino acids preferentially (but not necessarily) with one or more of the amino acids being the D-stereoisomer of the amino acid, and possessing hydrophobic domains to permit lipid protein interactions, and hydrophilic domains to permit a degree of water solubility also possess significant anti-inflammatory properties and are useful in treating one or more of the pathologies described herein. The "small peptides" typically range in length from 2 amino acids to about 15 amino acids, more preferably from about 3 amino acids to about 10 or 11 amino acids, and most preferably from about 4 to about 8 or 10 amino acids. In various embodiments the peptides are typically characterized by having hydrophobic terminal amino acids or terminal amino acids rendered hydrophobic by the attachment of one or more hydrophobic "protecting" groups. Various "small peptides" are described in copending applications U.S. Ser. No. 10/649,378, filed Aug. 26, 2003, and in U.S. Ser. No. 10/913,800, filed on Aug. 6, 2004, and in PCT Application PCT/US2004/026288.

In certain embodiments, the peptides can be characterized by Formula XXV, below:

$$X^1\text{—}X^2\text{—}X^3{}_n\text{—}X^4 \qquad XXV$$

where, n is 0 or 1, $X^1$ is a hydrophobic amino acid and/or bears a hydrophobic protecting group, $X^4$ is a hydrophobic amino acid and/or bears a hydrophobic protecting group; and when n is 0 $X^2$ is an acidic or a basic amino acid; when n is 1: $X^2$ and $X^3$ are independently an acidic amino acid, a basic amino acid, an aliphatic amino acid, or an aromatic amino acid such that when $X^2$ is an acidic amino acid; $X^3$ is a basic amino acid, an aliphatic amino acid, or an aromatic amino acid; when $X^2$ is a basic amino acid; $X^3$ is an acidic amino acid, an aliphatic amino acid, or an aromatic amino acid; and when $X^2$ is an aliphatic or aromatic amino acid, $X^3$ is an acidic amino acid, or a basic amino acid.

Longer peptides (e.g., up to 10, 11, or 15 amino acids) are also contemplated within the scope of this invention. Typically where the shorter peptides (e.g., peptides according to Formula XXV) are characterized by an acidic, basic, aliphatic, or aromatic amino acid, the longer peptides are characterized by acidic, basic, aliphatic, or aromatic domains comprising two or more amino acids of that type.

1) Functional Properties of Active Small Peptides.

It was a surprising finding of this invention that a number of physical properties predict the ability of small peptides (e.g., less than 10 amino acids, preferably less than 8 amino acids, more preferably from about 3 to about 5 or 6 amino acids) of this invention to render HDL more anti-inflammatory and to mitigate atherosclerosis and/or other pathologies characterized by an inflammatory response in a mammal. The physical properties include high solubility in ethyl acetate (e.g., greater than about 4 mg/mL), and solubility in aqueous buffer at pH 7.0. Upon contacting phospholipids such as 1,2-Dimyristoyl-sn-glycero-3-phosphocholine (DMPC), in an aqueous environment, the particularly effective small peptides induce or participate in the formation of particles with a diameter of approximately 7.5 nm (±0.1 nm), and/or induce or participate in the formation of stacked bilayers with a bilayer dimension on the order of 3.4 to 4.1 nm with spacing between the bilayers in the stack of approximately 2 nm, and/or also induce or participate in the formation of vesicular structures of approximately 38 nm). In certain preferred embodiments, the small peptides have a molecular weight of less than about 900 Da.

Thus, in certain embodiments, this invention contemplates small peptides that ameliorate one or more symptoms of an indication/pathology described herein, e.g., an inflammatory condition, where the peptide(s): ranges in length from about 3 to about 8 amino acids, preferably from about 3 to about 6, or 7 amino acids, and more preferably from about 3 to about 5 amino acids; are soluble in ethyl acetate at a concentration greater than about 4 mg/mL; are soluble in aqueous buffer at pH 7.0; when contacted with a phospholipid in an aqueous environment, form particles with a diameter of approximately 7.5 nm and/or form stacked bilayers with a bilayer dimension on the order of 3.4 to 4.1 nm with spacing between the bilayers in the stack of approximately 2 nm; have a molecular weight less than about 900 daltons; convert pro-inflammatory HDL to anti-inflammatory HDL or make anti-inflammatory HDL more anti-inflammatory. In certain embodiments the peptides include, but are not limited to peptides having the amino acid sequence Lys-Arg-Asp-Ser (SEQ ID NO:621801), especially in which Lys-Arg-Asp and Ser are all L amino acids. In certain embodiments, these small peptides protect a phospholipid against oxidation by an oxidizing agent. In certain embodiments the compositions and methods described herein exclude the amino acid sequence Lys-Arg-Asp-Ser (SEQ ID NO:621), especially in which Lys-Arg-Asp and Ser are all L amino acids.

While these small peptides need not be so limited, in certain embodiments, these small peptides can include the small peptides described below.

2) Tripeptides.

It was discovered that certain tripeptides (3 amino acid peptides) can be synthesized that show desirable properties as described herein (e.g., the ability to convert pro-inflammatory HDL to anti-inflammatory HDL, the ability to decrease LDL-induced monocyte chemotactic activity generated by artery wall cells. In certain embodiments, the peptides are characterized by Formula XXV, wherein N is zero, shown below as Formula XXVI:

$$X^1\text{—}X^2\text{—}X^4 \qquad XXVI$$

where the end amino acids ($X^1$ and $X^4$) are hydrophobic either because of a hydrophobic side chain or because the side chain or the C and/or N terminus is blocked with one or more hydrophobic protecting group(s) (e.g., the N-terminus is blocked with Boc-, Fmoc-, nicotinyl-, etc., and the C-terminus blocked with (tBu)-OtBu, etc.). In certain embodiments, the $X^2$ amino acid is either acidic (e.g., aspartic acid, glutamic acid, etc.) or basic (e.g., histidine, arginine, lysine, etc.). The peptide can be all L-amino acids or include one or more or all D-amino acids.

Certain tripeptides of this invention include, but are not limited to the peptides shown in Table 7.

TABLE 7

Examples of certain preferred tripeptides bearing hydrophobic blocking groups and acidic, basic, or histidine central amino acids.

| $X^1$ | $X^2$ | $X^3$ | $X^4$ |
|---|---|---|---|
| Boc-Lys(εBoc) | Arg | | Ser(tBu)-OtBu |
| Boc-Lys(εBoc) | Arg | | Thr(tBu)-OtBu |
| Boc-Trp | Arg | | Ile-OtBu |
| Boc-Trp | Arg | | Leu-OtBu |
| Boc-Phe | Arg | | Ile OtBu |
| Boc-Phe | Arg | | Leu-OtBu |
| Boc-Lys(εBoc) | Glu | | Ser(tBu)-OtBu |
| Boc-Lys(εBoc) | Glu | | Thr(tBu)-OtBu |
| Boc-Lys(εBoc) | Asp | | Ser(tBu)-OtBu |
| Boc-Lys(εBoc) | Asp | | Thr(tBu)-OtBu |
| Boc-Lys(εBoc) | Arg | | Ser(tBu)-OtBu |
| Boc-Lys(εBoc) | Arg | | Thr(tBu)-OtBu |
| Boc-Leu | Glu | | Ser(tBu)-OtBu |
| Boc-Leu | Glu | | Thr(tBu)-OtBu |
| Fmoc-Trp | Arg | | Ser(tBu)-OtBu |
| Fmoc-Trp | Asp | | Ser(tBu)-OtBu |
| Fmoc-Trp | Glu | | Ser(tBu)-OtBu |

TABLE 7-continued

Examples of certain preferred tripeptides bearing hydrophobic blocking groups and acidic, basic, or histidine central amino acids.

| $X^1$ | $X^2$ | $X^3\ X^4$ |
|---|---|---|
| Fmoc-Trp | Arg | Ser(tBu)-OtBu |
| Boc-Lys(εBoc) | Glu | Leu-OtBu |
| Fmoc-Leu | Arg | Ser(tBu)-OtBu |
| Fmoc-Leu | Asp | Ser(tBu)-OtBu |
| Fmoc-Leu | Glu | Ser(tBu)-OtBu |
| Fmoc-Leu | Arg | Ser(tBu)-OtBu |
| Fmoc-Leu | Arg | Thr(tBu)-OtBu |
| Boc-Glu | Asp | Tyr(tBu)-OtBu |
| Fmoc-Lys(εFmoc) | Arg | Ser(tBu)-OtBu |
| Fmoc-Trp | Arg | Ile-OtBu |
| Fmoc-Trp | Arg | Leu-OtBu |
| Emoc-Phe | Arg | Ile-OtBu |
| Emoc-Phe | Arg | Leu-OtBu |
| Boc-Trp | Arg | Phe-OtBu |
| Boc-Trp | Arg | Tyr-OtBu |
| Fmoc-Trp | Arg | Phe-OtBu |
| Fmoc-Trp | Arg | Tyr-OtBu |
| Boc-Orn(δBoc) | Arg | Ser(tBu)-OtBu |
| Nicotinyl Lys(εBoc) | Arg | Ser(tBu)-OtBu |
| Nicotinyl Lys(εBoc) | Arg | Thr(tBu)-OtBu |
| Fmoc-Leu | Asp | Thr(tBu)-OtBu |
| Fmoc-Leu | Glu | Thr(tBu)-OtBu |
| Fmoc-Leu | Arg | Thr(tBu)-OtBu |
| Fmoc-norLeu | Arg | Ser(tBu)-OtBu |
| Fmoc-norLeu | Asp | Ser(tBu)-OtBu |
| Fmoc-norLeu | Glu | Ser(tBu)-OtBu |
| Fmoc-Lys(εBoc) | Arg | Ser(tBu)-OtBu |
| Fmoc-Lys(εBoc) | Arg | Thr(tBu)-OtBu |
| Fmoc-Lys(εBoc) | Glu | Ser(tBu)-OtBu |
| Fmoc-Lys(εBoc) | Glu | Thr(tBu)-OtBu |
| Fmoc-Lys(εBoc) | Asp | Ser(tBu)-OtBu |
| Fmoc-Lys(εBoc) | Asp | Thr(tBu)-OtBu |
| Fmoc-Lys(εBoc) | Glu | Leu-OtBu |
| Fmoc-Lys(εBoc) | Arg | Leu-OtBu |
| Fmoc-Lys(εFmoc) | Arg | Thr(tBu)-OtBu |
| Emoc-Lys(εFmoc) | Glu | Ser(tBu)-OtBu |
| Emoc-Lys(εFmoc) | Glu | Thr(tBu)-OtBu |
| Emoc-Lys(εFmoc) | Asp | Ser(tBu)-OtBu |
| Emoc-Lys(εFmoc) | Asp | Thr(tBu)-OtBu |
| Emoc-Lys(εFmoc) | Arg | Ser(tBu)-OtBu |
| Emoc-Lys(εFmoc)) | Glu | Leu-OtBu |
| Boc-Lys(εFmoc) | Asp | Ser(tBu)-OtBu |
| Boc-Lys(εFmoc) | Asp | Thr(tBu)-OtBu |
| Boc-Lys(εFmoc) | Arg | Thr(tBu)-OtBu |
| Boc-Lys(εFmoc) | Glu | Leu-OtBu |
| Boc-Orn(δFmoc) | Glu | Ser(tBu)-OtBu |
| Boc-Orn(δFmoc) | Asp | Ser(tBu)-OtBu |
| Boc-Orn(δFmoc) | Asp | Thr(tBu)-OtBu |
| Boc-Orn(δFmoc) | Arg | Thr(tBu)-OtBu |
| Boc-Orn(δFmoc) | Glu | Thr(tBu)-OtBu |
| Fmoc-Trp | Asp | Ile-OtBu |
| Fmoc-Trp | Arg | Ile-OtBu |
| Fmoc-Trp | Glu | Ile-OtBu |
| Fmoc-Trp | Asp | Leu-OtBu |
| Fmoc-Trp | Glu | Leu-OtBu |
| Emoc-Phe | Asp | Ile-OtBu |
| Emoc-Phe | Asp | Leu-OtBu |
| Emoc-Phe | Glu | Leu-OtBu |
| Fmoc-Trp | Arg | Phe-OtBu |
| Fmoc-Trp | Glu | Phe-OtBu |
| Fmoc-Trp | Asp | Phe-OtBu |
| Fmoc-Trp | Asp | Tyr-OtBu |
| Fmoc-Trp | Arg | Tyr-OtBu |
| Fmoc-Trp | Glu | Tyr-OtBu |
| Fmoc-Trp | Arg | Thr(tBu)-OtBu |
| Fmoc-Trp | Asp | Thr(tBu)-OtBu |
| Fmoc-Trp | Glu | Thr(tBu)-OtBu |
| Boc-Phe | Arg | norLeu-OtBu |
| Boc-Phe | Glu | norLeu-OtBu |
| Emoc-Phe | Asp | norLeu-OtBu |
| Boc-Glu | His | Tyr(tBu)-OtBu |
| Boc-Leu | His | Ser(tBu)-OtBu |
| Boc-Leu | His | Thr(tBu)-OtBu |
| Boc-Lys(εBoc) | His | Ser(tBu)-OtBu |

TABLE 7-continued

Examples of certain preferred tripeptides bearing hydrophobic blocking groups and acidic, basic, or histidine central amino acids.

| $X^1$ | $X^2$ | $X^3$ $X^4$ |
|---|---|---|
| Boc-Lys(εBoc) | His | Thr(tBu)-OtBu |
| Boc-Lys(εBoc) | His | Leu-OtBu |
| Boc-Lys(εFmoc) | His | Ser(tBu)-OtBu |
| Boc-Lys(εFmoc) | His | Thr(tBu)-OtBu |
| Boc-Lys(εFmoc) | His | Leu-OtBu |
| Boc-Orn(δBoc) | His | Ser(tBu)-OtBu |
| Boc-Orn(δFmoc) | His | Thr(tBu)-OtBu |
| Boc-Phe | His | Ile-OtBu |
| Boc-Phe | His | Leu-OtBu |
| Boc-Phe | His | norLeu-OtBu |
| Boc-Phe | Lys | Leu-OtBu |
| Boc-Trp | His | Ile-OtBu |
| Boc-Trp | His | Leu-OtBu |
| Boc-Trp | His | Phe-OtBu |
| Boc-Trp | His | Tyr-OtBu |
| Boc-Phe | Lys | Leu-OtBu |
| Fmoc-Lys(εFmoc) | His | Ser(tBu)-OtBu |
| Fmoc-Lys(εFmoc) | His | Thr(tBu)-OtBu |
| Fmoc-Lys(εFmoc) | His | Leu-OtBu |
| Fmoc-Leu | His | Ser(tBu)-OtBu |
| Fmoc-Leu | His | Thr(tBu)-OtBu |
| Fmoc-Lys(εBoc) | His | Ser(tBu)-OtBu |
| Fmoc-Lys(εBoc) | His | Thr(tBu)-OtBu |
| Fmoc-Lys(εBoc) | His | Leu-OtBu |
| Fmoc-Lys(εFmoc) | His | Ser(tBu)-OtBu |
| Fmoc-Lys(εFmoc) | His | Thr(tBu)-OtBu |
| Fmoc-norLeu | His | Ser(tBu)-OtBu |
| Emoc-Phe | His | Ile-OtBu |
| Emoc-Phe | His | Leu-OtBu |
| Emoc-Phe | His | norLeu-OtBu |
| Fmoc-Trp | His | Ser(tBu)-OtBu |
| Fmoc-Trp | His | Ile-OtBu |
| Fmoc-Trp | His | Leu-OtBu |
| Fmoc-Trp | His | Phe-OtBu |
| Fmoc-Trp | His | Tyr-OtBu |
| Fmoc-Trp | His | Thr(tBu)-OtBu |
| Nicotinyl Lys(εBoc) | His | Ser(tBu)-OtBu |
| Nicotinyl Lys(εBoc) | His | Thr(tBu)-OtBu |

While the peptides of Table 7 are illustrated with particular protecting groups, it is noted that any of these groups may be eliminated and/or substituted with other protecting groups as described herein.

3) Small Peptides with Central Acidic and Basic Amino Acids.

In certain embodiments, the peptides of this invention range from four amino acids to about ten amino acids. The terminal amino acids are typically hydrophobic either because of a hydrophobic side chain or because the terminal amino acids bear one or more hydrophobic protecting groups end amino acids ($X^1$ and $X^4$) are hydrophobic either because of a hydrophobic side chain or because the side chain or the C and/or N terminus is blocked with one or more hydrophobic protecting group(s) (e.g., the N-terminus is blocked with Boc-, Fmoc-, Nicotinyl-, etc., and the C-terminus blocked with (tBu)-OtBu, etc.). Typically, the central portion of the peptide comprises a basic amino acid and an acidic amino acid (e.g., in a 4 mer) or a basic domain and/or an acidic domain in a longer molecule.

These four-mers can be represented by Formula XXV in which $X^1$ and $X^4$ are hydrophobic and/or bear hydrophobic protecting group(s) as described herein and $X^2$ is acidic while $X^3$ is basic or $X^2$ is basic while $X^3$ is acidic. The peptide can be all L-amino acids or include one or more or all D-amino acids.

Certain preferred of this invention include, but are not limited to the peptides shown in Table 8.

TABLE 8

Illustrative examples of small peptides with central acidic and basic amino acids.

| $X^1$ | $X^2$ | $X^3$ | $X^4$ | SEQ ID NO |
|---|---|---|---|---|
| Boc-Lys(εBoc) | Arg | Asp | Ser(tBu)-OtBu | 621 |
| Boc-Lys(εBoc) | Arg | Asp | Thr(tBu)-OtBu | 622 |
| Boc-Trp | Arg | Asp | Ile-OtBu | 623 |
| Boc-Trp | Arg | Asp | Leu-OtBu | 624 |
| Boc-Phe | Arg | Asp | Leu-OtBu | 625 |
| Boc-Phe | Arg | Asp | Ile-OtBu | 626 |
| Boc-Phe | Arg | Asp | norLeu-OtBu | 627 |
| Boc-Phe | Arg | Glu | norLeu-OtBu | 628 |
| Boc-Phe | Arg | Glu | Ile-OtBu | 629 |
| Boc-Phe | Asp | Arg | Ile-OtBu | 630 |
| Boc-Phe | Glu | Arg | Ile-OtBu | 631 |
| Boc-Phe | Asp | Arg | Leu-OtBu | 632 |
| Boc-Phe | Arg | Glu | Leu-OtBu | 633 |

TABLE 8-continued

Illustrative examples of small peptides with central acidic and basic amino acids.

| X¹ | X² | X³ | X⁴ | SEQ ID NO |
|---|---|---|---|---|
| Boc-Phe | Glu | Arg | Leu-OtBu | 634 |
| Boc-Phe | Asp | Arg | norLeu-OtBu | 635 |
| Boc-Phe | Glu | Arg | norLeu-OtBu | 636 |
| Boc-Lys(εBoc) | Glu | Arg | Ser(tBu)-OtBu | 637 |
| Boc-Lys(εBoc) | Glu | Arg | Thr(tBu)-OtBu | 638 |
| Boc-Lys(εBoc) | Asp | Arg | Ser(tBu)-OtBu | 639 |
| Boc-Lys(εBoc) | Asp | Arg | Thr(tBu)-OtBu | 640 |
| Boc-Lys(εBoc) | Arg | Glu | Ser(tBu)-OtBu | 641 |
| Boc-Lys(εBoc) | Arg | Glu | Thr(tBu)-OtBu | 642 |
| Boc-Leu | Glu | Arg | Ser(tBu)-OtBu | 643 |
| Boc-Leu | Glu | Arg | Thr(tBu)-OtBu | 644 |
| Fmoc-Trp | Arg | Asp | Ser(tBu)-OtBu | 645 |
| Fmoc-Trp | Asp | Arg | Ser(tBu)-OtBu | 646 |
| Fmoc-Trp | Glu | Arg | Ser(tBu)-OtBu | 647 |
| Fmoc-Trp | Arg | Glu | Ser(tBu)-OtBu | 648 |
| Boc-Lys(εBoc) | Glu | Arg | Leu-OtBu | 649 |
| Fmoc-Leu | Arg | Asp | Ser(tBu)-OtBu | 650 |
| Fmoc-Leu | Asp | Arg | Ser(tBu)-OtBu | 651 |
| Fmoc-Leu | Glu | Arg | Ser(tBu)-OtBu | 652 |
| Fmoc-Leu | Arg | Glu | Ser(tBu)-OtBu | 653 |
| Fmoc-Leu | Arg | Asp | Thr(tBu)-OtBu | 654 |
| Boc-Glu | Asp | Arg | Tyr(tBu)-OtBu | 655 |
| Fmoc-Lys(εFmoc) | Arg | Asp | Ser(tBu)-OtBu | 656 |
| Fmoc-Trp | Arg | Asp | Ile-OtBu | 657 |
| Fmoc-Trp | Arg | Asp | Leu-OtBu | 658 |
| Emoc-Phe | Arg | Asp | Ile-OtBu | 659 |
| Emoc-Phe | Arg | Asp | Leu-OtBu | 660 |
| Boc-Trp | Arg | Asp | Phe-OtBu | 661 |
| Boc-Trp | Arg | Asp | Tyr-OtBu | 662 |
| Fmoc-Trp | Arg | Asp | Phe-OtBu | 663 |
| Fmoc-Trp | Arg | Asp | Tyr-OtBu | 664 |
| Boc-Orn(δBoc) | Arg | Glu | Ser(tBu)-OtBu | 665 |
| Nicotinyl Lys(εBoc) | Arg | Asp | Ser(tBu)-OtBu | 666 |
| Nicotinyl Lys(εBoc) | Arg | Asp | Thr(tBu)-OtBu | 667 |
| Fmoc-Leu | Asp | Arg | Thr(tBu)-OtBu | 668 |
| Fmoc-Leu | Glu | Arg | Thr(tBu)-OtBu | 669 |
| Fmoc-Leu | Arg | Glu | Thr(tBu)-OtBu | 670 |
| Fmoc-norLeu | Arg | Asp | Ser(tBu)-OtBu | 671 |
| Fmoc-norLeu | Asp | Arg | Ser(tBu)-OtBu | 672 |
| Fmoc-norLeu | Glu | Arg | Ser(tBu)-OtBu | 673 |
| Fmoc-norLeu | Arg | Glu | Ser(tBu)-OtBu | 674 |
| Fmoc-Lys(εBoc) | Arg | Asp | Ser(tBu)-OtBu | 675 |
| Fmoc-Lys(εBoc) | Arg | Asp | Thr(tBu)-OtBu | 676 |
| Fmoc-Lys(εBoc) | Glu | Arg | Ser(tBu)-OtBu | 677 |
| Fmoc-Lys(εBoc) | Glu | Arg | Thr(tBu)-OtBu | 678 |
| Fmoc-Lys(εBoc) | Asp | Arg | Ser(tBu)-OtBu | 679 |
| Fmoc-Lys(εBoc) | Asp | Arg | Thr(tBu)-OtBu | 680 |
| Fmoc-Lys(εBoc) | Arg | Glu | Ser(tBu)-OtBu | 681 |
| Fmoc-Lys(εBoc) | Arg | Glu | Thr(tBu)-OtBu | 682 |
| Fmoc-Lys(εBoc) | Glu | Arg | Leu-OtBu | 683 |
| Fmoc-Lys(εBoc) | Arg | Glu | Leu-OtBu | 684 |
| Fmoc-Lys(εFmoc) | Arg | Asp | Thr(tBu)-OtBu | 685 |
| Emoc-Lys(εFmoc) | Glu | Arg | Ser(tBu)-OtBu | 686 |
| Emoc-Lys(εFmoc) | Glu | Arg | Thr(tBu)-OtBu | 687 |
| Emoc-Lys(εFmoc) | Asp | Arg | Ser(tBu)-OtBu | 688 |
| Emoc-Lys(εFmoc) | Asp | Arg | Thr(tBu)-OtBu | 689 |
| Emoc-Lys(εFmoc) | Arg | Glu | Ser(tBu)-OtBu | 690 |
| Emoc-Lys(εFmoc) | Arg | Glu | Thr(tBu)-OtBu | 691 |
| Emoc-Lys(εFmoc)) | Glu | Arg | Leu-OtBu | 692 |
| Boc-Lys(εFmoc) | Arg | Asp | Ser(tBu)-OtBu | 693 |
| Boc-Lys(εFmoc) | Arg | Asp | Thr(tBu)-OtBu | 694 |
| Boc-Lys(εFmoc) | Glu | Arg | Ser(tBu)-OtBu | 695 |
| Boc-Lys(εFmoc) | Glu | Arg | Thr(tBu)-OtBu | 696 |
| Boc-Lys(εFmoc) | Asp | Arg | Ser(tBu)-OtBu | 697 |
| Boc-Lys(εFmoc) | Asp | Arg | Thr(tBu)-OtBu | 698 |
| Boc-Lys(εFmoc) | Arg | Glu | Ser(tBu)-OtBu | 699 |
| Boc-Lys(εFmoc) | Arg | Glu | Thr(tBu)-OtBu | 700 |
| Boc-Lys(εFmoc) | Glu | Arg | Leu-OtBu | 701 |
| Boc-Orn(δFmoc) | Arg | Glu | Ser(tBu)-OtBu | 702 |
| Boc-Orn(δFmoc) | Glu | Arg | Ser(tBu)-OtBu | 703 |
| Boc-Orn(δFmoc) | Arg | Asp | Ser(tBu)-OtBu | 704 |
| Boc-Orn(δFmoc) | Asp | Arg | Ser(tBu)-OtBu | 705 |
| Boc-Orn(δFmoc) | Asp | Arg | Thr(tBu)-OtBu | 706 |
| Boc-Orn(δFmoc) | Arg | Asp | Thr(tBu)-OtBu | 707 |

TABLE 8-continued

Illustrative examples of small peptides with central acidic and basic amino acids.

| $X^1$ | $X^2$ | $X^3$ | $X^4$ | SEQ ID NO |
|---|---|---|---|---|
| Boc-Orn(δFmoc) | Glu | Arg | Thr(tBu)-OtBu | 708 |
| Boc-Orn(δFmoc) | Arg | Glu | Thr(tBu)-OtBu | 709 |
| Fmoc-Trp | Asp | Arg | Ile-OtBu | 710 |
| Fmoc-Trp | Arg | Glu | Ile-OtBu | 711 |
| Fmoc-Trp | Glu | Arg | Ile-OtBu | 712 |
| Fmoc-Trp | Asp | Arg | Leu-OtBu | 713 |
| Fmoc-Trp | Arg | Glu | Leu-OtBu | 714 |
| Fmoc-Trp | Glu | Arg | Leu-OtBu | 715 |
| Emoc-Phe | Asp | Arg | Ile-OtBu | 716 |
| Emoc-Phe | Arg | Glu | Ile-OtBu | 717 |
| Emoc-Phe | Glu | Arg | Ile-OtBu | 718 |
| Emoc-Phe | Asp | Arg | Leu-OtBu | 719 |
| Emoc-Phe | Arg | Glu | Leu-OtBu | 720 |
| Emoc-Phe | Glu | Arg | Leu-OtBu | 721 |
| Fmoc-Trp | Arg | Asp | Phe-OtBu | 722 |
| Fmoc-Trp | Arg | Glu | Phe-OtBu | 723 |
| Fmoc-Trp | Glu | Arg | Phe-OtBu | 724 |
| Fmoc-Trp | Asp | Arg | Tyr-OtBu | 725 |
| Fmoc-Trp | Arg | Glu | Tyr-OtBu | 726 |
| Fmoc-Trp | Glu | Arg | Tyr-OtBu | 727 |
| Fmoc-Trp | Arg | Asp | Thr(tBu)-OtBu | 728 |
| Fmoc-Trp | Asp | Arg | Thr(tBu)-OtBu | 729 |
| Fmoc-Trp | Arg | Glu | Thr(tBu)-OtBu | 730 |
| Fmoc-Trp | Glu | Arg | Thr(tBu)-OtBu | 731 |
| Emoc-Phe | Arg | Asp | norLeu-OtBu | 732 |
| Emoc-Phe | Arg | Glu | norLeu-OtBu | 733 |
| Boc-Phe | Lys | Asp | Leu-OtBu | 734 |
| Boc-Phe | Asp | Lys | Leu-OtBu | 735 |
| Boc-Phe | Lys | Glu | Leu-OtBu | 736 |
| Boc-Phe | Glu | Lys | Leu-OtBu | 737 |
| Boc-Phe | Lys | Asp | Ile-OtBu | 738 |
| Boc-Phe | Asp | Lys | Ile-OtBu | 739 |
| Boc-Phe | Lys | Glu | Ile-OtBu | 740 |
| Boc-Phe | Glu | Lys | Ile-OtBu | 741 |
| Boc-Phe | Lys | Asp | norLeu-OtBu | 742 |
| Boc-Phe | Asp | Lys | norLeu-OtBu | 743 |
| Boc-Phe | Lys | Glu | norLeu-OtBu | 744 |
| Boc-Phe | Glu | Lys | norLeu-OtBu | 745 |
| Boc-Phe | His | Asp | Leu-OtBu | 746 |
| Boc-Phe | Asp | His | Leu-OtBu | 747 |
| Boc-Phe | His | Glu | Leu-OtBu | 748 |
| Boc-Phe | Glu | His | Leu-OtBu | 749 |
| Boc-Phe | His | Asp | Ile-OtBu | 750 |
| Boc-Phe | Asp | His | Ile-OtBu | 751 |
| Boc-Phe | His | Glu | Ile-OtBu | 752 |
| Boc-Phe | Glu | His | Ile-OtBu | 753 |
| Boc-Phe | His | Asp | norLeu-OtBu | 754 |
| Boc-Phe | Asp | His | norLeu-OtBu | 755 |
| Boc-Phe | His | Glu | norLeu-OtBu | 756 |
| Boc-Phe | Glu | His | norLeu-OtBu | 757 |
| Boc-Lys(εBoc) | Lys | Asp | Ser(tBu)-OtBu | 758 |
| Boc-Lys(εBoc) | Asp | Lys | Ser(tBu)-OtBu | 759 |
| Boc-Lys(εBoc) | Lys | Glu | Ser(tBu)-OtBu | 760 |
| Boc-Lys(εBoc) | Glu | Lys | Ser(tBu)-OtBu | 761 |
| Boc-Lys(εBoc) | His | Asp | Ser(tBu)-OtBu | 762 |
| Boc-Lys(εBoc) | Asp | His | Ser(tBu)-OtBu | 763 |
| Boc-Lys(εBoc) | His | Glu | Ser(tBu)-OtBu | 764 |
| Boc-Lys(εBoc) | Glu | His | Ser(tBu)-OtBu | 765 |

While the peptides of Table 8 are illustrated with particular protecting groups, it is noted that these groups may be substituted with other protecting groups as described herein and/or one or more of the shown protecting group can be eliminated.

4) Small Peptides Having Either an Acidic or Basic Amino Acid in the Center to 2Ether with a Central Aliphatic Amino Acid.

In certain embodiments, the peptides of this invention range from four amino acids to about ten amino acids. The terminal amino acids are typically hydrophobic either because of a hydrophobic side chain or because the terminal amino acids bear one or more hydrophobic protecting groups. End amino acids ($X^1$ and $X^4$) are hydrophobic either because of a hydrophobic side chain or because the side chain or the C and/or N terminus is blocked with one or more hydrophobic protecting group(s) (e.g., the N-terminus is blocked with Boc-, Fmoc-, Nicotinyl-, etc., and the C-terminus blocked with (tBu)-OtBu, etc.). Typically, the central portion of the peptide comprises a basic or acidic amino acid and an aliphatic amino acid (e.g., in a 4 mer) or a basic domain or an acidic domain and an aliphatic domain in a longer molecule.

These four-mers can be represented by Formula XXV in which $X^1$ and $X^4$ are hydrophobic and/or bear hydrophobic protecting group(s) as described herein and $X^2$ is acidic or basic while $X^3$ is aliphatic or $X^2$ is aliphatic while $X^3$ is acidic or basic. The peptide can be all L-amino acids or include one, or more, or all D-amino acids.

Certain preferred peptides of this invention include, but are not limited to the peptides shown in Table 9.

TABLE 9

Examples of certain preferred peptides having either an acidic or basic amino acid in the center together with a central aliphatic amino acid.

| $X^1$ | $X^2$ | $X^3$ | $X^4$ | SEQ ID NO |
|---|---|---|---|---|
| Fmoc-Lys(εBoc) | Leu | Arg | Ser(tBu)-OtBu | 766 |
| Fmoc-Lys(εBoc) | Arg | Leu | Ser(tBu)-OtBu | 767 |
| Fmoc-Lys(εBoc) | Leu | Arg | Thr(tBu)-OtBu | 768 |
| Fmoc-Lys(εBoc) | Arg | Leu | Thr(tBu)-OtBu | 769 |
| Fmoc-Lys(εBoc) | Glu | Leu | Ser(tBu)-OtBu | 770 |
| Fmoc-Lys(εBoc) | Leu | Glu | Ser(tBu)-OtBu | 771 |
| Fmoc-Lys(εBoc) | Glu | Leu | Thr(tBu)-OtBu | 772 |
| Fmoc-Lys(εFmoc) | Leu | Arg | Ser(tBu)-OtBu | 773 |
| Fmoc-Lys(εFmoc) | Leu | Arg | Thr(tBu)-OtBu | 774 |
| Fmoc-Lys(εFmoc) | Glu | Leu | Ser(tBu)-OtBu | 775 |
| Fmoc-Lys(εFmoc) | Glu | Leu | Thr(tBu)-OtBu | 776 |
| Boc-Lys(Fmoc) | Glu | Ile | Thr(tBu)-OtBu | 777 |
| Boc-Lys(εFmoc) | Leu | Arg | Ser(tBu)-OtBu | 778 |
| Boc-Lys(εFmoc) | Leu | Arg | Thr(tBu)-OtBu | 779 |
| Boc-Lys(εFmoc) | Glu | Leu | Ser(tBu)-OtBu | 780 |
| Boc-Lys(εFmoc) | Glu | Leu | Thr(tBu)-OtBu | 781 |
| Boc-Lys(εBoc) | Leu | Arg | Ser(tBu)-OtBu | 782 |
| Boc-Lys(εBoc) | Arg | Phe | Thr(tBu)-OtBu | 783 |
| Boc-Lys(εBoc) | Leu | Arg | Thr(tBu)-OtBu | 784 |
| Boc-Lys(εBoc) | Glu | Ile | Thr(tBu) | 785 |
| Boc-Lys(εBoc) | Glu | Val | Thr(tBu) | 786 |
| Boc-Lys(εBoc) | Glu | Ala | Thr(tBu) | 787 |
| Boc-Lys(εBoc) | Glu | Gly | Thr(tBu) | 788 |
| Boc--Lys(εBoc) | Glu | Leu | Ser(tBu)-OtBu | 789 |
| Boc-Lys(εBoc) | Glu | Leu | Thr(tBu)-OtBu | 790 |

While the peptides of Table 9 are illustrated with particular protecting groups, it is noted that these groups may be substituted with other protecting groups as described herein and/or one or more of the shown protecting group can be eliminated.

5) Small Peptides Having Either an Acidic or Basic Amino Acid in the Center Together with a Central Aromatic Amino Acid.

In certain embodiments, the "small" peptides of this invention range from four amino acids to about ten amino acids. The terminal amino acids are typically hydrophobic either because of a hydrophobic side chain or because the terminal amino acids bear one or more hydrophobic protecting groups end amino acids ($X^1$ and $X^4$) are hydrophobic either because of a hydrophobic side chain or because the side chain or the C and/or N terminus is blocked with one or more hydrophobic protecting group(s) (e.g., the N-terminus is blocked with Boc-, Fmoc-, Nicotinyl-, etc., and the C-terminus blocked with (tBu)-OtBu, etc.). Typically, the central portion of the peptide comprises a basic or acidic amino acid and an aromatic amino acid (e.g., in a 4 mer) or a basic domain or an acidic domain and an aromatic domain in a longer molecule.

These four-mers can be represented by Formula XXV in which $X^1$ and $X^4$ are hydrophobic and/or bear hydrophobic protecting group(s) as described herein and $X^2$ is acidic or basic while $X^3$ is aromatic or $X^2$ is aromatic while $X^3$ is acidic or basic. The peptide can be all L-amino acids or include one, or more, or all D-amino acids. Five-mers can be represented by a minor modification of Formula XXV in which $X^5$ is inserted as shown in Table 10 and in which $X^5$ is typically an aromatic amino acid, e.g., $$X^1-X^2-X^3{}_n-X^5{}_p-X^4 \qquad \text{XXVII}$$

where $X^1$, $X^2$, $X^3$, and $X^4$ are as described above, p is 0 or 1 and $X^5$ is typically an aromatic amino acid.

Certain preferred peptides of this invention include, but are not limited to the peptides shown in Table 10.

TABLE 10

Examples of certain preferred peptides having either an acidic or basic amino acid in the center together with a central aromatic amino acid.

| $X^1$ | $X^2$ | $X^3$ | $X^5$ | $X^4$ | SEQ ID NO |
|---|---|---|---|---|---|
| Fmoc-Lys(εBoc) | Arg | Trp | | Tyr(tBu)-OtBu | 791 |
| Fmoc-Lys(εBoc) | Trp | Arg | | Tyr(tBu)-OtBu | 792 |
| Fmoc-Lys(εBoc) | Arg | Tyr | | Trp-OtBu | 793 |
| Fmoc-Lys(εBoc) | Tyr | Arg | | Trp-OtBu | 794 |
| Fmoc-Lys(εBoc) | Arg | Tyr | Trp | Thr(tBu)-OtBu | 795 |
| Fmoc-Lys(εBoc) | Arg | Tyr | | Thr(tBu)-OtBu | 796 |
| Fmoc-Lys(εBoc) | Arg | Trp | | Thr(tBu)-OtBu | 797 |
| Fmoc-Lys(εFmoc) | Arg | Trp | | Tyr(tBu)-OtBu | 798 |
| Fmoc-Lys(εFmoc) | Arg | Tyr | | Trp-OtBu | 799 |
| Fmoc-Lys(εFmoc) | Arg | Tyr | Trp | Thr(tBu)-OtBu | 800 |
| Fmoc-Lys(εFmoc) | Arg | Tyr | | Thr(tBu)-OtBu | 801 |
| Fmoc-Lys(εFmoc) | Arg | Trp | | Thr(tBu)-OtBu | 802 |
| Boc-Lys(εFmoc) | Arg | Trp | | Tyr(tBu)-OtBu | 803 |
| Boc-Lys(εFmoc) | Arg | Tyr | | Trp-OtBu | 804 |
| Boc-Lys(εFmoc) | Arg | Tyr | Trp | Thr(tBu)-OtBu | 805 |
| Boc-Lys(εFmoc) | Arg | Tyr | | Thr(tBu)-OtBu | 806 |
| Boc-Lys(εFmoc) | Arg | Trp | | Thr(tBu)-OtBu | 807 |
| Boc-Glu | Lys(εFmoc) | Arg | | Tyr(tBu)-OtBu | 808 |
| Boc-Lys(εBoc) | Arg | Trp | | Tyr(tBu)-OtBu | 809 |
| Boc-Lys(εBoc) | Arg | Tyr | | Trp-OtBu | 810 |
| Boc-Lys(εBoc) | Arg | Tyr | Trp | Thr(tBu)-OtBu | 811 |

TABLE 10-continued

Examples of certain preferred peptides having either an acidic or basic amino acid in the center together with a central aromatic amino acid.

| X¹ | X² | X³ | X⁵ | X⁴ | SEQ ID NO |
|---|---|---|---|---|---|
| Boc-Lys(εBoc) | Arg | Tyr | | Thr(tBu)-OtBu | 812 |
| Boc-Lys(εBoc) | Arg | Phe | | Thr(tBu)-OtBu | 813 |
| Boc-Lys(εBoc) | Arg | Trp | | Thr(tBu)-OtBu | 814 |

While the peptides of Table 10 are illustrated with particular protecting groups, it is noted that these groups may be substituted with other protecting groups as described herein and/or one or more of the shown protecting groups can be eliminated.

6) Small Peptides Having Aromatic Amino Acids or Aromatic Amino Acids Separated by Histidine(s) at the Center.

In certain embodiments, the peptides of this invention are characterized by π electrons that are exposed in the center of the molecule which allow hydration of the particle and that allow the peptide particles to trap pro-inflammatory oxidized lipids such as fatty acid hydroperoxides and phospholipids that contain an oxidation product of arachidonic acid at the sn-2 position.

In certain embodiments, these peptides consist of a minimum of 4 amino acids and a maximum of about 10 amino acids, preferentially (but not necessarily) with one or more of the amino acids being the D-sterioisomer of the amino acid, with the end amino acids being hydrophobic either because of a hydrophobic side chain or because the terminal amino acid(s) bear one or more hydrophobic blocking group(s), (e.g., an N-terminus blocked with Boc-, Fmoc-, Nicotinyl-, and the like, and a C-terminus blocked with (tBu)-OtBu groups and the like). Instead of having an acidic or basic amino acid in the center, these peptides generally have an aromatic amino acid at the center or have aromatic amino acids separated by histidine in the center of the peptide.

Certain preferred peptides of this invention include, but are not limited to the peptides shown in Table 11.

TABLE 11

Examples of peptides having aromatic amino acids in the center or aromatic amino acids or aromatic domains separated by one or more histidines.

| X¹ | X² | X³ | X⁴ | X⁵ | SEQ ID NO |
|---|---|---|---|---|---|
| Boc-Lys(εBoc) | Phe | Trp | Phe | Ser(tBu)-OtBu | 815 |
| Boc-Lys(εBoc) | Phe | Trp | Phe | Thr(tBu)-OtBu | 816 |
| Boc-Lys(εBoc) | Phe | Tyr | Phe | Ser(tBu)-OtBu | 817 |
| Boc-Lys(εBoc) | Phe | Tyr | Phe | Thr(tBu)-OtBu | 818 |
| Boc-Lys(εBoc) | Phe | His | Phe | Ser(tBu)-OtBu | 819 |
| Boc-Lys(εBoc) | Phe | His | Phe | Thr(tBu)-OtBu | 820 |
| Boc-Lys(εBoc) | Val Phe | Phe-Tyr | Ser(tBu)-OtBu | | 821 |
| Nicotinyl-Lys(εBoc) | Phe | Trp | Phe | Ser(tBu)-OtBu | 822 |
| Nicotinyl-Lys(εBoc) | Phe | Trp | Phe | Thr(tBu)-OtBu | 823 |
| Nicotinyl-Lys(εBoc) | Phe | Tyr | Phe | Ser(tBu)-OtBu | 824 |
| Nicotinyl-Lys(εBoc) | Phe | Tyr | Phe | Thr(tBu)-OtBu | 825 |
| Nicotinyl-Lys(εBoc) | Phe | His | Phe | Ser(tBu)-OtBu | 826 |
| Nicotinyl-Lys(εBoc) | Phe | His | Phe | Thr(tBu)-OtBu | 827 |
| Boc-Leu | Phe | Trp | Phe | Thr(tBu)-OtBu | 828 |
| Boc-Leu | Phe | Trp | Phe | Ser(tBu)-OtBu | 829 |

While the peptides of Table 11 are illustrated with particular protecting groups, it is noted that these groups may be substituted with other protecting groups as described herein and/or one or more of the shown protecting group can be eliminated.

7) Summary of Tripeptides and Tetrapeptides.

For the sake of clarity, a number of tripeptides and tetrapeptides of this invention are generally summarized below in Table 12.

TABLE 12

General structure of certain peptides of this invention.

| X¹ | X² | X³ | X⁴ |
|---|---|---|---|
| hydrophobic side chain or hydrophobic protecting group(s) | Acidic or Basic | — | hydrophobic side chain or hydrophobic protecting group(s) |
| hydrophobic side chain or hydrophobic protecting group(s) | Basic | Acidic | hydrophobic side chain or hydrophobic protecting group(s) |
| hydrophobic side chain or hydrophobic protecting group(s) | Acidic | Basic | hydrophobic side chain or hydrophobic protecting group(s) |
| hydrophobic side chain or hydrophobic protecting group(s) | Acidic or Basic | Aliphatic | hydrophobic side chain or hydrophobic protecting group(s) |
| hydrophobic side chain or hydrophobic protecting group(s) | Aliphatic | Acidic or Basic | hydrophobic side chain or hydrophobic protecting group(s) |
| hydrophobic side chain or hydrophobic protecting group(s) | Acidic or Basic | Aromatic | hydrophobic side chain or hydrophobic protecting group(s) |
| hydrophobic side chain or hydrophobic protecting group(s) | Aromatic | Acidic or Basic | hydrophobic side chain or hydrophobic protecting group(s) |
| hydrophobic side chain or hydrophobic protecting group(s) | Aromatic | His Aromatic | hydrophobic side chain or hydrophobic protecting group(s) |

Where longer peptides are desired, $X^2$ and $X^3$ can represent domains (e.g., regions of two or more amino acids of the specified type) rather than individual amino acids. Table 12 is intended to be illustrative and not limiting. Using the teaching provided herein, other suitable peptides can readily be identified.

8) Paired Amino Acids and Dipeptides.

In certain embodiments, this invention pertains to the discovery that certain pairs of amino acids, administered in conjunction with each other or linked to form a dipeptide have one or more of the properties described herein. Thus, without being bound to a particular theory, it is believed that when the pairs of amino acids are administered in conjunction with each other, as described herein, they are capable participating in or inducing the formation of micelles in vivo.

Similar to the other small peptides described herein, it is believed that the pairs of peptides will associate in vivo, and demonstrate physical properties including high solubility in ethyl acetate (e.g., greater than about 4 mg/mL), solubility in aqueous buffer at pH 7.0. Upon contacting phospholipids such as 1,2-Dimyristoyl-sn-glycero-3-phosphocholine (DMPC), in an aqueous environment, it is believed the pairs of amino acids induce or participate in the formation of particles with a diameter of approximately 7.5 nm (±0.1 nm), and/or induce or participate in the formation of stacked bilayers with a bilayer dimension on the order of 3.4 to 4.1 nm with spacing between the bilayers in the stack of approximately 2 nm, and/or also induce or participate in the formation of vesicular structures of approximately 38 nm).

Moreover, it is further believed that the pairs of amino acids can display one or more of the following physiologically relevant properties:

1. They convert pro-inflammatory HDL to anti-inflammatory HDL or make anti-inflammatory HDL more anti-inflammatory;
2. They decrease LDL-induced monocyte chemotactic activity generated by artery wall cells;
3. They stimulate the formation and cycling of pre-β HDL;
4. They raise HDL cholesterol; and/or
5. They increase HDL paraoxonase activity.

The pairs of amino acids can be administered as separate amino acids (administered sequentially or simultaneously, e.g., in a combined formulation) or they can be covalently coupled directly or through a linker (e.g., a PEG linker, a carbon linker, a branched linker, a straight chain linker, a heterocyclic linker, a linker formed of derivatized lipid, etc.). In certain embodiments, the pairs of amino acids are covalently linked through a peptide bond to form a dipeptide. In various embodiments while the dipeptides will typically comprise two amino acids each bearing an attached protecting group, this invention also contemplates dipeptides wherein only one of the amino acids bears one or more protecting groups.

The pairs of amino acids typically comprise amino acids where each amino acid is attached to at least one protecting group (e.g., a hydrophobic protecting group as described herein). The amino acids can be in the D or the L form. In certain embodiments, where the amino acids comprising the pairs are not attached to each other, each amino acid bears two protecting groups (e.g., such as molecules 1 and 2 in Table 13).

TABLE 13

Illustrative amino acid pairs of this invention.

| | Amino Acid Pair/dipeptide |
|---|---|
| 1. | Boc-Arg-OtBu* |
| 2. | Boc-Glu-OtBu* |
| 3. | Boc-Phe-Arg-OtBu** |

TABLE 13-continued

Illustrative amino acid pairs of this invention.

| | Amino Acid Pair/dipeptide |
|---|---|
| 4. | Boc-Glu-Leu-OtBu** |
| 5. | Boc-Arg-Glu-OtBu*** |

*This would typically be administered in conjunction with a second amino acid.
**In certain embodiments, these dipeptides would be administered in conjunction with each other.
***In certain embodiments, this peptide would be administered either alone or in combination with one of the other peptides described herein..

Suitable pairs of amino acids can readily be identified by providing the pair of protected amino acids and/or a dipeptide and then screening the pair of amino acids/dipeptide for one or more of the physical and/or physiological properties described above. In certain embodiments, this invention excludes pairs of amino acids and/or dipeptides comprising aspartic acid and phenylalanine. In certain embodiments, this invention excludes pairs of amino acids and/or dipeptides in which one amino acid is (−)-N-[(trans-4-isopropylcyclohexane)carbonyl]-D-phenylalanine (nateglinide).

In certain embodiments, the amino acids comprising the pair are independently selected from the group consisting of an acidic amino acid (e.g., aspartic acid, glutamic acid, etc.), a basic amino acid (e.g., lysine, arginine, histidine, etc.), and a non-polar amino acid (e.g., alanine, valine, leucine, isoleucine, proline, phenylalanine, tryptophan, methionine, etc.). In certain embodiments, where the first amino acid is acidic or basic, the second amino acid is non-polar and where the second amino acid is acidic or basic, the first amino acid is non-polar. In certain embodiments, where the first amino acid is acidic, the second amino acid is basic, and vice versa. (see, e.g., Table 14).

Similar combinations can be obtained by administering pairs of dipeptides. Thus, for example in certain embodiments, molecules 3 and 4 in Table 13 would be administered in conjunction with each other.

TABLE 14

Certain generalized amino acid pairs/dipeptides.

| | First Amino acid | Second Amino acid |
|---|---|---|
| 1. | Acidic | Basic |
| 2. | Basic | Acidic |
| 3. | Acidic | Non-polar |
| 4. | Non-polar | Acidic |
| 5. | Basic | Non-polar |
| 6. | Non-polar | Basic |

It is noted that these amino acid pairs/dipeptides are intended to be illustrative and not limiting. Using the teaching provided herein other suitable amino acid pairs/dipeptides can readily be determined.

In certain embodiments, however, dipeptides and/or amino acid pairs comprising L-Glu-L-Trp, e.g., as described in U.S. Pat. No. 5,807,830 and/or any other peptides disclosed in this patent, are expressly excluded from the methods and/or formulations described herein.

E) Apo-J (G* Peptides).

It was also a discovery of this invention that peptides that mimicking the amphipathic helical domains of apo J are capable of mitigating one or more symptoms of atherosclerosis and/or other pathologies described herein. Apolipoprotein J possesses a wide nonpolar face termed globular protein-like, or G* amphipathic helical domains. The class G amphipathic helix is found in globular proteins, and thus, the name class G. This class of amphipathic helix is characterized by a random distribution of positively charged and negatively charged residues on the polar face with a narrow nonpolar face. Because of the narrow nonpolar face this class does not readily associate with phospholipids. The G* of amphipathic helix possesses similar, but not identical, characteristics to the G amphipathic helix. Similar to the class G amphipathic helix, the G* class peptides possesses a random distribution of positively and negatively charged residues on the polar face. However, in contrast to the class G amphipathic helix which has a narrow nonpolar face, this class has a wide nonpolar face that allows this class to readily bind phospholipid and the class is termed G* to differentiate it from the G class of amphipathic helix.

A number of suitable G* amphipathic peptides are described in copending applications U.S. Ser. No. 10/120, 508, filed Apr. 5, 2002, U.S. Ser. No. 10/520,207, filed Apr. 1, 2003, and PCT Application PCT/US03/09988, filed Apr. 1, 2003. In addition, a variety of suitable peptides of this invention that are related to G* amphipathic helical domains of apo J are illustrated in Table 15.

TABLE 15

Certain peptides for use in this invention related to G* amphipathic helical domains of apo J.

| Amino Acid Sequence | SEQ ID NO |
|---|---|
| LLEQLNEQFNWVSRLANLTQGE | 830 |
| LLEQLNEQFNWVSRLANL | 831 |
| NELQEMSNQGSKYVNKEIQNAVNGV | 832 |
| IQNAVNGVKQIKTLIEKTNEE | 833 |
| RKTLLSNLEEAKKKKEDALNETRESETKLKEL | 834 |
| PGVCNETMMALWEECK | 835 |
| PCLKQTCMKFYARVCR | 836 |
| ECKPCLKQTCMKFYARVCR | 837 |
| LVGRQLEEFL | 838 |
| MNGDRIDSLLEN | 839 |
| QQTHMLDVMQD | 840 |
| FSRASSIIDELFQD | 841 |
| PFLEMIHEAQQAMDI | 842 |
| PTEFIREGDDD | 843 |
| RMKDQCDKCREILSV | 844 |
| PSQAKLRRELDESLQVAERLTRKYNELLKSYQ | 845 |
| LLEQLNEQFNWVSRLANLTEGE | 846 |
| DQYYLRVTTVA | 847 |
| PSGVTEVVVKLFDS | 848 |
| PKFMETVAEKALQEYRKKHRE | 849 |

The peptides of this invention, however, are not limited to G* variants of apo J. Generally speaking G* domains from essentially any other protein preferably apo proteins are also suitable. The particular suitability of such proteins can readily be determined using assays for protective activity (e.g., protecting LDL from oxidation, and the like), e.g., as illustrated herein in the Examples. Some particularly preferred proteins include G* amphipathic helical domains or variants thereof (e.g., conservative substitutions, and the like) of proteins including, but not limited to apo AI, apo AIV, apo E, apo CII, apo CIII, and the like.

Certain preferred peptides for related to G* amphipathic helical domains related to apoproteins other than apo J are illustrated in Table 16.

TABLE 16

Certain peptides for use in this invention related to G* amphipathic helical domains related to apoproteins other than apo J.

| Amino Acid Sequence | SEQ ID NO |
|---|---|
| WDRVKDLATVYVDVLKDSGRDYVSQF (Related to the 8 to 33 region of apo AI) | 850 |
| VATVMWDYFSQLSNNAKEAVEHLQK (Related to the 7 to 31 region of apo AIV) | 851 |
| RWELALGRFWDYLRWVQTLSEQVQEEL (Related to the 25 to 51 region of apo E) | 852 |
| LSSQVTQELRALMDETMKELKELKAYKSELEEQLT (Related to the 52 to 83 region of apo E) | 853 |
| ARLSKELQAAQARLGADMEDVCGRLV (Related to the 91 to 116 region of apo E) | 854 |
| VRLASHLRKLRKRLLRDADDLQKRLA (Related to the13S to 160 region of apo E) | 855 |
| PLVEDMQRQWAGLVEKVQA (267 to 285 of apo E.27) | 856 |
| MSTYTGIFTDQVLSVLK (Related to the 60 to 76 region of apo CII) | 857 |
| LLSFMQGYMKHATKTAKDALSS (Related to the 8 to 29 region of apo CIII) | 858 |

Additional illustrative G* peptides are shown in Table 17.

TABLE 17

Additional illustrative G* peptides.

| Peptide | SEQ ID NO |
|---|---|
| Ac-Lys-Trp-Ile-Tyr-His-Leu-Thr-Glu-Gly-Ser-Thr-Asp-Leu-Arg-Thr-Glu-Gly-NH$_2$ | 859 |
| Ac-Lys-Trp-Phe-Tyr-His-Leu-Thr-Glu-Gly-Ser-Thr-Asp-Leu-Arg-Thr-Glu-Gly-NH$_2$ | 860 |
| Ac-Lys-Trp-Leu-Tyr-His-Leu-Thr-Glu-Gly-Ser-Thr-Asp-Leu-Arg-Thr-Glu-Gly-NH$_2$ | 861 |
| Ac-Lys-Trp-Val-Tyr-His-Leu-Thr-Glu-Gly-Ser-Thr-Asp-Leu-Arg-Thr-Glu-Gly-NH$_2$ | 862 |
| Ac-Lys-Tyr-Ile-Trp-His-Leu-Thr-Glu-Gly-Ser-Thr-Asp-Leu-Arg-Thr-Glu-Gly-NH$_2$ | 863 |
| Ac-Lys-Trp-Ile-Tyr-His-Phe-Thr-Glu-Gly-Ser-Thr-Asp-Leu-Arg-Thr-Glu-Gly-NH$_2$ | 864 |
| Ac-Lys-Trp-Phe-Tyr-His-Ile-Thr-Glu-Gly-Ser-Thr-Asp-Leu-Arg-Thr-Glu-Gly-NH$_2$ | 865 |
| Ac-Lys-Trp-Leu-Tyr-His-Val-Thr-Glu-Gly-Ser-Thr-Asp-Leu-Arg-Thr-Glu-Gly-NH$_2$ | 866 |

TABLE 17-continued

Additional illustrative G* peptides.

| Peptide | SEQ ID NO |
|---|---|
| Ac-Lys-Trp-Val-Tyr-His-Tyr-Thr-Glu-Gly-Ser-Thr-Asp-Leu-Arg-Thr-Glu-Gly-NH$_2$ | 867 |
| Ac-Lys-Tyr-Ile-Trp-His-Phe-Thr-Glu-Gly-Ser-Thr-Asp-Leu-Arg-Thr-Glu-Gly-NH$_2$ | 868 |
| Ac-Lys-Tyr-Ile-Trp-His-Ile-Thr-Glu-Gly-Ser-Thr-Asp-Leu-Arg-Thr-Glu-Gly-NH$_2$ | 869 |
| Ac-Lys-Tyr-Ile-Trp-His-Val-Thr-Glu-Gly-Ser-Thr-Asp-Leu-Arg-Thr-Glu-Gly-NH$_2$ | 870 |
| Ac-Lys-Tyr-Ile-Trp-His-Tyr-Thr-Glu-Gly-Ser-Thr-Asp-Leu-Arg-Thr-Glu-Gly-NH$_2$ | 871 |
| Ac-Lys-Phe-Ile-Trp-His-Leu-Thr-Glu-Gly-Ser-Thr-Asp-Leu-Arg-Thr-Glu-Gly-NH$_2$ | 872 |
| Ac-Lys-Leu-Ile-Trp-His-Leu-Thr-Glu-Gly-Ser-Thr-Asp-Leu-Arg-Thr-Glu-Gly-NH$_2$ | 873 |
| Ac-Lys-Ile-Ile-Trp-His-Leu-Thr-Glu-Gly-Ser-Thr-Asp-Leu-Arg-Thr-Glu-Gly-NH$_2$ | 874 |
| Ac-Lys-Tyr-Ile-Trp-Phe-Leu-Thr-Glu-Gly-Ser-Thr-Asp-Leu-Arg-Thr-Glu-Gly-NH$_2$ | 875 |
| Ac-Lys-Trp-Ile-Tyr-Phe-Leu-Thr-Glu-Gly-Ser-Thr-Asp-Leu-Arg-Thr-Glu-Gly-NH$_2$ | 876 |
| Ac-Lys-Trp-Ile-Tyr-Leu-Leu-Thr-Glu-Gly-Ser-Thr-Asp-Leu-Arg-Thr-Glu-Gly-NH$_2$ | 877 |
| Ac-Lys-Trp-Ile-Tyr-His-Phe-Thr-Glu-Gly-Ser-Thr-Asp-Leu-Arg-Thr-Glu-Gly-NH$_2$ | 878 |
| Ac-Lys-Trp-Ile-Tyr-His-Tyr-Thr-Glu-Gly-Ser-Thr-Asp-Leu-Arg-Thr-Glu-Gly-NH$_2$ | 879 |
| Ac-Lys-Trp-Ile-Tyr-His-Ile-Thr-Glu-Gly-Ser-Thr-Asp-Leu-Arg-Thr-Glu-Gly-NH$_2$ | 880 |
| Ac-Lys-Trp-Ile-Tyr-His-Leu-Ser-Glu-Gly-Ser-Thr-Asp-Leu-Arg-Thr-Glu-Gly-NH$_2$ | 881 |
| Ac-Lys-Trp-Ile-Tyr-His-Leu-Thr-Asp-Gly-Ser-Thr-Asp-Leu-Arg-Thr-Glu-Gly-NH$_2$ | 882 |
| Ac-Lys-Trp-Ile-Tyr-His-Leu-Thr-Glu-Gly-Thr-Ser-Asp-Leu-Arg-Thr-Glu-Gly-NH$_2$ | 883 |
| Ac-Lys-Trp-Ile-Tyr-His-Leu-Thr-Glu-Gly-Ser-Thr-Glu-Leu-Arg-Thr-Glu-Gly-NH$_2$ | 884 |
| Ac-Lys-Trp-Ile-Tyr-His-Leu-Thr-Glu-Gly-Ser-Thr-Asp-Phe-Arg-Thr-Glu-Gly-NH$_2$ | 885 |
| Ac-Lys-Trp-Ile-Tyr-His-Leu-Thr-Glu-Gly-Ser-Thr-Asp-Tyr-Arg-Thr-Glu-Gly-NH$_2$ | 886 |
| Ac-Lys-Trp-Ile-Tyr-His-Leu-Thr-Glu-Gly-Ser-Thr-Asp-Ile-Arg-Thr-Glu-Gly-NH$_2$ | 887 |
| Ac-Lys-Trp-Ile-Tyr-His-Leu-Thr-Glu-Gly-Ser-Thr-Asp-Val-Arg-Thr-Glu-Gly-NH$_2$ | 888 |
| Ac-Lys-Trp-Ile-Tyr-His-Leu-Thr-Glu-Gly-Ser-Thr-Asp-Leu-Lys-Thr-Glu-Gly-NH$_2$ | 889 |
| Ac-Lys-Trp-Ile-Tyr-His-Leu-Thr-Glu-Gly-Ser-Thr-Asp-Leu-Arg-Ser-Glu-Gly-NH$_2$ | 890 |
| Ac-Lys-Trp-Ile-Tyr-His-Leu-Thr-Glu-Gly-Ser-Thr-Asp-Leu-Arg-Thr-Asp-Gly-NH$_2$ | 891 |
| Ac-Lys-Trp-Ile-Tyr-His-Leu-Thr-Glu-Gly-Ser-Thr-Asp-Ile-Lys-Thr-Glu-Gly-NH$_2$ | 892 |
| Ac-Lys-Trp-Ile-Tyr-His-Leu-Thr-Glu-Gly-Ser-Thr-Asp-Ile-Arg-Ser-Glu-Gly-NH$_2$ | 893 |
| Ac-Lys-Trp-Ile-Tyr-His-Leu-Thr-Glu-Gly-Ser-Thr-Asp-Ile-Lys-Ser-Glu-Gly-NH$_2$ | 894 |
| Ac-Lys-Trp-Ile-Tyr-His-Leu-Thr-Glu-Gly-Ser-Thr-Asp-Ile-Lys-Ser-Asp-Gly-NH$_2$ | 895 |
| Ac-Arg-Trp-Ile-Tyr-His-Leu-Thr-Glu-Gly-Ser-Thr-Asp-Leu-Arg-Thr-Glu-Gly-NH$_2$ | 896 |
| Ac-Arg-Tyr-Ile-Trp-His-Leu-Thr-Glu-Gly-Ser-Thr-Asp-Ile-Arg-Thr-Glu-Gly-NH$_2$ | 897 |
| Ac-Arg-Trp-Ile-Tyr-His-Leu-Thr-Glu-Gly-Ser-Thr-Asp-Ile-Arg-Thr-Asp-Gly-NH$_2$ | 898 |
| Ac-Arg-Trp-Ile-Phe-His-Leu-Thr-Glu-Gly-Ser-Thr-Asp-Ile-Arg-Thr-Glu-Gly-NH$_2$ | 899 |
| Ac-Arg-Trp-Ile-Tyr-His-Leu-Thr-Glu-Gly-Ser-Thr-Asp-Leu-Lys-Thr-Glu-Gly-NH$_2$ | 900 |
| Ac-Arg-Trp-Ile-Tyr-His-Leu-Thr-Asp-Gly-Ser-Thr-Asp-Ile-Arg-Thr-Glu-Gly-NH$_2$ | 901 |
| Ac-Arg-Trp-Ile-Tyr-His-Leu-Thr-Asp-Gly-Ser-Thr-Asp-Leu-Arg-Thr-Glu-Gly-NH$_2$ | 902 |
| Ac-Arg-Trp-Ile-Tyr-Phe-Leu-Thr-Glu-Gly-Ser-Thr-Asp-Ile-Arg-Thr-Glu-Gly-NH$_2$ | 903 |
| Ac-Arg-Trp-Ile-Tyr-Phe-Leu-Thr-Glu-Gly-Ser-Thr-Asp-Leu-Arg-Thr-Glu-Gly-NH$_2$ | 904 |
| Ac-Lys-Trp-Phe-Tyr-His-Leu-Thr-Glu-Gly-Ser-Thr-Asp-Phe-Arg-Thr-Glu-Gly-NH$_2$ | 905 |
| Ac-Arg-Trp-Phe-Tyr-His-Leu-Thr-Glu-Gly-Ser-Thr-Asp-Leu-Arg-Thr-Glu-Gly-NH$_2$ | 906 |
| Ac-Lys-Trp-Ile-Phe-His-Leu-Thr-Glu-Gly-Ser-Thr-Asp-Ile-Arg-Thr-Asp-Gly-NH$_2$ | 907 |
| Ac-Arg-Trp-Ile-Tyr-His-Leu-Thr-Glu-Gly-Ser-Thr-Asp-Ile-Arg-Thr-Asp-Gly-NH$_2$ | 908 |
| Ac-Arg-Trp-Ile-Tyr-His-Leu-Thr-Glu-Gly-Ser-Thr-Asp-Leu-Arg-Thr-Asp-Gly-NH$_2$ | 909 |
| Ac-Lys-Trp-Ile-Tyr-His-Leu-Thr-Glu-Gly-Ser-Thr-Asp-Ile-Lys-Thr-Glu-Gly-NH$_2$ | 910 |
| Ac-Lys-Trp-Ile-Tyr-His-Leu-Thr-Glu-Gly-Ser-Thr-Asp-Ile-Lys-Thr-Asp-Gly-NH$_2$ | 911 |
| Ac-Lys-Trp-Ile-Tyr-His-Leu-Thr-Glu-Gly-Ser-Thr-Asp-Phe-Lys-Thr-Glu-Gly-NH$_2$ | 912 |
| Ac-Lys-Trp-Ile-Tyr-His-Leu-Thr-Glu-Gly-Ser-Thr-Asp-Tyr-Lys-Thr-Glu-Gly-NH$_2$ | 913 |
| Ac-Lys-Trp-Ile-Tyr-His-Leu-Thr-Glu-Gly-Ser-Thr-Asp-Ile-Arg-Thr-Glu-Gly-NH$_2$ | 914 |
| Ac-Lys-Trp-Phe-Tyr-His-Phe-Thr-Glu-Gly-Ser-Thr-Asp-Leu-Arg-Thr-Glu-Gly-NH$_2$ | 915 |
| Ac-Arg-Trp-Phe-Tyr-His-Phe-Thr-Glu-Gly-Ser-Thr-Asp-Leu-Arg-Thr-Glu-Gly-NH$_2$ | 916 |

TABLE 17-continued

Additional illustrative G* peptides.

| Peptide | SEQ ID NO |
|---|---|
| Ac-Lys-Trp-Phe-Tyr-His-Phe-Thr-Glu-Gly-Ser-Thr-Asp-Phe-Arg-Thr-Glu-Gly-NH$_2$ | 917 |
| Ac-Lys-Trp-Phe-Tyr-His-Phe-Thr-Asp-Gly-Ser-Thr-Asp-Ile-Arg-Thr-Glu-Gly-NH$_2$ | 918 |
| Ac-Arg-Trp-Phe-Tyr-His-Phe-Thr-Glu-Gly-Ser-Thr-Asp-Leu-Arg-Thr-Glu-Gly-NH$_2$ | 919 |
| Ac-Arg-Trp-Phe-Tyr-His-Phe-Thr-Glu-Gly-Ser-Thr-Asp-Phe-Arg-Thr-Glu-Gly-NH$_2$ | 920 |
| Ac-Arg-Trp-Phe-Tyr-His-Phe-Thr-Glu-Gly-Ser-Thr-Asp-Phe-Arg-Thr-Asp-Gly-NH$_2$ | 921 |
| Ac-Glu-Lys-Cys-Val-Glu-Glu-Phe-Lys-Ser-Leu-Thr-Ser-Cys-Leu-Asp-Ser-Lys-Ala-Phe-NH$_2$ | 922 |
| Ac-Asp-Lys-Cys-Val-Glu-Glu-Phe-Lys-Ser-Leu-Thr-Ser-Cys-Leu-Asp-Ser-Lys-Ala-Phe-NH$_2$ | 923 |
| Ac-Glu-Lys-Cys-Val-Asp-Glu-Phe-Lys-Ser-Leu-Thr-Ser-Cys-Leu-Asp-Ser-Lys-Ala-Phe-NH$_2$ | 924 |
| Ac-Glu-Lys-Cys-Val-Glu-Asp-Phe-Lys-Ser-Leu-Thr-Ser-Cys-Leu-Asp-Ser-Lys-Ala-Phe-NH$_2$ | 925 |
| Ac-Glu-Arg-Cys-Val-Glu-Glu-Phe-Lys-Ser-Leu-Thr-Ser-Cys-Leu-Asp-Ser-Lys-Ala-Phe-NH$_2$ | 926 |
| Ac-Asp-Lys-Cys-Val-Asp-Asp-Phe-Lys-Ser-Leu-Thr-Ser-Cys-Leu-Asp-Ser-Lys-Ala-Phe-NH$_2$ | 927 |
| Ac-Asp-Arg-Cys-Val-Glu-Glu-Phe-Lys-Ser-Leu-Thr-Ser-Cys-Leu-Asp-Ser-Lys-Ala-Phe-NH$_2$ | 928 |
| Ac-Glu-Arg-Cys-Val-Asp-Asp-Phe-Lys-Ser-Leu-Thr-Ser-Cys-Leu-Asp-Ser-Lys-Ala-Phe-NH$_2$ | 929 |
| Ac-Glu-Lys-Cys-Val-Glu-Glu-Phe-Lys-Ser-Phe-Thr-Ser-Cys-Leu-Asp-Ser-Lys-Ala-Phe-NH$_2$ | 930 |
| Ac-Glu-Lys-Cys-Val-Glu-Glu-Phe-Lys-Ser-Ile-Thr-Ser-Cys-Leu-Asp-Ser-Lys-Ala-Phe-NH$_2$ | 931 |
| Ac-Glu-Lys-Cys-Val-Glu-Glu-Phe-Lys-Ser-Val-Thr-Ser-Cys-Leu-Asp-Ser-Lys-Ala-Phe-NH$_2$ | 932 |
| Ac-Glu-Arg-Cys-Val-Glu-Glu-Phe-Lys-Ser-Tyr-Thr-Ser-Cys-Leu-Asp-Ser-Lys-Ala-Phe-NH$_2$ | 933 |
| Ac-Glu-Arg-Cys-Val-Glu-Glu-Phe-Lys-Ser-Phe-Thr-Ser-Cys-Leu-Asp-Ser-Lys-Ala-Phe-NH$_2$ | 934 |
| Ac-Glu-Arg-Cys-Val-Glu-Glu-Phe-Lys-Ser-Ile-Thr-Ser-Cys-Leu-Asp-Ser-Lys-Ala-Phe-NH$_2$ | 935 |
| Ac-Glu-Arg-Cys-Val-Glu-Glu-Phe-Lys-Ser-Val-Thr-Ser-Cys-Leu-Asp-Ser-Lys-Ala-Phe-NH$_2$ | 936 |
| Ac-Glu-Arg-Cys-Val-Glu-Glu-Phe-Lys-Ser-Tyr-Thr-Ser-Cys-Leu-Asp-Ser-Lys-Ala-Phe-NH$_2$ | 937 |
| Ac-Glu-Lys-Cys-Val-Glu-Glu-Phe-Lys-Ser-Phe-Thr-Thr-Cys-Leu-Asp-Ser-Lys-Ala-Phe-NH$_2$ | 938 |
| Ac-Glu-Lys-Cys-Val-Glu-Glu-Phe-Lys-Ser-Ile-Ser-Ser-Cys-Leu-Asp-Ser-Lys-Ala-Phe-NH$_2$ | 939 |
| Ac-Glu-Lys-Cys-Val-Glu-Glu-Phe-Lys-Ser-Val-Ser-Thr-Cys-Leu-Asp-Ser-Lys-Ala-Phe-NH$_2$ | 940 |
| Ac-Glu-Lys-Cys-Val-Glu-Glu-Phe-Lys-Ser-Tyr-Thr-Ser-Cys-Leu-Asp-Ser-Lys-Ala-Phe-NH$_2$ | 941 |
| Ac-Glu-Lys-Cys-Val-Glu-Glu-Phe-Lys-Ser-Phe-Thr-Thr-Cys-Leu-Asp-Ser-Lys-Ala-Phe-NH$_2$ | 942 |
| Ac-Glu-Lys-Cys-Val-Glu-Glu-Phe-Lys-Ser-Phe-Ser-Ser-Cys-Leu-Asp-Ser-Lys-Ala-Phe-NH$_2$ | 943 |
| Ac-Glu-Lys-Cys-Val-Glu-Glu-Phe-Lys-Ser-Phe-Thr-Ser-Cys-Leu-Asp-Ser-Lys-Ala-Phe-NH$_2$ | 944 |
| Ac-Glu-Lys-Cys-Val-Glu-Glu-Phe-Lys-Ser-Phe-Thr-Ser-Cys-Leu-Asp-Ser-Lys-Ala-Phe-NH$_2$ | 945 |
| Ac-Glu-Lys-Cys-Val-Glu-Glu-Phe-Lys-Ser-Phe-Thr-Ser-Cys-Leu-Asp-Ser-Lys-Ala-Phe-NH$_2$ | 946 |
| Ac-Glu-Lys-Cys-Val-Glu-Glu-Phe-Lys-Ser-Phe-Thr-Ser-Cys-Phe-Asp-Ser-Lys-Ala-Phe-NH$_2$ | 947 |
| Ac-Glu-Lys-Cys-Val-Glu-Glu-Phe-Lys-Ser-Phe-Thr-Ser-Cys-Phe-Glu-Ser-Lys-Ala-Phe-NH$_2$ | 948 |
| Ac-Glu-Lys-Cys-Val-Glu-Glu-Phe-Lys-Ser-Phe-Thr-Ser-Cys-Leu-Glu-Ser-Lys-Ala-Phe-NH$_2$ | 949 |
| Ac-Glu-Lys-Cys-Val-Glu-Glu-Phe-Lys-Ser-Phe-Thr-Ser-Cys-Ile-Asp-Ser-Lys-Ala-Phe-NH$_2$ | 950 |
| Ac-Glu-Lys-Cys-Val-Glu-Glu-Leu-Lys-Ser-Phe-Thr-Ser-Cys-Phe-Asp-Ser-Lys-Ala-Phe-NH$_2$ | 951 |
| Ac-Asp-Lys-Cys-Val-Glu-Glu-Phe-Lys-Ser-Phe-Thr-Ser-Cys-Phe-Asp-Ser-Lys-Ala-Phe-NH$_2$ | 952 |
| Ac-Asp-Lys-Cys-Val-Glu-Glu-Phe-Lys-Ser-Phe-Thr-Ser-Cys-Phe-Glu-Ser-Lys-Ala-Phe-NH$_2$ | 953 |
| Ac-Glu-Arg-Cys-Val-Glu-Glu-Phe-Lys-Ser-Phe-Thr-Ser-Cys-Phe-Asp-Ser-Lys-Ala-Phe-NH$_2$ | 954 |
| Ac-Glu-Lys-Cys-Phe-Glu-Glu-Phe-Lys-Ser-Phe-Thr-Ser-Cys-Phe-Asp-Ser-Lys-Ala-Phe-NH$_2$ | 955 |
| Ac-Glu-Lys-Cys-Val-Glu-Glu-Phe-Lys-Ser-Phe-Thr-Ser-Cys-Phe-Glu-Ser-Lys-Ala-Phe-NH$_2$ | 956 |
| Ac-Glu-Lys-Cys-Val-Glu-Glu-Phe-Lys-Ser-Phe-Ser-Ser-Cys-Phe-Glu-Ser-Lys-Ala-Phe-NH$_2$ | 957 |
| Ac-Glu-Lys-Cys-Val-Glu-Glu-Phe-Lys-Ser-Phe-Gln-Ser-Cys-Phe-Asp-Ser-Lys-Ala-Phe-NH$_2$ | 958 |
| Ac-Glu-Lys-Cys-Phe-Glu-Glu-Phe-Lys-Ser-Phe-Gln-Ser-Cys-Phe-Asp-Ser-Lys-Ala-Phe-NH$_2$ | 959 |
| Ac-Glu-Lys-Cys-Val-Glu-Glu-Phe-Lys-Gln-Phe-Thr-Ser-Cys-Phe-Asp-Ser-Lys-Ala-Phe-NH$_2$ | 960 |
| Ac-Glu-Lys-Cys-Val-Glu-Glu-Phe-Lys-Gln-Leu-Thr-Ser-Cys-Leu-Asp-Ser-Lys-Ala-Phe-NH$_2$ | 961 |
| Ac-Glu-Lys-Cys-Phe-Glu-Glu-Phe-Lys-Ser-Phe-Gln-Ser-Cys-Leu-Asp-Ser-Lys-Ala-Phe-NH$_2$ | 962 |
| Ac-Glu-Lys-Cys-Val-Glu-Glu-Phe-Lys-Gln-Phe-Thr-Ser-Cys-Phe-Asp-Ser-Lys-Ala-Phe-NH$_2$ | 963 |
| Ac-Glu-Lys-Cys-Val-Glu-Glu-Phe-Lys-Ser-Phe-Thr-Ser-Cys-Phe-Glu-Ser-Lys-Ala-Phe-NH$_2$ | 964 |
| Ac-Glu-Arg-Cys-Phe-Glu-Glu-Phe-Lys-Ser-Phe-Thr-Ser-Cys-Phe-Asp-Ser-Lys-Ala-Phe-NH$_2$ | 965 |
| Ac-Asp-Lys-Cys-Phe-Glu-Glu-Phe-Lys-Ser-Phe-Thr-Ser-Cys-Phe-Asp-Ser-Lys-Ala-Phe-NH$_2$ | 966 |

TABLE 17-continued

Additional illustrative G* peptides.

| Peptide | SEQ ID NO |
|---|---|
| Ac-Glu-Arg-Cys-Val-Glu-Glu-Phe-Lys-Ser-Leu-Thr-Ser-Cys-Leu-Glu-Ser-Lys-Ala-Phe-NH$_2$ | 967 |
| Ac-Glu-Lys-Cys-Val-Glu-Glu-Phe-Lys-Ser-Leu-Thr-Ser-Cys-Leu-Asp-Ser-Lys-Phe-Phe-NH$_2$ | 968 |
| Ac-Glu-Lys-Cys-Phe-Glu-Glu-Phe-Lys-Ser-Phe-Thr-Ser-Cys-Phe-Asp-Ser-Lys-Phe-Phe-NH$_2$ | 969 |
| Ac-Asp-Lys-Cys-Phe-Glu-Glu-Phe-Lys-Ser-Phe-Thr-Ser-Cys-Leu-Asp-Ser-Lys-Phe-Phe-NH$_2$ | 970 |
| Ac-Asp-Lys-Cys-Phe-Glu-Glu-Phe-Lys-Ser-Phe-Thr-Ser-Cys-Leu-Glu-Ser-Lys-Phe-Phe-NH$_2$ | 971 |
| Ac-Asp-Lys-Cys-Phe-Glu-Glu-Leu-Lys-Ser-Phe-Thr-Ser-Cys-Leu-Asp-Ser-Lys-Phe-Phe-NH$_2$ | 972 |
| Ac-Asp-Lys-Cys-Trp-Glu-Glu-Phe-Lys-Ser-Phe-Thr-Ser-Cys-Leu-Asp-Ser-Lys-Phe-Phe-NH$_2$ | 982 |
| Ac-Glu-Lys-Cys-Phe-Glu-Glu-Phe-Lys-Ser-Tyr-Thr-Ser-Cys-Leu-Asp-Ser-Lys-Phe-Phe-NH$_2$ | 983 |
| Ac-Glu-Lys-Cys-Phe-Glu-Glu-Phe-Lys-Ser-Trp-Thr-Ser-Cys-Leu-Asp-Ser-Lys-Phe-Phe-NH$_2$ | 984 |
| Ac-Glu-Lys-Cys-Val-Glu-Glu-Phe-Lys-Ser-Trp-Thr-Ser-Cys-Leu-Asp-Ser-Lys-Ala-Phe-NH$_2$ | 985 |
| Ac-Asp-Lys-Cys-Phe-Glu-Glu-Phe-Lys-Ser-Trp-Thr-Ser-Cys-Leu-Asp-Ser-Lys-Ala-Phe-NH$_2$ | 986 |
| Ac-Glu-Arg-Cys-Phe-Glu-Glu-Phe-Lys-Ser-Phe-Thr-Ser-Cys-Leu-Asp-Ser-Lys-Phe-Phe-NH$_2$ | 973 |
| Ac-Glu-Lys-Ala-Val-Glu-Glu-Phe-Lys-Ser-Phe-Thr-Ser-Cys-Leu-Asp-Ser-Lys-Ala-Phe-NH$_2$ | 974 |
| Ac-Asp-Lys-Ala-Val-Glu-Glu-Phe-Lys-Ser-Phe-Thr-Ser-Cys-Leu-Asp-Ser-Lys-Phe-Phe-NH$_2$ | 975 |
| Ac-Glu-Lys-Ala-Val-Glu-Glu-Phe-Lys-Ser-Phe-Thr-Ser-Ala-Leu-Asp-Ser-Lys-Ala-Phe-NH$_2$ | 976 |
| Ac-Asp-Lys-Ala-Val-Glu-Glu-Phe-Lys-Ser-Phe-Thr-Ser-Ala-Leu-Asp-Ser-Lys-Ala-Phe-NH$_2$ | 977 |
| Ac-Asp-Arg-Ala-Phe-Glu-Glu-Phe-Lys-Ser-Phe-Thr-Ser-Cys-Leu-Asp-Ser-Lys-Phe-Phe-NH$_2$ | 978 |
| Ac-Asp-Arg-Ala-Phe-Glu-Glu-Phe-Lys-Ser-Phe-Thr-Ser-Ala-Leu-Asp-Ser-Lys-Phe-Phe-NH$_2$ | 979 |
| Ac-Asp-Lys-Cys-Phe-Glu-Glu-Phe-Lys-Ser-Phe-Thr-Ser-Cys-Phe-Glu-Ser-Lys-Phe-Phe-NH$_2$ | 980 |
| Ac-Glu-Lys-Cys-Tyr-Glu-Glu-Phe-Lys-Ser-Phe-Thr-Ser-Cys-Leu-Asp-Ser-Lys-Phe-Phe-NH$_2$ | 981 |

Other suitable peptides include, but are not limited to the peptides of Table 18.

TABLE 18

Illustrative peptides having an improved hydrophobic phase.

| Name | Sequence | SEQ ID NO |
|---|---|---|
| V2W3A5F1017-D-4F | Ac-Asp-Val-Trp-Lys-Ala-Ala-Tyr-Asp-Lys-Phe-Ala-Glu-Lys-Phe-Lys-Glu-Phe-Phe-NH$_2$ | 987 |
| V2W3F10-D-4F | Ac-Asp-Val-Trp-Lys-Ala-Phe-Tyr-Asp-Lys-Phe-Ala-Glu-Lys-Phe-Lys-Glu-Ala-Phe-NH$_2$ | 988 |
| W3-D-4F | Ac-Asp-Phe-Trp-Lys-Ala-Phe-Tyr-Asp-Lys-Val-Ala-Glu-Lys-Phe-Lys-Glu-Ala-Phe-NH$_2$ | 989 |

The peptides described here (V2W3A5F10, 17-D-4F; V2W3F10-D-4F; W3-D-4F) may be more potent than the original D-4F.

Still other suitable peptides include, but are not limited to: P$^1$-Dimethyltyrosine-D-Arg-Phe-Lys-P$^2$ (SEQ ID NO:990) and P$^1$-Dimethyltyrosine-Arg-Glu-Leu-P$^2$ (SEQ ID NO:991) where P1 and P2 are protecting groups as described herein. In certain embodiments, these peptides include, but are not limited to BocDimethyltyrosine-D-Arg-Phe-Lys(OtBu) (SEQ ID NO:990) and BocDimethyltyrosine-Arg-Glu-Leu(OtBu) (SEQ ID NO:991).

In certain embodiments, the peptides of this invention include peptides comprising or consisting of the amino acid sequence LAEYHAK (SEQ ID NO:992) comprising at least one D amino acid and/or at least one or two terminal protecting groups. In certain embodiments, this invention includes a peptide that ameliorates one or more symptoms of an inflammatory condition, wherein the peptide: ranges in length from about 3 to about 10 amino acids; comprises an amino acid sequence where the sequence comprises acidic or basic amino acids alternating with aromatic or hydrophobic amino acids; comprises hydrophobic terminal amino acids or terminal amino acids bearing a hydrophobic protecting group. In certain embodiments, the peptide is not the sequence LAEYHAK (SEQ ID NO:992) comprising all L amino acids; where the peptide converts pro-inflammatory HDL to anti-inflammatory HDL and/or makes anti-inflammatory HDL more anti-inflammatory.

It is also noted that the peptides listed in the Tables herein are not fully inclusive. Using the teaching provided herein, other suitable peptides can routinely be produced (e.g., by conservative or semi-conservative substitutions (e.g., D replaced by E), extensions, deletions, and the like). Thus, for example, one embodiment utilizes truncations of any one or more of peptides identified by SEQ ID Nos:830-858.

Longer peptides are also suitable. Such longer peptides may entirely form a class G or G* amphipathic helix, or the G amphipathic helix (helices) can form one or more domains of the peptide. In addition, this invention contemplates multimeric versions of the peptides. Thus, for example, the peptides illustrated in the tables herein can be coupled together (directly or through a linker (e.g., a carbon linker, or one or more amino acids) with one or more intervening amino acids). Suitable linkers include, but are not limited to Proline (-Pro-), Gly$_4$Ser$_3$ (SEQ ID NO:993), and the like. Thus, one illustrative multimeric peptide according to this invention is (D-J336)-P-(D-J336) (i.e. Ac-L-L-E-Q-L-N-E-Q-F-N-W-V-S-R-L-A-N-L-T-Q-G-E-P-L-L-E-Q-L-N-E-Q-F-N-W-V-S-R-L-A-N-L-T-Q-G-E-NH$_2$, SEQ ID NO:994).

This invention also contemplates the use of "hybrid" peptides comprising a one or more G or G* amphipathic helical domains and one or more class A amphipathic helices. Suitable class A amphipathic helical peptides are described in PCT publication WO 02/15923. Thus, by way of illustration, one such "hybrid" peptide is (D-J336)-Pro-(4F) (i.e. Ac-L-L-E-Q-L-N-E-Q-F-N-W-V-S-R-L-A-N-L-T-Q-G-E-P-D-W-F-K-A-F-Y-D-K-V-A-E-K-F-K-E-A-F-NH$_2$, SEQ ID NO:995), and the like.

Using the teaching provided herein, one of skill can routinely modify the illustrated amphipathic helical peptides to produce other suitable apo J variants and/or amphipathic G and/or A helical peptides of this invention. For example, routine conservative or semi-conservative substitutions (e.g., E for D) can be made of the existing amino acids. The effect of various substitutions on lipid affinity of the resulting peptide can be predicted using the computational method described by Palgunachari et al. (1996) *Arteriosclerosis, Thrombosis, & Vascular Biology* 16: 328-338. The peptides can be lengthened or shortened as long as the class helix structure(s) are preserved. In addition, substitutions can be made to render the resulting peptide more similar to peptide(s) endogenously produced by the subject species.

While, in preferred embodiments, the peptides of this invention utilize naturally-occurring amino acids or D forms of naturally occurring amino acids, substitutions with non-naturally occurring amino acids (e.g., methionine sulfoxide, methionine methylsulfonium, norleucine, episilon-aminocaproic acid, 4-aminobutanoic acid, tetrahydroisoquinoline-3-carboxylic acid, 8-aminocaprylic acid, 4-aminobutyric acid, Lys(N(epsilon)-trifluoroacetyl), α-aminoisobutyric acid, and the like) are also contemplated.

New peptides can be designed and/or evaluated using computational methods. Computer programs to identify and classify amphipathic helical domains are well known to those of skill in the art and many have been described by Jones et al. (1992) *J. Lipid Res.* 33: 287-296). Such programs include, but are not limited to the helical wheel program (WHEEL or WHEEL/SNORKEL), helical net program (HELNET, HELNET/SNORKEL, HELNET/Angle), program for addition of helical wheels (COMBO or COMBO/SNORKEL), program for addition of helical nets (COMNET, COMNET/SNORKEL, COMBO/SELECT, COMBO/NET), consensus wheel program (CONSENSUS, CONSENSUS/SNORKEL), and the like.

F) Blocking Groups and D Residues.

While the various peptides and/or amino acid pairs described herein may be shown with no protecting groups, in certain embodiments (e.g., for oral administration), they can bear one, two, three, four, or more protecting groups. The protecting groups can be coupled to the C- and/or N-terminus of the peptide(s) and/or to one or more internal residues comprising the peptide(s) (e.g., one or more R-groups on the constituent amino acids can be blocked). Thus, for example, in certain embodiments, any of the peptides described herein can bear, e.g., an acetyl group protecting the amino terminus and/or an amide group protecting the carboxyl terminus. One example of such a "dual protected peptide is Ac-L-L-E-Q-L-N-E-Q-F-N-W-V-S-R-L-A-N-L-T-Q-G-E-NH$_2$ (SEQ ID NO:830 with blocking groups), either or both of these protecting groups can be eliminated and/or substituted with another protecting group as described herein.

Without being bound by a particular theory, it was a discovery of this invention that blockage, particularly of the amino and/or carboxyl termini of the subject peptides of this invention greatly improves oral delivery and significantly increases serum half-life. It was also a surprising discovery, however, that in certain embodiments, particular when used in conjunction with the salicylanilides (e.g., niclosamide) and other delivery agents described herein, any or all of the protecting groups can be omitted and the peptides are still orally administrable. Nevertheless, in certain embodiments the peptides, even when formulated with and/or administered in conjunction with a salicylanilide or other delivery agent as described herein bears one or more protecting groups (e.g., terminal protecting groups).

A wide number of protecting groups are suitable for this purpose. Such groups include, but are not limited to acetyl, amide, and alkyl groups with acetyl and alkyl groups being particularly preferred for N-terminal protection and amide groups being preferred for carboxyl terminal protection. In certain particularly preferred embodiments, the protecting groups include, but are not limited to alkyl chains as in fatty acids, propeonyl, formyl, and others. Particularly preferred carboxyl protecting groups include amides, esters, and ether-forming protecting groups. In one preferred embodiment, an acetyl group is used to protect the amino terminus and an amide group is used to protect the carboxyl terminus. These blocking groups enhance the helix-forming tendencies of the peptides. Certain particularly preferred blocking groups include alkyl groups of various lengths, e.g., groups having the formula: $CH_3$—$(CH_2)_n$—CO— where n ranges from about 1 to about 20, preferably from about 1 to about 16 or 18, more preferably from about 3 to about 13, and most preferably from about 3 to about 10.

In certain particularly preferred embodiments, the protecting groups include, but are not limited to alkyl chains as in fatty acids, propeonyl, formyl, and others. Particularly preferred carboxyl protecting groups include amides, esters, and ether-forming protecting groups. In one preferred embodiment, an acetyl group is used to protect the amino terminus and an amide group is used to protect the carboxyl terminus. These blocking groups enhance the helix-forming tendencies of the peptides. Certain particularly preferred blocking groups include alkyl groups of various lengths, e.g., groups having the formula: $CH_3$—$(CH_2)_n$—CO— where n ranges from about 3 to about 20, preferably from about 3 to about 16, more preferably from about 3 to about 13, and most preferably from about 3 to about 10.

Other protecting groups include, but are not limited to Fmoc, t-butoxycarbonyl (t-BOC), 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), Benzyloxymethyl (Bom), cyclohexyloxy (cHxO), t-butoxymethyl (Bum), t-butoxy (tBuO), t-Butyl (tBu), Acetyl (Ac), and Trifluoroacetyl (TFA).

Protecting/blocking groups are well known to those of skill as are methods of coupling such groups to the appropriate residue(s) comprising the peptides of this invention (see, e.g., Greene et al., (1991) *Protective Groups in Organic Synthesis*, 2nd ed., John Wiley & Sons, Inc. Somerset, N.J.). In one preferred embodiment, for example, acetylation is accomplished during the synthesis when the peptide is on the resin using acetic anhydride. Amide protection can be achieved by the selection of a proper resin for the synthesis. During the synthesis of the peptides described herein in the examples, rink amide resin was used. After the completion of the synthesis, the semipermanent protecting groups on acidic bifunctional amino acids such as Asp and Glu and basic amino acid Lys, hydroxyl of Tyr are all simultaneously removed. The peptides released from such a resin using acidic treatment comes out with the n-terminal protected as acetyl and the carboxyl protected as $NH_2$ and with the simultaneous removal of all of the other protecting groups.

In certain particularly preferred embodiments, the peptides comprise one or more D-form (dextro rather than levo) amino acids as described herein. In certain embodiments at least two enantiomeric amino acids, more preferably at least 4 enantiomeric amino acids and most preferably at least 8 or 10 enantiomeric amino acids are "D" form amino acids. In certain embodiments every other, or even every amino acid (e.g., every enantiomeric amino acid) of the peptides described herein is a D-form amino acid.

In certain embodiments at least 50% of the enantiomeric amino acids are "D" form, more preferably at least 80% of the enantiomeric amino acids are "D" form, and most preferably at least 90% or even all of the enantiomeric amino acids are "D" form amino acids.

G) Peptide Mimetics.

In addition to the peptides described herein, it is believed that the salicylanilides (e.g., niclosamide) and other delivery agents described herein are also useful to improve in vivo activity of orally delivered peptide mimetics. Peptide analogs are commonly used in the pharmaceutical industry as non-peptide drugs with properties analogous to those of the template peptide. These types of non-peptide compound are termed "peptide mimetics" or "peptidomimetics" (Fauchere (1986) *Adv. Drug Res.* 15: 29; Veber and Freidinger (1985) *TINS* p. 392; and Evans et al. (1987) *J. Med. Chem.* 30: 1229) and are usually developed with the aid of computerized molecular modeling. Peptide mimetics that are structurally similar to therapeutically useful peptides may be used to produce an equivalent therapeutic or prophylactic effect.

Generally, peptidomimetics are structurally similar to a paradigm polypeptide (e.g., SEQ ID NO:5 shown in Table 1), but have one or more peptide linkages optionally replaced by a linkage selected from the group consisting of: —$CH_2NH$—, —$CH_2S$—, —$CH_2$—$CH_2$—, —CH=CH— (cis and trans), —$COCH_2$—, —$CH(OH)CH_2$—, —$CH_2SO$—, etc. by methods known in the art and further described in the following references: Spatola (1983) p. 267 in *Chemistry and Biochemistry of Amino Acids, Peptides, and Proteins*, B. Weinstein, eds., Marcel Dekker, New York; Spatola (1983) *Vega Data* 1(3) *Peptide Backbone Modifications*. (general review); Morley (1980) *Trends Pharm Sci* pp. 463-468 (general review); Hudson et al. (1979) *Int J Pept Prot Res* 14:177-185 (—$CH_2NH$—, $CH_2CH_2$—); Spatola et al. (1986) *Life Sci* 38:1243-1249 (—$CH_2$—S); Hann, (1982) *J Chem Soc Perkin Trans* I 307-314 (—CH—CH—, cis and trans); Almquist et al. (1980) *J Med. Chem.* 23:1392-1398 (—$COCH_2$—); Jennings-White et al. (1982) *Tetrahedron Lett.* 23:2533 (—$COCH_2$—); Szelke et al., European Appln. EP 45665 (1982) CA: 97:39405 (1982) (—CH(OH)CH2-); Holladay et al. (1983) *Tetrahedron Lett* 24:4401-4404 (—C(OH)$CH_2$—); and Hruby (1982) *Life Sci.*, 31:189-199 (—$CH_2$—S—)).

One particularly preferred non-peptide linkage is —$CH_2NH$—. Such peptide mimetics may have significant advantages over polypeptide embodiments, including, for example: more economical production, greater chemical stability, enhanced pharmacological properties (half-life, absorption, potency, efficacy, etc.), reduced antigenicity, and others.

In addition, circularly permutations of the peptides described herein or constrained peptides (including cyclized peptides) comprising a consensus sequence or a substantially identical consensus sequence variation may be generated by methods known in the art (Rizo and Gierasch (1992) *Ann. Rev. Biochem.* 61: 387); for example, by adding internal cysteine residues capable of forming intramolecular disulfide bridges which cyclize the peptide.

H) Small Organic Molecules.

In addition to the peptides described herein, it is believed that the salicylanilides (e.g., niclosamide) and other delivery agents described herein are also useful to improve in vivo activity (apparent activity) of orally delivered small organic molecules, e.g., as described in copending application U.S. Ser. No. 60/600,925, filed Aug. 11, 2004. In various embodiments the small organic molecules are similar to, and in certain cases, mimetics of the tetra- and penta-peptides described in copending application U.S. Ser. No. 10/649,378, filed on Aug. 26, 2003 and U.S. Ser. No. 60/494,449, filed on August 11.

The small organic molecules of this invention typically have molecular weights less than about 900 Daltons. Typically the molecules are highly soluble in ethyl acetate (e.g., at concentrations equal to or greater than 4 mg/mL), and also are soluble in aqueous buffer at pH 7.0.

Contacting phospholipids such as 1,2-dimyristoyl-sn-glycero-3-phosphocholine (DMPC), with the small organic molecules of this invention in an aqueous environment typically results in the formation of particles with a diameter of approximately 7.5 nm (±0.1 nm). In addition, stacked bilayers are often formed with a bilayer dimension on the order of 3.4 to 4.1 nm with spacing between the bilayers in the stack of approximately 2 nm. Vesicular structures of approximately 38 nm are also often formed. Moreover, when the molecules of this invention are administered to a mammal they render HDL more anti-inflammatory and mitigate one or more symptoms of atherosclerosis and/or other conditions characterized by an inflammatory response.

Thus, in certain embodiments, the small organic molecule is one that ameliorates one or more symptoms of a pathology characterized by an inflammatory response in a mammal (e.g., atherosclerosis), where the small molecule is soluble in ethyl acetate at a concentration greater than 4 mg/mL, is soluble in aqueous buffer at pH 7.0, and, when contacted with a phospholipid in an aqueous environment, forms particles with a diameter of approximately 7.5 nm and forms stacked bilayers with a bilayer dimension on the order of 3.4 to 4.1 nm with spacing between the bilayers in the stack of approximately 2 nm, and has a molecular weight less than 900 daltons.

In certain embodiment, the molecule has the formula:

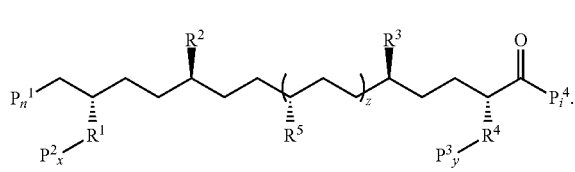

I where $P^1$, $P^2$, $P^3$, and $P^4$ are independently selected hydrophobic protecting groups; $R^1$ and $R^4$ are independently selected amino acid R groups; n, i, x, y, and z are independently zero or 1 such that when n and x are both zero, $R^1$ is a hydrophobic group and when y and i are both zero, $R^4$ is a hydrophobic group; $R^2$ and $R^3$ are acidic or basic groups at pH 7.0 such that when $R^2$ is acidic, $R^3$ is basic and when $R^2$ is basic, $R^3$ is acidic; and $R^5$, when present is selected from the group consisting of an aromatic group, an aliphatic group, a positively charged group, or a negatively charged group. In certain embodiments, $R^2$ or $R^3$ is —(CH$_2$)j-COOH where j=1, 2, 3, or 4 and/or —(CH$_2$)j-NH$_2$ where j=1, 2, 3, 4, or 5, or —(CH$_2$)j-NH—C(=NH)—NH$_2$ where n=1, 2, 3 or 4. In certain embodiments, $R^2$, $R^3$, and $R^5$, when present, are amino acid R groups. Thus, for example, In various embodiments $R^2$ and $R^3$ are independently an aspartic acid R group, a glutamic acid R group, a lysine R group, a histidine R group, or an arginine R group (e.g., as illustrated in Table 1).

In certain embodiments, $R^1$ is selected from the group consisting of a Lys R group, a Trp R group, a Phe R group, a Leu R group, an Orn R group, pr a norLeu R group. In certain embodiments, $R^4$ is selected from the group consisting of a Ser R group, a Thr R group, an Ile R group, a Leu R group, a norLeu R group, a Phe R group, or a Tyr R group.

In various embodiments x is 1, and $R^5$ is an aromatic group (e.g., a Trp R group).

In various embodiments at least one of n, x, y, and i is 1 and $P^1$, $P^2$, $P^3$, and $P^4$ when present, are independently selected from the group consisting of polyethylene glycol (PEG), an acetyl, amide, a 3 to 20 carbon alkyl group, fmoc, 9-fluoreneacetyl group, 1-fluorenecarboxylic group, 9-fluorenecarboxylic, 9-fluorenone-1-carboxylic group, benzyloxycarbonyl, xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), -4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), benzyloxy (BzlO), benzyl (Bzl), benzoyl (Bz), 3-nitro-2-pyridinesulphenyl (Npys), 1-(4,4-dimethyl-2,6-dioxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), benzyloxymethyl (Bom), t-butoxycarbonyl (Boc), cyclohexyloxy (cHxO), t-butoxymethyl (Bum), t-butoxy (tBuO), t-Butyl (tBu), a propyl group, a butyl group, a pentyl group, a hexyl group, and trifluoroacetyl (TFA). In certain embodiments, $P^1$ when present and/or $P^2$ when present are independently selected from the group consisting of Boc-, Fmoc-, and Nic- otinyl- and/or $P^3$ when present and/or $P^4$ when present are independently selected from the group consisting of tBu, and OtBu.

While a number of protecting groups ($P^1$, $P^2$, $P^3$, $P^4$) are illustrated above, this list is intended to be illustrative and not limiting. In view of the teachings provided herein, a number of other protecting/blocking groups will also be known to one of skill in the art. Such blocking groups can be selected to minimize digestion (e.g., for oral pharmaceutical delivery), and/or to increase uptake/bioavailability (e.g., through mucosal surfaces in nasal delivery, inhalation therapy, rectal administration), and/or to increase serum/plasma half-life. In certain embodiments, the protecting groups can be provided as an excipient or as a component of an excipient.

In certain embodiments, z is zero and the molecule has the formula:

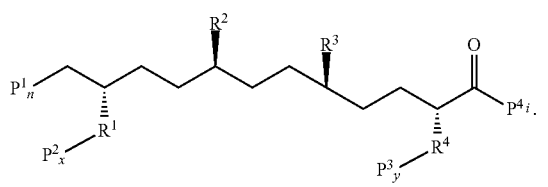

II where $P^1$, $P^2$, $P^3$, $P^4$, $R^1$, $R^2$, $R^3$, $R^4$, n, x, y, and i are as described above.

In certain embodiments, z is zero and the molecule has the formula:

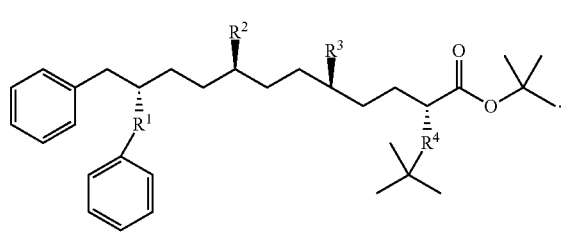

III where $R^1$, $R^2$, $R^3$, and $R^4$ are as described above.

In one embodiment, the molecule has the formula:

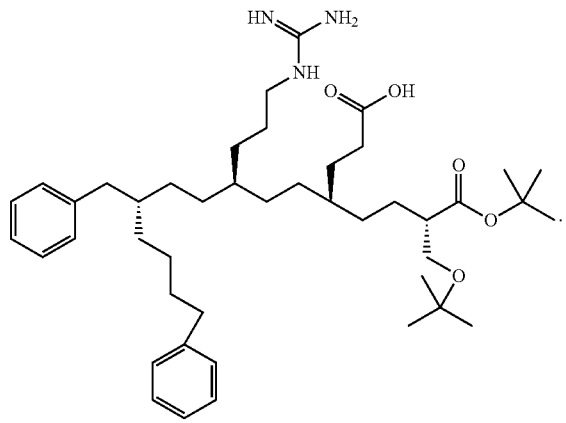

In certain embodiments, this invention contemplates small molecules having one or more of the physical and/or functional properties described herein and having the formula:

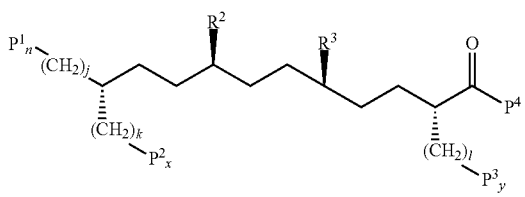

where $P^1$, $P^2$, $P^3$, and $P^4$ are independently selected hydrophobic protecting groups as described above, n, x, and y are independently zero or 1; j, k, and l are independently zero, 1, 2, 3, 4, or 5; and $R^2$ and $R^3$ are acidic or basic groups at pH 7.0 such that when $R^2$ is acidic, $R^3$ is basic and when $R^2$ is basic, $R^3$ is acidic. In certain preferred embodiments, the small molecule is soluble in water; and the small molecule has a molecular weight less than about 900 Daltons. In certain embodiments, n, x, y, j, and l are 1; and k is 4.

In certain embodiments, $P^1$ and/or $P^2$ are aromatic protecting groups. In certain embodiments, $R^2$ and $R^3$ are amino acid R groups, e.g., as described above. In various embodiments least one of n, x, and y, is 1 and $P^1$, $P^2$, $P^3$ and $P^4$ when present, are independently protecting groups, e.g., as described above. In certain embodiments the protecting groups, when present, are independently selected from the group consisting of polyethylene glycol (PEG), an acetyl, amide, 3 to 20 carbon alkyl groups, Fmoc, 9-fluoreneacetyl group, 1-fluorenecarboxylic group, 9-fluorenecarboxylic, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), -4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), benzyloxy (BzlO), benzyl (Bzl), benzoyl (Bz), 3-nitro-2-pyridinesulphenyl (Npys), 1-(4,4-dimethyl-2,6-dioxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), benzyloxymethyl (Bom), t-butoxycarbonyl (Boc), cyclohexyloxy (cHxO), t-butoxymethyl (Bum), t-butoxy (tBuO), t-Butyl (tBu), a propyl group, a butyl group, a pentyl group, a hexyl group, and trifluoroacetyl (TFA). In certain embodiments, $P^1$ when present and/or $P^2$ when present are independently selected from the group consisting of Boc-, Fmoc-, and Nicotinyl- and/or $P^3$ when present and/or $P^4$ when present are independently selected from the group consisting of tBu, and OtBu.

IV. Pharmaceutical Formulations.

A) Pharmaceutical Formulations.

In order to carry out the methods of the invention, one or more therapeutic peptides, mimetics, or small organic molecules described herein are administered in conjunction with a salicylanilide (e.g., niclosamide or niclosamide analogue) or one of the other delivery agents described herein to a mammal, e.g., to an individual diagnosed as having one or more symptoms of atherosclerosis, or as being at risk for atherosclerosis and or the various other pathologies described herein.

In various embodiments the "active agent(s)", therapeutic peptides, mimetics, or small organic molecules described herein, are formulated in combination with one or more of the salicylanilides (e.g., niclosamide or niclosamide analogue) or one of the other delivery agents described herein. In certain embodiments one or more active agent(s) are combined with one or more salicylanilides (e.g., niclosamide or niclosamide analogs) to form an adduct. The active agent(s) can be administered in the "native" form or, if desired, in the form of salts, esters, amides, prodrugs, derivatives, and the like, provided the salt, ester, amide, prodrug or derivative is suitable pharmacologically, i.e., effective in the present method. Salts, esters, amides, prodrugs and other derivatives of the active agents can be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience.

Similarly, the delivery agent(s) can also be formulated as salts, esters, amides, and the like.

Methods of formulating such derivatives are known to those of skill in the art. For example, the disulfide salts of a number of delivery agents are described in PCT Publication WO 00/059863 which is incorporated herein by reference. Similarly, acid salts of therapeutic peptides, mimetics, and small organic molecules can be prepared from the free base using conventional methodology, that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

Preparation of Esters Typically Involves Functionalization of Hydroxyl and/or carboxyl groups which may be present within the molecular structure of the drug. The esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides and prodrugs can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety that results in a compound that is therapeutically inactive until modified by an individual's metabolic system.

The active agents identified herein are useful for parenteral, topical, oral, nasal (or otherwise inhaled), rectal, or local administration, such as by aerosol or transdermally, for prophylactic and/or therapeutic treatment of one or more of the pathologies/indications described herein (e.g., atherosclerosis and/or symptoms thereof). The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectibles, implantable sustained-release formulations, lipid complexes, etc.

In addition to administration in conjunction with or formulation with one or more delivery agents, the active agents of this invention can also be combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers.

Other physiologically acceptable compounds, particularly of use in the preparation of tablets, capsules, gel caps, and the like include, but are not limited to binders, diluent/fillers, disentegrants, lubricants, susupending agents, and the like.

In certain embodiments, to manufacture an oral dosage form (e.g., a tablet), an excipient (e.g., lactose, sucrose, starch, mannitol, etc.), an optional disintegrator (e.g. calcium carbonate, carboxymethylcellulose calcium, sodium starch glycollate, crospovidone etc.), a binder (e.g. alpha-starch, gum arabic, microcrystalline cellulose, carboxymethylcellulose, polyvinylpyrrolidone, hydroxypropylcellulose, cyclodextrin, etc.), and an optional lubricant (e.g., talc, magnesium stearate, polyethylene glycol 6000, etc.), for instance, are added to the active component or components (e.g., active peptide and salicylanilide) and the resulting composition is compressed. Where necessary, the compressed product is coated, e.g., known methods for masking the taste or for enteric dissolution or sustained release. Suitable coating materials include, but are not limited to ethyl-cellulose, hydroxymethylcellulose, polyoxyethylene glycol, cellulose acetate phthalate, hydroxypropylmethylcellulose phthalate, and Eudragit (Rohm & Haas, Germany; methacrylic-acrylic copolymer).

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s).

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

In therapeutic applications, the compositions of this invention are administered, e.g., orally administered, to a patient suffering from one or more symptoms of the one or more pathologies described herein, or at risk for one or more of the pathologies described herein in an amount sufficient to prevent and/or cure and/or or at least partially prevent or arrest the disease and/or its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the active agents of the formulations of this invention to effectively treat (ameliorate one or more symptoms) the patient.

The concentration of active agent(s) can vary widely, and will be selected primarily based on activity of the active ingredient(s), body weight and the like in accordance with the particular mode of administration selected and the patient's needs. Concentrations, however, will typically be selected to provide dosages ranging from about 0.1 or 1 mg/kg/day to about 50 mg/kg/day and sometimes higher. Typical dosages range from about 3 mg/kg/day to about 3.5 mg/kg/day, preferably from about 3.5 mg/kg/day to about 7.2 mg/kg/day, more preferably from about 7.2 mg/kg/day to about 11.0 mg/kg/day, and most preferably from about 11.0 mg/kg/day to about 15.0 mg/kg/day. In certain preferred embodiments, dosages range from about 10 mg/kg/day to about 50 mg/kg/day. In certain embodiments, dosages range from about 20 mg to about 50 mg given orally twice daily. It will be appreciated that such dosages may be varied to optimize a therapeutic regimen in a particular subject or group of subjects.

In certain embodiments, the active agents of this invention are administered orally (e.g., via a tablet, capsule, caplet, gel cap, etc.). It was a surprising discovery that therapeutic peptides can be orally administered and achieve therapeutically effective levels, particularly when administered with a salicylanilide (e.g., niclosamide or a niclosamide analogue) or one of the other delivery agents described herein. It was particularly surprising that when so administered, the therapeutic peptide can be an L-form peptide and need not bear protecting groups. The combination of therapeutic peptide with a salicylanilide or other delivery agent is not limited to unprotected L-form peptides. To the contrary, the use salicylanilides and/or other delivery agent(s) with L-form peptides bearing one or more protecting groups, D-form peptides, and D-form peptides bearing one or more protecting groups is also contemplated.

In certain embodiments the active agents of this invention are administered as an injectable in accordance with standard methods well known to those of skill in the art. In other preferred embodiments, the agents, can also be delivered through the skin using conventional transdermal drug delivery systems, i.e., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

Other formulations for topical drug delivery include, but are not limited to, ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

As indicated above, various buccal, and sublingual formulations are also contemplated.

The use of salicylanilide or other delivery agents as described herein need not be limited to oral delivery. In certain embodiments the use of such delivery agents is also contemplated in formulations intended for transdermal delivery, injectable delivery, surgical implantation, nasal delivery, rectal delivery, and the like.

In another embodiment, one or more components of the formulation (e.g., delivery agent and/or active agent) can be provided as a "concentrate", e.g., in a storage container (e.g., in a premature volume) ready for dilution, or in a soluble capsule ready for addition to a volume of water. In certain embodiments the salicylanilide or other delivery agent and the therapeutic agent are provided separately. Thus for example, salicylanilide or other delivery agent is provided as a solution that is administered immediately or some time prior to administration of the therapeutic agent (e.g., therapeutic peptide), or the salicylanilide or other delivery agent is provided as a solution used while swallowing the active agent(s) formulated as a capsule, tablet, gel cap, etc.

The foregoing formulations and administration methods are intended to be illustrative and not limiting. It will be appreciated that, using the teaching provided herein, other suitable formulations and modes of administration can be readily devised.

B) Lipid-Based Formulations.

In certain embodiments, the active agents and/or salicylanilide or other delivery agent(s) of this invention are administered in conjunction with one or more lipids. The lipids can be formulated as an excipient to protect and/or enhance transport/uptake of the active agents or they can be administered separately.

Without being bound by a particular theory, it was discovered of this invention that administration (e.g., oral administration) of certain phospholipids can significantly increase HDL/LDL ratios. In addition, it is believed that certain medium-length phospholipids are transported by a process different than that involved in general lipid transport. Thus, co-administration of certain medium-length phospholipids with the active agents of this invention confer a number of advantages: They protect the active agents from digestion or hydrolysis, they improve uptake, and they improve HDL/LDL ratios.

The lipids can be formed into liposomes that encapsulate the active agents of this invention and/or they can be complexed/admixed with the active agents and/or they can be covalently coupled to the active agents. Methods of making liposomes and encapsulating reagents are well known to those of skill in the art (see, e.g., Martin and Papahadjopoulos (1982) *J. Biol. Chem.*, 257: 286-288; Papahadjopoulos et al. (1991) *Proc. Natl. Acad. Sci. USA*, 88: 11460-11464; Huang et al. (1992) *Cancer Res.*, 52:6774-6781; Lasic et al. (1992) *FEBS Lett.*, 312: 255-258., and the like).

Preferred phospholipids for use in these methods have fatty acids ranging from about 4 carbons to about 24 carbons in the sn-1 and sn-2 positions. In certain preferred embodiments, the fatty acids are saturated. In other preferred embodiments, the fatty acids can be unsaturated. Various preferred fatty acids are illustrated in Table 19.

TABLE 19

Preferred fatty acids in the sn-1 and/or sn-2 position of the preferred phospholipids for administration of active agents described herein.

| Carbon No. | Common Name | IUPAC Name |
|---|---|---|
| 3:0 | Propionoyl | Trianoic |
| 4:0 | Butanoyl | Tetranoic |
| 5:0 | Pentanoyl | Pentanoic |
| 6:0 | Caproyl | Hexanoic |
| 7:0 | Heptanoyl | Heptanoic |
| 8:0 | Capryloyl | Octanoic |
| 9:0 | Nonanoyl | Nonanoic |
| 10:0 | Capryl | Decanoic |
| 11:0 | Undcanoyl | Undecanoic |
| 12:0 | Lauroyl | Dodecanoic |
| 13:0 | Tridecanoyl | Tridecanoic |
| 14:0 | Myristoyl | Tetradecanoic |
| 15:0 | Pentadecanoyl | Pentadecanoic |
| 16:0 | Palmitoyl | Hexadecanoic |
| 17:0 | Heptadecanoyl | Heptadecanoic |
| 18:0 | Stearoyl | Octadecanoic |
| 19:0 | Nonadecanoyl | Nonadecanoic |
| 20:0 | Arachidoyl | Eicosanoic |
| 21:0 | Heniecosanoyl | Heniecosanoic |
| 22:0 | Behenoyl | Docosanoic |
| 23:0 | Trucisanoyl | Trocosanoic |
| 24:0 | Lignoceroyl | Tetracosanoic |
| 14:1 | Myristoleoyl (9-cis) | |
| 14:1 | Myristelaidoyl (9-trans) | |
| 16:1 | Palmitoleoyl (9-cis) | |
| 16:1 | Palmitelaidoyl (9-trans) | |

The fatty acids in these positions can be the same or different. Particularly preferred phospholipids have phosphorylcholine at the sn-3 position.

V. Additional Pharmacologically Active Agents.

A) Combined Active Agents

In various embodiments, the use of combinations of two or more active agents described is contemplated in the treatment of the various pathologies/indications described herein. The use of combinations of active agents can alter pharmacological activity, bioavailability, and the like.

By way of illustration, it is noted that D-4F and L-4F rapidly associates with pre-beta HDL and HDL and then are rapidly cleared from the circulation (it is essentially nondetectable 6 hours after an oral dose), while D-[113-122]apoJ slowly associates with pre-beta HDL and to a lesser extent with HDL but remains associated with these HDL fractions for at least 36 hours. FREL associates with HDL and only HDL but remains detectable in HDL for much longer than D-4F (i.e., it is detectable in HDL 48 hours after a single oral dose in mice). In certain embodiments this invention thus contemplates combinations of, for example, these three peptides to reduce the amount to reduce production expense, and/or to optimize dosage regimen, therapeutic profile, and the like. In certain embodiments combinations of the active agents described herein can be simply coadministered and/or added together to form a single pharmaceutical formulation. In certain embodiments the various active agent(s) can be complexed together (e.g., via hydrogen bonding) to form active agent complexes that are more effective than the parent agents.

B) Use with Additional Pharmacologically Active Materials.

Additional pharmacologically active materials (i.e., drugs) can be delivered in conjunction with one or more of the active agents described herein. In certain embodiments, such agents include, but are not limited to agents that reduce the risk of atherosclerotic events and/or complications thereof. Such agents include, but are not limited to beta blockers, beta blockers and thiazide diuretic combinations, statins, aspirin, ace inhibitors, ace receptor inhibitors (ARBs), and the like.

It was discovered that, adding a low dosage active agent (e.g., of D-4F) (1 µg/ml) to the drinking water of apoE null mice for 24 hours did not significantly improve HDL function (see, e.g., related application U.S. Ser. No. 10/423,830, filed on Apr. 25, 2003, which is incorporated herein by reference). In addition, adding 0.05 mg/ml of atorvastatin or pravastatin alone to the drinking water of the apoE null mice for 24 hours did not improve HDL function. However, when D-4F1 µg/ml was added to the drinking water together with 0.05 mg/ml of atorvastatin or pravastatin there was a significant improvement in HDL function). Indeed the pro-inflammatory apoE null HDL became as anti-inflammatory as 350 µg/ml of normal human HDL (h, HDL see, e.g., related application U.S. Ser. No. 10/423,830).

Thus, doses of D-4F alone, or statins alone, which by themselves had no effect on HDL function when given together acted synergistically. When D-4F and a statin were given together to apo E null mice, their pro-inflammatory HDL at 50 µg/ml of HDL-cholesterol became as effective as normal human HDL at 350 µg/ml of HDL-cholesterol in preventing the inflammatory response induced by the action of HPODE oxidizing PAPC in cocultures of human artery wall cells.

Thus, in certain embodiments this invention provides methods for enhancing the activity of statins. The methods generally involve administering one or more of the active agents described herein, as described herein in conjunction with one or more statins. The active agents achieve synergistic action between the statin and the agent(s) to ameliorate one or more symptoms of atherosclerosis. In this context statins can be administered at significantly lower dosages thereby avoiding various harmful side effects (e.g., muscle wasting) associated with high dosage statin use and/or the anti-inflammatory properties of statins at any given dose are significantly enhanced.

Suitable statins include, but are not limited to pravastatin (Pravachol/Bristol-Myers Squibb), simvastatin (Zocor/Merck), lovastatin (Mevacor/Merck), and the like.

In various embodiments the active agent(s) described herein are administered in conjunction with one or more beta blockers. Suitable beta blockers include, but are not limited to cardioselective (selective beta 1 blockers), e.g., acebutolol (Sectral™), atenolol (Tenormin™), betaxolol (Kerlone™), bisoprolol (Zebeta™), metoprolol (Lopressor™), and the like. Suitable non-selective blockers (block beta 1 and beta 2 equally) include, but are not limited to carteolol (Cartrol™), nadolol (Corgard™), penbutolol (Levatol™), pindolol (Visken™), propranolol (Inderal™), timolol (Blockadren™), labetalol (Normodyne™, Trandate™), and the like.

Suitable beta blocker thiazide diuretic combinations include, but are not limited to Lopressor HCT, ZIAC, Tenoretic, Corzide, Timolide, Inderal LA 40/25, Inderide, Normozide, and the like.

Suitable ace inhibitors include, but are not limited to captopril (e.g., Capoten™ by Squibb), benazepril (e.g., Lotensin™ by Novartis), enalapril (e.g., Vasotec™ by Merck), fosinopril (e.g., Monopril™ by Bristol-Myers), lisinopril (e.g., Prinivil™ by Merck or Zestril™ by Astra-Zeneca), quinapril (e.g., Accupril™ by Parke-Davis), ramipril (e.g., Altace™ by Hoechst Marion Roussel, King Pharmaceuticals), imidapril, perindopril erbumine (e.g., Aceon™ by Rhone-Polenc Rorer), trandolapril (e.g., Mavik™ by Knoll Pharmaceutical), and the like. Suitable ARBS (Ace Receptor Blockers) include but are not limited to losartan (e.g., Cozaar™ by Merck), irbesartan (e.g., Avapro™ by Sanofi), candesartan (e.g., Atacand™ by Astra Merck), valsartan (e.g., Diovan™ by Novartis), and the like.

In various embodiments, one or more agents described herein are administered with one or more of the drugs identified below.

Thus, in certain embodiments one or more active agents are administered in conjunction with cholesteryl ester transfer protein (CETP) inhibitors (e.g., torcetrapib, JTT-705. CP-529414) and/or acyl-CoA:cholesterol O-acyltransferase (ACAT) inhibitors (e.g., Avasimibe (CI-1011), CP 113818, F-1394, and the like), and/or immunomodulators (e.g., FTY720 (sphingosine-1-phosphate receptor agonist), Thalomid (thalidomide), Imuran (azathioprine), Copaxone (glatiramer acetate), Certican® (everolimus), Neoral® (cyclosporine), antd the like), and/or dipeptidyl-peptidase-4 (DPP4) inhibitors (e.g., 2-Pyrrolidinecarbonitrile, 1-[[[2-[(5-cyano-2-pyridinyl)amino]ethyl]amino]acetyl], see also U.S. Patent Publication 2005-0070530), and/or calcium channel blockers (e.g., Adalat, Adalat CC, Calan, Calan SR, Cardene, Cardizem, Cardizem CD, Cardizem SR, Dilacor-XR, DynaCirc, Isoptin, Isoptin SR, Nimotop, Norvasc, Plendil, Procardia, Procardia XL, Vascor, Verelan), and/or peroxisome proliferator-activated receptor (PPAR) agonists for, e.g., α, γ; δ receptors (e.g., Azelaoyl PAF, 2-Bromohexadecanoic acid, Ciglitizone, Clofibrate, 15-Deoxy-$\delta^{12,14}$-prostaglandin J$_2$, Fenofibrate, Fmoc-Leu-OH, GW1929, GW7647, 8(S)-Hydroxy-(5Z,9E,11Z,14Z)-eicosatetraenoic acid (8(S)-HETE), Leukotriene B$_4$, LY-171,883 (Tomelukast), Prostaglandin A$_2$, Prostaglandin J$_2$, Tetradecylthioacetic acid (TTA), Troglitazone (CS-045), WY-14643 (Pirinixic acid)), and the like.

In certain embodiments one or more of the active agents are administered in conjunction with fibrates (e.g., clofibrate (atromid), gemfibrozil (lopid), fenofibrate (tricor), etc.), bile acid sequestrants (e.g., cholestyramine, colestipol, etc.), cholesterol absorption blockers (e.g., ezetimibe (Zetia), etc.), Vytorin ((ezetimibe/simvastatin combination), and/or steroids, warfarin, and/or aspirin, and/or Bcr-Abl inhibitors/antagonists (e.g., Gleevec (Imatinib Mesylate), AMN107, STI571 (CGP57148B), ON 012380, PLX225, and the like), and/or renin angiotensin pathway blockers (e.g., Losartan (Cozaar®), Valsartan (Diovan®), Irbesartan (Avapro®), Candesartan (Atacand®), and the like), and/or angiotensin II receptor antagonists (e.g., losartan (Cozaar), valsartan (Diovan), irbesartan (Avapro), candesartan (Atacand) and telmisartan (Micardis), etc.), and/or PKC inhibitors (e.g., Calphostin C, Chelerythrine chloride, Chelerythrine. chloride, Copper bis-3,5-diisopropylsalicylate, Ebselen, EGF Receptor (human) (651-658) (N-Myristoylated), Gö 6976, H-7. dihydrochloride, 1-O-Hexadecyl-2-O-methyl-rac-glycerol, Hexadecyl-phosphocholine ($C_{16:0}$); Miltefosine, Hypericin, Melittin (natural), Melittin (synthetic), ML-7. hydrochloride, ML-9. hydrochloride, Palmitoyl-DL-carnitine. hydrochloride, Protein Kinase C (19-31), Protein Kinase C (19-36), Quercetin. dihydrate, Quercetin. dihydrate, D-erythro-Sphingosine (isolated), D-erythro-Sphingosine (synthetic), Sphingosine, N,N-dimethyl, D-erythro-Sphingosine, Dihydro-, D-erythro-Sphingosine, N,N-Dimethyl-, D-erythro-Sphingosine chloride, N,N,N-Trimethyl-, Staurosporine, Bisindolylmaleimide I, G-6203, and the like).

In certain embodiments, one or more of the active agents are administered in conjunction with ApoAI, Apo A-I derivatives and/or agonists (e.g., ApoAI milano, see, e.g., U.S. Patent Publications 20050004082, 20040224011, 20040198662, 20040181034, 20040122091, 20040082548, 20040029807, 20030149094, 20030125559, 20030109442, 20030065195, 20030008827, and 20020071862, and U.S. Pat. Nos. 6,831,105, 6,790,953, 6,773,719, 6,713,507, 6,703,422, 6,699,910, 6,680,203, 6,673,780, 6,646,170, 6,617,134, 6,559,284, 6,506,879, 6,506,799, 6,459,003, 6,423,830, 6,410,802, 6,376,464, 6,367,479, 6,329,341, 6,287,590, 6,090,921, 5,990,081, and the like), renin inhibitors (e.g., SPP630 and SPP635, SPP100, Aliskiren, and the like), and/or MR antagonist (e.g., spironolactone, aldosterone glucuronide, and the like), and/or aldosterone synthase inhibitors, and/or alpha-adrenergic antagonists (e.g., Aldomet® (Methyldopa), Cardura® (Doxazosin), Catapres®; Catapres-TTS®; Duraclon™ (Clonidine), Dibenzyline® (Phenoxybenzamine), Hylorel® (Guanadrel), Hytrin® (Terazosin), Minipress® (Prazosin), Tenex® (Guanfacine), Guanabenz, Phentolamine, Reserpine, and the like), and/or liver X receptor (LXR) agonists (e.g., T0901317, GW3965, ATI-829, acetyl-podocarpic dimer (APD), and the like), and/or farnesoid X receptor (FXR) agonists (e.g., GW4064, 6alpha-ethylchenodeoxycholic acid (6-ECDCA), T0901317, and the like), and/or plasminogen activator-1 (PAI-1) inhibitors (see, e.g., oxime-based PAI-1 inhibitors, see also U.S. Pat. No. 5,639,726, and the like), and/or low molecular weight heparin, and/or AGE inhibitorsibreakers (e.g., Benfotiamine, aminoguanidine, pyridoxamine, Tenilsetam, Pimagedine, and the like) and/or ADP receptor blockers (e.g., Clopidigrel, AZD6140, and the like), and/or ABCA1 agonists, and/or scavenger receptor B1 agonists, and/or Adiponectic receptor agonist or adiponectin inducers, and/or stearoyl-CoA Desaturase I (SCD1) inhibitors, and/or Cholesterol synthesis inhibitors (non-statins), and/or Diacylglycerol Acyltransferase I (DGAT1) inhibitors, and/or Acetyl CoA Carboxylase 2 inhibitors, and/or LP-PLA2 inhibitors, and/or GLP-1, and/or glucokinase activator, and/or CB-1 agonists, and/or anti-thrombotic/coagulants, and/or Factor Xa inhibitors, and/or GPIIb/IIIa inhibitors, and/or Factor VIIa inhibitors, and/or Tissue factor inhibitors, and/or anti-inflammatory drugs, and/or Probucol and derivatives (e.g., AGI-1067, etc.), and/or CCR2 antagonists, and/or CX3CR1 antagonists, and/or IL-1 antagonists, and/or nitrates and NO donors, and/or phosphodiesterase inhibitors, and the like.

C) Administration.

Typically the active agent(s) described hereinwill be administered (typically in conjunction with a salicylanilide (e.g., niclosamide or niclosamide analogue) or other delivery agent as described herein) to a mammal (e.g., a human) in need thereof. Such a mammal will typically include a mammal (e.g., a human) having or at risk for one or more of the pathologies described herein.

The active agent(s) can be administered, as described herein, according to any of a number of standard methods including, but not limited to injection, suppository, nasal spray, time-release implant, transdermal patch, and the like. In one particularly preferred embodiment, the peptide(s) are administered orally (e.g., as a syrup, capsule, or tablet).

The methods involve the administration of a single active agent of this invention or the administration of two or more different active agents, typically in conjunction with a salicylanilide (e.g., niclosamide or niclosamide analogue) or other delivery agent as described herein. The active agents can be provided as monomers (e.g., in separate or combined formulations), or in dimeric, oligomeric or polymeric forms. In certain embodiments, the multimeric forms may comprise associated monomers (e.g., ionically or hydrophobically linked) while certain other multimeric forms comprise covalently linked monomers (directly linked or through a linker).

While the invention is described with respect to use in humans, it is also suitable for animal, e.g., veterinary use. Thus certain preferred organisms include, but are not limited to humans, non-human primates, canines, equines, felines, porcines, ungulates, largomorphs, and the like.

The methods of this invention are not limited to humans or non-human animals showing one or more symptom(s) of the pathologies described herein, but are also useful in a prophylactic context. Thus, the active agents of this invention can be administered to organisms to prevent the onset/development of one or more symptoms of the pathologies described herein (e.g., atherosclerosis, stroke, etc.). Particularly preferred subjects in this context are subjects showing one or more risk factors for the pathology. Thus, for example, in the case of atherosclerosis risk factors include family history, hypertension, obesity, high alcohol consumption, smoking, high blood cholesterol, high blood triglycerides, elevated blood LDL, VLDL, IDL, or low HDL, diabetes, or a family history of diabetes, high blood lipids, heart attack, angina or stroke, etc.

VI. Kits for the Treatment of One or More Indications.

In another embodiment this invention provides kits for amelioration of one or more symptoms of atherosclerosis or for the prophylactic treatment of a subject (human or animal) at risk for atherosclerosis and/or the treatment or prophylaxis of one or more of the conditions described herein. The kits preferably comprise a container containing one or more of the active agents described herein. The active agent(s) can be provided in a unit dosage formulation (e.g., suppository, tablet, caplet, patch, etc.) and/or may be optionally combined with one or more pharmaceutically acceptable excipients.

In various embodiments the kits typically additionally comprise a salicylanilide or other delivery agent described herein. The salicylanilide or other delivery agent can be formulated as a compound formulation with one or more of the active agents described herein. Alternatively, the salicylanilide or other delivery agent can be provided separately, e.g., in a separate container.

The kit can, optionally, further comprise one or more other agents used in the treatment of the condition/pathology of interest. Such agents include, but are not limited to, beta blockers, vasodilators, aspirin, statins, ace inhibitors or ace receptor inhibitors (ARBs) and the like, e.g., as described above.

In addition, the kits optionally include labeling and/or instructional materials providing directions (i.e., protocols)

for the practice of the methods or use of the "therapeutics" or "prophylactics" of this invention. Preferred instructional materials describe the use of one or more active agent(s) of this invention to mitigate one or more symptoms of atherosclerosis (or other pathologies described herein) and/or to prevent the onset or increase of one or more of such symptoms in an individual at risk for atherosclerosis (or other pathologies described herein). The instructional materials may also, optionally, teach preferred dosages/therapeutic regiment, counter indications and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

VII. Indications.

The active agents (e.g., peptides, small organic molecules, amino acid pairs, etc.) described herein are effective for mitigating one or more symptoms and/or reducing the rate of onset and/or severity of one or more indications described herein. In particular, the active agents (e.g., peptides, small organic molecules, amino acid pairs, etc.) described herein are effective for mitigating one or more symptoms of atherosclerosis. Without being bound to a particular theory, it is believed that the peptides bind the "seeding molecules" required for the formation of pro-inflammatory oxidized phospholipids such as Ox-PAPC, POVPC, PGPC, and PEIPC.

In addition, since many inflammatory conditions and/or other pathologies are mediated at least in part by oxidized lipids, we believe that the peptides of this invention are effective in ameliorating conditions that are characterized by the formation of biologically active oxidized lipids. In addition, there are a number of other conditions for which the active agents described herein appear to be efficacious.

A number of pathologies for which the active agents described herein appear to be a palliative and/or a preventative are shown in Table 20.

TABLE 20

Summary of conditions in which the active agents (e.g., D-4F) have been shown to be or are believed to be effective.

atherosclerosis/symptoms/consequences thereof
   plaque formation
   lesion formation
   myocardial infarction
   stroke
   congestive heart failure
   vascular function:
      arteriole function
      arteriolar disease
         associated with aging
         associated with Alzheimer's disease
         associated with chronic kidney disease
         associated with hypertension
         associated with multi-infarct dementia
         associated with subarachnoid hemorrhage
      peripheral vascular disease
   pulmonary disease:
      chronic obstructive pulmonary disease (COPD),
      emphysema
      asthma
      idiopathic pulmonary fibrosis
      Pulmonary fibrosis
      adult respiratory distress syndrome TABLE 20-continued Summary of conditions in which the active agents (e.g., D-4F) have been shown to be or are believed to be effective.

osteoporosis
   Paget's disease
   coronary calcification
   autoimmune:
      rheumatoid arthritis
      polyarteritis nodosa
      polymyalgia rheumatica
      lupus erythematosus
      multiple sclerosis
      Wegener's granulomatosis
      central nervous system vasculitis (CNSV)
      Sjögren's syndrome
      Scleroderma
      polymyositis.
AIDS inflammatory response
infections:
   bacterial
   fungal
   viral
   parasitic
   influenza
      avian flu
   viral pneumonia
   endotoxic shock syndrome
   sepsis
   sepsis syndrome
   (clinical syndrome where it appears that the patient is septic but no organisms are recovered from the blood)
trauma/wound:
   organ transplant
   transplant atherosclerosis
   transplant rejection
   corneal ulcer
   chronic/non-healing wound
   ulcerative colitis
   reperfusion injury (prevent and/or treat)
   ischemic reperfusion injury (prevent and/or treat)
   spinal cord injuries (mitigating effects)
cancers
   myeloma/multiple myeloma
   ovarian cancer
   breast cancer
   colon cancer
   bone cancer
osteoarthritis
inflammatory bowel disease
allergic rhinitis
cachexia
diabetes
Alzheimer's disease
implanted prosthesis
biofilm formation
Crohns' disease
dermatitis, acute and chronic
   eczema
   psoriasis
   contact dermatitis
   scleroderma
diabetes and related conditions
   Type I Diabetes
   Type II Diabetes
   Juvenile Onset Diabetes
   Prevention of the onset of diabetes
   Diabetic Nephropathy
   Diabetic Neuropathy
   Diabetic Retinopathy
erectile dysfunction
macular degeneration
multiple sclerosis
nephropathy
neuropathy
Parkinson's Disease
peripheral Vascular Disease
meningitis
Specific biological activities:
   increase Heme Oxygenase 1
   increase extracellular superoxide dismutase

TABLE 20-continued

Summary of conditions in which the active agents (e.g., D-4F) have been shown to be or are believed to be effective.

prevent endothelial sloughing
prevent the association of myeloperoxidase with ApoA-I
prevent the nitrosylation of tyrosine in ApoA-I
render HDL anti-inflammatory
improve vasoreactivity
increase the formation of pre-beta HDL
promote reverse cholesterol transport
promote reverse cholesterol transport from macrophages
synergize the action of statins It is noted that the conditions listed in Table 20 are intended to be illustrative and not limiting.

EXAMPLES

The following examples are offered to illustrate, but not to limit the claimed invention.

Example 1

Niclosamide Enhances Uptake/Bioavailability of Orally Administered Peptides

We previously reported that the amino acid sequence D-W—F—K-A-F—Y-D-K—V-A-E-KF—K-E-A-F (SEQ-ID-NO:5) bearing at least one protecting group (see, e.g., U.S. Pat. No. 6,933,279) when synthesized from all L-amino acids (L-4F) and administered orally to mice was rapidly degraded and did not significantly alter the protective capacity of HDL to inhibit LDL-induced monocyte chemotactic activity in cultures of human artery wall cells (Navab et al. (2002) *Circulation* 105: 290-292).

It was a surprising finding of this invention that administering L-4F with niclosamide orally to mice resulted in significant improvement in the ability of HDL from these mice to inhibit LDL-induced monocyte chemotactic activity. In contrast orally administering either agent alone was ineffective or significantly less effective.

Figure 8:
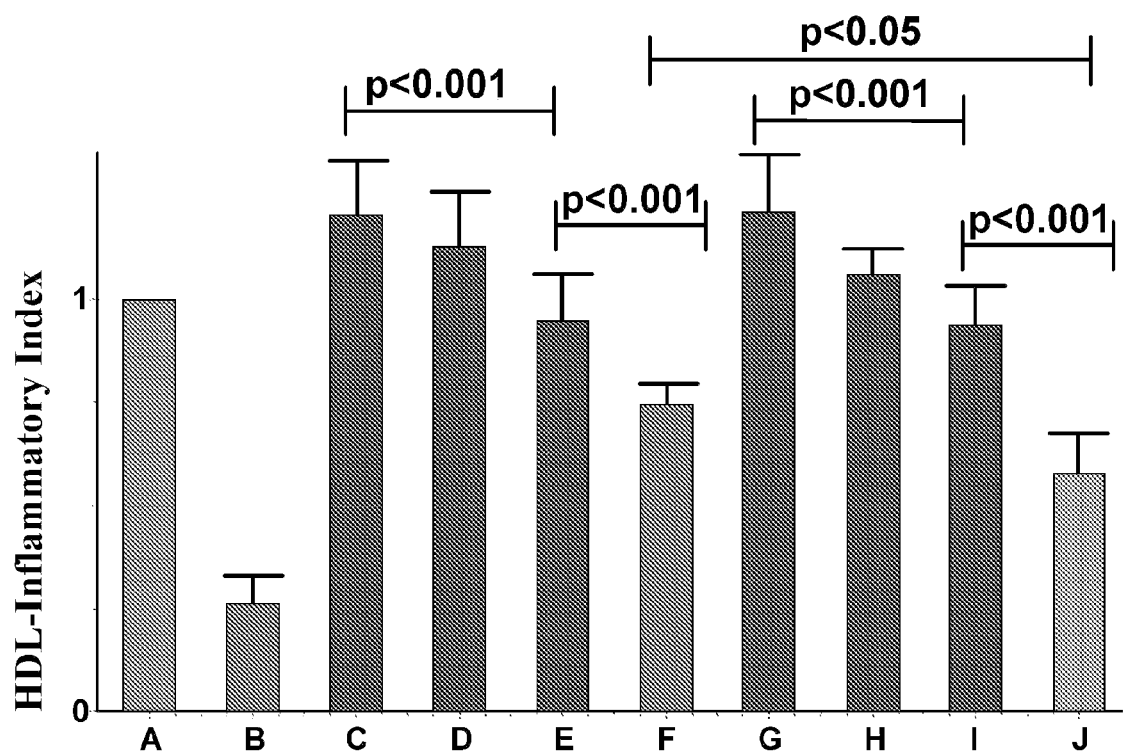
FIG. 8 shows HDL inflammatory index for apoE null mice fed chow containing or not containing additions. C: Mice were given chow alone; D: Mice given chow supplemented with 8.0 micrograms of niclosamide; E: Mice given chow supplemented with 2.0 micrograms of L-4F; F: Mice given chow supplemented with 8.0 micrograms of Niclosamide together with 2.0 micrograms of L-4F (free base) per gram of chow. The mouse HDL (C-J) was also compared to a standard human HDL (B) that was added at the same concentrations as the mouse HDL. The resulting monocyte chemotactic activity was normalized to the standard control LDL added alone (A). The results are plotted as the HDL-inflammatory index, which is the result of dividing the monocyte chemotactic activity measured for each condition by the monocyte chemotactic activity obtained by the standard control LDL added alone, which was normalized to 1.0. G-I: A second experiment. G: Chow alone; H: chow supplemented with 100 micrograms of Niclosamide per gram of chow; I: Chow supplemented with 10 micrograms of L-4F (free base) per gram of mouse chow; J: Chow supplemented with 10 micrograms of L-4F (free base) together with 100 micrograms of Niclosamide per gram of chow. The data shown are the Mean±S.D.

As shown in FIG. 8, the combination of oral Niclosamide and L-4F was potent in a mouse model of atherosclerosis. 11-month-old female apoE null mice were fasted during the day. At night the mice were provided chow containing or not containing additions. In the first experiment the mice were given chow alone (C) or chow supplemented with 8.0 micrograms of Niclosamide (2',5-Dichloro-4'-nitrosalicylanilide; Niclosamide, Sigma catalog number N-3510 Page 1711 2006-2007 catalog Empirical Formula (Hill Notation): $C_{13}H_8Cl_2N_2O_4$ Formula Weight: 327.12, CAS Number: 50-65-7 Batch 105K0666 EC 200-056-8) per gram of chow (D) or chow supplemented with 2.0 micrograms of L-4F (free base) per gram of chow (E), or chow supplemented with 8.0 micrograms of Niclosamide together with 2.0 micrograms of L-4F (free base) per gram of chow (F). The mice were only given one gram of chow per mouse (n=8 mice per group) so that they would consume all of the chow. In the morning after the chow was consumed the mice were bled and their plasma was sucrose cryopreserved and fractionated by FPLC and the HDL-containing fractions were tested for their ability to inhibit monocyte chemotactic activity induced by a standard control human LDL (A) in cultures of human aortic endothelial cells. The mouse HDL (C-J) was also compared to a standard human HDL (B) that was added at the same concentrations as the mouse HDL. The resulting monocyte chemotactic activity was normalized to the standard control LDL added alone (A). The results are plotted as the HDL-inflammatory index, which is the result of dividing the monocyte chemotactic activity measured for each condition by the monocyte chemotactic activity obtained by the standard control LDL added alone, which was normalized to 1.0 as described previously (Navab et al. (2004) *J Lipid Res,* 45: 993-1007).

A second experiment was performed as described for the first experiment with 8 mice in each group except that the additions to the chow were different. Chow alone in the second experiment (G) was compared to chow supplemented with 100 micrograms of Niclosamide per gram of chow (H), or supplemented with 10 micrograms of L-4F (free base) per gram of mouse chow (I), or supplemented with 10 micrograms of L-4F (free base) together with 100 micrograms of Niclosamide per gram of chow (J). As in the first experiment the mice were only given one gram of chow per mouse so that they would consume all of the chow. In the morning this second group of mice were bled and their HDL tested in the human artery wall cell culture together with the HDL from the first experiment.

The data indicate that addition of either 2 (E) or 10 (I) micrograms of L-4F to the chow slightly but significantly improved the HDL-inflammatory index and the difference between these two doses in the absence of Niclosamide was not significant confirming our previous report (Navab et al. (2002) *Circulation,* 105: 290-292). As shown in FIG. 1 (D) and (H), administering Niclosamide by itself was ineffective. Surprisingly the oral combination of Niclosamide with L-4F in each case resulted in dramatic statistically significant improvement in the HDL-inflammatory index. The use of 10 micrograms of L-4F together with 100 micrograms of Niclosamide (J) was significantly better than 2 micrograms of L-4F together with 8 micrograms of Niclosamide (F).

Figure 9:
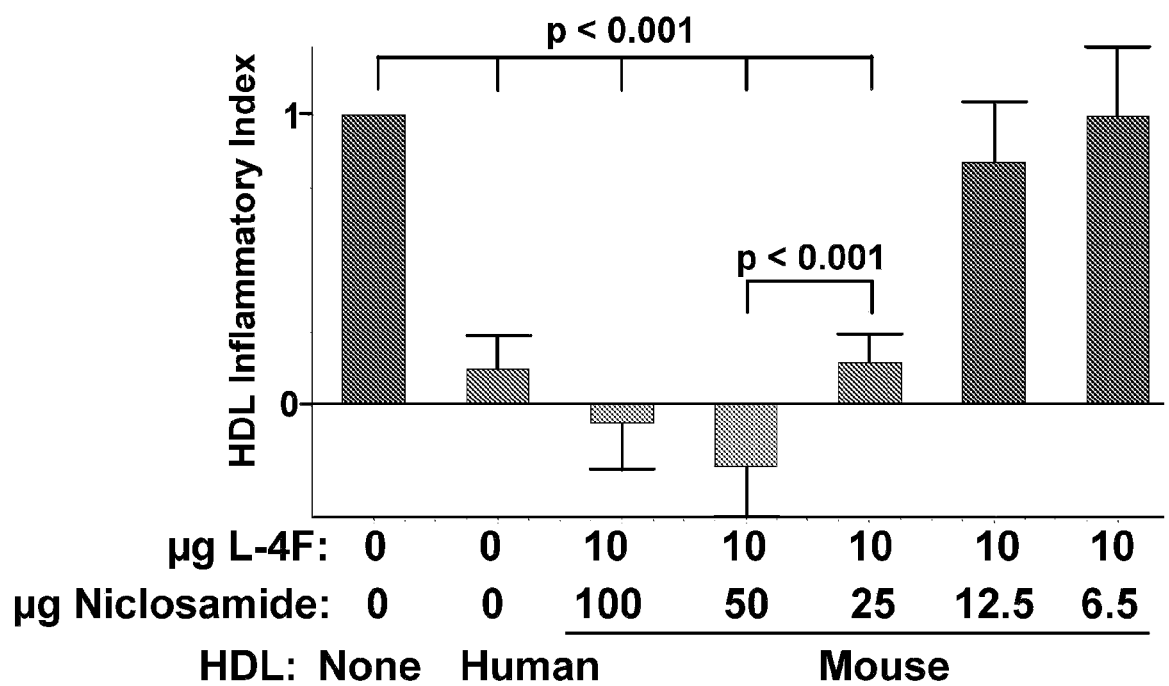
FIG. 9 shows that administration of niclosamide as an oral bolus by gastric gavage (stomach tube) immediately followed by administration of L-4F as an oral bolus by stomach tube rendered apoE null mouse HDL anti-inflammatory. the HDL-containing fractions were tested for their ability to inhibit the induction of monocyte chemotactic activity by a standard control human LDL, which was added to cultures of human aortic endothelial cells. The values obtained after the addition of the standard control HDL or the mouse HDL were compared to the values obtained by the standard control LDL alone to give the HDL Inflammatory Index. The values shown are the Mean±S.D.

As shown in FIG. 9, administration of Niclosamide as an oral bolus by gastric gavage (stomach tube) immediately followed by administration of L-4F as an oral bolus by stomach tube rendered apoE null mouse HDL anti-inflammatory. Ten mg of Niclosamide was placed in a glass-glass homogenizer with mortar and round bottom pestle (Kontes Dounce Tissue grinder, K885300-0015 available from Fisher, VWR) and 200 µL of ethanol was added. The Niclosamide ethanol mixture was homogenized using 2-3 strokes and distilled water was added and the mixture further homogenized using 5-10 strokes and the volume was adjusted to 10 mL with distilled water. Serial dilutions of this mixture were made using distilled water to give the micrograms of Niclosamide shown on the x-axis, which were contained in 100 µL. L-4F (free base) was diluted with water to give 10 µg per 100 µL of water. One hundred microliters of the Niclosamide solution was given by stomach tube to each mouse in each group of twelve-month-old non-fasting female apoE null mice (n=4 per group) and immediately followed by 100 µL containing 10 µg of L-4F (free base) in water. The mice were fasted and after 7 hours they were bled and their plasma was sucrose cryopreserved. The plasma was fractionated by FPLC and the HDL-containing fractions were tested for their ability to inhibit the induction of monocyte chemotactic activity by a standard control human LDL, which was added to cultures of human aortic endothelial cells. The standard control human LDL was also added by itself or with a standard control human HDL. The values obtained by the standard control human LDL alone were normalized to 1.0. The values obtained after the addition of the standard control HDL or the mouse HDL were compared to the values obtained by the standard control LDL alone to give the HDL Inflammatory Index.

Figure 10:
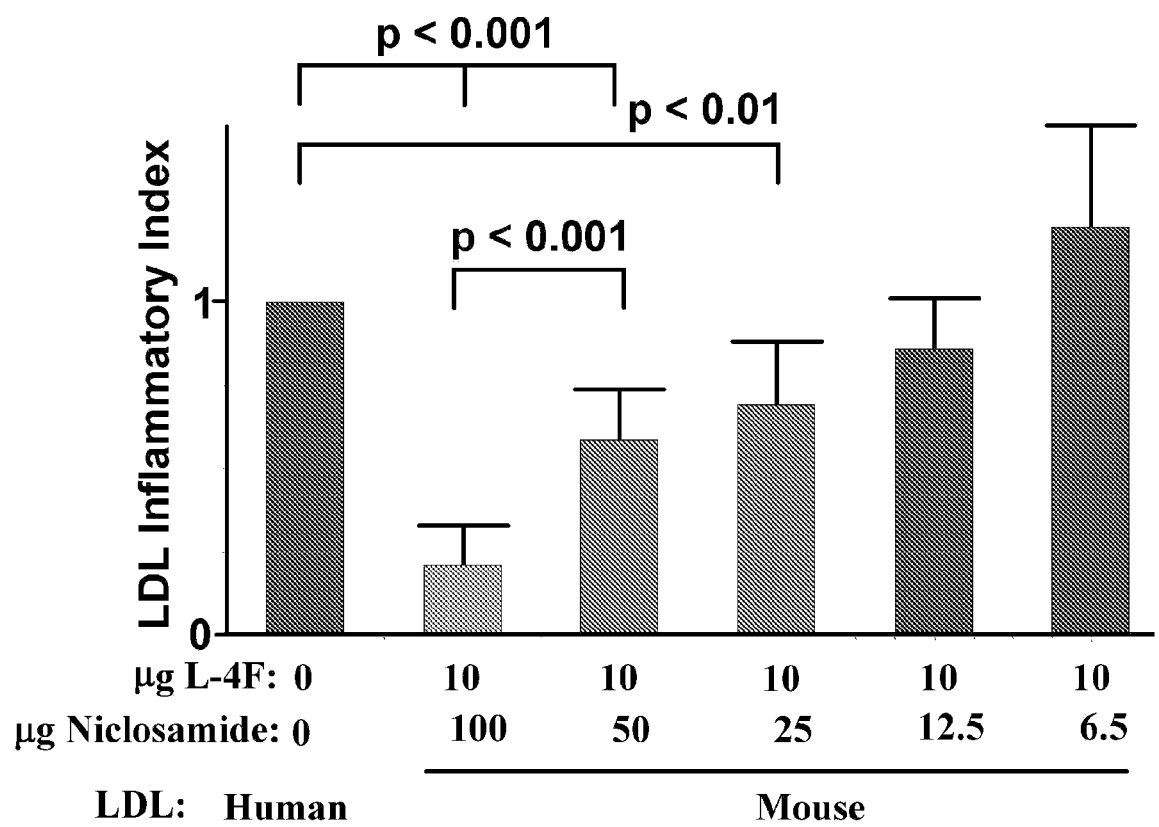
FIG. 10 shows that administration of Niclosamide as an oral bolus by stomach tube immediately followed by administration of L-4F as an oral bolus by stomach tube significantly reduced the ability of apoE null mouse LDL to induce monocyte chemotactic activity in cultures of human aortic endothelial cells. The LDL fractions from the mice described in FIG. 9 were tested for their ability to induce monocyte chemotactic activity in cultures of human aortic endothelial cells and compared to a standard control human LDL whose values were normalized to 1.0 for the LDL-inflammatory index. The data shown are the Mean±S.D.

FIG. 10 shows that Administration of Niclosamide as an oral bolus by stomach tube immediately followed by administration of L-4F as an oral bolus by stomach tube significantly reduced the ability of apoE null mouse LDL to induce monocyte chemotactic activity in cultures of human aortic endothelial cells. The LDL fractions from the mice described in FIG. 9 were tested for their ability to induce monocyte chemotactic activity in cultures of human aortic endothelial cells and compared to a standard control human LDL whose values were normalized to 1.0 for the LDL-inflammatory index.

Figure 11:
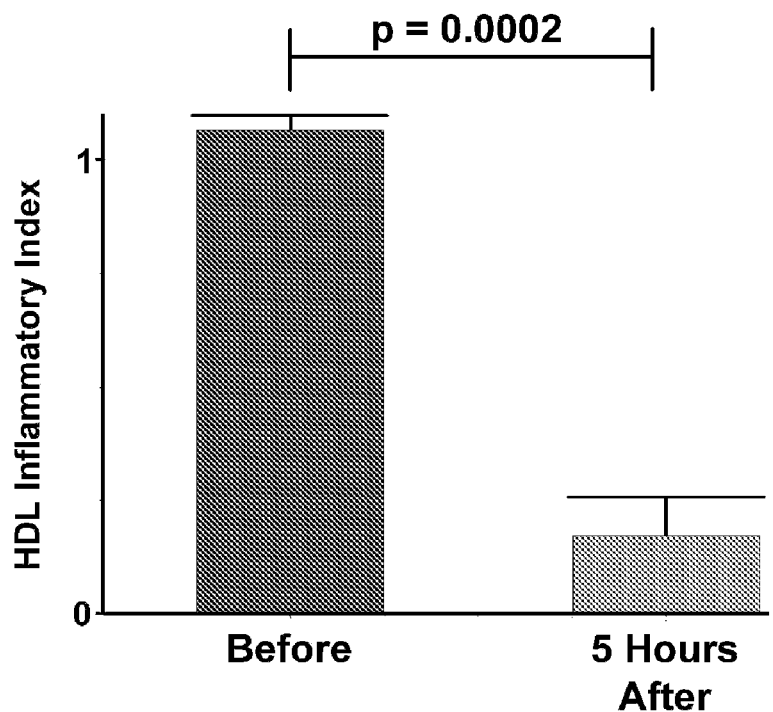
FIG. 11 shows that oral administration of niclosamide (5.0 mg/kg body weight) immediately followed by oral administration of L-4F (0.5 mg/kg/body weight) renders monkey HDL anti-inflammatory. The data shown are the Mean±S.D. for the HDL

FIG. 11 shows that oral administration of niclosamide (5.0 mg/kg body weight) immediately followed by oral administration of L-4F (0.5 mg/kg/body weight) renders monkey HDL anti-inflammatory. One hundred mg of niclosamide was placed in a glass-glass homogenizer with mortar and round bottom pestle (Kontes Dounce Tissue grinder, K885300-0015 available from Fisher, VWR) and 200 µL of ethanol was added. The Niclosamide ethanol mixture was homogenized using 2-3 strokes and distilled water was added and the mixture further homogenized using 5-10 strokes and the volume was adjusted to 10 mL with distilled water. The niclosamide mixture was again mixed immediately before the dose was removed as the Niclosamide tends to settle out. Each of 4 monkeys (2 Female and 2 Male) were given 5.0 mg/kg body weight of Niclosamide contained in 2.5 mL of the mixture by stomach tube. L-4F (free base) was added to 10 mL of distilled water in the glass-glass homogenizer and homogenized using 5-10 strokes. Immediately after administration of the Niclosamide mixture each monkey was given 0.5 mg/kg body weight of L-4F (free base) contained in 2.5 mL water by stomach tube. Blood was obtained 5 hours later and the plasma was separated by FPLC and the lipoproteins tested as described in FIG. 8 for the HDL-inflammatory index and FIG. 10 for the LDL-inflammatory index. The data shown are the Mean±S.D. for the HDL Inflammatory Index for monkey HDL before and 5 hours after treatment (the data for the standard control human LDL alone and the standard control human LDL plus the standard control human HDL are not shown in the figure).

Figure 12:
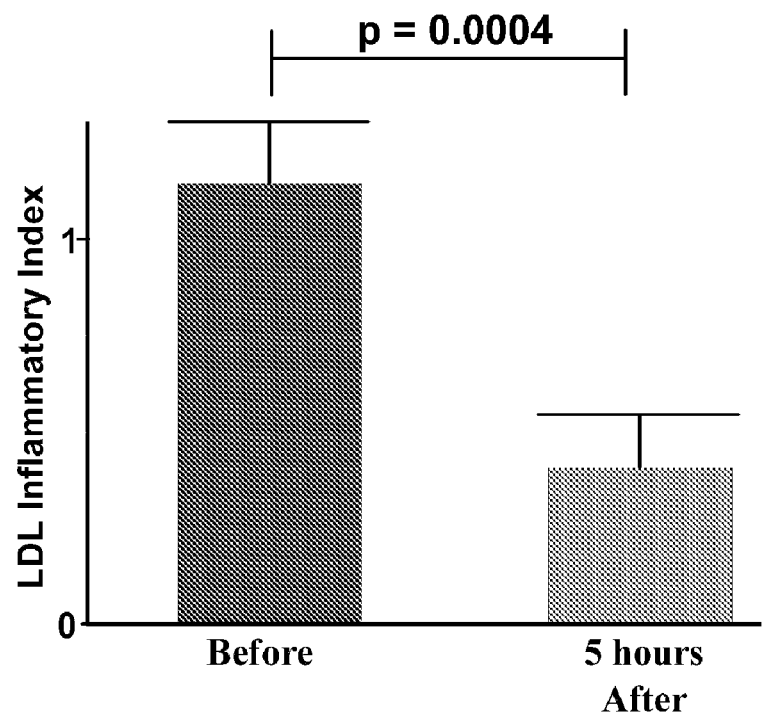
FIG. 12 shows that oral administration of niclosamide (5.0 mg/kg body weight) immediately followed by oral administration of L-4F (0.5 mg/kg/body weight) significantly reduced the ability of monkey LDL to induce monocyte chemotactic activity in cultures of human aortic endothelial cells. The LDL fractions from the monkey plasma described in FIG. 11 were tested as described in FIG. 10. The data shown are the Mean±S.D.

Oral administration of niclosamide (5.0 mg/kg body weight) immediately followed by oral administration of L-4F (0.5 mg/kg/body weight) significantly reduced the ability of monkey LDL to induce monocyte chemotactic activity in cultures of human aortic endothelial cells (see, e.g., FIG. 12). The LDL fractions from the monkey plasma described in FIG. 11 were tested as described in FIG. 10.

Figure 13:
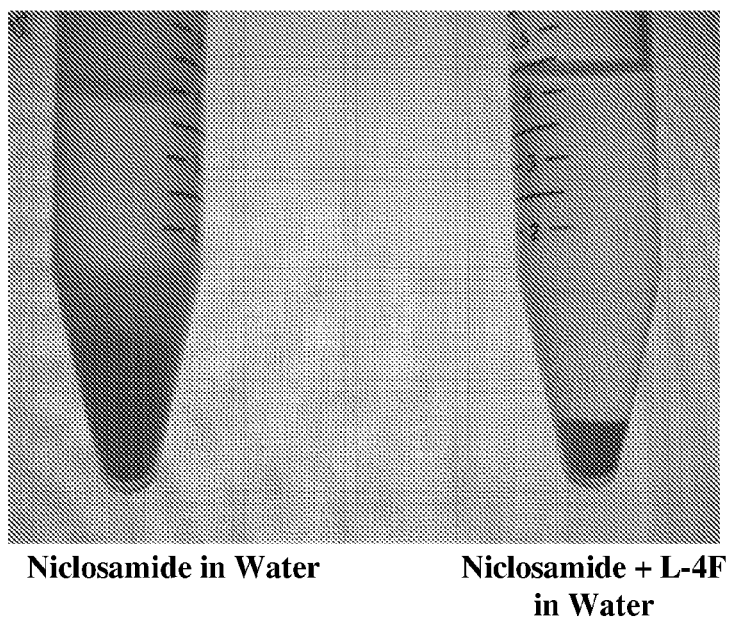
FIG. 13 shows that an amphipathic helical peptide (L-4F) increases the solubility of niclosamide in an aqueous system. Niclosamide at 10 mg per mL was added to water, or to water containing 1.0 mg/mL L-4F (free base) and was homogenized in a glass-glass homogenizer. The solutions were stored at 4° C. for ten days and photographed

Niclosamide is relatively insoluble in aqueous solutions even when added in ethanol and homogenized. It was a surprising finding of this invention that L-4F solubilized niclosamide in aqueous solution as shown in FIG. 13. Niclosamide at 10 mg per mL was added to water, or to water containing 1.0 mg/mL L-4F (free base) and was homogenized in a glass-glass homogenizer. The solutions were stored at 4° C. for ten days and photographed (see FIG. 13).

The solutions of Niclosamide with or without L-4F shown above in FIG. 13 were serially diluted and given by gastric gavage (stomach tube) to fasting seven month old female apoE null mice in a volume of 100 µL per mouse (n=8 per group). Blood was collected 6 hrs following treatment while the mice were still fasting and the plasma was separated by FPLC and the HDL fractions were tested as described in FIG. 8 and the data are shown in FIG. 14.

The micrograms of L-4F and/or niclosamides are shown on the X-axis. Six hours after administration the mice were bled and the ability of mouse HDL (m) or human HDL (h) to inhibit LDL-induced monocyte chemotactic activity in cultures of human aortic endothelial cells was determined and plotted as the HDL-inflammatory index as described for FIG. 8.

Figure 15:
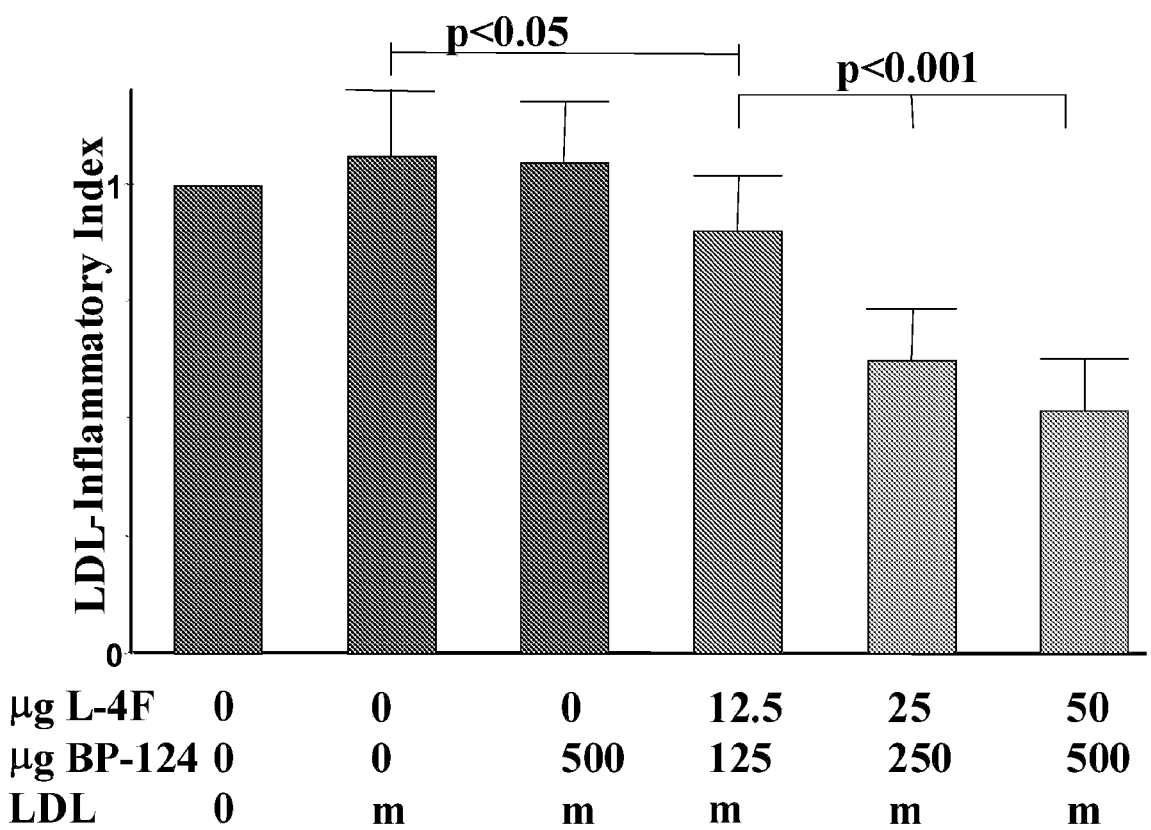
FIG. 15 LDL from the mice described in FIG. 14 was tested for its ability to induce human aortic endothelial cells to produce monocyte chemotactic activity. The data are plotted as the LDL-inflammatory index as described for FIG. 10. The values shown are the Mean±S.D.

As shown in FIG. 15, administration of the L-4F together with the solubilized niclosamide resulted in a significant reduction in the ability of mouse LDL to induce monocyte chemotactic activity in cultures of human aortic endothelial cells.

Figure 14:
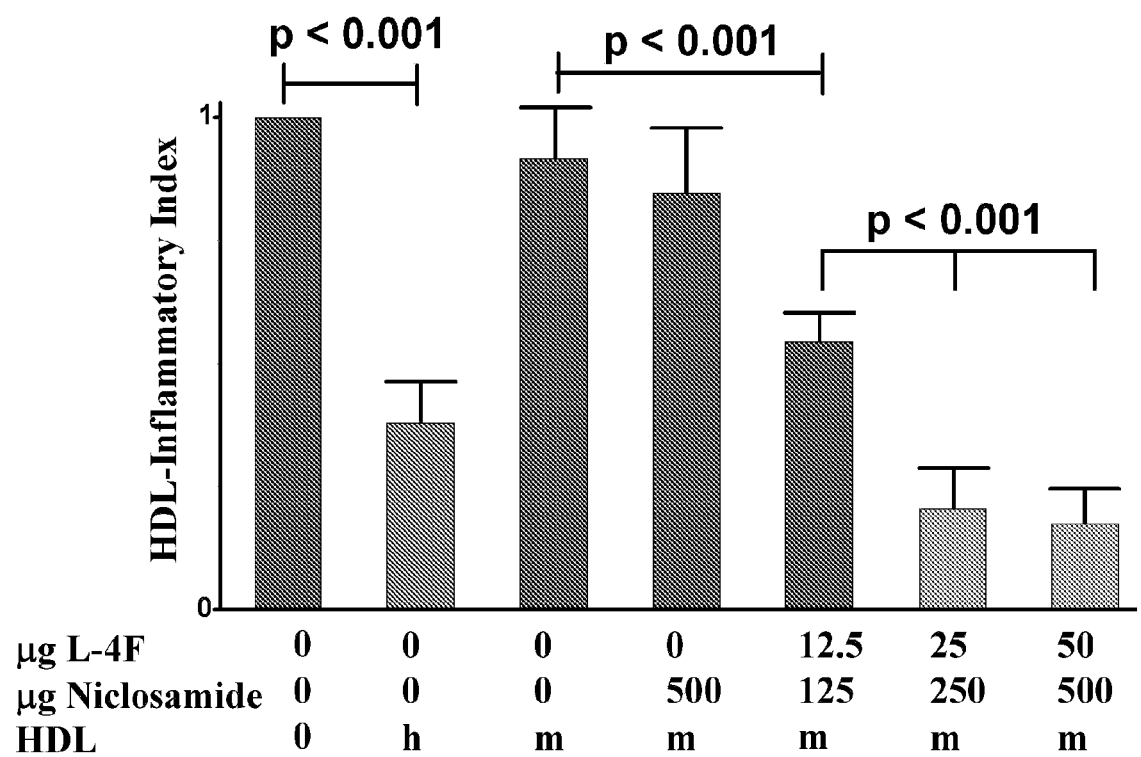
FIG. 14 shows the HDL inflammatory index for female apoE null mice that were given by gastric gavage (stomach tube) 100 μL water alone or 100 μL water containing niclosamide or containing niclosamide in combination with L-4F at the doses shown on the X-axis. The solutions of niclosamide with or without L-4F shown in FIG. 13 were serially diluted and given by gastric gavage (stomach tube) to fasting seven month old female apoE null mice in a volume of 100 microliters per mouse (n=8 per group). Blood was collected 6 hours following treatment while the mice were still fasting and the plasma was separated by FPLC and the HDL fractions were tested as described in FIG. 8. The data shown are the Mean±S.D, h=human, m=mouse.

The data in FIGS. 14 and 15 demonstrate the remarkable, novel, and unexpected findings that the peptide L-4F solubilizes niclosamide and results in a therapeutic combination that renders HDL anti-inflammatory and significantly reduces the inflammatory properties of LDL in a mouse model of atherosclerosis.

Figure 16:
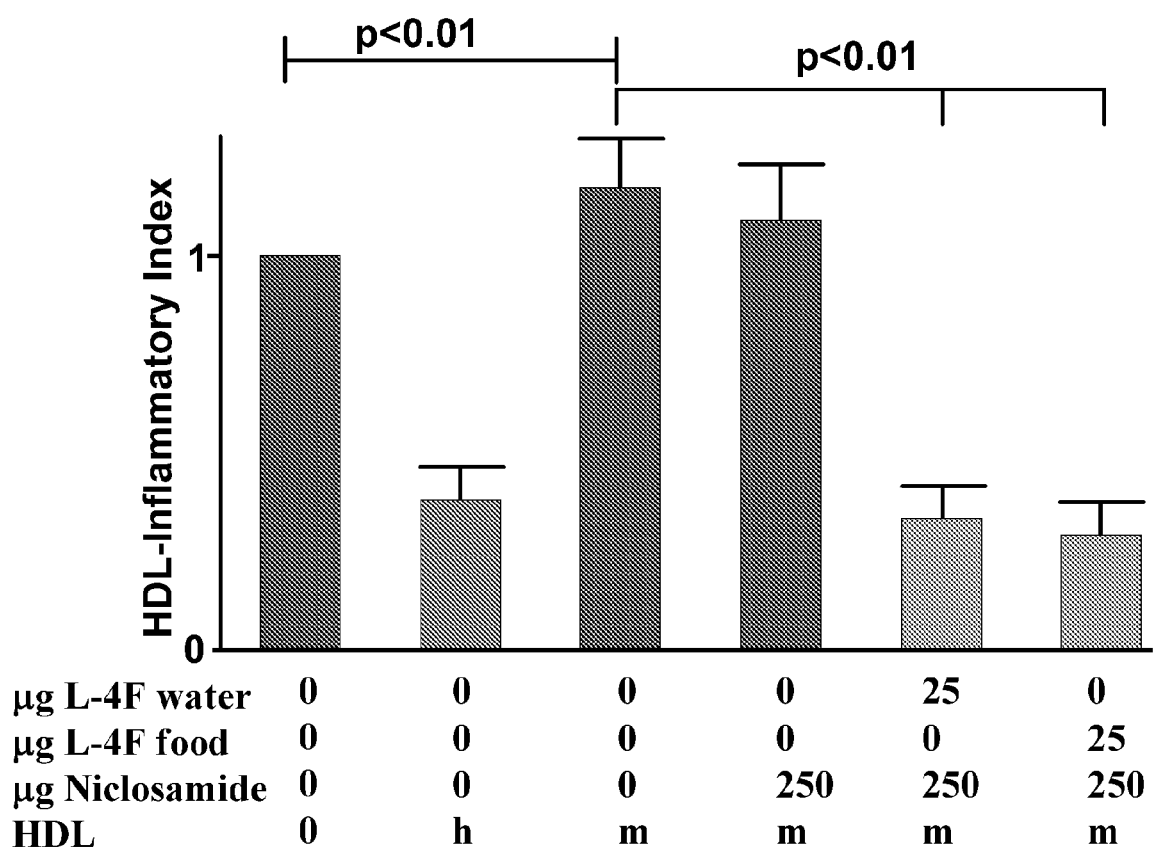
FIG. 16 shows the HDL from mice that were given niclosamide in mouse chow at 250 μg per day per mouse with or without L-4F (free base). Seven month old female apoE null mice (n=8 per treatment group) were given niclosamide in mouse chow at 250 micrograms per day per mouse with or without L-4F (free base) at 25 micrograms per day per mouse in the drinking water or in mouse chow (food) with the niclosamide. After three days the mice were bled, their plasma was fractionated by FPLC and the ability of the mouse HDL (m) to inhibit LDL-induced monocyte chemotactic activity was determined in cultures of human aortic endothelial cells and calculated as the HDL-inflammatory index as described in FIG. 8. Normal anti-inflammatory human (h) HDL was included in the assays as a positive control. The values shown are the Mean±S.D.
Figure 17:
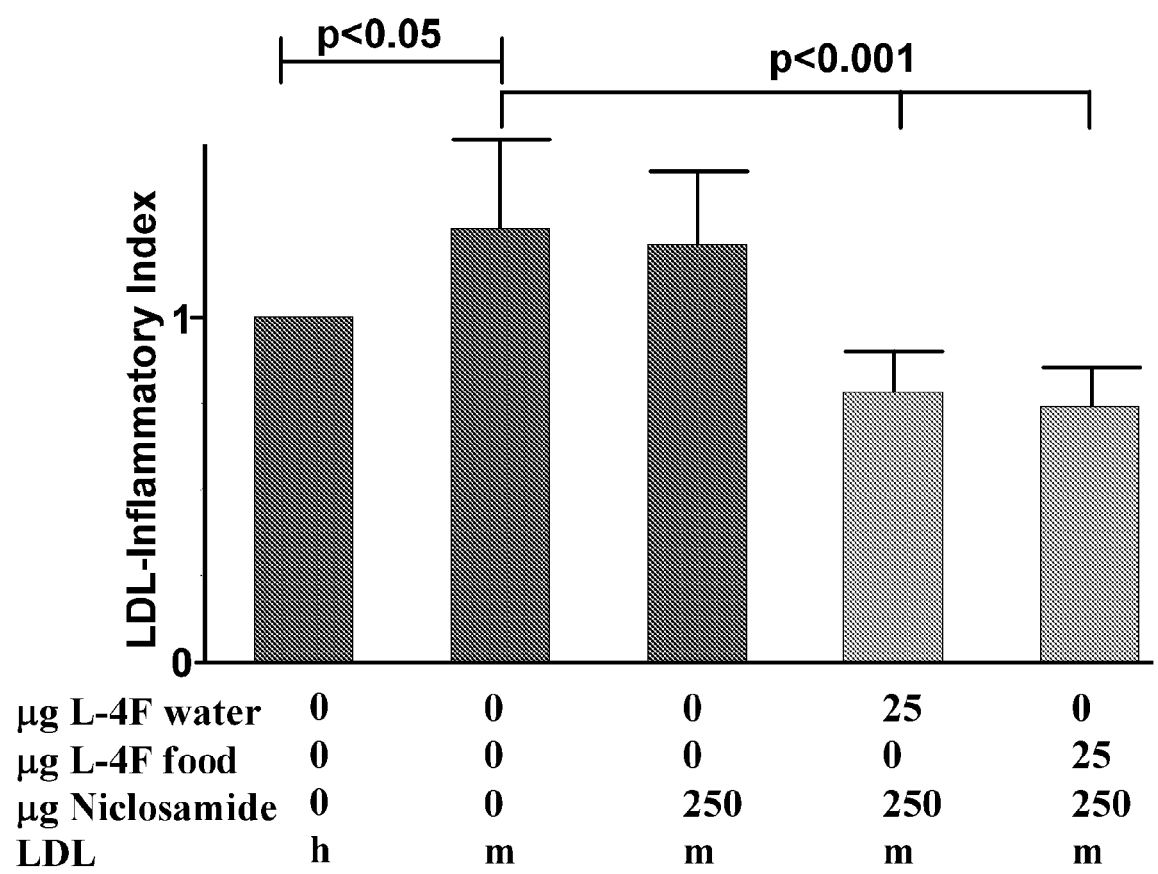
FIG. 17 shows the results of LDL from the mice (m) in FIG. 16 tested for its ability to induce monocyte chemotactic activity in cultures of human aortic endothelial cells. The data is expressed as the LDL-inflammatory index by comparing the results to the monocyte chemotactic activity induced by a standard control human (h) LDL alone, which was normalized to 1.0. The values shown are the Mean±S.D; h=human, m=mouse.

It was also a surprising finding of this invention that administration of Niclosamide in mouse chow greatly enhanced the ability of L-4F to render HDL anti-inflammatory and to decrease the ability of LDL to induce monocyte chemotactic activity in cultures of human aortic endothelial cells even when the L-4F was administered in the drinking water (see, e.g., FIGS. 16 and 17).

L-4F was previously thought to be ineffective in rendering HDL anti-inflammatory and ineffective in reducing the ability of LDL to induce monocyte chemotactic activity in cultures of human aortic endothelial cells if the peptide was given orally (see, e.g., Navab et al. (2002) Circulation, 105: 290-292). The data in FIGS. 8-17 demonstrate the surprising and unexpected finding that if L-4F is given orally with niclosamide it is highly effective in rendering HDL anti-inflammatory and highly effective in reducing the inflammatory properties of LDL. This invention also demonstrates the surprising and unexpected finding that L-4F solubilizes niclosamide.

Example 2

Salicylanilides Combined with L-4F Enhance Formation of Pre-Beta HDL

Figure 18:
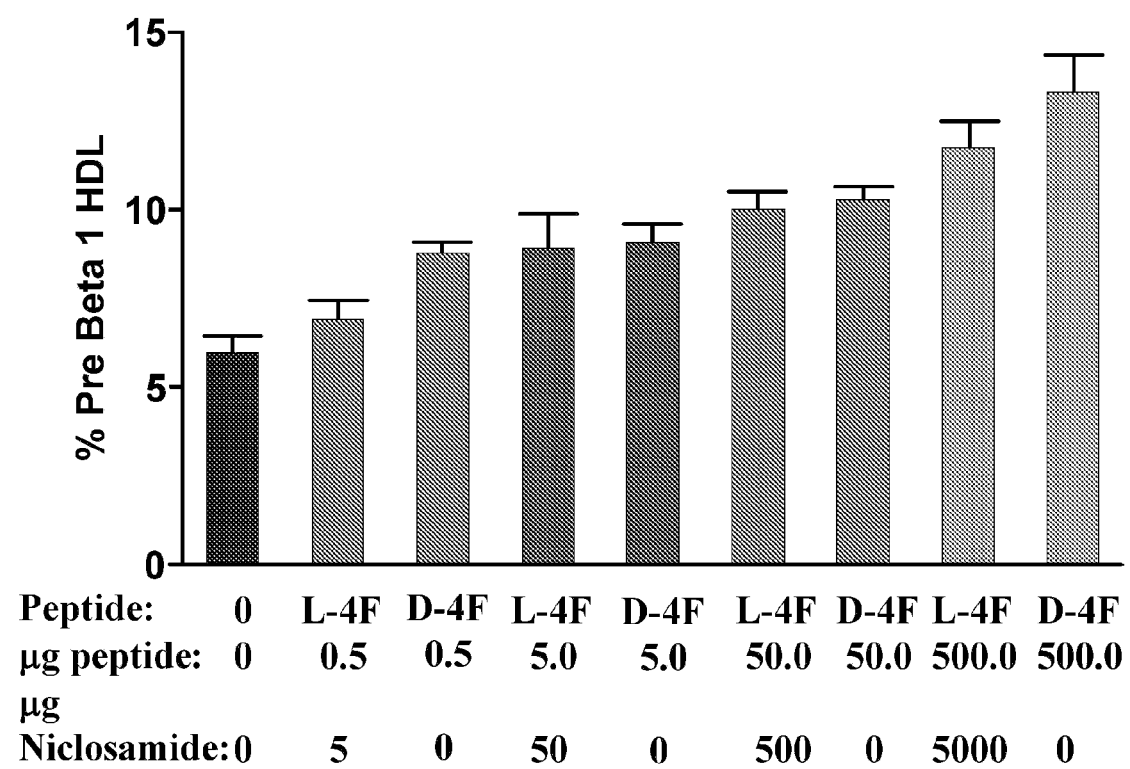
FIG. 18 shows pre-beta HDL formation in mice administered niclosamide with L-4F compared to D-4F.

Niclosamide plus L-4F causes the formation of pre-β HDL in apoE null mice after oral administration (see, e.g., FIG. 18). D-4F (free base) was dissolved in 0.1% Tween20 in ammonium bicarbonate buffer (ABCT) pH 7.0. L-4F (free base) plus niclosamide were dissolved in ABCT in a ratio of 1:10 (L-4F:Niclosamide; wt:wt). ABCT alone or ABCT containing the micrograms of L-4F or D-4F with or without the micrograms of niclosamide shown in FIG. 18 on the X-axis were administered in 100 µL by stomach tube to 8 month old female apoE null mice that were fasted overnight (n=8 per group). Thirty to forty minutes later the mice were bled and the percent of apolipoprotein A-I contained in pre-β-1 HDL was determined in triplicate 2-dimensional gels by scanning. The data shown are the Mean±S.D.

Figure 19:
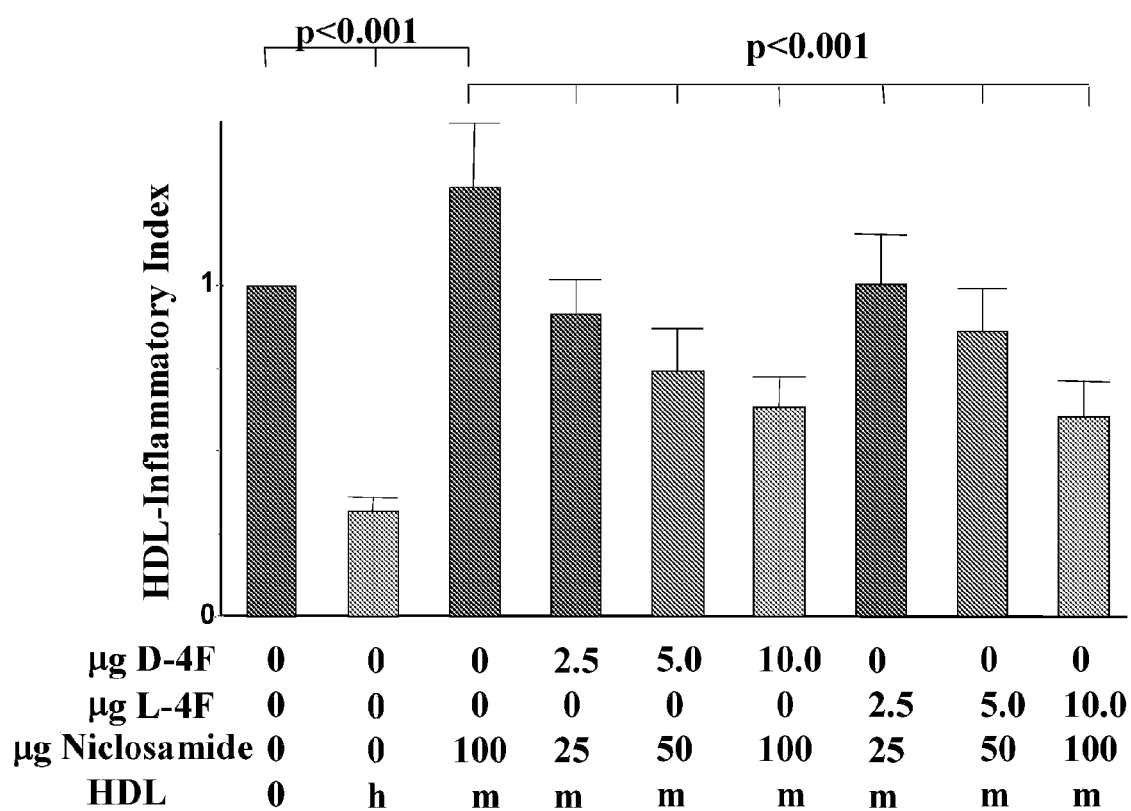
FIG. 19 shows the HDL-inflammatory index after oral administration of D-4F or L-4F. Niclosamide was homogenized with or without D-4F or L-4F (both as the free-base) in a ratio of 10:1 (nicolsamide:peptipde; wt:wt) in ABCT buffer pH 7.0 and incubated at 37° C. for 1 hour. The buffer without peptide or with the peptides at 2.5, 5.0, or 10 μg was administered to 3 month old fasting female apoE null mice (n=8 per group) in 100 μL by stomach tube. Six hours later the mice were bled and their plasma separated by FPLC and the HDL fractions from the mice were tested in cultures of human aortic endothelial cells exposed to normal human LDL to determine the HDL-inflammatory index as described in FIG. 8. In the absence of added HDL (0) the monocyte chemotactic activity obtained after addition of the normal control LDL was normalized to 1.0. The monocyte chemotactic activity after addition of the human LDL plus a normal control human HDL (h) or mouse HDL (m) was divided by the monocyte chemotactic activity obtained following addition of the human LDL without HDL to give the HDL-inflammatory index. The data shown are the Mean±S.D; h=human, m=mouse.

It was also a surprising discovery that oral co-administration of niclosamide and L-4F improved the inflammatory properties of apoE null mouse HDL (as measured in a cell-based assay) to a degree similar to that seen when niclosamide was administered with D-4F (see, e.g., FIG. 19).

Figure 20:
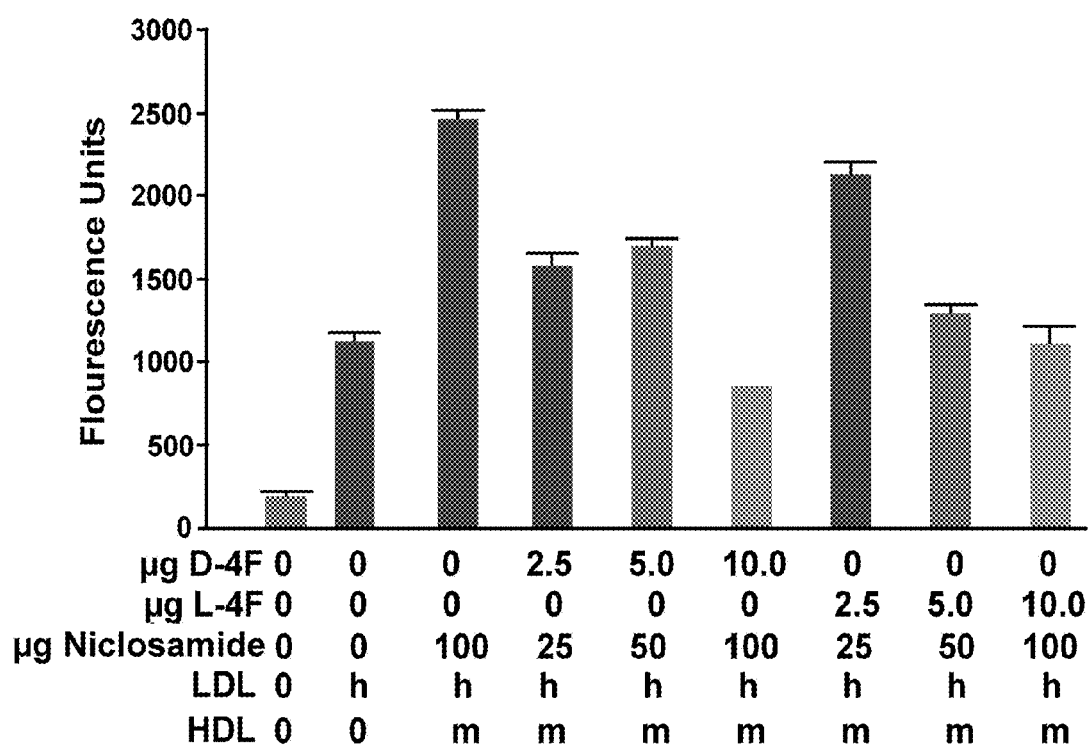
FIG. 20 shows the results of a cell-free assay of HDL taken from mice receiving oral D-4F or L-4F. The HDL from the mice described in FIG. 19 was tested in the cell-free assay. The data shown are the Mean±S.D.

Similar results were obtained when the inflammatory properties of HDL were measured by a cell-free assay (see, e.g., FIG. 20).

Figure 21:
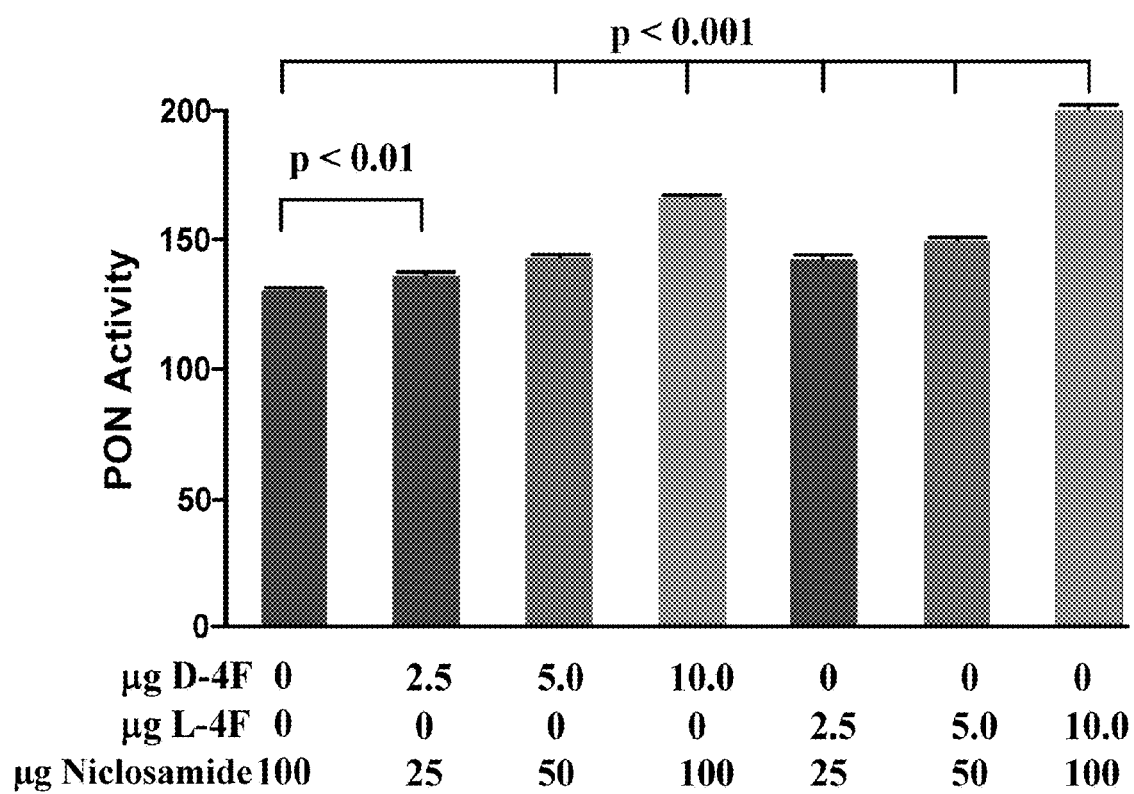
FIG. 21 shows plasma paraoxonase activity from the mice described in FIG. 19. The data shown are the Mean±S.D.

It was also a surprising discovery that when niclosamide and L-4F were co-administered orally to apoE null mice the increase in paraoxonase activity was similar to that seen when niclosamide was co-administered with D-4F (see, e.g., FIG. 21).

Figure 22:
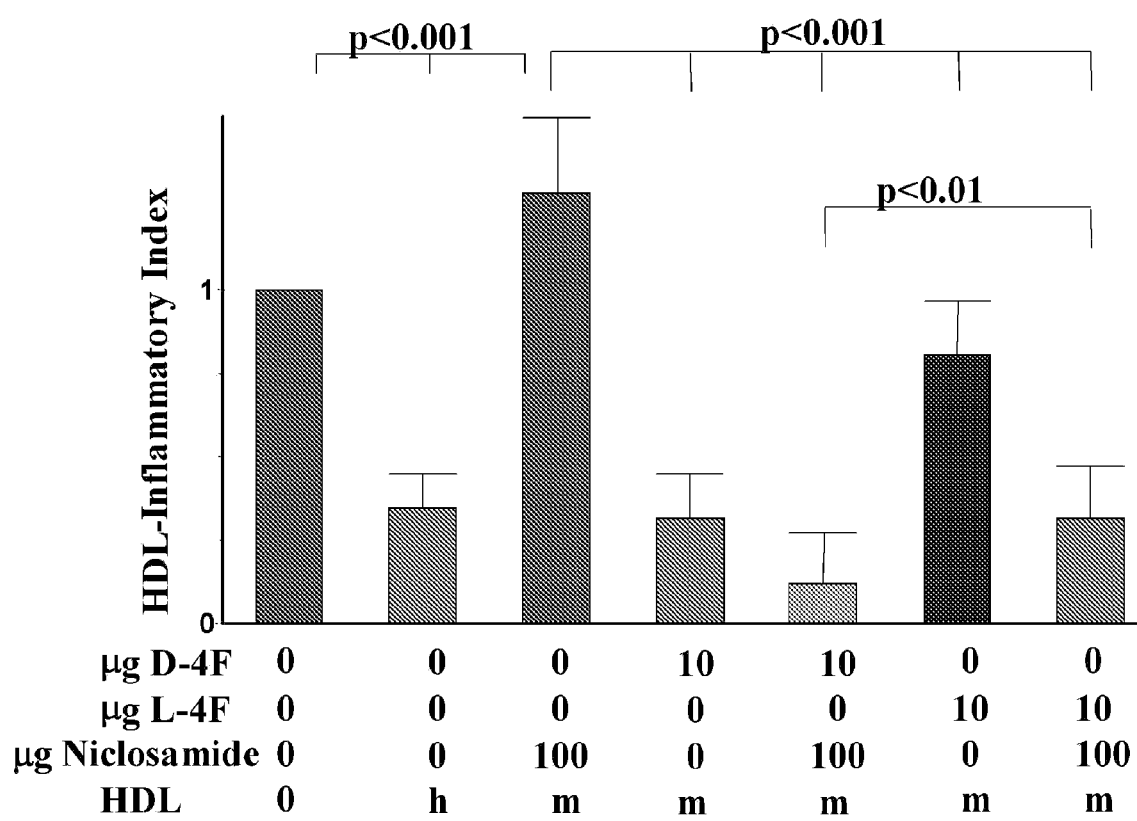
FIG. 22 shows that co-administration of niclosamide with L-4F renders apoE null mouse HDL anti-inflammatory to a degree that is similar to normal human HDL. Free base D-4F or L-4F were homogenized with or without niclosamide in a ratio of 10:1 (niclosamide:peptide; wt:wt) in ABCT buffer adjusted to pH 8.0 using 0.1 NaOH. The buffer without peptide or with the peptides at 10 μg in 100 μL was administered to 4-month-old fasting apoE null female mice (n=8 per group) by stomach tube. Seven hours later the mice were bled and their plasma separated by FPLC and the HDL fractions from the mice were tested in cultures of human aortic endothelial cells exposed to normal human LDL to determine the HDL-inflammatory index as described in FIG. 8. The data shown are the Mean±S.D; h=human, m=mouse.

Oral co-administration of niclosamide with either D-4F or L-4F enhanced the ability of both peptides to improve HDL inflammatory properties in apoE null mice. In the absence of niclosamide, however, D-4F was able to render apoE null mouse HDL anti-inflammatory to a degree comparable to normal human HDL while L-4F was only able to achieve this degree of efficacy when co-administered with niclosamide (see, e.g., FIG. 22).

Figure 23:
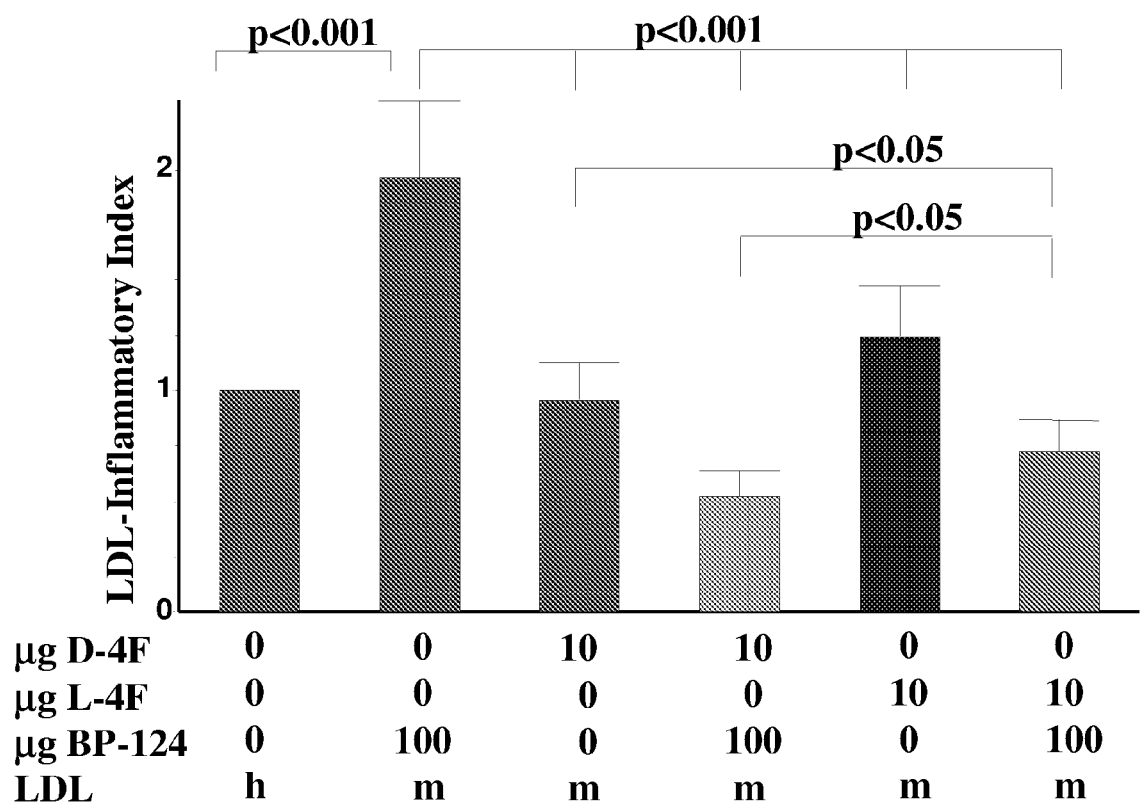
FIG. 23. The LDL-inflammatory index from the mice described in FIG. 22 was determined. The data shown are the Mean±S.D; h=human, m=mouse.

As shown in FIG. 23 the inflammatory properties of LDL from apoE null mice were reduced by the co-administration orally of niclosamide and L-4F.

Figure 24:
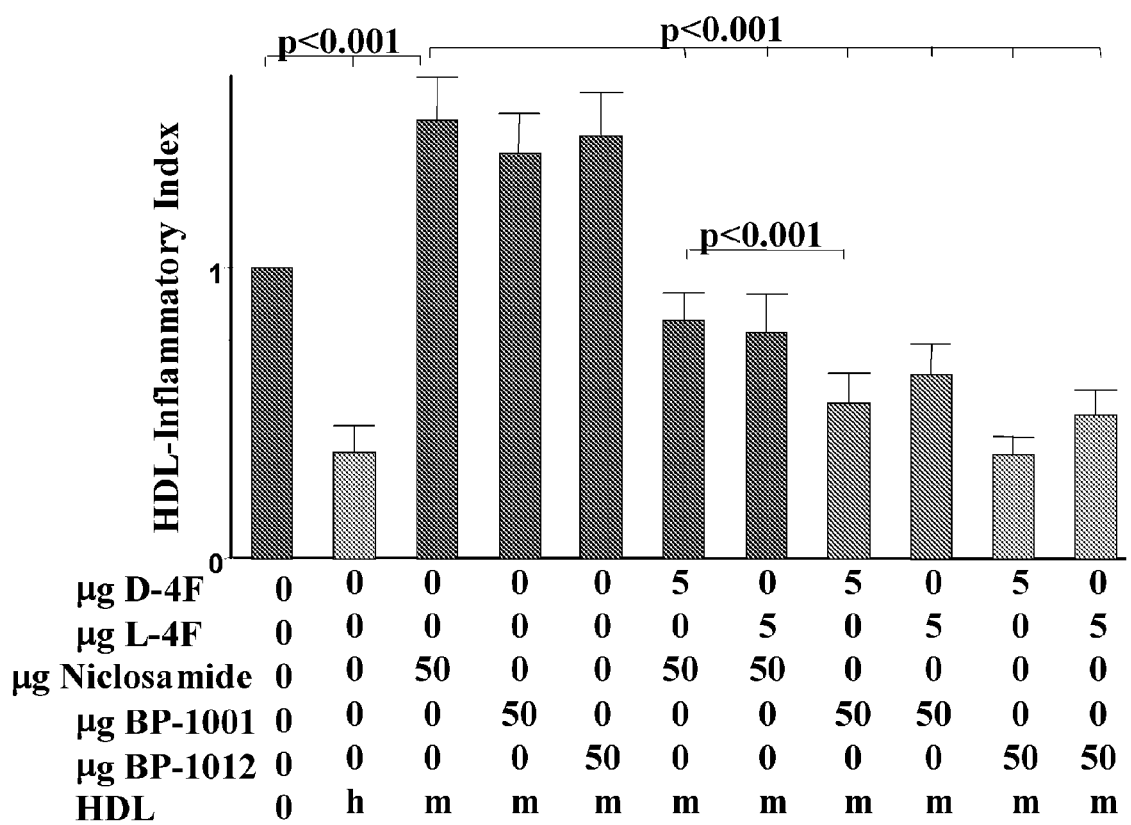
FIG. 24 shows that new salicylanilides (BP-1001 and BP-1012) are more potent than niclosamide in improving the HDL-inflammatory index. Niclosamide (BP-124) or BP-1001, or BP-1012 were homogenized with or without D-4F or L-4F (both as the free base) in a ratio of 10:1 (wt:wt) in ABCT buffer. The buffer without peptide or with peptide at 5 μg in 100 μL was administered to 4-month-old fasting apoE null mice (n=4 per group) by stomach tube. Six hours later the mice were bled and their plasma separated by FPLC and the HDL fractions from the mice were tested in cultures of human aortic endothelial cells exposed to normal human LDL to determine the HDL-inflammatory index as described in FIG. 8. The data shown are the Mean±S.D; h=human, m=mouse.
Figure 25:
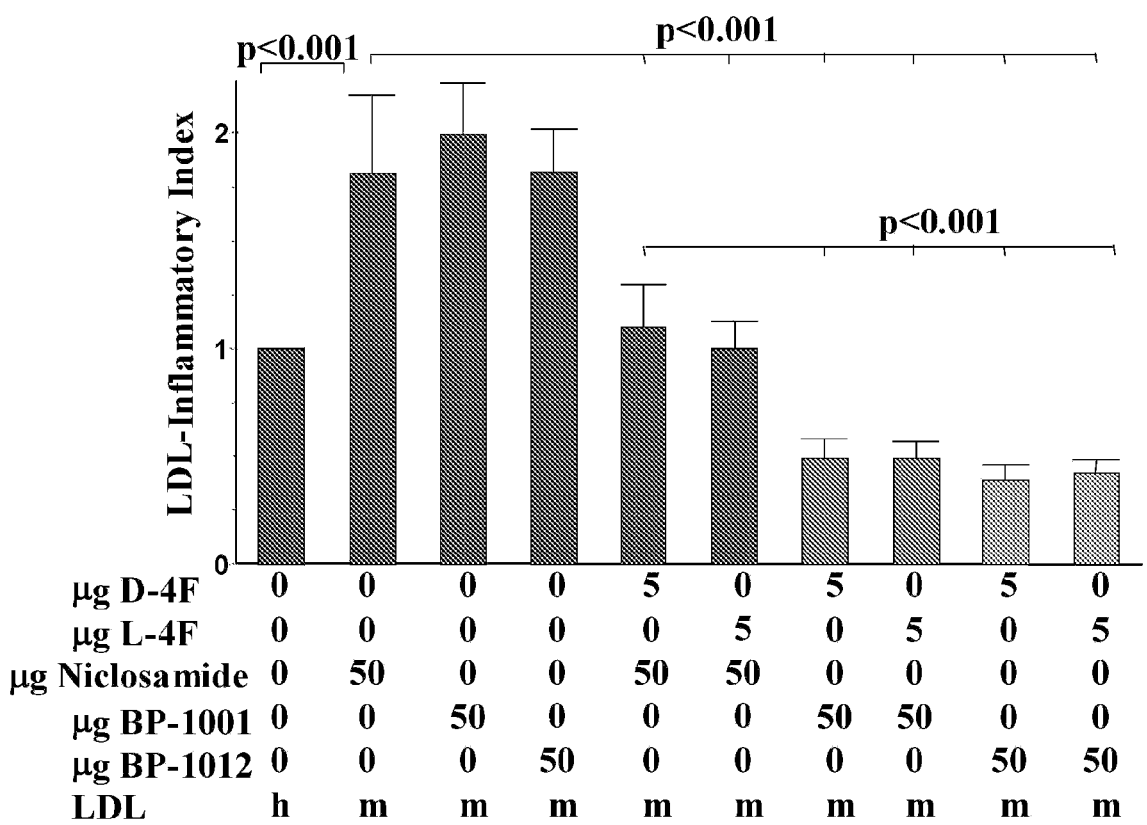
FIG. 25. The LDL-inflammatory index for LDL taken from the mice described in FIG. 24 was determined as described in FIG. 10. The data shown are the Mean±S.D; h=human, m=mouse.
Figure 26:
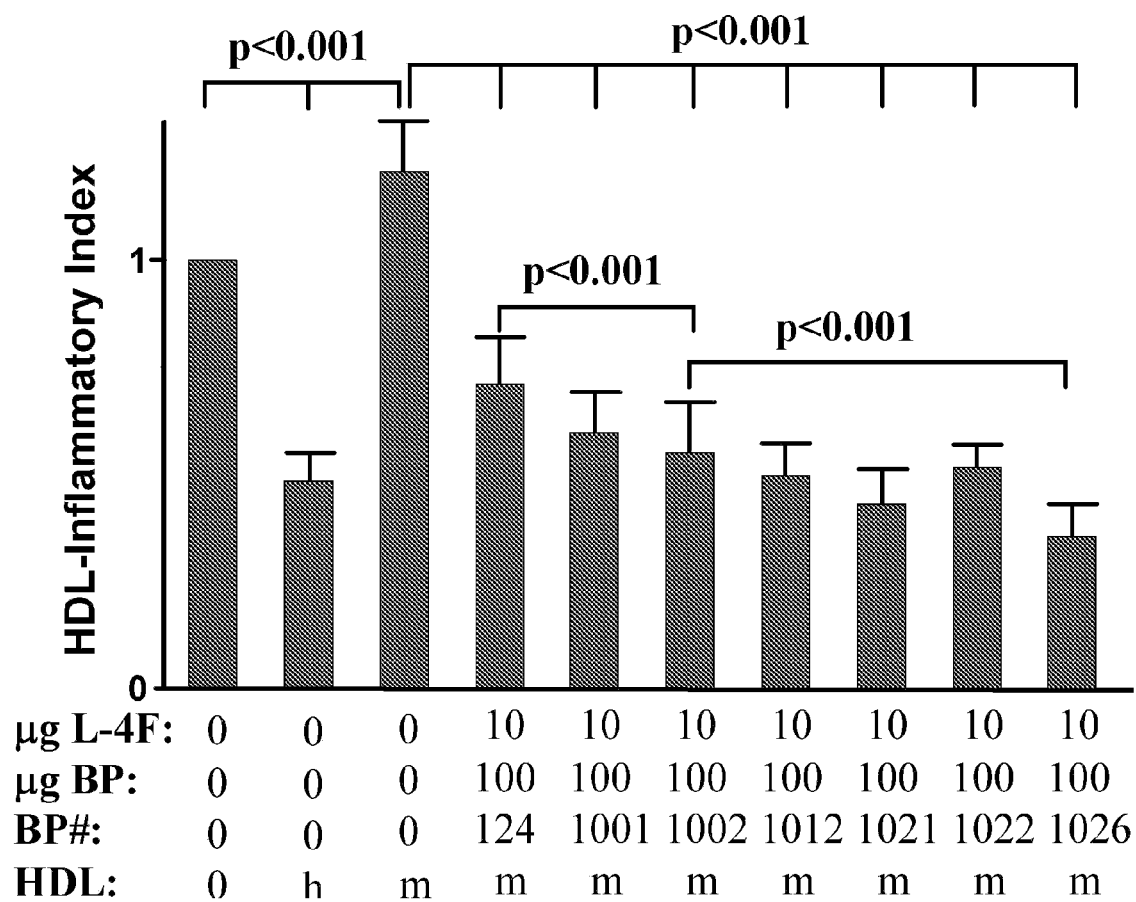
FIG. 26 shows a comparison of niclosamide (BP-124) with other salicylanilides. Niclosamide (BP-124) or the salicylanilides whose numbers (BP#) are shown on the X-axis were homogenized with L-4F (as the free base) in a ratio of 10:1 (salicylanilide:L-4F; wt:wt) in ABCT buffer which was adjusted to pH 8.0 with 0.1N NaOH. The buffer without peptide or salicylanilide or with salicylanilide at 100 μg together with L-4F at 10 μg in 100 μL was administered to 5-month-old fasting male apoE null mice (n=4 per group) by stomach tube. Eight hours later the mice were bled and their plasma separated by FPLC and the HDL fractions from the mice were tested in cultures of human aortic endothelial cells exposed to normal human LDL to determine the HDL-inflammatory index as described in FIG. 8. The data shown are the Mean±S.D; h=human, m=mouse.

It was a surprising discovery of this invention that some of the salicylanilides described in FIGS. 24-26 were even more potent than niclosamide in rendering apoE null mouse HDL anti-inflammatory when administered orally together with either D-4F or L-4F. As shown in FIG. 24 neither niclosamide nor the new salicylanilides were anti-inflammatory when administered without the peptides.

As shown in FIG. 25 the new salicylanilides (BP-1001 and BP-1012) were also more potent in reducing the inflammatory properties of LDL than niclosamide when co-administered with D-4F or L-4F.

As shown in FIG. 26, other salicylanilides were similar to niclosamide (BP-124) in bioactivity while still others were more potent.

Example 3

Niclosamide Increases L-4F Absorption in Apoe Null Mice

L-4F absorption was determined with and without niclosamide (BP-124) using $^{14}$C-L-4F. Fasted female apoE null mice 6-months of age (n=4 per group) were administered by stomach tube L-4F (21,000 dpm containing 10 micrograms of L-4F per mouse) with or without 100 micrograms of niclosamide in 200 µL 0.1% Tween20 in ammonium bicarbonate at pH 7.0. Fasting was continued and the mice were bled at the time points shown on the X-axis in FIG. 27 and the dpm per mL plasma determined. The area under the curve (AUC) in FIG. 27 for the mice receiving L-4F+niclosamide was 4.4 times greater than the AUC for the mice receiving L-4F without niclosamide.

The data indicate that one of the mechanisms by which niclosamide enhances the in vivo bioactivity of L-4F is by increasing the absorption of L-4F.

The foregoing data (Examples 1, 2, and 3) show that the combination of niclosamide or other salicylanilides with L-4F, and presumably other therapeutic peptides, appears to have great potential for oral therapy. Based on these data it is believed that the use of niclosamide or other salicylanilides with other peptides or proteins will make new oral therapeutics possible.

Figure 27:
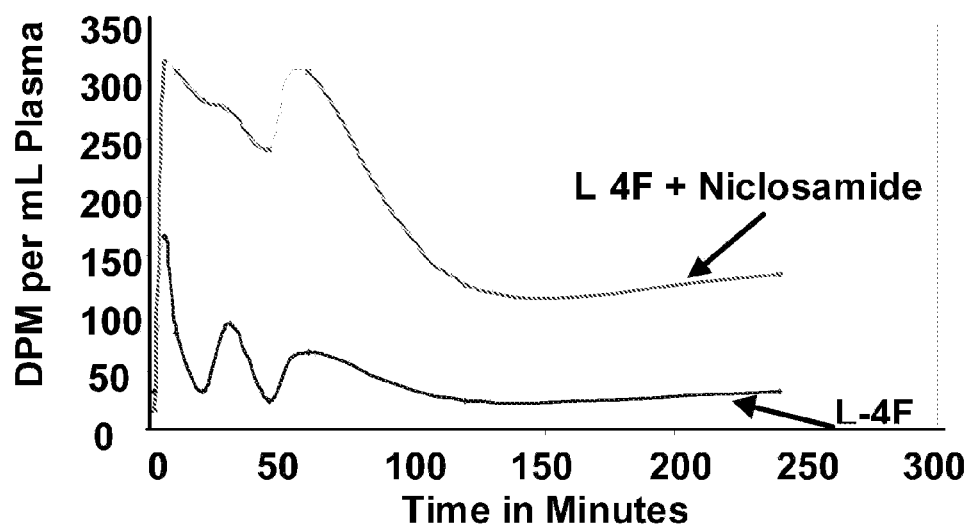
FIG. 27 shows that niclosamide increases L-4F absorption in apoE null mice. Fasted apoE null mice 6-months of age (n=4 per group) were administered by stomach tube $^{14}$C-L-4F (21,000 dpm containing 10 micrograms of L-4F per mouse) with or without 100 micrograms of niclosamide in 200 microliters. Fasting was continued and the mice were bled at the time points shown on the X-axis and the dpm per mL plasma determined.

The data in FIG. 27 indicate that without niclosamide administration of $^{14}$C-L-4F by stomach tube resulted in low plasma levels that lasted no more than 5 minutes. In contrast, when $^{14}$C-L-4F was administered with niclosamide a $C_{max}$ of approximately 150 nanograms/mL was achieved which persisted for more than an hour and at a lower level for up to four hours.

Figure 28:
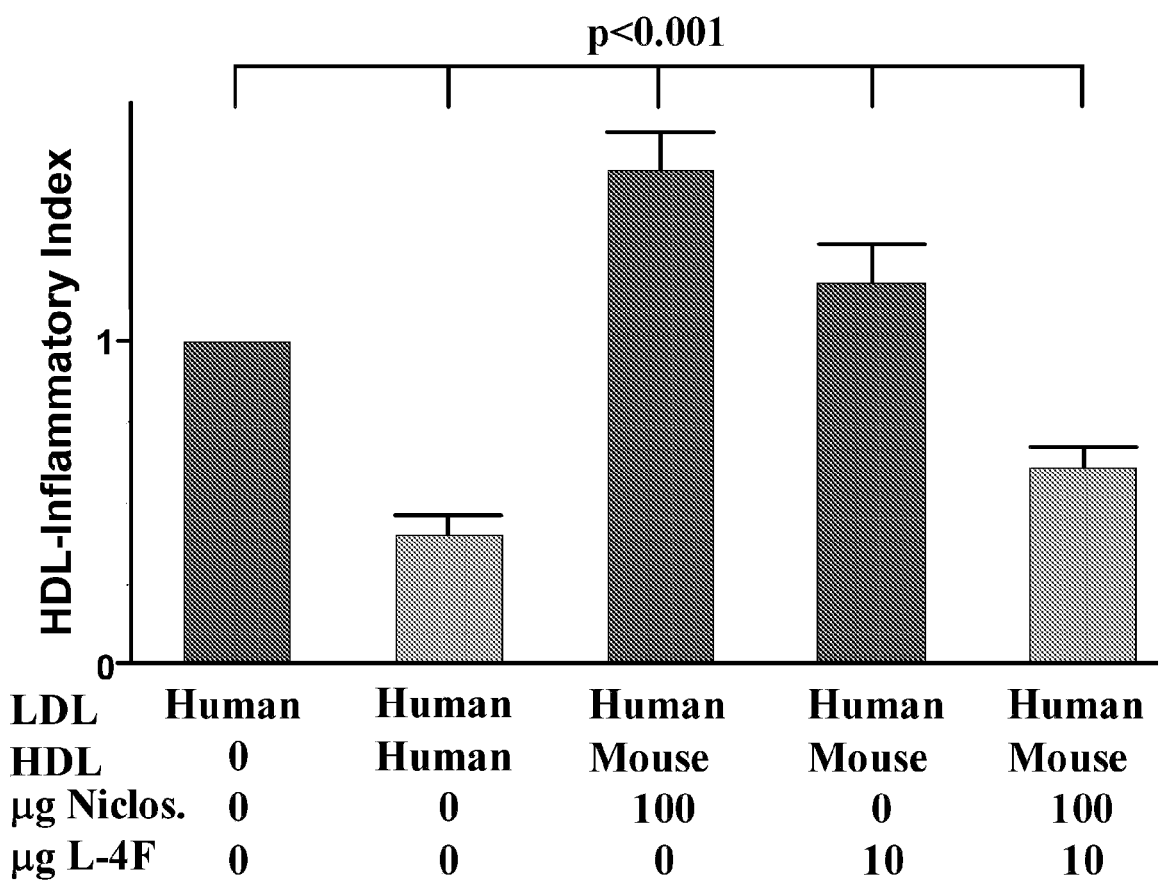
FIG. 28 demonstrates that the $^{14}$C-L-4F used in FIG. 27 was biologically active. The HDL inflammatory index was determined as described in FIG. 8 after administration of the compounds shown in FIG. 27.

The data in FIG. 28 demonstrate that the $^{14}$C-L-4F used in FIG. 28 was biologically active when given with niclosamide. Fasted apoE null mice 5-months of age (n=4 per group) were administered by stomach tube $^{14}$C-L-4F (21,000 dpm containing 10 µg of L-4F per mouse) with or without 100 µg of niclosamide (Niclos.) in 200 µL. Fasting was continued and the mice were bled 5 hours later and the HDL inflammatory index determined in cultures of human aortic endothelial cells as described in FIG. 8. Briefly, To determine the HDL-inflammatory index lipoproteins were added to human aortic endothelial cell cultures as described previously (Navab et al. (2005) *Circulation Research* 97: 524-532). A normal control human LDL was added to each well in triplicate at a final concentration of 100 µg/mL of LDL-cholesterol. A normal human HDL was added to three wells containing human LDL at a final concentration of 50 µg/mL HDL-cholesterol as a positive control. HDL from the mice at a final concentration of 50 µg/mL HDL-cholesterol was added in triplicate to other wells containing human LDL. After 8 hours of culture the supernatants were removed and monocyte chemotactic activity was determined as previously described (Navab et al. (2001) *J. Lipid Res.*, 42: 1308-1317; Danciger et al. (2004) *J. Immunol. Meth.*, 288: 123-124). The values obtained from wells containing the human LDL but no HDL were normalized to 1.0. The values obtained from wells containing the human LDL with either human or mouse HDL were divided by the values obtained from wells with human LDL without added HDL to give the HDL-inflammatory index as previously described (Ansell et al. (2003) *Circulation* 108: 2751-2756). The data in FIG. 28 demonstrate that the $^{14}$C-L-4F used in the experiments described in FIG. 27 was biologically active.

Example 4

Figure 29:
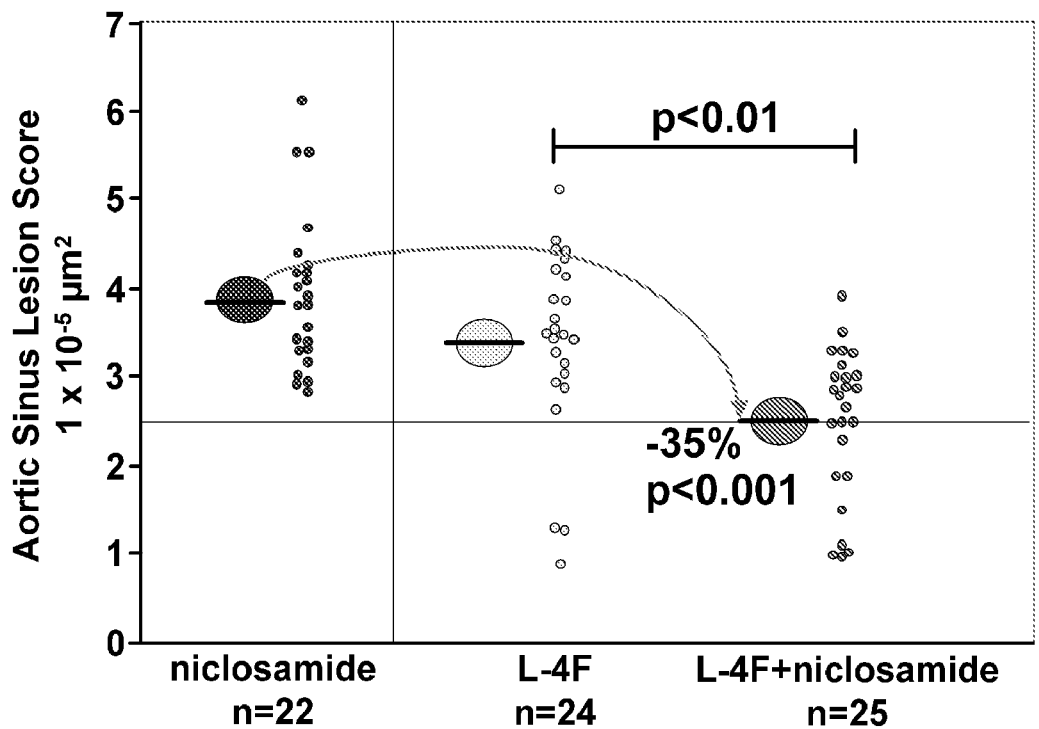
FIG. 29 shows aortic sinus lesion score in apoE null mice receiving oral doses of niclosamide, L-4F, or niclosamide together with L-4F. Seventeen week old female apoE null mice who were on chow were divided into three groups and the following additions were made to the chow for each group: Group I: Niclosamide at 250 micrograms/mouse/day; Group II: L-4F at 25 micrograms/mouse/day; Group III: L-4F at 25 micrograms/mouse/day plus Niclosamide at 250 micrograms/mouse/day. All groups received 50 micrograms/mouse/day of pravastatin in their drinking water. After 14 weeks the mice were sacrificed and aortic sinus lesion area was determined as described previously (Navab et al. (2005) *Arterioscler. Thromb. Vasc. Biol.*, 25: 1426-1432).
Figure 30:
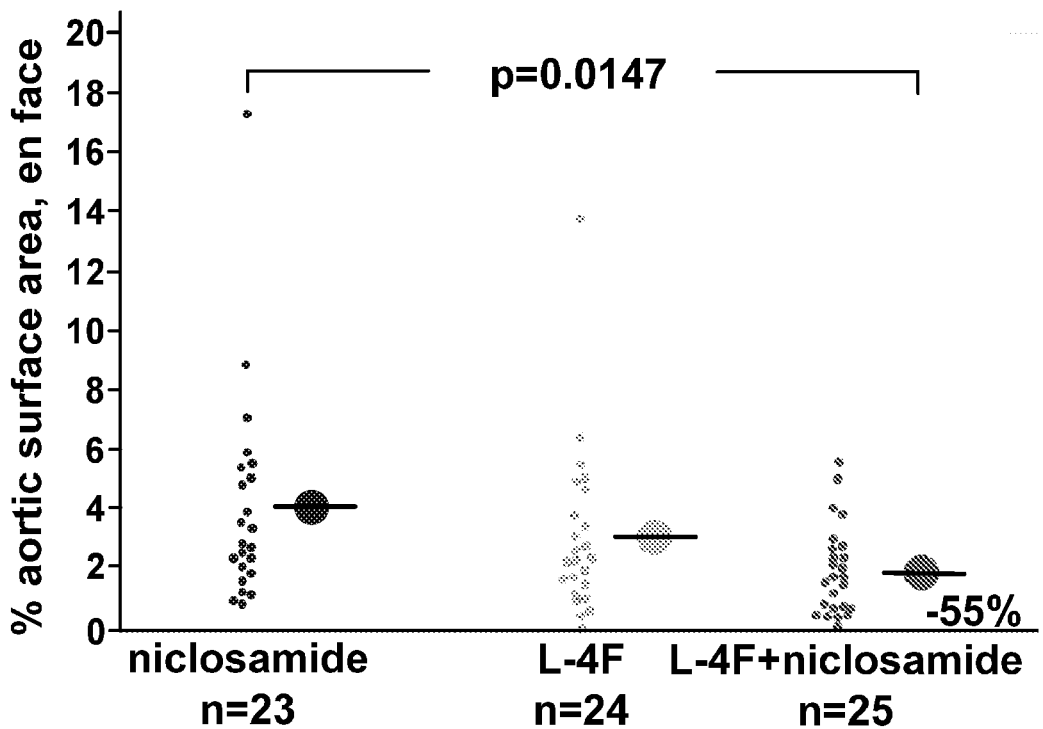
FIG. 30 shows the percent aortic surface area determined by en face analysis for the mice described in FIG. 29.
Figure 31:
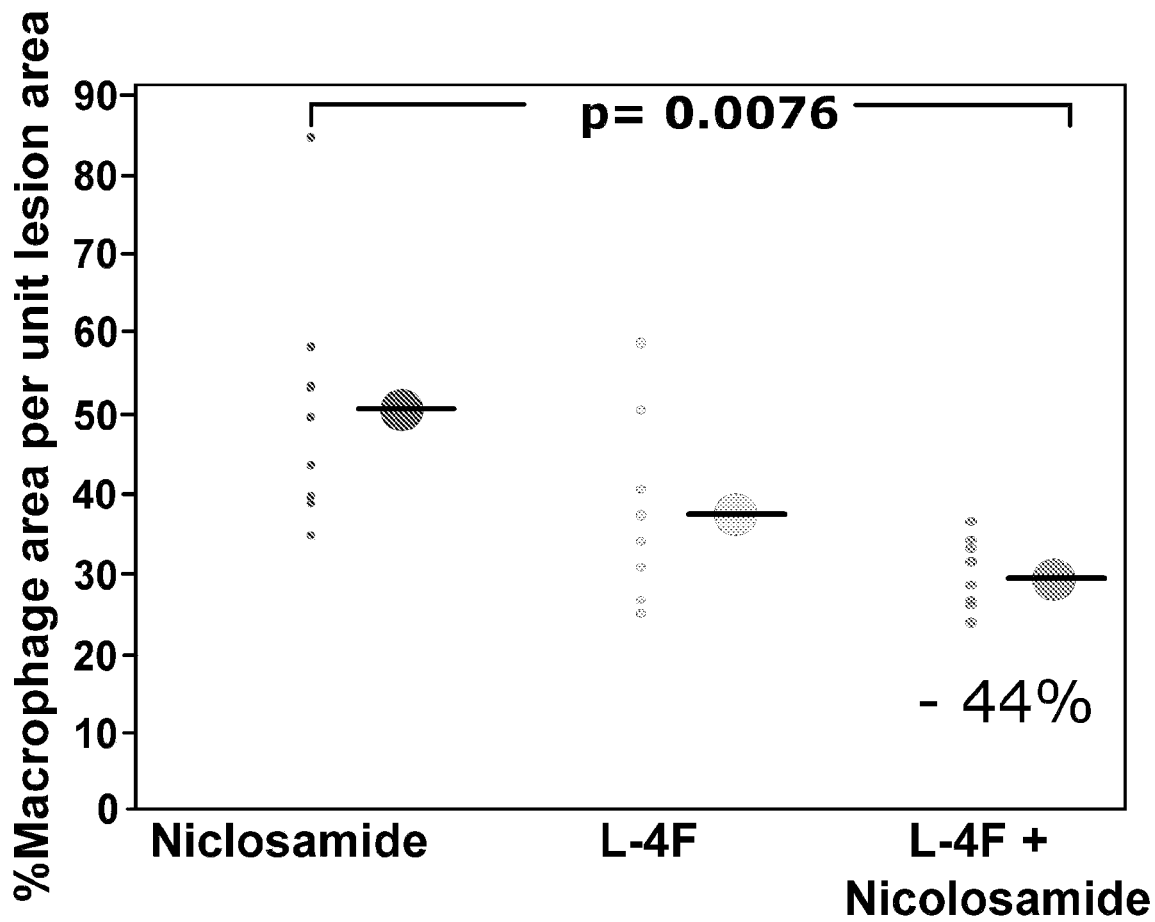
FIG. 31 shows the percent macrophage lesion area for the mice described in FIG. 29.

Niclosamide Plus L-4F Administered Orally (but not L-4F Alone) Reduces Lesions in Mouse Models of Atherosclerosis In another experiment, seventeen week old female apoE null mice were divided into three groups: Group I received niclosamide 250 µg/mouse/day in rodent chow. Group II received L-4F at 25 µg/mouse/day in rodent chow. Group III received niclosamide at 250 µg/mouse/day together with L-4F 25 µg/mouse/day in rodent chow. All three groups received pravastatin 50 µg/mouse/day in drinking water. After 14 weeks the mice were sacrificed and aortic sinus lesion area was determined. As shown in FIGS. 29-31 oral administration of L-4F together with niclosamide but not without niclosamide significantly inhibits atherosclerosis in apoE Null mice.

Figure 32:
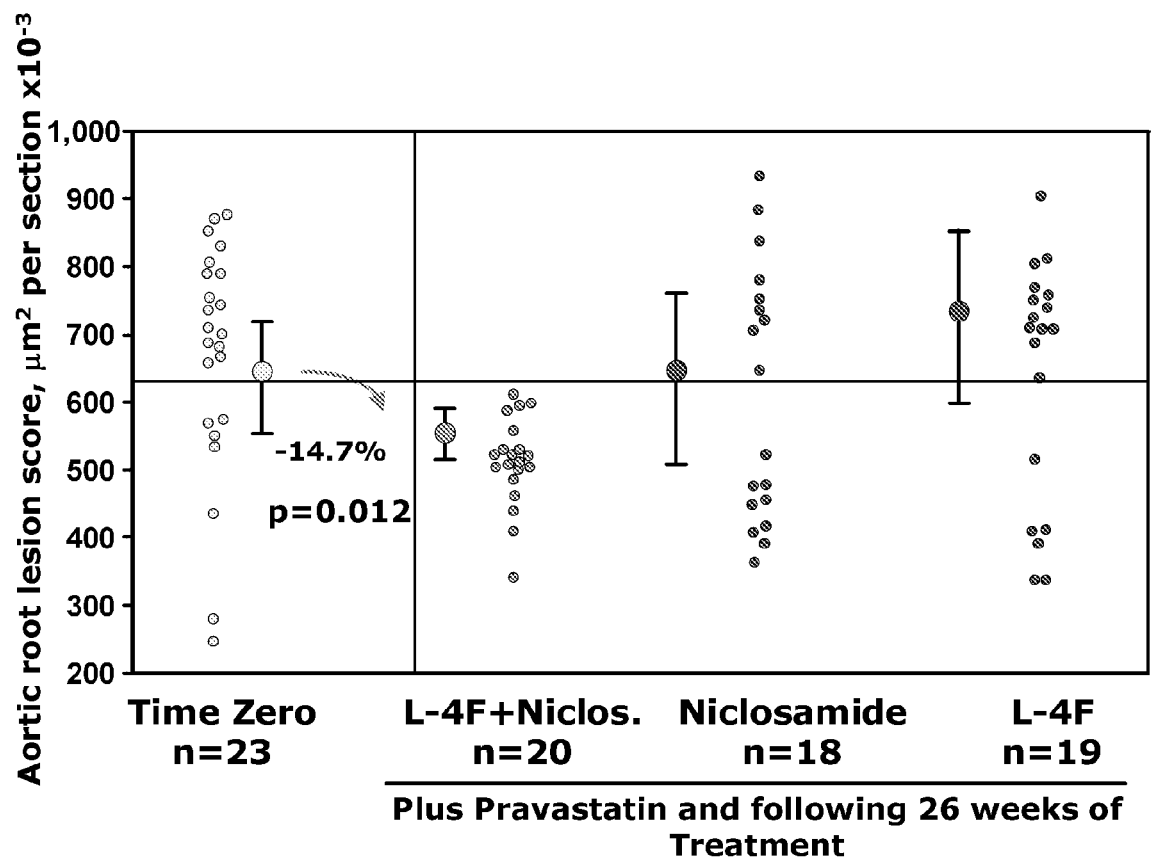
FIG. 32 shows that oral administration of L-4F together with niclosamide causes lesion regression in old apoE null mice. Ninety-five female apoE null mice age 9.5 months from the UCLA breeding colony were identified. Twenty-three were sacrificed at time Zero (Group I) to establish lesion area at the start of the experiment. The remainder of the mice were divided into three groups of 24 mice each and the following additions were made to the chow for each group: Group II: Niclosamide at 2,000 micrograms/mouse/day; Group III: L-4F at 200 micrograms/mouse/day; Group IV: L-4F at 200 micrograms/mouse/day plus Niclosamide at 2,000 micrograms/mouse/day. All groups received 50 micrograms/mouse/day of pravastatin in their drinking water. At the veterinarian's request because of fighting and/or ulcerative dermatitis mice were euthanized prior to the end of the experiment as follows: 6 mice from Group II; 5 mice from Group III; 4 mice from Group IV. After six months the remaining mice were sacrificed and aortic sinus lesion area was determined as described previously (Id.).
Figure 33:
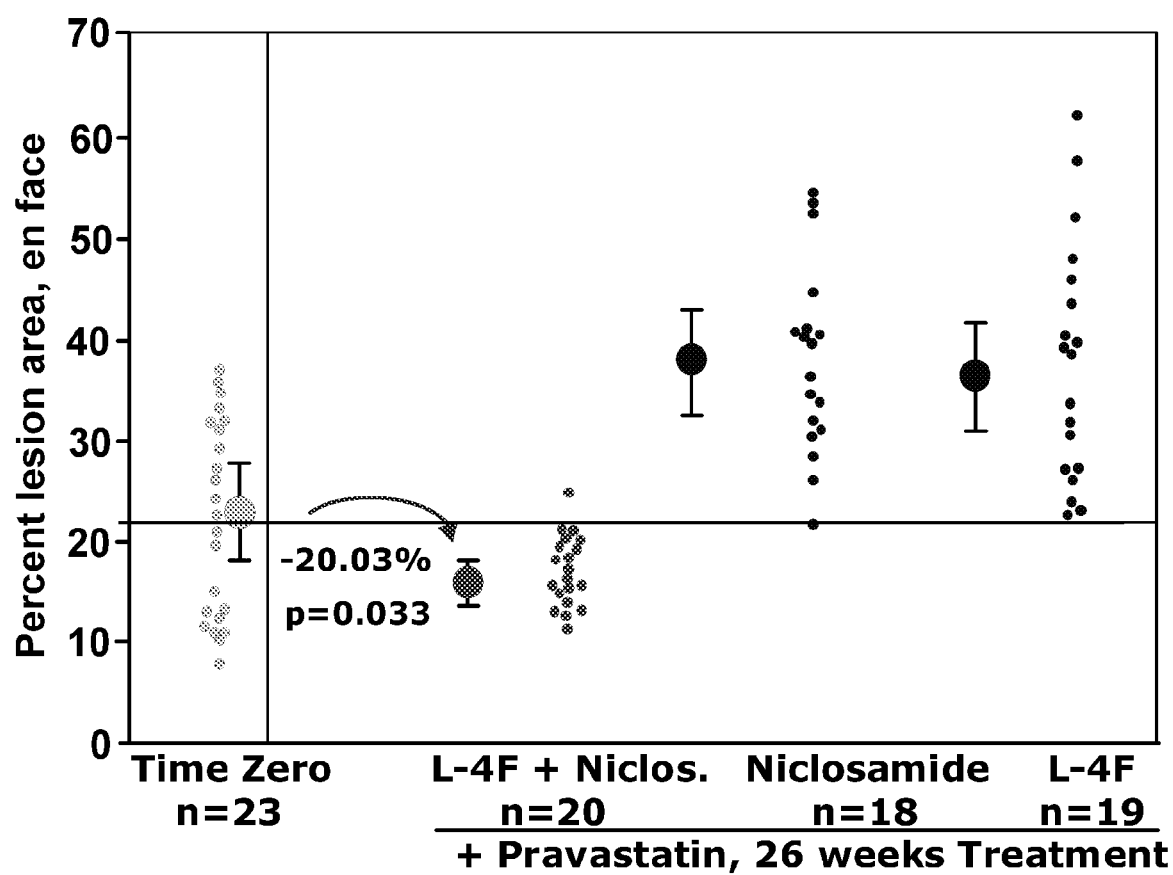
FIG. 33 shows the percent aortic surface lesion area determined by en face analysis for the mice described in FIG. 32.
Figure 34:
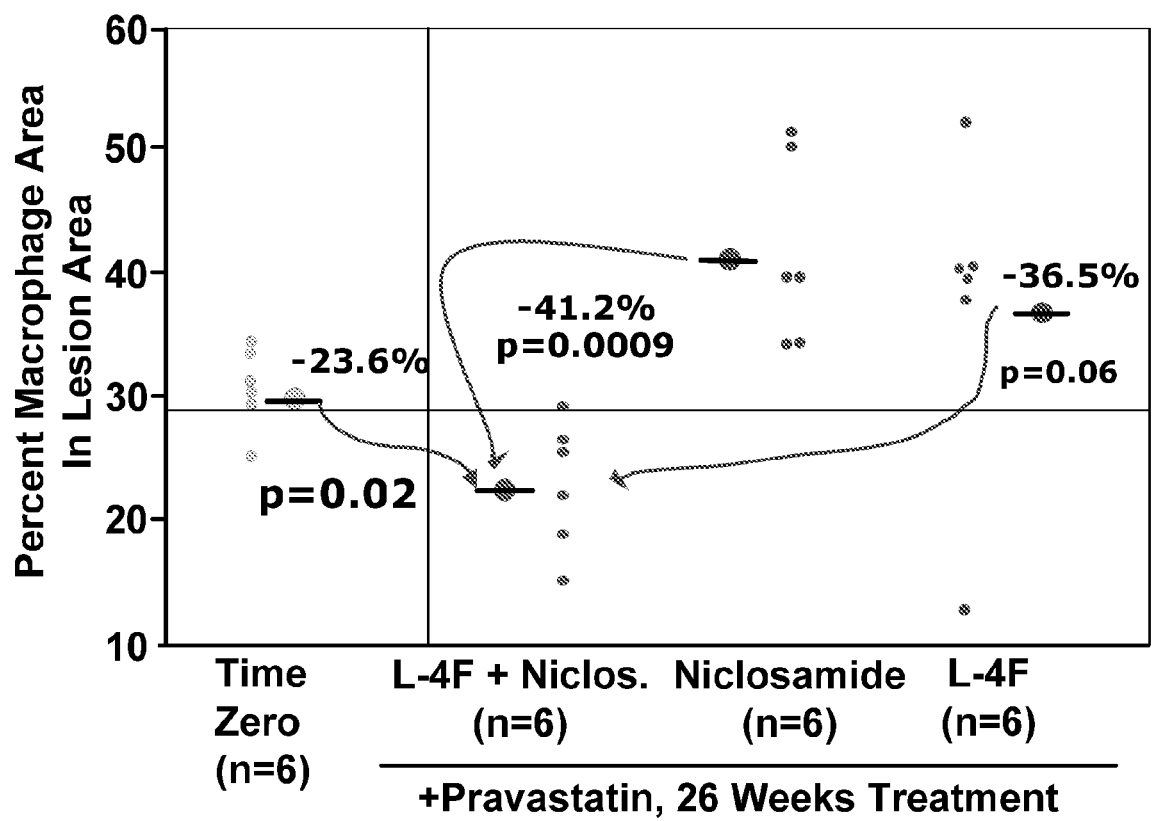
FIG. 34 shows the percent macrophage lesion area for the mice described in FIG. 32.

In still another experiments, nine and half months-old female apoE null mice were divided into four groups: Group I was sacrificed to establish base line lesion area (Time Zero). Group II received niclosamide at 2 mg/mouse/day in rodent chow. Group III received L-4F at 200 µg/mouse/day in rodent chow. Group IV received niclosamide (Niclos.) at 2 mg/mouse/day together with L-4F 200 µg/mouse/day in rodent chow. Groups II-IV received pravastatin 50 µg/mouse/day in drinking water. After 26 weeks the mice were sacrificed and aortic sinus lesion area was determined. The data in FIGS. 32-34 demonstrate that the combination of L-4F plus niclosamide caused lesion regression in old apoE null mice. In contrast, neither niclosamide nor L-4F without niclosamide significantly reduced lesions.

L-4F forms a class A amphipathic helix. The sequence comprising residues 113-122 in apolipoprotein J (apoJ) comprises a potential G* helix. Administration of this peptide synthesized from all D-amino acids, D-[113-122]apoJ, dramatically improved HDL inflammatory properties and reduced atherosclerosis in apoE null mice (Navab et al. (2005) *Arterioscler. Thromb. Vasc. Biol.* 25: 1932-1937).

Figure 35:
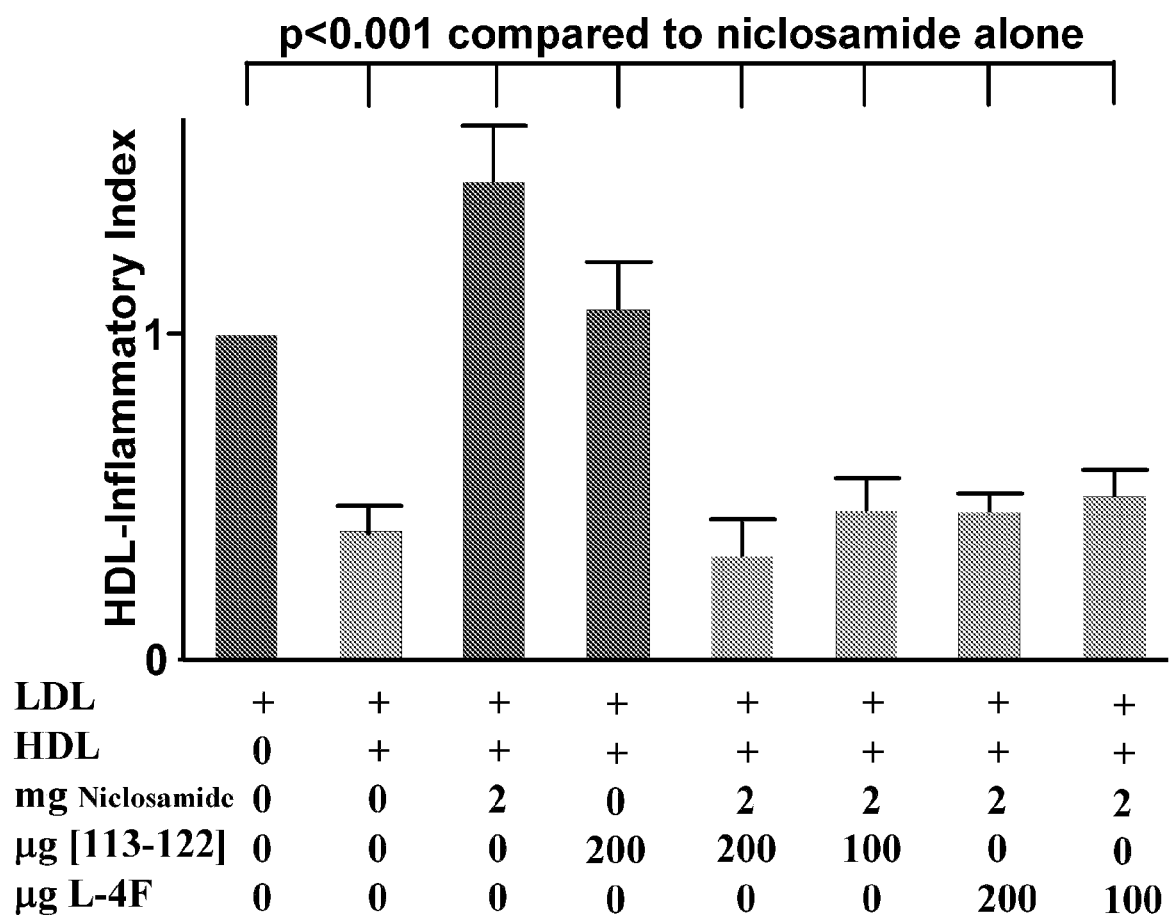
FIG. 35 shows the HDL-inflammatory index determined for apoE-null mice administered L-[113-122]apoJ or L-4F with and without niclosamide. Ten month old apoE null mice (n=4 per group) were administered by stomach tube 2 mg of niclosamide or 200 micrograms of L-[113-122]apoJ or 2 mg of niclosamide plus 200 micrograms of L-[113-122]apoJ. Eight hours later the mice were bled, their plasma separated by FPLC and the HDL-inflammatory index determined as described in FIG. 8. The data shown are Mean±S.D.

To determine whether niclosamide could improve activity of the L-form of apoJ, ten month old apoE null mice (n=4 per group) were administered by stomach tube 2 mg of niclosamide or 200 µg of L-[113-122]apoJ or 2 mg of niclosamide together with 100 or 200 µg of L-[113-122]apoJ or were administered 2 mg of niclosamide together with 100 or 200 µg of L-4F. Eight hours later the mice were bled and the HDL inflammatory index was determined in cultures of human aortic endothelial cells as described in FIG. 8. As shown in FIG. 35 oral administration of the same peptide but synthesized from all L-amino acids and administered with niclosamide rendered apoE null mouse HDL anti-inflammatory to the same degree as normal human HDL, but when the peptide was administered orally without niclosamide this was not the case.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of mitigating one or more symptoms of atherosclerosis in a mammal, said method comprising:

orally administering to said mammal an effective amount of a "D" or "L" peptide and niclosamide, wherein said peptide ranges in length from about 18 to about 50 amino acids and comprises an amino acid sequence selected from the group consisting of peptide D-W-F-K-A-F-Y-D-K-V-A-E-K-F-K-E-A-F (4F, SEQ ID NO:5), F-A-E-K-F-K-E-A-V-K-D-Y-F-A-K-F-W-D (retro 4F, SEQ ID NO: 104), D-W-L-K-A-F-Y-D-K-F-F-E-K-F-K-E-F-F (6F, SEQ ID NO:7), and F-F-E-K-F-K-E-F-F-K-D-Y-F-A-K-L-W-D (retro 6F, SEQ ID NO:537).

2. The method of claim 1, wherein said niclosamide is administered before said peptide.

3. The method of claim 1, wherein said niclosamide is administered simultaneously with peptide.

4. The method of claim 1, wherein said niclosamide and said peptide are administered as a single formulation.

5. The method of claim 1, wherein said niclosamide and said peptide are combined to form an adduct prior to administration.

6. The method of claim 1, wherein all the amino acids of said peptide are "D" amino acids.

7. The method of claim 1, wherein all the amino acids of said peptide are "L" amino acids.

8. The method of claim 1, wherein said peptide comprises a protecting group at the amino or carboxyl terminus.

9. The method of claim 8, wherein said protecting group is a protecting group selected from the group consisting of acetyl, amide, and 3 to 20 carbon alkyl groups, Fmoc, Tboc, 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethylbenzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), Benzyloxymethyl (Bom), t-butoxycarbonyl (Boc), cyclohexyloxy (cHxO),t-butoxymethyl (Bum), t-butoxy (tBuO), t-Butyl (tBu), Acetyl (Ac), and Trifluoroacetyl (TFA).

10. The method of claim 8, wherein said peptide comprises a first protecting attached to the amino terminus and a second protecting group attached to the carboxyl terminus.

11. The method of claim 10, wherein said first protecting group is a protecting group selected from the group consisting of acetyl, propionyl, and a 3 to 20 carbon alkyl.

12. The method of claim 10, wherein said second protecting group is an amide.

13. The method of claim 1, wherein said niclosamide and said peptide are administered as a unit dosage formulation.

14. The method of claim 1, wherein said niclosamide and said peptide are administered as a unit dosage formulation formulated so that the niclosamide is released or solubilized before the peptide.

15. The method of claim 1, wherein said peptide has a formula selected from the group consisting of Ac-D-W-F-K-A-F-Y-D-K-V-A-E-K-F-K-E-A-F-NH$_2$ (4F, SEQ ID NO:5), Ac-F-A-E-K-F-K-E-A-V-K-D-Y-F-A-K-F-W-D-NH$_2$ (retro 4F, SEQ ID NO: 104), Ac-D-W-L-K-A-F-Y-D-K-F-F-E-K-F-K-E-F-F-NH$_2$ (6F, SEQ ID NO:7), and Ac-F-F-E-K-F-K-E-F-F-K-D-Y-F-A-K-L-W-D-NH$_2$ (retro 6F, SEQ ID NO:537).

16. The method of claim 1, wherein said peptide consists of all "L" amino acids and the amino acid sequence of said peptide consists of the sequence D-W-L-K-A-F-Y-D-K-F-F-E-K-F-K-E-F-F (SEQ ID NO:7).

17. The method of claim 16, wherein said peptide has the formula: Ac-D-W-L-K-A-F-Y-D-K-F-F-E-K-F-K-E-F-F-NH$_2$ (6F, SEQ ID NO:7).

18. The method of claim 1, wherein said peptide consists of all "L" amino acids and the amino acid sequence of said peptide consists of the sequence F-F-E-K-F-K-E-F-F-K-D-Y-F-A-K-L-W-D (SEQ ID NO:537).

19. The method of claim 18, wherein said peptide has the formula Ac-F-F-E-K-F-K-E-F-F-K-D-Y-F-A-K-L-W-D-NH$_2$(SEQ ID NO:537).

20. The method of claim 1, wherein said peptide consists of all "L" amino acids and the amino acid sequence of said peptide consists of the sequence D-W-F-K-A-F-Y-D-K-V-A-E-K-F-K-E-A-F (SEQ ID NO:5).

21. The method of claim 1, wherein said peptide has the formula Ac-D-W-F-K-A-F-Y-D-K-V-A-E-K-F-K-E-A-F-NH$_2$ (SEQ ID NO:5).

22. The method of claim 1, wherein said peptide consists of all "L" amino acids and the amino acid sequence of said peptide consists of the sequence F-A-E-K-F-K-E-A-V-K-D-Y-F-A-K-F-W-D (SEQ ID NO: 104).

23. The method of claim 22, wherein said peptide has the formula Ac-F-A-E-K-F-K-E-A-V-K-D-Y-F-A-K-F-W-D-NH$_2$ (SEQ ID NO: 104).

* * * * *

UNITED STATES PATENT AND TRADEMARK OFFICE
CERTIFICATE OF CORRECTION

| | | |
|---|---|---|
| PATENT NO. | : 8,148,328 B2 | |
| APPLICATION NO. | : 11/835338 | |
| DATED | : April 3, 2012 | |
| INVENTOR(S) | : Alan M. Fogelman and Mohamad Navab | |

It is certified that error appears in the above-identified patent and that said Letters Patent is hereby corrected as shown below:

Column 1, lines 16-18, change "This work was supported, in part, by USPHS Grant 2 P01 HL-030568. The government of the United States of America may possess certain rights in this invention." to -- This invention was made with Government support under Grant No. HL030568 awarded by the National Institutes of Health. The Government has certain rights in this invention. --.

Signed and Sealed this
Twenty-seventh Day of November, 2012

David J. Kappos
*Director of the United States Patent and Trademark Office*

```
                              SEQUENCE LISTING

<160> NUMBER OF SEQ ID NOS: 995

<210> SEQ ID NO 1
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 1

Asp Trp Leu Lys Ala Phe Tyr Asp Lys Val Ala Glu Lys Leu Lys Glu
1               5                   10                  15

Ala Phe

<210> SEQ ID NO 2
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 2

Asp Trp Leu Lys Ala Phe Tyr Asp Lys Val Ala Glu Lys Leu Lys Glu
1               5                   10                  15

Ala Phe

<210> SEQ ID NO 3
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 3

Asp Trp Phe Lys Ala Phe Tyr Asp Lys Val Ala Glu Lys Leu Lys Glu
1               5                   10                  15

Ala Phe

<210> SEQ ID NO 4
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 4

Asp Trp Leu Lys Ala Phe Tyr Asp Lys Val Ala Glu Lys Phe Lys Glu
1               5                   10                  15

Ala Phe
```

```
<210> SEQ ID NO 5
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 5

Asp Trp Phe Lys Ala Phe Tyr Asp Lys Val Ala Glu Lys Phe Lys Glu
1               5                   10                  15

Ala Phe

<210> SEQ ID NO 6
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 6

Asp Trp Leu Lys Ala Phe Tyr Asp Lys Val Phe Glu Lys Phe Lys Glu
1               5                   10                  15

Phe Phe

<210> SEQ ID NO 7
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 7

Asp Trp Leu Lys Ala Phe Tyr Asp Lys Phe Phe Glu Lys Phe Lys Glu
1               5                   10                  15

Phe Phe

<210> SEQ ID NO 8
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 8

Asp Trp Phe Lys Ala Phe Tyr Asp Lys Phe Phe Glu Lys Phe Lys Glu
1               5                   10                  15

Phe Phe

<210> SEQ ID NO 9
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 9

Asp Trp Leu Lys Ala Phe Tyr Asp Lys Val Ala Glu Lys Leu Lys Glu
1               5                   10                  15

Phe Phe
```

```
<210> SEQ ID NO 10
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 10

Asp Trp Leu Lys Ala Phe Tyr Asp Lys Val Phe Glu Lys Phe Lys Glu
1               5                   10                  15

Ala Phe

<210> SEQ ID NO 11
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 11

Asp Trp Leu Lys Ala Phe Tyr Asp Lys Val Phe Glu Lys Leu Lys Glu
1               5                   10                  15

Phe Phe

<210> SEQ ID NO 12
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 12

Asp Trp Leu Lys Ala Phe Tyr Asp Lys Val Ala Glu Lys Phe Lys Glu
1               5                   10                  15

Phe Phe

<210> SEQ ID NO 13
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 13

Asp Trp Leu Lys Ala Phe Tyr Asp Lys Val Phe Glu Lys Phe Lys Glu
1               5                   10                  15

Phe Phe

<210> SEQ ID NO 14
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 14

Glu Trp Leu Lys Leu Phe Tyr Glu Lys Val Leu Glu Lys Phe Lys Glu
1               5                   10                  15

Ala Phe
```

```
<210> SEQ ID NO 15
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 15

Glu Trp Leu Lys Ala Phe Tyr Asp Lys Val Ala Glu Lys Phe Lys Glu
1               5                   10                  15

Ala Phe

<210> SEQ ID NO 16
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 16

Glu Trp Leu Lys Ala Phe Tyr Asp Lys Val Ala Glu Lys Leu Lys Glu
1               5                   10                  15

Phe Phe

<210> SEQ ID NO 17
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 17

Glu Trp Leu Lys Ala Phe Tyr Asp Lys Val Phe Glu Lys Phe Lys Glu
1               5                   10                  15

Ala Phe

<210> SEQ ID NO 18
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 18

Glu Trp Leu Lys Ala Phe Tyr Asp Lys Val Phe Glu Lys Leu Lys Glu
1               5                   10                  15

Phe Phe

<210> SEQ ID NO 19
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 19

Glu Trp Leu Lys Ala Phe Tyr Asp Lys Val Ala Glu Lys Phe Lys Glu
1               5                   10                  15

Phe Phe
```

```
<210> SEQ ID NO 20
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 20

Glu Trp Leu Lys Ala Phe Tyr Asp Lys Val Phe Glu Lys Phe Lys Glu
1               5                   10                  15

Phe Phe

<210> SEQ ID NO 21
<211> LENGTH: 14
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 21

Ala Phe Tyr Asp Lys Val Ala Glu Lys Leu Lys Glu Ala Phe
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 22

Ala Phe Tyr Asp Lys Val Ala Glu Lys Phe Lys Glu Ala Phe
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 23

Ala Phe Tyr Asp Lys Val Ala Glu Lys Phe Lys Glu Ala Phe
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 24

Ala Phe Tyr Asp Lys Phe Phe Glu Lys Phe Lys Glu Phe Phe
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Synthetic D or L peptide with optional
      protecting groups.
```

```
<400> SEQUENCE: 25

Ala Phe Tyr Asp Lys Phe Phe Glu Lys Phe Lys Glu Phe Phe
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 26

Ala Phe Tyr Asp Lys Val Ala Glu Lys Phe Lys Glu Ala Phe
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 27

Ala Phe Tyr Asp Lys Val Ala Glu Lys Leu Lys Glu Phe Phe
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 28

Ala Phe Tyr Asp Lys Val Phe Glu Lys Phe Lys Glu Ala Phe
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 29

Ala Phe Tyr Asp Lys Val Phe Glu Lys Leu Lys Glu Phe Phe
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 30

Ala Phe Tyr Asp Lys Val Ala Glu Lys Phe Lys Glu Phe Phe
1               5                   10

<210> SEQ ID NO 31
<211> LENGTH: 14
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 31

Lys Ala Phe Tyr Asp Lys Val Phe Glu Lys Phe Lys Glu Phe
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 32

Leu Phe Tyr Glu Lys Val Leu Glu Lys Phe Lys Glu Ala Phe
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 33

Ala Phe Tyr Asp Lys Val Ala Glu Lys Phe Lys Glu Ala Phe
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 34

Ala Phe Tyr Asp Lys Val Ala Glu Lys Leu Lys Glu Phe Phe
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 35

Ala Phe Tyr Asp Lys Val Phe Glu Lys Phe Lys Glu Ala Phe
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 36

Ala Phe Tyr Asp Lys Val Phe Glu Lys Leu Lys Glu Phe Phe
1               5                   10
```

```
<210> SEQ ID NO 37
<211> LENGTH: 14
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 37

Ala Phe Tyr Asp Lys Val Ala Glu Lys Phe Lys Glu Phe Phe
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 38

Ala Phe Tyr Asp Lys Val Phe Glu Lys Phe Lys Glu Phe Phe
1               5                   10

<210> SEQ ID NO 39
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 39

Asp Trp Leu Lys Ala Leu Tyr Asp Lys Val Ala Glu Lys Leu Lys Glu
1               5                   10                  15

Ala Leu

<210> SEQ ID NO 40
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 40

Asp Trp Phe Lys Ala Phe Tyr Glu Lys Val Ala Glu Lys Leu Lys Glu
1               5                   10                  15

Phe Phe

<210> SEQ ID NO 41
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 41

Asp Trp Phe Lys Ala Phe Tyr Glu Lys Phe Phe Glu Lys Phe Lys Glu
1               5                   10                  15

Phe Phe

<210> SEQ ID NO 42
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 42

Glu Trp Leu Lys Ala Leu Tyr Glu Lys Val Ala Glu Lys Leu Lys Glu
1               5                   10                  15

Ala Leu

<210> SEQ ID NO 43
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 43

Glu Trp Leu Lys Ala Phe Tyr Glu Lys Val Ala Glu Lys Leu Lys Glu
1               5                   10                  15

Ala Phe

<210> SEQ ID NO 44
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 44

Glu Trp Phe Lys Ala Phe Tyr Glu Lys Val Ala Glu Lys Leu Lys Glu
1               5                   10                  15

Phe Phe

<210> SEQ ID NO 45
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 45

Glu Trp Leu Lys Ala Phe Tyr Glu Lys Val Phe Glu Lys Phe Lys Glu
1               5                   10                  15

Phe Phe

<210> SEQ ID NO 46
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 46

Glu Trp Leu Lys Ala Phe Tyr Glu Lys Phe Phe Glu Lys Phe Lys Glu
1               5                   10                  15

Phe Phe

<210> SEQ ID NO 47
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 47

Glu Trp Phe Lys Ala Phe Tyr Glu Lys Phe Phe Glu Lys Phe Lys Glu
1               5                   10                  15
Phe Phe

<210> SEQ ID NO 48
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 48

Asp Phe Leu Lys Ala Trp Tyr Asp Lys Val Ala Glu Lys Leu Lys Glu
1               5                   10                  15
Ala Trp

<210> SEQ ID NO 49
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 49

Glu Phe Leu Lys Ala Trp Tyr Glu Lys Val Ala Glu Lys Leu Lys Glu
1               5                   10                  15
Ala Trp

<210> SEQ ID NO 50
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 50

Asp Phe Trp Lys Ala Trp Tyr Asp Lys Val Ala Glu Lys Leu Lys Glu
1               5                   10                  15
Trp Trp

<210> SEQ ID NO 51
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 51

Glu Phe Trp Lys Ala Trp Tyr Glu Lys Val Ala Glu Lys Leu Lys Glu
1               5                   10                  15
Trp Trp

<210> SEQ ID NO 52
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 52

Asp Lys Leu Lys Ala Phe Tyr Asp Lys Val Phe Glu Trp Ala Lys Glu
1               5                   10                  15

Ala Phe

<210> SEQ ID NO 53
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 53

Asp Lys Trp Lys Ala Val Tyr Asp Lys Phe Ala Glu Ala Phe Lys Glu
1               5                   10                  15

Phe Leu

<210> SEQ ID NO 54
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 54

Glu Lys Leu Lys Ala Phe Tyr Glu Lys Val Phe Glu Trp Ala Lys Glu
1               5                   10                  15

Ala Phe

<210> SEQ ID NO 55
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 55

Glu Lys Trp Lys Ala Val Tyr Glu Lys Phe Ala Glu Ala Phe Lys Glu
1               5                   10                  15

Phe Leu

<210> SEQ ID NO 56
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 56

Asp Trp Leu Lys Ala Phe Val Asp Lys Phe Ala Glu Lys Phe Lys Glu
1               5                   10                  15

Ala Tyr

<210> SEQ ID NO 57
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 57

Glu Lys Trp Lys Ala Val Tyr Glu Lys Phe Ala Glu Ala Phe Lys Glu
1               5                   10                  15

Phe Leu

<210> SEQ ID NO 58
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 58

Asp Trp Leu Lys Ala Phe Val Tyr Asp Lys Val Phe Lys Leu Lys Glu
1               5                   10                  15

Phe Phe

<210> SEQ ID NO 59
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 59

Glu Trp Leu Lys Ala Phe Val Tyr Glu Lys Val Phe Lys Leu Lys Glu
1               5                   10                  15

Phe Phe

<210> SEQ ID NO 60
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 60

Asp Trp Leu Arg Ala Phe Tyr Asp Lys Val Ala Glu Lys Leu Lys Glu
1               5                   10                  15

Ala Phe

<210> SEQ ID NO 61
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 61

Glu Trp Leu Arg Ala Phe Tyr Glu Lys Val Ala Glu Lys Leu Lys Glu
1               5                   10                  15

Ala Phe

<210> SEQ ID NO 62
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 62

Asp Trp Leu Lys Ala Phe Tyr Asp Arg Val Ala Glu Lys Leu Lys Glu
1               5                   10                  15

Ala Phe

<210> SEQ ID NO 63
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 63

Glu Trp Leu Lys Ala Phe Tyr Glu Arg Val Ala Glu Lys Leu Lys Glu
1               5                   10                  15

Ala Phe

<210> SEQ ID NO 64
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 64

Asp Trp Leu Lys Ala Phe Tyr Asp Lys Val Ala Glu Arg Leu Lys Glu
1               5                   10                  15

Ala Phe

<210> SEQ ID NO 65
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 65

Glu Trp Leu Lys Ala Phe Tyr Glu Lys Val Ala Glu Arg Leu Lys Glu
1               5                   10                  15

Ala Phe

<210> SEQ ID NO 66
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 66

Asp Trp Leu Lys Ala Phe Tyr Asp Lys Val Ala Glu Lys Leu Arg Glu
1               5                   10                  15

Ala Phe

<210> SEQ ID NO 67
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 67

Glu Trp Leu Lys Ala Phe Tyr Glu Lys Val Ala Glu Lys Leu Arg Glu
1               5                   10                  15

Ala Phe

<210> SEQ ID NO 68
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 68

Asp Trp Leu Lys Ala Phe Tyr Asp Arg Val Ala Glu Arg Leu Lys Glu
1               5                   10                  15

Ala Phe

<210> SEQ ID NO 69
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 69

Glu Trp Leu Lys Ala Phe Tyr Glu Arg Val Ala Glu Arg Leu Lys Glu
1               5                   10                  15

Ala Phe

<210> SEQ ID NO 70
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 70

Asp Trp Leu Arg Ala Phe Tyr Asp Lys Val Ala Glu Lys Leu Arg Glu
1               5                   10                  15

Ala Phe

<210> SEQ ID NO 71
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 71

Glu Trp Leu Arg Ala Phe Tyr Glu Lys Val Ala Glu Lys Leu Arg Glu
1               5                   10                  15

Ala Phe

<210> SEQ ID NO 72
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 72

Asp Trp Leu Arg Ala Phe Tyr Asp Arg Val Ala Glu Lys Leu Lys Glu
1               5                   10                  15

Ala Phe

<210> SEQ ID NO 73
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 73

Glu Trp Leu Arg Ala Phe Tyr Glu Arg Val Ala Glu Lys Leu Lys Glu
1               5                   10                  15

Ala Phe

<210> SEQ ID NO 74
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 74

Asp Trp Leu Lys Ala Phe Tyr Asp Lys Val Ala Glu Arg Leu Arg Glu
1               5                   10                  15

Ala Phe

<210> SEQ ID NO 75
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 75

Glu Trp Leu Lys Ala Phe Tyr Glu Lys Val Ala Glu Arg Leu Arg Glu
1               5                   10                  15

Ala Phe

<210> SEQ ID NO 76
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 76

Asp Trp Leu Arg Ala Phe Tyr Asp Lys Val Ala Glu Arg Leu Lys Glu
1               5                   10                  15

Ala Phe

<210> SEQ ID NO 77
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 77

Glu Trp Leu Arg Ala Phe Tyr Glu Lys Val Ala Glu Arg Leu Lys Glu
1               5                   10                  15

Ala Phe

<210> SEQ ID NO 78
<211> LENGTH: 37
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 78

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Asp Lys Val Ala Glu Lys
                20                  25                  30

Leu Lys Glu Ala Phe
            35

<210> SEQ ID NO 79
<211> LENGTH: 37
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 79

Asp Trp Leu Lys Ala Phe Tyr Asp Lys Val Ala Glu Lys Leu Lys Glu
1               5                   10                  15

Phe Phe Pro Asp Trp Leu Lys Ala Phe Tyr Asp Lys Val Ala Glu Lys
                20                  25                  30

Leu Lys Glu Phe Phe
            35

<210> SEQ ID NO 80
<211> LENGTH: 37
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 80

Asp Trp Phe Lys Ala Phe Tyr Asp Lys Val Ala Glu Lys Leu Lys Glu
1               5                   10                  15

Ala Phe Pro Asp Trp Phe Lys Ala Phe Tyr Asp Lys Val Ala Glu Lys
                20                  25                  30

Leu Lys Glu Ala Phe
            35

<210> SEQ ID NO 81
<211> LENGTH: 37
<212> TYPE: PRT
<213> ORGANISM: Artificial Sequence
<220> FEATURE:
<223> OTHER INFORMATION: Synthetic D or L peptide with optional
      protecting groups.
```

-continued

```
<400> SEQUENCE: 81

Asp Lys Leu Lys Ala Phe Tyr Asp Lys Val Phe Glu Trp Ala Lys Glu
1               5                   10                  15

Ala Phe Pro Asp Lys Leu Lys Ala Phe Tyr Asp Lys Val Phe Glu Trp
            20                  25                  30

Leu Lys Glu Ala Phe
            35

<210> SEQ ID NO 82
<211> LENGTH: 37
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 82

Asp Lys Trp Lys Ala Val Tyr Asp Lys Phe Ala Glu Ala Phe Lys Glu
1               5                   10                  15

Phe Leu Pro Asp Lys Trp Lys Ala Val Tyr Asp Lys Phe Ala Glu Ala
            20                  25                  30

Phe Lys Glu Phe Leu
            35

<210> SEQ ID NO 83
<211> LENGTH: 37
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 83

Asp Trp Phe Lys Ala Phe Tyr Asp Lys Val Ala Glu Lys Phe Lys Glu
1               5                   10                  15

Ala Phe Pro Asp Trp Phe Lys Ala Phe Tyr Asp Lys Val Ala Glu Lys
            20                  25                  30

Phe Lys Glu Ala Phe
            35

<210> SEQ ID NO 84
<211> LENGTH: 37
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 84

Asp Trp Leu Lys Ala Phe Val Tyr Asp Lys Val Phe Lys Leu Lys Glu
1               5                   10                  15

Phe Phe Pro Asp Trp Leu Lys Ala Phe Val Tyr Asp Lys Val Phe Lys
            20                  25                  30

Leu Lys Glu Phe Phe
            35

<210> SEQ ID NO 85
<211> LENGTH: 37
<212> TYPE: PRT
<213> ORGANISM: Artificial Sequence
<220> FEATURE:
<223> OTHER INFORMATION: Synthetic D or L peptide with optional
      protecting groups.
```

```
<400> SEQUENCE: 85

Asp Trp Leu Lys Ala Phe Tyr Asp Lys Phe Ala Glu Lys Phe Lys Glu
1               5                   10                  15

Phe Phe Pro Asp Trp Leu Lys Ala Phe Tyr Asp Lys Phe Ala Glu Lys
            20                  25                  30

Phe Lys Glu Phe Phe
            35

<210> SEQ ID NO 86
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 86

Glu Trp Phe Lys Ala Phe Tyr Glu Lys Val Ala Glu Lys Phe Lys Glu
1               5                   10                  15

Ala Phe

<210> SEQ ID NO 87
<211> LENGTH: 14
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 87

Asp Trp Phe Lys Ala Phe Tyr Asp Lys Val Ala Glu Lys Phe
1               5                   10

<210> SEQ ID NO 88
<211> LENGTH: 14
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 88

Phe Lys Ala Phe Tyr Asp Lys Val Ala Glu Lys Phe Lys Glu
1               5                   10

<210> SEQ ID NO 89
<211> LENGTH: 14
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 89

Phe Lys Ala Phe Tyr Glu Lys Val Ala Glu Lys Phe Lys Glu
1               5                   10

<210> SEQ ID NO 90
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 90
```

Asn Met Ala Phe Lys Ala Phe Tyr Asp Lys Val Ala Glu Lys Phe Lys
1               5                   10                  15

Glu

<210> SEQ ID NO 91
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 91

Asn Met Ala Phe Lys Ala Phe Tyr Glu Lys Val Ala Glu Lys Phe Lys
1               5                   10                  15

Glu

<210> SEQ ID NO 92
<211> LENGTH: 21
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 92

Asn Met Ala Asp Trp Phe Lys Ala Phe Tyr Asp Lys Val Ala Glu Lys
1               5                   10                  15

Phe Lys Glu Ala Phe
            20

<210> SEQ ID NO 93
<211> LENGTH: 21
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 93

Asn Met Ala Glu Trp Phe Lys Ala Phe Tyr Glu Lys Val Ala Glu Lys
1               5                   10                  15

Phe Lys Glu Ala Phe
            20

<210> SEQ ID NO 94
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 94

Asn Met Ala Ala Phe Tyr Asp Lys Val Ala Glu Lys Phe Lys Glu Ala
1               5                   10                  15

Phe

<210> SEQ ID NO 95
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

```
<400> SEQUENCE: 95

Asn Met Ala Asp Trp Phe Lys Ala Phe Tyr Asp Lys Val Ala Glu Lys
1               5                   10                  15
Phe

<210> SEQ ID NO 96
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 96

Asp Trp Leu Lys Ala Phe Tyr Asp Lys Val Phe Glu Lys Phe Lys Glu
1               5                   10                  15
Phe Phe

<210> SEQ ID NO 97
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 97

Glu Trp Leu Lys Ala Phe Tyr Glu Lys Val Phe Glu Lys Phe Lys Glu
1               5                   10                  15
Phe Phe

<210> SEQ ID NO 98
<211> LENGTH: 14
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 98

Ala Phe Tyr Asp Lys Val Phe Glu Lys Phe Lys Glu Phe Phe
1               5                   10

<210> SEQ ID NO 99
<211> LENGTH: 14
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 99

Ala Phe Tyr Glu Lys Val Phe Glu Lys Phe Lys Glu Phe Phe
1               5                   10

<210> SEQ ID NO 100
<211> LENGTH: 14
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 100

Asp Trp Leu Lys Ala Phe Tyr Asp Lys Val Phe Glu Lys Phe
1               5                   10
```

<210> SEQ ID NO 101
<211> LENGTH: 14
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 101

Glu Trp Leu Lys Ala Phe Tyr Glu Lys Val Phe Glu Lys Phe
1               5                   10

<210> SEQ ID NO 102
<211> LENGTH: 14
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 102

Leu Lys Ala Phe Tyr Asp Lys Val Phe Glu Lys Phe Lys Glu
1               5                   10

<210> SEQ ID NO 103
<211> LENGTH: 14
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 103

Leu Lys Ala Phe Tyr Glu Lys Val Phe Glu Lys Phe Lys Glu
1               5                   10

<210> SEQ ID NO 104
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 104

Phe Ala Glu Lys Phe Lys Glu Ala Val Lys Asp Tyr Phe Ala Lys Phe
1               5                   10                  15

Trp Asp

<210> SEQ ID NO 105
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 105

Asp Lys Trp Lys Ala Val Tyr Asp Lys Phe Ala Glu Ala Phe Lys Glu
1               5                   10                  15

Phe Leu

<210> SEQ ID NO 106
<211> LENGTH: 18
<212> TYPE: PRT
<213> ORGANISM: Artificial Sequence

```
<220> FEATURE:
<223> OTHER INFORMATION: Synthetic D or L peptide with optional
      protecting groups.

<400> SEQUENCE: 106

Asp Lys Leu Lys Ala Phe Tyr Asp Lys Val Phe Glu Trp Ala Lys Glu
1               5                   10                  15

Ala Phe

<210> SEQ ID NO 107
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 107

Glu Trp Phe Lys Ala Phe Tyr Glu Lys Val Ala Asp Lys Phe Lys Asp
1               5                   10                  15

Ala Phe

<210> SEQ ID NO 108
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 108

Glu Trp Phe Lys Ala Phe Tyr Asp Lys Val Ala Asp Lys Phe Lys Glu
1               5                   10                  15

Ala Phe

<210> SEQ ID NO 109
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 109

Asp Trp Phe Lys Ala Phe Tyr Glu Lys Val Ala Asp Lys Phe Lys Glu
1               5                   10                  15

Ala Phe

<210> SEQ ID NO 110
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 110

Asp Trp Phe Lys Ala Phe Tyr Glu Lys Val Ala Glu Lys Phe Lys Asp
1               5                   10                  15

Ala Phe

<210> SEQ ID NO 111
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 111

Asp Phe Trp Lys Ala Phe Tyr Asp Lys Val Ala Glu Lys Phe Lys Glu
1               5                   10                  15

Ala Phe

<210> SEQ ID NO 112
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 112

Glu Phe Trp Lys Ala Phe Tyr Glu Lys Val Ala Asp Lys Phe Lys Asp
1               5                   10                  15

Ala Phe

<210> SEQ ID NO 113
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 113

Glu Phe Trp Lys Ala Phe Tyr Asp Lys Val Ala Asp Lys Phe Lys Glu
1               5                   10                  15

Ala Phe

<210> SEQ ID NO 114
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 114

Asp Phe Trp Lys Ala Phe Tyr Glu Lys Val Ala Asp Lys Phe Lys Glu
1               5                   10                  15

Ala Phe

<210> SEQ ID NO 115
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 115

Asp Phe Trp Lys Ala Phe Tyr Glu Lys Val Ala Glu Lys Phe Lys Asp
1               5                   10                  15

Ala Phe

<210> SEQ ID NO 116
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 116

Asp Trp Phe Lys Ala Tyr Phe Asp Lys Val Ala Glu Lys Phe Lys Glu
1               5                   10                  15

Ala Phe

<210> SEQ ID NO 117
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 117

Glu Trp Phe Lys Ala Tyr Phe Glu Lys Val Ala Asp Lys Phe Lys Asp
1               5                   10                  15

Ala Phe

<210> SEQ ID NO 118
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 118

Glu Trp Phe Lys Ala Tyr Phe Asp Lys Val Ala Asp Lys Phe Lys Glu
1               5                   10                  15

Ala Phe

<210> SEQ ID NO 119
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 119

Asp Trp Phe Lys Ala Tyr Phe Glu Lys Val Ala Asp Lys Phe Lys Glu
1               5                   10                  15

Ala Phe

<210> SEQ ID NO 120
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 120

Asp Trp Phe Lys Ala Tyr Phe Glu Lys Val Ala Glu Lys Phe Lys Asp
1               5                   10                  15

Ala Phe

<210> SEQ ID NO 121
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 121

Asp Trp Phe Lys Ala Phe Val Asp Lys Tyr Ala Glu Lys Phe Lys Glu
1               5                   10                  15

Ala Phe

<210> SEQ ID NO 122
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 122

Glu Trp Phe Lys Ala Phe Val Glu Lys Tyr Ala Asp Lys Phe Lys Asp
1               5                   10                  15

Ala Phe

<210> SEQ ID NO 123
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 123

Glu Trp Phe Lys Ala Phe Val Asp Lys Tyr Ala Asp Lys Phe Lys Glu
1               5                   10                  15

Ala Phe

<210> SEQ ID NO 124
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 124

Asp Trp Phe Lys Ala Phe Val Glu Lys Tyr Ala Asp Lys Phe Lys Glu
1               5                   10                  15

Ala Phe

<210> SEQ ID NO 125
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 125

Asp Trp Phe Lys Ala Phe Val Glu Lys Tyr Ala Glu Lys Phe Lys Asp
1               5                   10                  15

Ala Phe

<210> SEQ ID NO 126
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 126

Asp Trp Phe Lys Ala Phe Tyr Asp Lys Ala Val Glu Lys Phe Lys Glu
1               5                   10                  15

Ala Phe

<210> SEQ ID NO 127
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 127

Glu Trp Phe Lys Ala Phe Tyr Glu Lys Ala Val Asp Lys Phe Lys Asp
1               5                   10                  15

Ala Phe

<210> SEQ ID NO 128
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 128

Glu Trp Phe Lys Ala Phe Tyr Asp Lys Ala Val Asp Lys Phe Lys Glu
1               5                   10                  15

Ala Phe

<210> SEQ ID NO 129
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 129

Asp Trp Phe Lys Ala Phe Tyr Glu Lys Ala Val Asp Lys Phe Lys Glu
1               5                   10                  15

Ala Phe

<210> SEQ ID NO 130
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 130

Asp Trp Phe Lys Ala Phe Tyr Glu Lys Ala Val Glu Lys Phe Lys Asp
1               5                   10                  15

Ala Phe

<210> SEQ ID NO 131
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 131

Asp Trp Phe Lys Ala Phe Tyr Asp Lys Val Phe Glu Lys Ala Lys Glu
1               5                   10                  15

Ala Phe

<210> SEQ ID NO 132
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 132

Glu Trp Phe Lys Ala Phe Tyr Glu Lys Val Phe Asp Lys Ala Lys Asp
1               5                   10                  15

Ala Phe

<210> SEQ ID NO 133
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 133

Glu Trp Phe Lys Ala Phe Tyr Asp Lys Val Phe Asp Lys Ala Lys Glu
1               5                   10                  15

Ala Phe

<210> SEQ ID NO 134
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 134

Asp Trp Phe Lys Ala Phe Tyr Glu Lys Val Phe Asp Lys Ala Lys Glu
1               5                   10                  15

Ala Phe

<210> SEQ ID NO 135
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 135

Asp Trp Phe Lys Ala Phe Tyr Glu Lys Val Phe Glu Lys Ala Lys Asp
1               5                   10                  15

Ala Phe

<210> SEQ ID NO 136
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 136

Asp Trp Phe Lys Ala Phe Tyr Asp Lys Val Ala Glu Lys Ala Lys Glu
1               5                   10                  15

Phe Phe

<210> SEQ ID NO 137
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 137

Glu Trp Phe Lys Ala Phe Tyr Glu Lys Val Ala Asp Lys Ala Lys Asp
1               5                   10                  15

Phe Phe

<210> SEQ ID NO 138
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 138

Glu Trp Phe Lys Ala Phe Tyr Asp Lys Val Ala Asp Lys Ala Lys Glu
1               5                   10                  15

Phe Phe

<210> SEQ ID NO 139
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 139

Asp Trp Phe Lys Ala Phe Tyr Glu Lys Val Ala Asp Lys Ala Lys Glu
1               5                   10                  15

Phe Phe

<210> SEQ ID NO 140
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 140

Asp Trp Phe Lys Ala Phe Tyr Glu Lys Val Ala Glu Lys Ala Lys Asp
1               5                   10                  15

Phe Phe

<210> SEQ ID NO 141
<211> LENGTH: 18
<212> TYPE: PRT
<213> ORGANISM: Artificial Sequence
```

<220> FEATURE:
<223> OTHER INFORMATION: Synthetic D or L peptide with optional
      protecting groups.

<400> SEQUENCE: 141

Asp Trp Phe Lys Ala Phe Tyr Asp Lys Val Ala Glu Lys Phe Lys Glu
1               5                   10                  15

Phe Ala

<210> SEQ ID NO 142
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 142

Glu Trp Phe Lys Ala Phe Tyr Glu Lys Val Ala Asp Lys Phe Lys Asp
1               5                   10                  15

Phe Ala

<210> SEQ ID NO 143
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 143

Glu Trp Phe Lys Ala Phe Tyr Asp Lys Val Ala Asp Lys Phe Lys Glu
1               5                   10                  15

Phe Ala

<210> SEQ ID NO 144
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 144

Asp Trp Phe Lys Ala Phe Tyr Glu Lys Val Ala Asp Lys Phe Lys Glu
1               5                   10                  15

Phe Ala

<210> SEQ ID NO 145
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 145

Asp Trp Phe Lys Ala Phe Tyr Glu Lys Val Ala Glu Lys Phe Lys Asp
1               5                   10                  15

Phe Ala

<210> SEQ ID NO 146
<211> LENGTH: 18
<212> TYPE: PRT
<213> ORGANISM: Artificial Sequence

```
<220> FEATURE:
<223> OTHER INFORMATION: Synthetic D or L peptide with optional
      protecting groups.

<400> SEQUENCE: 146

Asp Ala Phe Lys Ala Phe Tyr Asp Lys Val Ala Glu Lys Phe Lys Glu
1               5                   10                  15

Trp Phe

<210> SEQ ID NO 147
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 147

Glu Ala Phe Lys Ala Phe Tyr Glu Lys Val Ala Asp Lys Phe Lys Asp
1               5                   10                  15

Trp Phe

<210> SEQ ID NO 148
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 148

Glu Ala Phe Lys Ala Phe Tyr Asp Lys Val Ala Asp Lys Phe Lys Glu
1               5                   10                  15

Trp Phe

<210> SEQ ID NO 149
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 149

Asp Ala Phe Lys Ala Phe Tyr Glu Lys Val Ala Asp Lys Phe Lys Glu
1               5                   10                  15

Trp Phe

<210> SEQ ID NO 150
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 150

Asp Ala Phe Lys Ala Phe Tyr Glu Lys Val Ala Glu Lys Phe Lys Asp
1               5                   10                  15

Trp Phe

<210> SEQ ID NO 151
<211> LENGTH: 18
<212> TYPE: PRT
<213> ORGANISM: Artificial Sequence
```

<220> FEATURE:
<223> OTHER INFORMATION: Synthetic D or L peptide with optional
     protecting groups.

<400> SEQUENCE: 151

Asp Ala Phe Lys Ala Phe Tyr Asp Lys Val Trp Glu Lys Phe Lys Glu
1               5                   10                  15

Ala Phe

<210> SEQ ID NO 152
<211> LENGTH: 18
<212> TYPE: PRT
<213> ORGANISM: Artificial Sequence
<220> FEATURE:
<223> OTHER INFORMATION: Synthetic D or L peptide with optional
     protecting groups.

<400> SEQUENCE: 152

Glu Ala Phe Lys Ala Phe Tyr Glu Lys Val Trp Asp Lys Phe Lys Asp
1               5                   10                  15

Ala Phe

<210> SEQ ID NO 153
<211> LENGTH: 18
<212> TYPE: PRT
<213> ORGANISM: Artificial Sequence
<220> FEATURE:
<223> OTHER INFORMATION: Synthetic D or L peptide with optional
     protecting groups.

<400> SEQUENCE: 153

Glu Ala Phe Lys Ala Phe Tyr Asp Lys Val Trp Asp Lys Phe Lys Glu
1               5                   10                  15

Ala Phe

<210> SEQ ID NO 154
<211> LENGTH: 18
<212> TYPE: PRT
<213> ORGANISM: Artificial Sequence
<220> FEATURE:
<223> OTHER INFORMATION: Synthetic D or L peptide with optional
     protecting groups.

<400> SEQUENCE: 154

Asp Ala Phe Lys Ala Phe Tyr Glu Lys Val Trp Asp Lys Phe Lys Glu
1               5                   10                  15

Ala Phe

<210> SEQ ID NO 155
<211> LENGTH: 18
<212> TYPE: PRT
<213> ORGANISM: Artificial Sequence
<220> FEATURE:
<223> OTHER INFORMATION: Synthetic D or L peptide with optional
     protecting groups.

<400> SEQUENCE: 155

Asp Ala Phe Lys Ala Phe Tyr Glu Lys Val Trp Glu Lys Phe Lys Asp
1               5                   10                  15

Ala Phe

<210> SEQ ID NO 156
<211> LENGTH: 18
<212> TYPE: PRT
<213> ORGANISM: Artificial Sequence

```
<220> FEATURE:
<223> OTHER INFORMATION: Synthetic D or L peptide with optional
      protecting groups.

<400> SEQUENCE: 156

Asp Tyr Phe Lys Ala Phe Trp Asp Lys Val Ala Glu Lys Phe Lys Glu
1               5                   10                  15

Ala Phe

<210> SEQ ID NO 157
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 157

Glu Tyr Phe Lys Ala Phe Trp Glu Lys Val Ala Asp Lys Phe Lys Asp
1               5                   10                  15

Ala Phe

<210> SEQ ID NO 158
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 158

Glu Tyr Phe Lys Ala Phe Trp Asp Lys Val Ala Asp Lys Phe Lys Glu
1               5                   10                  15

Ala Phe

<210> SEQ ID NO 159
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 159

Asp Tyr Phe Lys Ala Phe Trp Glu Lys Val Ala Asp Lys Phe Lys Glu
1               5                   10                  15

Ala Phe

<210> SEQ ID NO 160
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 160

Asp Tyr Phe Lys Ala Phe Trp Glu Lys Val Ala Glu Lys Phe Lys Asp
1               5                   10                  15

Ala Phe

<210> SEQ ID NO 161
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 161

Asp Trp Ala Lys Ala Phe Tyr Asp Lys Val Ala Glu Lys Phe Lys Glu
1               5                   10                  15

Phe Phe

<210> SEQ ID NO 162
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 162

Glu Trp Ala Lys Ala Phe Tyr Glu Lys Val Ala Asp Lys Phe Lys Asp
1               5                   10                  15

Phe Phe

<210> SEQ ID NO 163
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 163

Glu Trp Ala Lys Ala Phe Tyr Asp Lys Val Ala Asp Lys Phe Lys Glu
1               5                   10                  15

Phe Phe

<210> SEQ ID NO 164
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 164

Asp Trp Ala Lys Ala Phe Tyr Glu Lys Val Ala Asp Lys Phe Lys Glu
1               5                   10                  15

Phe Phe

<210> SEQ ID NO 165
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 165

Asp Trp Ala Lys Ala Phe Tyr Glu Lys Val Ala Glu Lys Phe Lys Asp
1               5                   10                  15

Phe Phe

<210> SEQ ID NO 166
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 166

Asp Trp Phe Lys Ala Ala Tyr Asp Lys Val Ala Glu Lys Phe Lys Glu
1               5                   10                  15

Phe Phe

<210> SEQ ID NO 167
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 167

Glu Trp Phe Lys Ala Ala Tyr Glu Lys Val Ala Asp Lys Phe Lys Asp
1               5                   10                  15

Phe Phe

<210> SEQ ID NO 168
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 168

Glu Trp Phe Lys Ala Ala Tyr Asp Lys Val Ala Asp Lys Phe Lys Glu
1               5                   10                  15

Phe Phe

<210> SEQ ID NO 169
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 169

Asp Trp Phe Lys Ala Ala Tyr Glu Lys Val Ala Asp Lys Phe Lys Glu
1               5                   10                  15

Phe Phe

<210> SEQ ID NO 170
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 170

Asp Trp Phe Lys Ala Ala Tyr Glu Lys Val Ala Glu Lys Phe Lys Asp
1               5                   10                  15

Phe Phe

<210> SEQ ID NO 171
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 171

Asp Trp Phe Lys Ala Phe Ala Asp Lys Val Ala Glu Lys Phe Lys Glu
1               5                   10                  15

Tyr Phe

<210> SEQ ID NO 172
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 172

Glu Trp Phe Lys Ala Phe Ala Glu Lys Val Ala Asp Lys Phe Lys Asp
1               5                   10                  15

Tyr Phe

<210> SEQ ID NO 173
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 173

Glu Trp Phe Lys Ala Phe Ala Asp Lys Val Ala Asp Lys Phe Lys Glu
1               5                   10                  15

Tyr Phe

<210> SEQ ID NO 174
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 174

Asp Trp Phe Lys Ala Phe Ala Glu Lys Val Ala Asp Lys Phe Lys Glu
1               5                   10                  15

Tyr Phe

<210> SEQ ID NO 175
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 175

Asp Trp Phe Lys Ala Phe Ala Glu Lys Val Ala Glu Lys Phe Lys Asp
1               5                   10                  15

Tyr Phe

<210> SEQ ID NO 176
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 176

Asp Trp Phe Lys Ala Phe Tyr Asp Lys Ala Ala Glu Lys Phe Lys Glu
1               5                   10                  15

Val Phe

<210> SEQ ID NO 177
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 177

Glu Trp Phe Lys Ala Phe Tyr Glu Lys Ala Ala Asp Lys Phe Lys Asp
1               5                   10                  15

Val Phe

<210> SEQ ID NO 178
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 178

Glu Trp Phe Lys Ala Phe Tyr Asp Lys Ala Ala Asp Lys Phe Lys Glu
1               5                   10                  15

Val Phe

<210> SEQ ID NO 179
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 179

Asp Trp Phe Lys Ala Phe Tyr Glu Lys Ala Ala Asp Lys Phe Lys Glu
1               5                   10                  15

Val Phe

<210> SEQ ID NO 180
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 180

Asp Trp Phe Lys Ala Phe Tyr Glu Lys Ala Ala Glu Lys Phe Lys Asp
1               5                   10                  15

Val Phe

<210> SEQ ID NO 181
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 181

Asp Trp Tyr Lys Ala Phe Phe Asp Lys Val Ala Glu Lys Phe Lys Glu
1               5                   10                  15

Ala Phe

<210> SEQ ID NO 182
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 182

Glu Trp Tyr Lys Ala Phe Phe Glu Lys Val Ala Asp Lys Phe Lys Asp
1               5                   10                  15

Ala Phe

<210> SEQ ID NO 183
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 183

Glu Trp Tyr Lys Ala Phe Phe Asp Lys Val Ala Asp Lys Phe Lys Glu
1               5                   10                  15

Ala Phe

<210> SEQ ID NO 184
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 184

Asp Trp Tyr Lys Ala Phe Phe Glu Lys Val Ala Asp Lys Phe Lys Glu
1               5                   10                  15

Ala Phe

<210> SEQ ID NO 185
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 185

Asp Trp Tyr Lys Ala Phe Phe Glu Lys Val Ala Glu Lys Phe Lys Asp
1               5                   10                  15

Ala Phe

<210> SEQ ID NO 186
<211> LENGTH: 18
<212> TYPE: PRT
<213> ORGANISM: Artificial Sequence
```

<220> FEATURE:
<223> OTHER INFORMATION: Synthetic D or L peptide with optional
      protecting groups.

<400> SEQUENCE: 186

Asp Trp Val Lys Ala Phe Tyr Asp Lys Phe Ala Glu Lys Phe Lys Glu
1               5                   10                  15

Ala Phe

<210> SEQ ID NO 187
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 187

Glu Trp Val Lys Ala Phe Tyr Glu Lys Phe Ala Asp Lys Phe Lys Asp
1               5                   10                  15

Ala Phe

<210> SEQ ID NO 188
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 188

Glu Trp Val Lys Ala Phe Tyr Asp Lys Phe Ala Asp Lys Phe Lys Glu
1               5                   10                  15

Ala Phe

<210> SEQ ID NO 189
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 189

Asp Trp Val Lys Ala Phe Tyr Glu Lys Phe Ala Asp Lys Phe Lys Glu
1               5                   10                  15

Ala Phe

<210> SEQ ID NO 190
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 190

Asp Trp Val Lys Ala Phe Tyr Glu Lys Phe Ala Glu Lys Phe Lys Asp
1               5                   10                  15

Ala Phe

<210> SEQ ID NO 191
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 191

Asp Trp Phe Lys Ala Phe Phe Asp Lys Val Ala Glu Lys Tyr Lys Glu
1               5                   10                  15

Ala Phe

<210> SEQ ID NO 192
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 192

Glu Trp Phe Lys Ala Phe Phe Glu Lys Val Ala Asp Lys Tyr Lys Asp
1               5                   10                  15

Ala Phe

<210> SEQ ID NO 193
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 193

Glu Trp Phe Lys Ala Phe Phe Asp Lys Val Ala Asp Lys Tyr Lys Glu
1               5                   10                  15

Ala Phe

<210> SEQ ID NO 194
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 194

Asp Trp Phe Lys Ala Phe Phe Glu Lys Val Ala Asp Lys Tyr Lys Glu
1               5                   10                  15

Ala Phe

<210> SEQ ID NO 195
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 195

Asp Trp Phe Lys Ala Phe Phe Glu Lys Val Ala Asp Lys Tyr Lys Glu
1               5                   10                  15

Ala Phe

<210> SEQ ID NO 196
<211> LENGTH: 18
<212> TYPE: PRT
<213> ORGANISM: Artificial Sequence -continued

```
<220> FEATURE:
<223> OTHER INFORMATION: Synthetic D or L peptide with optional
      protecting groups.

<400> SEQUENCE: 196

Asp Trp Phe Lys Ala Phe Phe Asp Lys Val Ala Glu Lys Phe Lys Glu
1               5                   10                  15

Ala Tyr

<210> SEQ ID NO 197
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 197

Glu Trp Phe Lys Ala Phe Phe Glu Lys Val Ala Asp Lys Phe Lys Asp
1               5                   10                  15

Ala Tyr

<210> SEQ ID NO 198
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 198

Glu Trp Phe Lys Ala Phe Phe Asp Lys Val Ala Asp Lys Phe Lys Glu
1               5                   10                  15

Ala Tyr

<210> SEQ ID NO 199
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 199

Asp Trp Phe Lys Ala Phe Phe Glu Lys Val Ala Asp Lys Phe Lys Glu
1               5                   10                  15

Ala Tyr

<210> SEQ ID NO 200
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 200

Asp Trp Phe Lys Ala Phe Phe Glu Lys Val Ala Glu Lys Phe Lys Asp
1               5                   10                  15

Ala Tyr

<210> SEQ ID NO 201
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 201

Asp Trp Phe Lys Ala Phe Tyr Asp Lys Phe Ala Glu Lys Phe Lys Glu
1               5                   10                  15

Ala Val

<210> SEQ ID NO 202
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 202

Glu Trp Phe Lys Ala Phe Tyr Glu Lys Phe Ala Asp Lys Phe Lys Asp
1               5                   10                  15

Ala Val

<210> SEQ ID NO 203
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 203

Glu Trp Phe Lys Ala Phe Tyr Asp Lys Phe Ala Asp Lys Phe Lys Glu
1               5                   10                  15

Ala Val

<210> SEQ ID NO 204
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 204

Asp Trp Phe Lys Ala Phe Tyr Glu Lys Phe Ala Asp Lys Phe Lys Glu
1               5                   10                  15

Ala Val

<210> SEQ ID NO 205
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 205

Asp Trp Phe Lys Ala Phe Tyr Glu Lys Phe Ala Glu Lys Phe Lys Asp
1               5                   10                  15

Ala Val

<210> SEQ ID NO 206
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 206

Asp Lys Phe Lys Ala Phe Tyr Asp Lys Val Ala Glu Lys Phe Trp Glu
1               5                   10                  15

Ala Phe

<210> SEQ ID NO 207
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 207

Glu Lys Phe Lys Ala Phe Tyr Glu Lys Val Ala Asp Lys Phe Trp Asp
1               5                   10                  15

Ala Phe

<210> SEQ ID NO 208
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 208

Glu Lys Phe Lys Ala Phe Tyr Asp Lys Val Ala Asp Lys Phe Trp Glu
1               5                   10                  15

Ala Phe

<210> SEQ ID NO 209
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 209

Asp Lys Phe Lys Ala Phe Tyr Glu Lys Val Ala Asp Lys Phe Trp Glu
1               5                   10                  15

Ala Phe

<210> SEQ ID NO 210
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 210

Asp Lys Phe Lys Ala Phe Tyr Glu Lys Val Ala Glu Lys Phe Trp Asp
1               5                   10                  15

Ala Phe

<210> SEQ ID NO 211
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 211

Asp Lys Trp Lys Ala Phe Tyr Asp Lys Val Ala Glu Lys Phe Glu
1               5                   10                  15

Ala Phe

<210> SEQ ID NO 212
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 212

Glu Lys Trp Lys Ala Phe Tyr Glu Lys Val Ala Asp Lys Phe Asp
1               5                   10                  15

Ala Phe

<210> SEQ ID NO 213
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 213

Glu Lys Trp Lys Ala Phe Tyr Asp Lys Val Ala Asp Lys Phe Glu
1               5                   10                  15

Ala Phe

<210> SEQ ID NO 214
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 214

Asp Lys Trp Lys Ala Phe Tyr Glu Lys Val Ala Asp Lys Phe Glu
1               5                   10                  15

Ala Phe

<210> SEQ ID NO 215
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 215

Asp Lys Trp Lys Ala Phe Tyr Glu Lys Val Ala Glu Lys Phe Asp
1               5                   10                  15

Ala Phe

<210> SEQ ID NO 216
<211> LENGTH: 18
<212> TYPE: PRT
<213> ORGANISM: Artificial Sequence
```

<220> FEATURE:
<223> OTHER INFORMATION: Synthetic D or L peptide with optional
     protecting groups.

<400> SEQUENCE: 216

Asp Lys Phe Lys Ala Phe Tyr Asp Lys Trp Ala Glu Val Phe Lys Glu
1               5                   10                  15

Ala Phe

<210> SEQ ID NO 217
<211> LENGTH: 18
<212> TYPE: PRT
<213> ORGANISM: Artificial Sequence
<220> FEATURE:
<223> OTHER INFORMATION: Synthetic D or L peptide with optional
     protecting groups.

<400> SEQUENCE: 217

Glu Lys Phe Lys Ala Phe Tyr Glu Lys Trp Ala Asp Val Phe Lys Asp
1               5                   10                  15

Ala Phe

<210> SEQ ID NO 218
<211> LENGTH: 18
<212> TYPE: PRT
<213> ORGANISM: Artificial Sequence
<220> FEATURE:
<223> OTHER INFORMATION: Synthetic D or L peptide with optional
     protecting groups.

<400> SEQUENCE: 218

Glu Lys Phe Lys Ala Phe Tyr Asp Lys Trp Ala Asp Val Phe Lys Glu
1               5                   10                  15

Ala Phe

<210> SEQ ID NO 219
<211> LENGTH: 18
<212> TYPE: PRT
<213> ORGANISM: Artificial Sequence
<220> FEATURE:
<223> OTHER INFORMATION: Synthetic D or L peptide with optional
     protecting groups.

<400> SEQUENCE: 219

Asp Lys Phe Lys Ala Phe Tyr Glu Lys Trp Ala Asp Val Phe Lys Glu
1               5                   10                  15

Ala Phe

<210> SEQ ID NO 220
<211> LENGTH: 18
<212> TYPE: PRT
<213> ORGANISM: Artificial Sequence
<220> FEATURE:
<223> OTHER INFORMATION: Synthetic D or L peptide with optional
     protecting groups.

<400> SEQUENCE: 220

Asp Lys Phe Lys Ala Phe Tyr Glu Lys Trp Ala Glu Val Phe Lys Asp
1               5                   10                  15

Ala Phe

<210> SEQ ID NO 221
<211> LENGTH: 18
<212> TYPE: PRT
<213> ORGANISM: Artificial Sequence

```
<220> FEATURE:
<223> OTHER INFORMATION: Synthetic D or L peptide with optional
      protecting groups.

<400> SEQUENCE: 221

Asp Lys Phe Lys Ala Phe Tyr Asp Lys Val Ala Glu Phe Trp Lys Glu
1               5                   10                  15

Ala Phe

<210> SEQ ID NO 222
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 222

Glu Lys Phe Lys Ala Phe Tyr Glu Lys Val Ala Asp Phe Trp Lys Asp
1               5                   10                  15

Ala Phe

<210> SEQ ID NO 223
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 223

Glu Lys Phe Lys Ala Phe Tyr Asp Lys Val Ala Asp Phe Trp Lys Glu
1               5                   10                  15

Ala Phe

<210> SEQ ID NO 224
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 224

Asp Lys Phe Lys Ala Phe Tyr Glu Lys Val Ala Asp Phe Trp Lys Glu
1               5                   10                  15

Ala Phe

<210> SEQ ID NO 225
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 225

Asp Lys Phe Lys Ala Phe Tyr Glu Lys Val Ala Glu Phe Trp Lys Asp
1               5                   10                  15

Ala Phe

<210> SEQ ID NO 226
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 226

Phe Ala Glu Lys Phe Lys Glu Ala Val Lys Asp Tyr Phe Ala Lys Phe
1               5                   10                  15

Trp Asp

<210> SEQ ID NO 227
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 227

Phe Ala Asp Lys Phe Lys Asp Ala Val Lys Glu Tyr Phe Ala Lys Phe
1               5                   10                  15

Trp Glu

<210> SEQ ID NO 228
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 228

Phe Ala Asp Lys Phe Lys Glu Ala Val Lys Asp Tyr Phe Ala Lys Phe
1               5                   10                  15

Trp Glu

<210> SEQ ID NO 229
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 229

Phe Ala Glu Lys Phe Lys Asp Ala Val Lys Glu Tyr Phe Ala Lys Phe
1               5                   10                  15

Trp Asp

<210> SEQ ID NO 230
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 230

Phe Ala Glu Lys Phe Lys Asp Ala Val Lys Asp Tyr Phe Ala Lys Phe
1               5                   10                  15

Trp Glu

<210> SEQ ID NO 231
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 231

Phe Trp Glu Lys Phe Lys Glu Ala Val Lys Asp Tyr Phe Ala Lys Phe
1               5                   10                  15

Ala Asp

<210> SEQ ID NO 232
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 232

Phe Trp Asp Lys Phe Lys Asp Ala Val Lys Glu Tyr Phe Ala Lys Phe
1               5                   10                  15

Ala Glu

<210> SEQ ID NO 233
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 233

Phe Ala Asp Lys Phe Lys Glu Ala Val Lys Asp Tyr Phe Ala Lys Phe
1               5                   10                  15

Trp Glu

<210> SEQ ID NO 234
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 234

Phe Ala Glu Lys Phe Lys Asp Ala Val Lys Glu Tyr Phe Ala Lys Phe
1               5                   10                  15

Trp Asp

<210> SEQ ID NO 235
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 235

Phe Ala Glu Lys Phe Lys Asp Ala Val Lys Asp Tyr Phe Ala Lys Phe
1               5                   10                  15

Trp Glu

<210> SEQ ID NO 236
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 236

Phe Phe Glu Lys Phe Lys Glu Ala Val Lys Asp Tyr Phe Ala Lys Ala
1               5                   10                  15

Trp Asp

<210> SEQ ID NO 237
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 237

Phe Phe Asp Lys Phe Lys Asp Ala Val Lys Glu Tyr Phe Ala Lys Ala
1               5                   10                  15

Trp Glu

<210> SEQ ID NO 238
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 238

Phe Phe Asp Lys Phe Lys Glu Ala Val Lys Asp Tyr Phe Ala Lys Ala
1               5                   10                  15

Trp Glu

<210> SEQ ID NO 239
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 239

Phe Phe Glu Lys Phe Lys Asp Ala Val Lys Glu Tyr Phe Ala Lys Ala
1               5                   10                  15

Trp Asp

<210> SEQ ID NO 240
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 240

Phe Phe Glu Lys Phe Lys Asp Ala Val Lys Asp Tyr Phe Ala Lys Ala
1               5                   10                  15

Trp Glu

<210> SEQ ID NO 241
<211> LENGTH: 18
<212> TYPE: PRT
<213> ORGANISM: Artificial Sequence
```

-continued

```
<220> FEATURE:
<223> OTHER INFORMATION: Synthetic D or L peptide with optional
      protecting groups.

<400> SEQUENCE: 241

Phe Ala Glu Lys Ala Lys Glu Phe Val Lys Asp Tyr Phe Ala Lys Phe
1               5                   10                  15

Trp Asp

<210> SEQ ID NO 242
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 242

Phe Ala Asp Lys Ala Lys Asp Phe Val Lys Glu Tyr Phe Ala Lys Phe
1               5                   10                  15

Trp Glu

<210> SEQ ID NO 243
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 243

Phe Ala Asp Lys Ala Lys Glu Phe Val Lys Asp Tyr Phe Ala Lys Phe
1               5                   10                  15

Trp Glu

<210> SEQ ID NO 244
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 244

Phe Ala Glu Lys Ala Lys Asp Phe Val Lys Glu Tyr Phe Ala Lys Phe
1               5                   10                  15

Trp Asp

<210> SEQ ID NO 245
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 245

Phe Ala Glu Lys Ala Lys Asp Phe Val Lys Asp Tyr Phe Ala Lys Phe
1               5                   10                  15

Trp Glu

<210> SEQ ID NO 246
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 246

Phe Ala Glu Lys Phe Lys Glu Val Ala Lys Asp Tyr Phe Ala Lys Phe
1               5                   10                  15

Trp Asp

<210> SEQ ID NO 247
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 247

Phe Ala Asp Lys Phe Lys Asp Val Ala Lys Glu Tyr Phe Ala Lys Phe
1               5                   10                  15

Trp Glu

<210> SEQ ID NO 248
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 248

Phe Ala Asp Lys Phe Lys Glu Val Ala Lys Asp Tyr Phe Ala Lys Phe
1               5                   10                  15

Trp Glu

<210> SEQ ID NO 249
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 249

Phe Ala Glu Lys Phe Lys Asp Val Ala Lys Glu Tyr Phe Ala Lys Phe
1               5                   10                  15

Trp Asp

<210> SEQ ID NO 250
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 250

Phe Ala Glu Lys Phe Lys Asp Val Ala Lys Asp Tyr Phe Ala Lys Phe
1               5                   10                  15

Trp Glu

<210> SEQ ID NO 251
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 251

Phe Ala Glu Lys Phe Lys Glu Ala Tyr Lys Asp Val Phe Ala Lys Phe
1               5                   10                  15

Trp Asp

<210> SEQ ID NO 252
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 252

Phe Ala Asp Lys Phe Lys Asp Ala Tyr Lys Glu Val Phe Ala Lys Phe
1               5                   10                  15

Trp Glu

<210> SEQ ID NO 253
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 253

Phe Ala Asp Lys Phe Lys Glu Ala Tyr Lys Asp Val Phe Ala Lys Phe
1               5                   10                  15

Trp Glu

<210> SEQ ID NO 254
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 254

Phe Ala Glu Lys Phe Lys Asp Ala Tyr Lys Glu Val Phe Ala Lys Phe
1               5                   10                  15

Trp Asp

<210> SEQ ID NO 255
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 255

Phe Ala Glu Lys Phe Lys Asp Ala Tyr Lys Asp Val Phe Ala Lys Phe
1               5                   10                  15

Trp Glu

<210> SEQ ID NO 256
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 256

Phe Ala Glu Lys Phe Lys Glu Ala Val Lys Asp Phe Tyr Ala Lys Phe
1               5                   10                  15

Trp Asp

<210> SEQ ID NO 257
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 257

Phe Ala Asp Lys Phe Lys Asp Ala Val Lys Glu Phe Tyr Ala Lys Phe
1               5                   10                  15

Trp Glu

<210> SEQ ID NO 258
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 258

Phe Ala Asp Lys Phe Lys Glu Ala Val Lys Asp Phe Tyr Ala Lys Phe
1               5                   10                  15

Trp Glu

<210> SEQ ID NO 259
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 259

Phe Ala Glu Lys Phe Lys Asp Ala Val Lys Glu Phe Tyr Ala Lys Phe
1               5                   10                  15

Trp Asp

<210> SEQ ID NO 260
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 260

Phe Ala Glu Lys Phe Lys Asp Ala Val Lys Asp Phe Tyr Ala Lys Phe
1               5                   10                  15

Trp Glu

<210> SEQ ID NO 261
<211> LENGTH: 18
<212> TYPE: PRT
<213> ORGANISM: Artificial Sequence
```

<220> FEATURE:
<223> OTHER INFORMATION: Synthetic D or L peptide with optional
      protecting groups.

<400> SEQUENCE: 261

Phe Ala Glu Lys Phe Trp Glu Ala Val Lys Asp Tyr Phe Ala Lys Phe
1               5                   10                  15

Lys Asp

<210> SEQ ID NO 262
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 262

Phe Ala Asp Lys Phe Trp Asp Ala Val Lys Glu Tyr Phe Ala Lys Phe
1               5                   10                  15

Lys Glu

<210> SEQ ID NO 263
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 263

Phe Ala Asp Lys Phe Trp Glu Ala Val Lys Asp Tyr Phe Ala Lys Phe
1               5                   10                  15

Lys Glu

<210> SEQ ID NO 264
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 264

Phe Ala Glu Lys Phe Trp Asp Ala Val Lys Glu Tyr Phe Ala Lys Phe
1               5                   10                  15

Lys Asp

<210> SEQ ID NO 265
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 265

Phe Ala Glu Lys Phe Trp Asp Ala Val Lys Asp Tyr Phe Ala Lys Phe
1               5                   10                  15

Lys Glu

<210> SEQ ID NO 266
<211> LENGTH: 18
<212> TYPE: PRT
<213> ORGANISM: Artificial Sequence

```
<220> FEATURE:
<223> OTHER INFORMATION: Synthetic D or L peptide with optional
      protecting groups.

<400> SEQUENCE: 266

Ala Phe Glu Lys Phe Lys Glu Ala Val Lys Asp Tyr Phe Ala Lys Phe
1               5                   10                  15

Trp Asp

<210> SEQ ID NO 267
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 267

Ala Phe Asp Lys Phe Lys Asp Ala Val Lys Glu Tyr Phe Ala Lys Phe
1               5                   10                  15

Trp Glu

<210> SEQ ID NO 268
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 268

Ala Phe Asp Lys Phe Lys Glu Ala Val Lys Asp Tyr Phe Ala Lys Phe
1               5                   10                  15

Trp Glu

<210> SEQ ID NO 269
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 269

Ala Phe Glu Lys Phe Lys Asp Ala Val Lys Glu Tyr Phe Ala Lys Phe
1               5                   10                  15

Trp Asp

<210> SEQ ID NO 270
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 270

Ala Phe Glu Lys Phe Lys Asp Ala Val Lys Asp Tyr Phe Ala Lys Phe
1               5                   10                  15

Trp Glu

<210> SEQ ID NO 271
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 271

Val Ala Glu Lys Phe Lys Glu Ala Phe Lys Asp Tyr Phe Ala Lys Phe
1               5                   10                  15

Trp Asp

<210> SEQ ID NO 272
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 272

Val Ala Asp Lys Phe Lys Asp Ala Phe Lys Glu Tyr Phe Ala Lys Phe
1               5                   10                  15

Trp Glu

<210> SEQ ID NO 273
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 273

Val Ala Asp Lys Phe Lys Glu Ala Phe Lys Asp Tyr Phe Ala Lys Phe
1               5                   10                  15

Trp Glu

<210> SEQ ID NO 274
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 274

Val Ala Glu Lys Phe Lys Asp Ala Phe Lys Glu Tyr Phe Ala Lys Phe
1               5                   10                  15

Trp Asp

<210> SEQ ID NO 275
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 275

Val Ala Glu Lys Phe Lys Asp Ala Phe Lys Asp Tyr Phe Ala Lys Phe
1               5                   10                  15

Trp Glu

<210> SEQ ID NO 276
<211> LENGTH: 18
<212> TYPE: PRT
<213> ORGANISM: Artificial Sequence
```

-continued

<220> FEATURE:
<223> OTHER INFORMATION: Synthetic D or L peptide with optional
      protecting groups.

<400> SEQUENCE: 276

Tyr Ala Glu Lys Phe Lys Glu Ala Val Lys Asp Phe Phe Ala Lys Phe
1               5                   10                  15

Trp Asp

<210> SEQ ID NO 277
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 277

Tyr Ala Asp Lys Phe Lys Asp Ala Val Lys Glu Phe Phe Ala Lys Phe
1               5                   10                  15

Trp Glu

<210> SEQ ID NO 278
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 278

Tyr Ala Asp Lys Phe Lys Glu Ala Val Lys Asp Phe Phe Ala Lys Phe
1               5                   10                  15

Trp Glu

<210> SEQ ID NO 279
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 279

Tyr Ala Glu Lys Phe Lys Asp Ala Val Lys Glu Phe Phe Ala Lys Phe
1               5                   10                  15

Trp Asp

<210> SEQ ID NO 280
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 280

Tyr Ala Glu Lys Phe Lys Asp Ala Val Lys Asp Phe Phe Ala Lys Phe
1               5                   10                  15

Trp Glu

<210> SEQ ID NO 281
<211> LENGTH: 18
<212> TYPE: PRT
<213> ORGANISM: Artificial Sequence

```
<220> FEATURE:
<223> OTHER INFORMATION: Synthetic D or L peptide with optional
      protecting groups.

<400> SEQUENCE: 281

Ala Ala Glu Lys Phe Lys Glu Phe Val Lys Asp Tyr Phe Ala Lys Phe
1               5                   10                  15

Trp Asp

<210> SEQ ID NO 282
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 282

Ala Ala Asp Lys Phe Lys Asp Phe Val Lys Glu Tyr Phe Ala Lys Phe
1               5                   10                  15

Trp Glu

<210> SEQ ID NO 283
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 283

Ala Ala Asp Lys Phe Lys Glu Phe Val Lys Asp Tyr Phe Ala Lys Phe
1               5                   10                  15

Trp Glu

<210> SEQ ID NO 284
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 284

Ala Ala Glu Lys Phe Lys Asp Phe Val Lys Glu Tyr Phe Ala Lys Phe
1               5                   10                  15

Trp Asp

<210> SEQ ID NO 285
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 285

Ala Ala Glu Lys Phe Lys Asp Phe Val Lys Asp Tyr Phe Ala Lys Phe
1               5                   10                  15

Trp Glu

<210> SEQ ID NO 286
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 286

Phe Phe Glu Lys Ala Lys Glu Ala Val Lys Asp Tyr Phe Ala Lys Phe
1               5                   10                  15

Trp Asp

<210> SEQ ID NO 287
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 287

Phe Phe Asp Lys Ala Lys Asp Ala Val Lys Glu Tyr Phe Ala Lys Phe
1               5                   10                  15

Trp Glu

<210> SEQ ID NO 288
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 288

Phe Phe Asp Lys Ala Lys Glu Ala Val Lys Asp Tyr Phe Ala Lys Phe
1               5                   10                  15

Trp Glu

<210> SEQ ID NO 289
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 289

Phe Phe Glu Lys Ala Lys Asp Ala Val Lys Glu Tyr Phe Ala Lys Phe
1               5                   10                  15

Trp Asp

<210> SEQ ID NO 290
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 290

Phe Phe Glu Lys Ala Lys Asp Ala Val Lys Asp Tyr Phe Ala Lys Phe
1               5                   10                  15

Trp Glu

<210> SEQ ID NO 291
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 291

Phe Tyr Glu Lys Phe Lys Glu Ala Val Lys Asp Ala Phe Ala Lys Phe
1               5                   10                  15

Trp Asp

<210> SEQ ID NO 292
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 292

Phe Tyr Asp Lys Phe Lys Asp Ala Val Lys Glu Ala Phe Ala Lys Phe
1               5                   10                  15

Trp Glu

<210> SEQ ID NO 293
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 293

Phe Tyr Asp Lys Phe Lys Glu Ala Val Lys Asp Ala Phe Ala Lys Phe
1               5                   10                  15

Trp Glu

<210> SEQ ID NO 294
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 294

Phe Tyr Glu Lys Phe Lys Asp Ala Val Lys Glu Ala Phe Ala Lys Phe
1               5                   10                  15

Trp Asp

<210> SEQ ID NO 295
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 295

Phe Tyr Glu Lys Phe Lys Asp Ala Val Lys Asp Ala Phe Ala Lys Phe
1               5                   10                  15

Trp Glu

<210> SEQ ID NO 296
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 296

Phe Val Glu Lys Phe Lys Glu Ala Ala Lys Asp Tyr Phe Ala Lys Phe
1               5                   10                  15

Trp Asp

<210> SEQ ID NO 297
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 297

Phe Val Asp Lys Phe Lys Asp Ala Ala Lys Glu Tyr Phe Ala Lys Phe
1               5                   10                  15

Trp Glu

<210> SEQ ID NO 298
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 298

Phe Val Asp Lys Phe Lys Glu Ala Ala Lys Asp Tyr Phe Ala Lys Phe
1               5                   10                  15

Trp Glu

<210> SEQ ID NO 299
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 299

Phe Val Glu Lys Phe Lys Asp Ala Ala Lys Glu Tyr Phe Ala Lys Phe
1               5                   10                  15

Trp Asp

<210> SEQ ID NO 300
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 300

Phe Val Glu Lys Phe Lys Asp Ala Ala Lys Asp Tyr Phe Ala Lys Phe
1               5                   10                  15

Trp Glu

<210> SEQ ID NO 301
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 301

Phe Ala Glu Lys Tyr Lys Glu Ala Val Lys Asp Phe Phe Ala Lys Phe
1               5                   10                  15

Trp Asp

<210> SEQ ID NO 302
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 302

Phe Ala Asp Lys Tyr Lys Asp Ala Val Lys Glu Phe Phe Ala Lys Phe
1               5                   10                  15

Trp Glu

<210> SEQ ID NO 303
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 303

Phe Ala Asp Lys Tyr Lys Glu Ala Val Lys Asp Phe Phe Ala Lys Phe
1               5                   10                  15

Trp Glu

<210> SEQ ID NO 304
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 304

Phe Ala Glu Lys Tyr Lys Asp Ala Val Lys Glu Phe Phe Ala Lys Phe
1               5                   10                  15

Trp Asp

<210> SEQ ID NO 305
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 305

Phe Ala Glu Lys Tyr Lys Asp Ala Val Lys Asp Phe Phe Ala Lys Phe
1               5                   10                  15

Trp Glu

<210> SEQ ID NO 306
<211> LENGTH: 18
<212> TYPE: PRT
<213> ORGANISM: Artificial Sequence
```

<220> FEATURE:
<223> OTHER INFORMATION: Synthetic D or L peptide with optional
      protecting groups.

<400> SEQUENCE: 306

Phe Ala Glu Lys Val Lys Glu Ala Phe Lys Asp Tyr Phe Ala Lys Phe
1               5                   10                  15

Trp Asp

<210> SEQ ID NO 307
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 307

Phe Ala Asp Lys Val Lys Asp Ala Phe Lys Glu Tyr Phe Ala Lys Phe
1               5                   10                  15

Trp Glu

<210> SEQ ID NO 308
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 308

Phe Ala Asp Lys Val Lys Glu Ala Phe Lys Asp Tyr Phe Ala Lys Phe
1               5                   10                  15

Trp Glu

<210> SEQ ID NO 309
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 309

Phe Ala Glu Lys Val Lys Asp Ala Phe Lys Glu Tyr Phe Ala Lys Phe
1               5                   10                  15

Trp Asp

<210> SEQ ID NO 310
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 310

Phe Ala Glu Lys Val Lys Asp Ala Phe Lys Asp Tyr Phe Ala Lys Phe
1               5                   10                  15

Trp Glu

<210> SEQ ID NO 311
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 311

Phe Ala Glu Lys Phe Lys Glu Tyr Val Lys Asp Ala Phe Ala Lys Phe
1               5                   10                  15

Trp Asp

<210> SEQ ID NO 312
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 312

Phe Ala Asp Lys Phe Lys Asp Tyr Val Lys Glu Ala Phe Ala Lys Phe
1               5                   10                  15

Trp Glu

<210> SEQ ID NO 313
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 313

Phe Ala Asp Lys Phe Lys Glu Tyr Val Lys Asp Ala Phe Ala Lys Phe
1               5                   10                  15

Trp Glu

<210> SEQ ID NO 314
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 314

Phe Ala Glu Lys Phe Lys Asp Tyr Val Lys Glu Ala Phe Ala Lys Phe
1               5                   10                  15

Trp Asp

<210> SEQ ID NO 315
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 315

Phe Ala Glu Lys Phe Lys Asp Tyr Val Lys Asp Ala Phe Ala Lys Phe
1               5                   10                  15

Trp Glu

<210> SEQ ID NO 316
<211> LENGTH: 18
<212> TYPE: PRT
<213> ORGANISM: Artificial Sequence

```
<220> FEATURE:
<223> OTHER INFORMATION: Synthetic D or L peptide with optional
      protecting groups.

<400> SEQUENCE: 316

Phe Ala Glu Lys Phe Lys Glu Ala Phe Lys Asp Tyr Val Ala Lys Phe
1               5                  10                  15

Trp Asp

<210> SEQ ID NO 317
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 317

Phe Ala Asp Lys Phe Lys Asp Ala Phe Lys Glu Tyr Val Ala Lys Phe
1               5                  10                  15

Trp Glu

<210> SEQ ID NO 318
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 318

Phe Ala Asp Lys Phe Lys Glu Ala Phe Lys Asp Tyr Val Ala Lys Phe
1               5                  10                  15

Trp Glu

<210> SEQ ID NO 319
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 319

Phe Ala Glu Lys Phe Lys Asp Ala Phe Lys Glu Tyr Val Ala Lys Phe
1               5                  10                  15

Trp Asp

<210> SEQ ID NO 320
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 320

Phe Ala Glu Lys Phe Lys Asp Ala Phe Lys Asp Tyr Val Ala Lys Phe
1               5                  10                  15

Trp Glu

<210> SEQ ID NO 321
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 321

Phe Ala Glu Lys Phe Lys Glu Ala Phe Lys Asp Tyr Phe Ala Lys Val
1               5                   10                  15

Trp Asp

<210> SEQ ID NO 322
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 322

Phe Ala Asp Lys Phe Lys Asp Ala Phe Lys Glu Tyr Phe Ala Lys Val
1               5                   10                  15

Trp Glu

<210> SEQ ID NO 323
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 323

Phe Ala Asp Lys Phe Lys Glu Ala Phe Lys Asp Tyr Phe Ala Lys Val
1               5                   10                  15

Trp Glu

<210> SEQ ID NO 324
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 324

Phe Ala Glu Lys Phe Lys Asp Ala Phe Lys Glu Tyr Phe Ala Lys Val
1               5                   10                  15

Trp Asp

<210> SEQ ID NO 325
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 325

Phe Ala Glu Lys Phe Lys Asp Ala Phe Lys Asp Tyr Phe Ala Lys Val
1               5                   10                  15

Trp Glu

<210> SEQ ID NO 326
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 326

Phe Ala Glu Lys Phe Lys Glu Ala Val Lys Asp Phe Phe Ala Lys Tyr
1               5                   10                  15

Trp Asp

<210> SEQ ID NO 327
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 327

Phe Ala Asp Lys Phe Lys Asp Ala Val Lys Glu Phe Phe Ala Lys Tyr
1               5                   10                  15

Trp Glu

<210> SEQ ID NO 328
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 328

Phe Ala Asp Lys Phe Lys Glu Ala Val Lys Asp Phe Phe Ala Lys Tyr
1               5                   10                  15

Trp Glu

<210> SEQ ID NO 329
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 329

Phe Ala Glu Lys Phe Lys Asp Ala Val Lys Glu Phe Phe Ala Lys Tyr
1               5                   10                  15

Trp Asp

<210> SEQ ID NO 330
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 330

Phe Ala Glu Lys Phe Lys Asp Ala Val Lys Asp Phe Phe Ala Lys Tyr
1               5                   10                  15

Trp Glu

<210> SEQ ID NO 331
<211> LENGTH: 18
<212> TYPE: PRT
<213> ORGANISM: Artificial Sequence
```

<220> FEATURE:
<223> OTHER INFORMATION: Synthetic D or L peptide with optional
      protecting groups.

<400> SEQUENCE: 331

Trp Ala Glu Lys Phe Phe Glu Ala Val Lys Asp Tyr Phe Ala Lys Phe
1               5                   10                  15

Lys Asp

<210> SEQ ID NO 332
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 332

Trp Ala Asp Lys Phe Phe Asp Ala Val Lys Glu Tyr Phe Ala Lys Phe
1               5                   10                  15

Lys Glu

<210> SEQ ID NO 333
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 333

Trp Ala Asp Lys Phe Phe Glu Ala Val Lys Asp Tyr Phe Ala Lys Phe
1               5                   10                  15

Lys Glu

<210> SEQ ID NO 334
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 334

Trp Ala Glu Lys Phe Phe Asp Ala Val Lys Glu Tyr Phe Ala Lys Phe
1               5                   10                  15

Lys Asp

<210> SEQ ID NO 335
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 335

Trp Ala Glu Lys Phe Phe Asp Ala Val Lys Asp Tyr Phe Ala Lys Phe
1               5                   10                  15

Lys Glu

<210> SEQ ID NO 336
<211> LENGTH: 18
<212> TYPE: PRT
<213> ORGANISM: Artificial Sequence -continued

```
<220> FEATURE:
<223> OTHER INFORMATION: Synthetic D or L peptide with optional
      protecting groups.

<400> SEQUENCE: 336

Phe Ala Glu Lys Trp Phe Glu Ala Val Lys Asp Tyr Phe Ala Lys Phe
1               5                   10                  15

Lys Asp

<210> SEQ ID NO 337
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 337

Phe Ala Asp Lys Trp Phe Asp Ala Val Lys Glu Tyr Phe Ala Lys Phe
1               5                   10                  15

Lys Glu

<210> SEQ ID NO 338
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 338

Phe Ala Asp Lys Trp Phe Glu Ala Val Lys Asp Tyr Phe Ala Lys Phe
1               5                   10                  15

Lys Glu

<210> SEQ ID NO 339
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 339

Phe Ala Glu Lys Trp Phe Asp Ala Val Lys Glu Tyr Phe Ala Lys Phe
1               5                   10                  15

Lys Asp

<210> SEQ ID NO 340
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 340

Phe Ala Glu Lys Trp Phe Asp Ala Val Lys Asp Tyr Phe Ala Lys Phe
1               5                   10                  15

Lys Glu

<210> SEQ ID NO 341
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 341

Phe Ala Glu Lys Phe Val Glu Ala Trp Lys Asp Tyr Phe Ala Lys Phe
1               5                   10                  15

Lys Asp

<210> SEQ ID NO 342
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 342

Phe Ala Asp Lys Phe Val Asp Ala Trp Lys Glu Tyr Phe Ala Lys Phe
1               5                   10                  15

Lys Glu

<210> SEQ ID NO 343
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 343

Phe Ala Asp Lys Phe Val Glu Ala Trp Lys Asp Tyr Phe Ala Lys Phe
1               5                   10                  15

Lys Glu

<210> SEQ ID NO 344
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 344

Phe Ala Glu Lys Phe Val Asp Ala Trp Lys Glu Tyr Phe Ala Lys Phe
1               5                   10                  15

Lys Asp

<210> SEQ ID NO 345
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 345

Phe Ala Glu Lys Phe Val Asp Ala Trp Lys Asp Tyr Phe Ala Lys Phe
1               5                   10                  15

Lys Glu

<210> SEQ ID NO 346
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 346

Phe Tyr Glu Lys Phe Ala Glu Ala Val Lys Asp Trp Phe Ala Lys Phe
1               5                   10                  15

Lys Asp

<210> SEQ ID NO 347
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 347

Phe Tyr Asp Lys Phe Ala Asp Ala Val Lys Glu Trp Phe Ala Lys Phe
1               5                   10                  15

Lys Glu

<210> SEQ ID NO 348
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 348

Phe Tyr Asp Lys Phe Ala Glu Ala Val Lys Asp Trp Phe Ala Lys Phe
1               5                   10                  15

Lys Glu

<210> SEQ ID NO 349
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 349

Phe Tyr Glu Lys Phe Ala Asp Ala Val Lys Glu Trp Phe Ala Lys Phe
1               5                   10                  15

Lys Asp

<210> SEQ ID NO 350
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 350

Phe Tyr Glu Lys Phe Ala Asp Ala Val Lys Asp Trp Phe Ala Lys Phe
1               5                   10                  15

Lys Glu

<210> SEQ ID NO 351
<211> LENGTH: 18
<212> TYPE: PRT
<213> ORGANISM: Artificial Sequence
```

```
<220> FEATURE:
<223> OTHER INFORMATION: Synthetic D or L peptide with optional
      protecting groups.
<220> FEATURE:
<221> NAME/KEY: misc_feature
<222> LOCATION: (1)..(1)
<223> OTHER INFORMATION: Xaa is Asp or Glu
<220> FEATURE:
<221> NAME/KEY: misc_feature
<222> LOCATION: (2)..(3)
<223> OTHER INFORMATION: Xaa is Leu, norLeu, Val, Ile, Trp, Phe, Tyr,
      beta-Nal, or alpha-Nal.
<220> FEATURE:
<221> NAME/KEY: misc_feature
<222> LOCATION: (4)..(4)
<223> OTHER INFORMATION: Xaa is Lys or Arg
<220> FEATURE:
<221> NAME/KEY: misc_feature
<222> LOCATION: (5)..(5)
<223> OTHER INFORMATION: Xaa is Ala, His, Ser, Gln, Asn, or Thr
<220> FEATURE:
<221> NAME/KEY: misc_feature
<222> LOCATION: (6)..(7)
<223> OTHER INFORMATION: Xaa is Leu, norLeu, Val, Ile, Trp, Phe, Tyr,
      beta-Nal, or alpha-Nal.
<220> FEATURE:
<221> NAME/KEY: misc_feature
<222> LOCATION: (8)..(8)
<223> OTHER INFORMATION: Xaa is Asp or Glu
<220> FEATURE:
<221> NAME/KEY: misc_feature
<222> LOCATION: (9)..(9)
<223> OTHER INFORMATION: Xaa is Lys or Arg
<220> FEATURE:
<221> NAME/KEY: misc_feature
<222> LOCATION: (10)..(10)
<223> OTHER INFORMATION: Xaa is Leu, norLeu, Val, Ile, Trp, Phe, Tyr,
      beta-Nal, or alpha-Nal.
<220> FEATURE:
<221> NAME/KEY: misc_feature
<222> LOCATION: (11)..(11)
<223> OTHER INFORMATION: Xaa is Ala, His, Ser, Gln, Asn, or Thr
<220> FEATURE:
<221> NAME/KEY: misc_feature
<222> LOCATION: (12)..(12)
<223> OTHER INFORMATION: Xaa is Asp or Glu
<220> FEATURE:
<221> NAME/KEY: misc_feature
<222> LOCATION: (13)..(13)
<223> OTHER INFORMATION: Xaa is Lys or Arg
<220> FEATURE:
<221> NAME/KEY: misc_feature
<222> LOCATION: (14)..(14)
<223> OTHER INFORMATION: Xaa is Leu, norLeu, Val, Ile, Trp, Phe, Tyr,
      beta-Nal, or alpha-Nal.
<220> FEATURE:
<221> NAME/KEY: misc_feature
<222> LOCATION: (15)..(15)
<223> OTHER INFORMATION: Xaa is Lys or Arg
<220> FEATURE:
<221> NAME/KEY: misc_feature
<222> LOCATION: (16)..(16)
<223> OTHER INFORMATION: Xaa is Asp or Glu
<220> FEATURE:
<221> NAME/KEY: misc_feature
<222> LOCATION: (17)..(17)
<223> OTHER INFORMATION: Xaa is Ala, His, Ser, Gln, Asn, or Thr
<220> FEATURE:
<221> NAME/KEY: misc_feature
<222> LOCATION: (18)..(18)
<223> OTHER INFORMATION: Xaa is Leu, norLeu, Val, Ile, Trp, Phe, Tyr,
      beta-Nal, or alpha-Nal.

<400> SEQUENCE: 351

Xaa Xaa Xaa Xaa Xaa Xaa Xaa Xaa Xaa Xaa Xaa Xaa Xaa Xaa Xaa Xaa
1               5                   10                  15

Xaa Xaa
```

<210> SEQ ID NO 352
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 352

Asp Trp Phe Lys His Phe Tyr Asp Lys Val Ala Glu Lys Phe Lys Glu
1               5                   10                  15

Ala Phe

<210> SEQ ID NO 353
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 353

Glu Trp Phe Lys His Phe Tyr Glu Lys Val Ala Asp Lys Phe Lys Asp
1               5                   10                  15

Ala Phe

<210> SEQ ID NO 354
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 354

Glu Trp Phe Lys His Phe Tyr Asp Lys Val Ala Glu Lys Phe Lys Glu
1               5                   10                  15

Ala Phe

<210> SEQ ID NO 355
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 355

Asp Trp Phe Lys His Phe Tyr Glu Lys Val Ala Glu Lys Phe Lys Glu
1               5                   10                  15

Ala Phe

<210> SEQ ID NO 356
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 356

Asp Trp Phe Lys His Phe Tyr Asp Lys Val Ala Asp Lys Phe Lys Glu
1               5                   10                  15

Ala Phe

<210> SEQ ID NO 357
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 357

Asp Trp Phe Lys His Phe Tyr Asp Lys Val Ala Glu Lys Phe Lys Asp
1               5                   10                  15

Ala Phe

<210> SEQ ID NO 358
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 358

Asp Trp His Lys Phe Phe Tyr Asp Lys Val Ala Glu Lys Phe Lys Glu
1               5                   10                  15

Ala Phe

<210> SEQ ID NO 359
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 359

Glu Trp His Lys Phe Phe Tyr Glu Lys Val Ala Asp Lys Phe Lys Asp
1               5                   10                  15

Ala Phe

<210> SEQ ID NO 360
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 360

Glu Trp His Lys Phe Phe Tyr Asp Lys Val Ala Glu Lys Phe Lys Glu
1               5                   10                  15

Ala Phe

<210> SEQ ID NO 361
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 361

Asp Trp His Lys Phe Phe Tyr Glu Lys Val Ala Glu Lys Phe Lys Glu
1               5                   10                  15

Ala Phe

```
<210> SEQ ID NO 362
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 362

Asp Trp His Lys Phe Phe Tyr Asp Lys Val Ala Asp Lys Phe Lys Glu
1               5                   10                  15

Ala Phe

<210> SEQ ID NO 363
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 363

Asp Trp His Lys Phe Phe Tyr Asp Lys Val Ala Glu Lys Phe Lys Asp
1               5                   10                  15

Ala Phe

<210> SEQ ID NO 364
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 364

Asp Trp Phe Lys Phe His Tyr Asp Lys Val Ala Glu Lys Phe Lys Glu
1               5                   10                  15

Ala Phe

<210> SEQ ID NO 365
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 365

Glu Trp Phe Lys Phe His Tyr Glu Lys Val Ala Asp Lys Phe Lys Asp
1               5                   10                  15

Ala Phe

<210> SEQ ID NO 366
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 366

Glu Trp Phe Lys Phe His Tyr Asp Lys Val Ala Glu Lys Phe Lys Glu
1               5                   10                  15

Ala Phe
```

```
<210> SEQ ID NO 367
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 367

Asp Trp Phe Lys Phe His Tyr Glu Lys Val Ala Glu Lys Phe Lys Glu
1               5                   10                  15

Ala Phe

<210> SEQ ID NO 368
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 368

Asp Trp Phe Lys Phe His Tyr Asp Lys Val Ala Asp Lys Phe Lys Glu
1               5                   10                  15

Ala Phe

<210> SEQ ID NO 369
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 369

Asp Trp Phe Lys Phe His Tyr Asp Lys Val Ala Glu Lys Phe Lys Asp
1               5                   10                  15

Ala Phe

<210> SEQ ID NO 370
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 370

Asp Trp Phe Lys Val Phe Tyr Asp Lys His Ala Glu Lys Phe Lys Glu
1               5                   10                  15

Ala Phe

<210> SEQ ID NO 371
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 371

Glu Trp Phe Lys Val Phe Tyr Glu Lys His Ala Asp Lys Phe Lys Asp
1               5                   10                  15

Ala Phe
```

```
<210> SEQ ID NO 372
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 372

Glu Trp Phe Lys Val Phe Tyr Asp Lys His Ala Glu Lys Phe Lys Glu
1               5                   10                  15

Ala Phe

<210> SEQ ID NO 373
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 373

Asp Trp Phe Lys Val Phe Tyr Glu Lys His Ala Glu Lys Phe Lys Glu
1               5                   10                  15

Ala Phe

<210> SEQ ID NO 374
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 374

Asp Trp Phe Lys Val Phe Tyr Asp Lys His Ala Asp Lys Phe Lys Glu
1               5                   10                  15

Ala Phe

<210> SEQ ID NO 375
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 375

Asp Trp Phe Lys Val Phe Tyr Asp Lys His Ala Glu Lys Phe Lys Asp
1               5                   10                  15

Ala Phe

<210> SEQ ID NO 376
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 376

Asp Trp Phe Lys Ala Phe Tyr Asp Lys Val Ala Glu Lys Phe Lys Glu
1               5                   10                  15

His Phe
```

<210> SEQ ID NO 377
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 377

Glu Trp Phe Lys Ala Phe Tyr Glu Lys Val Ala Asp Lys Phe Lys Asp
1               5                   10                  15

His Phe

<210> SEQ ID NO 378
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 378

Glu Trp Phe Lys Ala Phe Tyr Asp Lys Val Ala Glu Lys Phe Lys Glu
1               5                   10                  15

His Phe

<210> SEQ ID NO 379
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 379

Asp Trp Phe Lys Ala Phe Tyr Glu Lys Val Ala Glu Lys Phe Lys Glu
1               5                   10                  15

His Phe

<210> SEQ ID NO 380
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 380

Asp Trp Phe Lys Ala Phe Tyr Asp Lys Val Ala Asp Lys Phe Lys Glu
1               5                   10                  15

His Phe

<210> SEQ ID NO 381
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 381

Asp Trp Phe Lys Ala Phe Tyr Asp Lys Val Ala Glu Lys Phe Lys Asp
1               5                   10                  15

His Phe

```
<210> SEQ ID NO 382
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 382

Asp Trp Phe Lys Ala Phe Tyr Asp Lys Val Ala Glu Lys Phe Lys Glu
1               5                   10                  15

Phe His

<210> SEQ ID NO 383
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 383

Glu Trp Phe Lys Ala Phe Tyr Glu Lys Val Ala Asp Lys Phe Lys Asp
1               5                   10                  15

Phe His

<210> SEQ ID NO 384
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 384

Glu Trp Phe Lys Ala Phe Tyr Asp Lys Val Ala Glu Lys Phe Lys Glu
1               5                   10                  15

Phe His

<210> SEQ ID NO 385
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 385

Asp Trp Phe Lys Ala Phe Tyr Asp Lys Val Ala Glu Lys Phe Lys Glu
1               5                   10                  15

Phe His

<210> SEQ ID NO 386
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 386

Asp Trp Phe Lys Ala Phe Tyr Glu Lys Val Ala Glu Lys Phe Lys Glu
1               5                   10                  15

Phe His
```

<210> SEQ ID NO 387
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 387

Asp Trp Phe Lys Ala Phe Tyr Asp Lys Val Ala Glu Lys Phe Lys Glu
1               5                   10                  15

Phe His

<210> SEQ ID NO 388
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 388

Asp Trp Phe Lys Ala Phe Tyr Asp Lys Val Ala Glu Lys Phe Lys Asp
1               5                   10                  15

Phe His

<210> SEQ ID NO 389
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 389

Phe Ala Glu Lys Phe Lys Glu Ala Val Lys Asp Tyr Phe Ala Lys Phe
1               5                   10                  15

Trp Asp

<210> SEQ ID NO 390
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 390

Phe His Glu Lys Phe Lys Glu Ala Val Lys Asp Tyr Phe Ala Lys Phe
1               5                   10                  15

Trp Asp

<210> SEQ ID NO 391
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 391

Phe His Glu Lys Phe Lys Glu Ala Val Lys Glu Tyr Phe Ala Lys Phe
1               5                   10                  15

Trp Glu

```
<210> SEQ ID NO 392
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 392

Phe His Asp Lys Phe Lys Asp Ala Val Lys Asp Tyr Phe Ala Lys Phe
1               5                   10                  15

Trp Asp

<210> SEQ ID NO 393
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 393

Phe His Asp Lys Phe Lys Asp Ala Val Lys Glu Tyr Phe Ala Lys Phe
1               5                   10                  15

Trp Glu

<210> SEQ ID NO 394
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 394

Phe His Asp Lys Phe Lys Glu Ala Val Lys Asp Tyr Phe Ala Lys Phe
1               5                   10                  15

Trp Asp

<210> SEQ ID NO 395
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 395

Phe His Glu Lys Phe Lys Asp Ala Val Lys Asp Tyr Phe Ala Lys Phe
1               5                   10                  15

Trp Asp

<210> SEQ ID NO 396
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 396

Phe His Glu Lys Phe Lys Glu Ala Val Lys Glu Tyr Phe Ala Lys Phe
1               5                   10                  15

Trp Asp
```

<210> SEQ ID NO 397
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 397

Phe His Glu Lys Phe Lys Glu Ala Val Lys Asp Tyr Phe Ala Lys Phe
1               5                   10                  15

Trp Glu

<210> SEQ ID NO 398
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 398

His Phe Glu Lys Phe Lys Glu Ala Val Lys Asp Tyr Phe Ala Lys Phe
1               5                   10                  15

Trp Asp

<210> SEQ ID NO 399
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 399

His Phe Asp Lys Phe Lys Asp Ala Val Lys Glu Tyr Phe Ala Lys Phe
1               5                   10                  15

Trp Glu

<210> SEQ ID NO 400
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 400

His Phe Glu Lys Phe Lys Glu Ala Val Lys Glu Tyr Phe Ala Lys Phe
1               5                   10                  15

Trp Glu

<210> SEQ ID NO 401
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 401

His Phe Asp Lys Phe Lys Glu Ala Val Lys Asp Tyr Phe Ala Lys Phe
1               5                   10                  15

Trp Asp

<210> SEQ ID NO 402
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 402

His Phe Glu Lys Phe Lys Asp Ala Val Lys Asp Tyr Phe Ala Lys Phe
1               5                   10                  15

Trp Asp

<210> SEQ ID NO 403
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 403

His Phe Glu Lys Phe Lys Glu Ala Val Lys Glu Tyr Phe Ala Lys Phe
1               5                   10                  15

Trp Asp

<210> SEQ ID NO 404
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 404

His Phe Glu Lys Phe Lys Glu Ala Val Lys Asp Tyr Phe Ala Lys Phe
1               5                   10                  15

Trp Glu

<210> SEQ ID NO 405
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 405

Phe Phe Glu Lys His Lys Glu Ala Val Lys Asp Tyr Phe Ala Lys Phe
1               5                   10                  15

Trp Asp

<210> SEQ ID NO 406
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 406

Phe Phe Asp Lys His Lys Asp Ala Val Lys Glu Tyr Phe Ala Lys Phe
1               5                   10                  15

Trp Glu

<210> SEQ ID NO 407
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 407

Phe Phe Glu Lys His Lys Glu Ala Val Lys Glu Tyr Phe Ala Lys Phe
1               5                   10                  15

Trp Glu

<210> SEQ ID NO 408
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 408

Phe Phe Asp Lys His Lys Asp Ala Val Lys Asp Tyr Phe Ala Lys Phe
1               5                   10                  15

Trp Asp

<210> SEQ ID NO 409
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 409

Phe Phe Asp Lys His Lys Glu Ala Val Lys Asp Tyr Phe Ala Lys Phe
1               5                   10                  15

Trp Asp

<210> SEQ ID NO 410
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 410

Phe Phe Glu Lys His Lys Glu Ala Val Lys Glu Tyr Phe Ala Lys Phe
1               5                   10                  15

Trp Asp

<210> SEQ ID NO 411
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 411

Phe Phe Glu Lys His Lys Glu Ala Val Lys Asp Tyr Phe Ala Lys Phe
1               5                   10                  15

Trp Glu

<210> SEQ ID NO 412
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 412

Phe Val Glu Lys Phe Lys Glu Ala His Lys Asp Tyr Phe Ala Lys Phe
1               5                   10                  15

Trp Asp

<210> SEQ ID NO 413
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 413

Phe Val Asp Lys Phe Lys Asp Ala His Lys Glu Tyr Phe Ala Lys Phe
1               5                   10                  15

Trp Glu

<210> SEQ ID NO 414
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 414

Phe Val Glu Lys Phe Lys Glu Ala His Lys Glu Tyr Phe Ala Lys Phe
1               5                   10                  15

Trp Glu

<210> SEQ ID NO 415
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 415

Phe Val Asp Lys Phe Lys Asp Ala His Lys Asp Tyr Phe Ala Lys Phe
1               5                   10                  15

Trp Asp

<210> SEQ ID NO 416
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 416

Phe Val Asp Lys Phe Lys Glu Ala His Lys Asp Tyr Phe Ala Lys Phe
1               5                   10                  15

Trp Asp

<210> SEQ ID NO 417
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 417

Phe Val Glu Lys Phe Lys Asp Ala His Lys Asp Tyr Phe Ala Lys Phe
1               5                   10                  15

Trp Asp

<210> SEQ ID NO 418
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 418

Phe Val Glu Lys Phe Lys Glu Ala His Lys Glu Tyr Phe Ala Lys Phe
1               5                   10                  15

Trp Asp

<210> SEQ ID NO 419
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 419

Phe Val Glu Lys Phe Lys Glu Ala His Lys Asp Tyr Phe Ala Lys Phe
1               5                   10                  15

Trp Glu

<210> SEQ ID NO 420
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 420

Phe Ala Glu Lys Phe Lys Glu His Val Lys Asp Tyr Phe Ala Lys Phe
1               5                   10                  15

Trp Asp

<210> SEQ ID NO 421
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 421

Phe Ala Asp Lys Phe Lys Asp His Val Lys Glu Tyr Phe Ala Lys Phe
1               5                   10                  15

Trp Glu

<210> SEQ ID NO 422
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 422

Phe Ala Glu Lys Phe Lys Glu His Val Lys Glu Tyr Phe Ala Lys Phe
1               5                   10                  15

Trp Glu

<210> SEQ ID NO 423
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 423

Phe Ala Asp Lys Phe Lys Asp His Val Lys Asp Tyr Phe Ala Lys Phe
1               5                   10                  15

Trp Asp

<210> SEQ ID NO 424
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 424

Phe Ala Asp Lys Phe Lys Glu His Val Lys Asp Tyr Phe Ala Lys Phe
1               5                   10                  15

Trp Asp

<210> SEQ ID NO 425
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 425

Phe Ala Glu Lys Phe Lys Asp His Val Lys Asp Tyr Phe Ala Lys Phe
1               5                   10                  15

Trp Asp

<210> SEQ ID NO 426
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 426

Phe Ala Glu Lys Phe Lys Glu His Val Lys Glu Tyr Phe Ala Lys Phe
1               5                   10                  15

Trp Asp

<210> SEQ ID NO 427
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 427

Phe Ala Glu Lys Phe Lys Glu His Val Lys Asp Tyr Phe Ala Lys Phe
1               5                   10                  15

Trp Glu

<210> SEQ ID NO 428
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 428

Phe Ala Glu Lys Phe Lys Glu Phe Val Lys Asp Tyr His Ala Lys Phe
1               5                   10                  15

Trp Asp

<210> SEQ ID NO 429
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 429

Phe Ala Asp Lys Phe Lys Asp Phe Val Lys Glu Tyr His Ala Lys Phe
1               5                   10                  15

Trp Glu

<210> SEQ ID NO 430
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 430

Phe Ala Asp Lys Phe Lys Glu Phe Val Lys Asp Tyr His Ala Lys Phe
1               5                   10                  15

Trp Asp

<210> SEQ ID NO 431
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 431

Phe Ala Glu Lys Phe Lys Asp Phe Val Lys Asp Tyr His Ala Lys Phe
1               5                   10                  15

Trp Asp

<210> SEQ ID NO 432
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 432

Phe Ala Asp Lys Phe Lys Asp Phe Val Lys Asp Tyr His Ala Lys Phe
1               5                   10                  15

Trp Asp

<210> SEQ ID NO 433
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 433

Phe Ala Glu Lys Phe Lys Glu Phe Val Lys Glu Tyr His Ala Lys Phe
1               5                   10                  15

Trp Glu

<210> SEQ ID NO 434
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 434

Phe Ala Glu Lys Phe Lys Glu Phe Val Lys Glu Tyr His Ala Lys Phe
1               5                   10                  15

Trp Asp

<210> SEQ ID NO 435
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 435

Phe Ala Glu Lys Phe Lys Glu Phe Val Lys Asp Tyr His Ala Lys Phe
1               5                   10                  15

Trp Glu

<210> SEQ ID NO 436
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 436

Phe Ala Glu Lys Phe Lys Glu Phe Val Lys Asp Tyr Phe Ala Lys His
1               5                   10                  15

Trp Asp

```
<210> SEQ ID NO 437
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 437

Phe Ala Asp Lys Phe Lys Asp Phe Val Lys Glu Tyr Phe Ala Lys His
1               5                  10                  15

Trp Glu

<210> SEQ ID NO 438
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 438

Phe Ala Glu Lys Phe Lys Glu Phe Val Lys Glu Tyr Phe Ala Lys His
1               5                  10                  15

Trp Glu

<210> SEQ ID NO 439
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 439

Phe Ala Asp Lys Phe Lys Asp Phe Val Lys Asp Tyr Phe Ala Lys His
1               5                  10                  15

Trp Asp

<210> SEQ ID NO 440
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 440

Phe Ala Asp Lys Phe Lys Glu Phe Val Lys Asp Tyr Phe Ala Lys His
1               5                  10                  15

Trp Asp

<210> SEQ ID NO 441
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 441

Phe Ala Glu Lys Phe Lys Asp Phe Val Lys Asp Tyr Phe Ala Lys His
1               5                  10                  15

Trp Asp
```

```
<210> SEQ ID NO 442
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 442

Phe Ala Glu Lys Phe Lys Glu Phe Val Lys Glu Tyr Phe Ala Lys His
1               5                   10                  15

Trp Asp

<210> SEQ ID NO 443
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 443

Phe Ala Glu Lys Phe Lys Glu Phe Val Lys Asp Tyr Phe Ala Lys His
1               5                   10                  15

Trp Glu

<210> SEQ ID NO 444
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (3)..(3)
<223> OTHER INFORMATION: Xaa is beta-napthalanine
<220> FEATURE:
<221> NAME/KEY: misc_feature
<222> LOCATION: (6)..(6)
<223> OTHER INFORMATION: Xaa is beta-napthalanine
<220> FEATURE:
<221> NAME/KEY: misc_feature
<222> LOCATION: (14)..(14)
<223> OTHER INFORMATION: Xaa is beta-napthalanine
<220> FEATURE:
<221> NAME/KEY: misc_feature
<222> LOCATION: (18)..(18)
<223> OTHER INFORMATION: Xaa is beta-napthalanine

<400> SEQUENCE: 444

Asp Trp Xaa Lys Ala Xaa Tyr Asp Lys Val Ala Glu Lys Xaa Lys Glu
1               5                   10                  15

Ala Xaa

<210> SEQ ID NO 445
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (3)..(3)
<223> OTHER INFORMATION: Xaa is beta-napthalanine
<220> FEATURE:
<221> NAME/KEY: misc_feature
<222> LOCATION: (6)..(6)
<223> OTHER INFORMATION: Xaa is beta-napthalanine
```

```
<220> FEATURE:
<221> NAME/KEY: misc_feature
<222> LOCATION: (14)..(14)
<223> OTHER INFORMATION: Xaa is beta-napthalanine
<220> FEATURE:
<221> NAME/KEY: misc_feature
<222> LOCATION: (18)..(18)
<223> OTHER INFORMATION: Xaa is beta-napthalanine

<400> SEQUENCE: 445

Glu Trp Xaa Lys Ala Xaa Tyr Glu Lys Val Ala Asp Lys Xaa Lys Asp
1               5                   10                  15

Ala Xaa

<210> SEQ ID NO 446
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (3)..(3)
<223> OTHER INFORMATION: Xaa is beta-napthalanine
<220> FEATURE:
<221> NAME/KEY: misc_feature
<222> LOCATION: (6)..(6)
<223> OTHER INFORMATION: Xaa is beta-napthalanine
<220> FEATURE:
<221> NAME/KEY: misc_feature
<222> LOCATION: (14)..(14)
<223> OTHER INFORMATION: Xaa is beta-napthalanine
<220> FEATURE:
<221> NAME/KEY: misc_feature
<222> LOCATION: (18)..(18)
<223> OTHER INFORMATION: Xaa is beta-napthalanine

<400> SEQUENCE: 446

Glu Trp Xaa Lys Ala Xaa Tyr Glu Lys Val Ala Glu Lys Xaa Lys Glu
1               5                   10                  15

Ala Xaa

<210> SEQ ID NO 447
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (3)..(3)
<223> OTHER INFORMATION: Xaa is beta-napthalanine
<220> FEATURE:
<221> NAME/KEY: misc_feature
<222> LOCATION: (6)..(6)
<223> OTHER INFORMATION: Xaa is beta-napthalanine
<220> FEATURE:
<221> NAME/KEY: misc_feature
<222> LOCATION: (14)..(14)
<223> OTHER INFORMATION: Xaa is beta-napthalanine
<220> FEATURE:
<221> NAME/KEY: misc_feature
<222> LOCATION: (18)..(18)
<223> OTHER INFORMATION: Xaa is beta-napthalanine

<400> SEQUENCE: 447

Asp Trp Xaa Lys Ala Xaa Tyr Asp Lys Val Ala Asp Lys Xaa Lys Asp
1               5                   10                  15

Ala Xaa
```

```
<210> SEQ ID NO 448
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (3)..(3)
<223> OTHER INFORMATION: Xaa is beta-napthalanine
<220> FEATURE:
<221> NAME/KEY: misc_feature
<222> LOCATION: (6)..(6)
<223> OTHER INFORMATION: Xaa is beta-napthalanine
<220> FEATURE:
<221> NAME/KEY: misc_feature
<222> LOCATION: (14)..(14)
<223> OTHER INFORMATION: Xaa is beta-napthalanine
<220> FEATURE:
<221> NAME/KEY: misc_feature
<222> LOCATION: (18)..(18)
<223> OTHER INFORMATION: Xaa is beta-napthalanine

<400> SEQUENCE: 448

Glu Trp Xaa Lys Ala Xaa Tyr Asp Lys Val Ala Glu Lys Xaa Lys Glu
1               5                   10                  15

Ala Xaa

<210> SEQ ID NO 449
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (3)..(3)
<223> OTHER INFORMATION: Xaa is beta-napthalanine
<220> FEATURE:
<221> NAME/KEY: misc_feature
<222> LOCATION: (6)..(6)
<223> OTHER INFORMATION: Xaa is beta-napthalanine
<220> FEATURE:
<221> NAME/KEY: misc_feature
<222> LOCATION: (14)..(14)
<223> OTHER INFORMATION: Xaa is beta-napthalanine
<220> FEATURE:
<221> NAME/KEY: misc_feature
<222> LOCATION: (18)..(18)
<223> OTHER INFORMATION: Xaa is beta-napthalanine

<400> SEQUENCE: 449

Asp Trp Xaa Lys Ala Xaa Tyr Glu Lys Val Ala Glu Lys Xaa Lys Glu
1               5                   10                  15

Ala Xaa

<210> SEQ ID NO 450
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (3)..(3)
<223> OTHER INFORMATION: Xaa is beta-napthalanine
<220> FEATURE:
<221> NAME/KEY: misc_feature
<222> LOCATION: (6)..(6)
<223> OTHER INFORMATION: Xaa is beta-napthalanine
```

```
<220> FEATURE:
<221> NAME/KEY: misc_feature
<222> LOCATION: (14)..(14)
<223> OTHER INFORMATION: Xaa is beta-napthalanine
<220> FEATURE:
<221> NAME/KEY: misc_feature
<222> LOCATION: (18)..(18)
<223> OTHER INFORMATION: Xaa is beta-napthalanine

<400> SEQUENCE: 450

Asp Trp Xaa Lys Ala Xaa Tyr Asp Lys Val Ala Asp Lys Xaa Lys Glu
1               5                   10                  15

Ala Xaa

<210> SEQ ID NO 451
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (3)..(3)
<223> OTHER INFORMATION: Xaa is beta-napthalanine
<220> FEATURE:
<221> NAME/KEY: misc_feature
<222> LOCATION: (6)..(6)
<223> OTHER INFORMATION: Xaa is beta-napthalanine
<220> FEATURE:
<221> NAME/KEY: misc_feature
<222> LOCATION: (14)..(14)
<223> OTHER INFORMATION: Xaa is beta-napthalanine
<220> FEATURE:
<221> NAME/KEY: misc_feature
<222> LOCATION: (18)..(18)
<223> OTHER INFORMATION: Xaa is beta-napthalanine

<400> SEQUENCE: 451

Asp Trp Xaa Lys Ala Xaa Tyr Asp Lys Val Ala Glu Lys Xaa Lys Asp
1               5                   10                  15

Ala Xaa

<210> SEQ ID NO 452
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (3)..(3)
<223> OTHER INFORMATION: Xaa is beta-napthalanine
<220> FEATURE:
<221> NAME/KEY: misc_feature
<222> LOCATION: (6)..(6)
<223> OTHER INFORMATION: Xaa is beta-napthalanine

<400> SEQUENCE: 452

Asp Trp Xaa Lys Ala Xaa Tyr Asp Lys Val Ala Glu Lys Phe Lys Glu
1               5                   10                  15

Ala Phe

<210> SEQ ID NO 453
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
```

```
<220> FEATURE:
<221> NAME/KEY: misc_feature
<222> LOCATION: (14)..(14)
<223> OTHER INFORMATION: Xaa is beta-napthalanine
<220> FEATURE:
<221> NAME/KEY: misc_feature
<222> LOCATION: (18)..(18)
<223> OTHER INFORMATION: Xaa is beta-napthalanine

<400> SEQUENCE: 453

Asp Trp Phe Lys Ala Phe Tyr Asp Lys Val Ala Glu Lys Xaa Lys Glu
1               5                   10                  15

Ala Xaa

<210> SEQ ID NO 454
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (3)..(3)
<223> OTHER INFORMATION: Xaa is beta-napthalanine

<400> SEQUENCE: 454

Asp Trp Xaa Lys Ala Phe Tyr Asp Lys Val Ala Glu Lys Phe Lys Glu
1               5                   10                  15

Ala Phe

<210> SEQ ID NO 455
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (6)..(6)
<223> OTHER INFORMATION: Xaa is beta-napthalanine

<400> SEQUENCE: 455

Asp Trp Phe Lys Ala Xaa Tyr Asp Lys Val Ala Glu Lys Phe Lys Glu
1               5                   10                  15

Ala Phe

<210> SEQ ID NO 456
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (14)..(14)
<223> OTHER INFORMATION: Xaa is beta-napthalanine

<400> SEQUENCE: 456

Asp Trp Phe Lys Ala Phe Tyr Asp Lys Val Ala Glu Lys Xaa Lys Glu
1               5                   10                  15

Ala Phe

<210> SEQ ID NO 457
<211> LENGTH: 18
<212> TYPE: PRT
```

```
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (18)..(18)
<223> OTHER INFORMATION: Xaa is beta-napthalanine

<400> SEQUENCE: 457

Asp Trp Phe Lys Ala Phe Tyr Asp Lys Val Ala Glu Lys Phe Lys Glu
1               5                   10                  15

Ala Xaa

<210> SEQ ID NO 458
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (1)..(1)
<223> OTHER INFORMATION: Xaa is beta-napthalanine
<220> FEATURE:
<221> NAME/KEY: misc_feature
<222> LOCATION: (5)..(5)
<223> OTHER INFORMATION: Xaa is beta-napthalanine
<220> FEATURE:
<221> NAME/KEY: misc_feature
<222> LOCATION: (13)..(13)
<223> OTHER INFORMATION: Xaa is beta-napthalanine
<220> FEATURE:
<221> NAME/KEY: misc_feature
<222> LOCATION: (16)..(16)
<223> OTHER INFORMATION: Xaa is beta-napthalanine

<400> SEQUENCE: 458

Xaa Ala Glu Lys Xaa Lys Glu Ala Val Lys Asp Tyr Xaa Ala Lys Xaa
1               5                   10                  15

Trp Asp

<210> SEQ ID NO 459
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (1)..(1)
<223> OTHER INFORMATION: Xaa is beta-napthalanine
<220> FEATURE:
<221> NAME/KEY: misc_feature
<222> LOCATION: (5)..(5)
<223> OTHER INFORMATION: Xaa is beta-napthalanine

<400> SEQUENCE: 459

Xaa Ala Glu Lys Xaa Lys Glu Ala Val Lys Asp Tyr Phe Ala Lys Phe
1               5                   10                  15

Trp Asp

<210> SEQ ID NO 460
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
```

```
<220> FEATURE:
<221> NAME/KEY: misc_feature
<222> LOCATION: (13)..(13)
<223> OTHER INFORMATION: Xaa is beta-napthalanine
<220> FEATURE:
<221> NAME/KEY: misc_feature
<222> LOCATION: (16)..(16)
<223> OTHER INFORMATION: Xaa is beta-napthalanine

<400> SEQUENCE: 460

Phe Ala Glu Lys Phe Lys Glu Ala Val Lys Asp Tyr Xaa Ala Lys Xaa
1               5                   10                  15

Trp Asp

<210> SEQ ID NO 461
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (1)..(1)
<223> OTHER INFORMATION: Xaa is beta-napthalanine

<400> SEQUENCE: 461

Xaa Ala Glu Lys Phe Lys Glu Ala Val Lys Asp Tyr Phe Ala Lys Phe
1               5                   10                  15

Trp Asp

<210> SEQ ID NO 462
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (5)..(5)
<223> OTHER INFORMATION: Xaa is beta-napthalanine

<400> SEQUENCE: 462

Phe Ala Glu Lys Xaa Lys Glu Ala Val Lys Asp Tyr Phe Ala Lys Phe
1               5                   10                  15

Trp Asp

<210> SEQ ID NO 463
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (13)..(13)
<223> OTHER INFORMATION: Xaa is beta-napthalanine

<400> SEQUENCE: 463

Phe Ala Glu Lys Phe Lys Glu Ala Val Lys Asp Tyr Xaa Ala Lys Phe
1               5                   10                  15

Trp Asp

<210> SEQ ID NO 464
<211> LENGTH: 18
<212> TYPE: PRT
```

<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (16)..(16)
<223> OTHER INFORMATION: Xaa is beta-napthalanine

<400> SEQUENCE: 464

Phe Ala Glu Lys Phe Lys Glu Ala Val Lys Asp Tyr Phe Ala Lys Xaa
1               5                   10                  15

Trp Asp

<210> SEQ ID NO 465
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 465

Phe Ala Glu Lys Phe Lys Glu Ala Val Lys Glu Tyr Phe Ala Lys Phe
1               5                   10                  15

Trp Glu

<210> SEQ ID NO 466
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 466

Phe Ala Asp Lys Phe Lys Asp Ala Val Lys Asp Tyr Phe Ala Lys Phe
1               5                   10                  15

Trp Asp

<210> SEQ ID NO 467
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 467

Phe Ala Glu Arg Phe Arg Glu Ala Val Lys Asp Tyr Phe Ala Lys Phe
1               5                   10                  15

Trp Asp

<210> SEQ ID NO 468
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 468

Phe Ala Glu Lys Phe Arg Glu Ala Val Lys Asp Tyr Phe Ala Lys Phe
1               5                   10                  15

Trp Asp

```
<210> SEQ ID NO 469
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 469

Phe Ala Glu Lys Phe Lys Glu Ala Val Arg Asp Tyr Phe Ala Lys Phe
1               5                   10                  15

Trp Asp

<210> SEQ ID NO 470
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 470

Phe Ala Glu Lys Phe Lys Glu Ala Val Lys Asp Tyr Phe Ala Arg Phe
1               5                   10                  15

Trp Asp

<210> SEQ ID NO 471
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 471

Phe Ala Glu Lys Phe Lys Glu Ala Val Lys Glu Tyr Phe Ala Lys Phe
1               5                   10                  15

Trp Glu

<210> SEQ ID NO 472
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 472

Phe Ala Asp Lys Phe Lys Asp Ala Val Lys Asp Tyr Phe Ala Lys Phe
1               5                   10                  15

Trp Asp

<210> SEQ ID NO 473
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 473

Phe Ala Glu Arg Phe Arg Glu Ala Val Lys Asp Tyr Phe Ala Lys Phe
1               5                   10                  15

Trp Asp
```

<210> SEQ ID NO 474
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 474

Phe Ala Glu Lys Phe Arg Glu Ala Val Lys Asp Tyr Phe Ala Lys Phe
1               5                   10                  15

Trp Asp

<210> SEQ ID NO 475
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 475

Phe Ala Glu Lys Phe Lys Glu Ala Val Arg Asp Tyr Phe Ala Lys Phe
1               5                   10                  15

Trp Asp

<210> SEQ ID NO 476
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 476

Phe Ala Glu Lys Phe Lys Glu Ala Val Lys Asp Tyr Phe Ala Arg Phe
1               5                   10                  15

Trp Asp

<210> SEQ ID NO 477
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 477

Phe Ala Glu Lys Phe Lys Glu Ala Val Lys Glu Tyr Phe Ala Lys Phe
1               5                   10                  15

Trp Glu

<210> SEQ ID NO 478
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 478

Phe Ala Asp Lys Phe Lys Asp Ala Val Lys Asp Tyr Phe Ala Lys Phe
1               5                   10                  15

Trp Asp

<210> SEQ ID NO 479
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 479

Phe Ala Glu Arg Phe Arg Glu Ala Val Lys Asp Tyr Phe Ala Lys Phe
1               5                   10                  15

Trp Asp

<210> SEQ ID NO 480
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 480

Phe Ala Glu Lys Phe Arg Glu Ala Val Lys Asp Tyr Phe Ala Lys Phe
1               5                   10                  15

Trp Asp

<210> SEQ ID NO 481
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 481

Phe Ala Glu Lys Phe Lys Glu Ala Val Arg Asp Tyr Phe Ala Lys Phe
1               5                   10                  15

Trp Asp

<210> SEQ ID NO 482
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 482

Phe Ala Glu Lys Phe Lys Glu Ala Val Lys Asp Tyr Phe Ala Arg Phe
1               5                   10                  15

Trp Asp

<210> SEQ ID NO 483
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 483

Phe Ala Glu Arg Phe Arg Glu Ala Val Lys Asp Tyr Phe Ala Lys Phe
1               5                   10                  15

Trp Asp

<210> SEQ ID NO 484
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 484

Phe Ala Glu Lys Phe Arg Glu Ala Val Lys Asp Tyr Phe Ala Lys Phe
1               5                   10                  15

Trp Asp

<210> SEQ ID NO 485
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 485

Phe Ala Glu Lys Phe Lys Glu Ala Val Arg Asp Tyr Phe Ala Lys Phe
1               5                   10                  15

Trp Asp

<210> SEQ ID NO 486
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 486

Phe Ala Glu Lys Phe Lys Glu Ala Val Lys Asp Tyr Phe Ala Arg Phe
1               5                   10                  15

Trp Asp

<210> SEQ ID NO 487
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 487

Phe Ala Glu Lys Phe Lys Glu Ala Val Lys Glu Tyr Phe Ala Lys Phe
1               5                   10                  15

Trp Glu

<210> SEQ ID NO 488
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 488

Phe Ala Asp Lys Phe Lys Asp Ala Val Lys Asp Tyr Phe Ala Lys Phe
1               5                   10                  15

Trp Asp

<210> SEQ ID NO 489
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 489

Phe Ala Glu Arg Phe Arg Glu Ala Val Lys Asp Tyr Phe Ala Lys Phe
1               5                   10                  15

Trp Asp

<210> SEQ ID NO 490
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 490

Phe Ala Glu Lys Phe Arg Glu Ala Val Lys Asp Tyr Phe Ala Lys Phe
1               5                   10                  15

Trp Asp

<210> SEQ ID NO 491
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 491

Phe Ala Glu Lys Phe Lys Glu Ala Val Arg Asp Tyr Phe Ala Lys Phe
1               5                   10                  15

Trp Asp

<210> SEQ ID NO 492
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 492

Phe Ala Glu Lys Phe Lys Glu Ala Val Lys Asp Tyr Phe Ala Arg Phe
1               5                   10                  15

Trp Asp

<210> SEQ ID NO 493
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 493

Leu Phe Glu Lys Phe Ala Glu Ala Phe Lys Asp Tyr Val Ala Lys Trp
1               5                   10                  15

Lys Asp

```
<210> SEQ ID NO 494
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 494

Leu Phe Glu Arg Phe Ala Glu Ala Phe Lys Asp Tyr Val Ala Lys Trp
1               5                   10                  15

Lys Asp

<210> SEQ ID NO 495
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 495

Leu Phe Glu Lys Phe Ala Glu Ala Phe Arg Asp Tyr Val Ala Lys Trp
1               5                   10                  15

Lys Asp

<210> SEQ ID NO 496
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 496

Leu Phe Glu Lys Phe Ala Glu Ala Phe Lys Asp Tyr Val Ala Arg Trp
1               5                   10                  15

Lys Asp

<210> SEQ ID NO 497
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 497

Leu Phe Glu Lys Phe Ala Glu Ala Phe Lys Asp Tyr Val Ala Lys Trp
1               5                   10                  15

Arg Asp

<210> SEQ ID NO 498
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 498

Leu Phe Glu Lys Phe Ala Glu Ala Phe Lys Glu Tyr Val Ala Lys Trp
1               5                   10                  15

Lys Glu
```

```
<210> SEQ ID NO 499
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 499

Leu Phe Asp Lys Phe Ala Asp Ala Phe Lys Asp Tyr Val Ala Lys Trp
1               5                   10                  15

Lys Asp

<210> SEQ ID NO 500
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 500

Leu Phe Asp Lys Phe Ala Glu Ala Phe Lys Asp Tyr Val Ala Lys Trp
1               5                   10                  15

Lys Asp

<210> SEQ ID NO 501
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 501

Leu Phe Glu Lys Phe Ala Asp Ala Phe Lys Asp Tyr Val Ala Lys Trp
1               5                   10                  15

Lys Asp

<210> SEQ ID NO 502
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 502

Leu Phe Glu Lys Phe Ala Glu Ala Phe Lys Glu Tyr Val Ala Lys Trp
1               5                   10                  15

Lys Asp

<210> SEQ ID NO 503
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 503

Leu Phe Glu Lys Phe Ala Glu Ala Phe Lys Asp Tyr Val Ala Lys Trp
1               5                   10                  15

Lys Glu
```

<210> SEQ ID NO 504
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 504

Phe Ala Glu Lys Ala Trp Glu Phe Val Lys Asp Tyr Phe Ala Lys Leu
1               5                   10                  15

Lys Asp

<210> SEQ ID NO 505
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 505

Phe Ala Glu Arg Ala Trp Glu Phe Val Lys Asp Tyr Phe Ala Lys Leu
1               5                   10                  15

Lys Asp

<210> SEQ ID NO 506
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 506

Phe Ala Glu Lys Ala Trp Glu Phe Val Lys Asp Tyr Phe Ala Lys Leu
1               5                   10                  15

Lys Asp

<210> SEQ ID NO 507
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 507

Phe Ala Glu Lys Ala Trp Glu Phe Val Lys Asp Tyr Phe Ala Lys Leu
1               5                   10                  15

Lys Asp

<210> SEQ ID NO 508
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 508

Phe Ala Glu Lys Ala Trp Glu Phe Val Lys Asp Tyr Phe Ala Lys Leu
1               5                   10                  15

Arg Asp

```
<210> SEQ ID NO 509
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 509

Phe Ala Glu Lys Ala Trp Glu Phe Val Lys Glu Tyr Phe Ala Lys Leu
1               5                   10                  15

Lys Glu

<210> SEQ ID NO 510
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 510

Phe Ala Asp Lys Ala Trp Asp Phe Val Lys Asp Tyr Phe Ala Lys Leu
1               5                   10                  15

Lys Asp

<210> SEQ ID NO 511
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 511

Phe Ala Asp Lys Ala Trp Glu Phe Val Lys Asp Tyr Phe Ala Lys Leu
1               5                   10                  15

Lys Asp

<210> SEQ ID NO 512
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 512

Phe Ala Glu Lys Ala Trp Asp Phe Val Lys Asp Tyr Phe Ala Lys Leu
1               5                   10                  15

Lys Asp

<210> SEQ ID NO 513
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 513

Phe Ala Glu Lys Ala Trp Glu Phe Val Lys Glu Tyr Phe Ala Lys Leu
1               5                   10                  15

Lys Asp
```

<210> SEQ ID NO 514
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 514

Phe Ala Glu Lys Ala Trp Glu Phe Val Lys Asp Tyr Phe Ala Lys Leu
1               5                   10                  15

Lys Glu

<210> SEQ ID NO 515
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 515

Phe Phe Glu Lys Phe Lys Glu Phe Val Lys Asp Tyr Phe Ala Lys Leu
1               5                   10                  15

Trp Asp

<210> SEQ ID NO 516
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 516

Phe Phe Glu Lys Phe Lys Glu Phe Val Lys Glu Tyr Phe Ala Lys Leu
1               5                   10                  15

Trp Glu

<210> SEQ ID NO 517
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 517

Phe Phe Asp Lys Phe Lys Asp Phe Val Lys Asp Tyr Phe Ala Lys Leu
1               5                   10                  15

Trp Asp

<210> SEQ ID NO 518
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 518

Phe Phe Glu Arg Phe Lys Glu Phe Val Lys Asp Tyr Phe Ala Lys Leu
1               5                   10                  15

Trp Asp

-continued

<210> SEQ ID NO 519
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 519

Phe Phe Glu Lys Phe Arg Glu Phe Val Lys Asp Tyr Phe Ala Lys Leu
1               5                   10                  15

Trp Asp

<210> SEQ ID NO 520
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 520

Phe Phe Glu Lys Phe Lys Glu Phe Val Arg Asp Tyr Phe Ala Lys Leu
1               5                   10                  15

Trp Asp

<210> SEQ ID NO 521
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 521

Phe Phe Glu Lys Phe Lys Glu Phe Val Lys Asp Tyr Phe Ala Arg Leu
1               5                   10                  15

Trp Asp

<210> SEQ ID NO 522
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 522

Phe Phe Asp Lys Phe Lys Glu Phe Val Lys Asp Tyr Phe Ala Lys Leu
1               5                   10                  15

Trp Asp

<210> SEQ ID NO 523
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 523

Phe Phe Glu Lys Phe Lys Asp Phe Val Lys Asp Tyr Phe Ala Lys Leu
1               5                   10                  15

Trp Asp

```
<210> SEQ ID NO 524
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 524

Phe Phe Glu Lys Phe Lys Glu Phe Val Lys Glu Tyr Phe Ala Lys Leu
1               5                   10                  15

Trp Asp

<210> SEQ ID NO 525
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 525

Phe Phe Glu Lys Phe Lys Glu Phe Val Lys Asp Tyr Phe Ala Lys Leu
1               5                   10                  15

Trp Glu

<210> SEQ ID NO 526
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 526

Phe Leu Glu Lys Phe Lys Glu Phe Val Lys Asp Tyr Phe Ala Lys Phe
1               5                   10                  15

Trp Asp

<210> SEQ ID NO 527
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 527

Phe Leu Glu Lys Phe Lys Glu Phe Val Lys Glu Tyr Phe Ala Lys Phe
1               5                   10                  15

Trp Glu

<210> SEQ ID NO 528
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 528

Phe Leu Asp Lys Phe Lys Glu Phe Val Lys Asp Tyr Phe Ala Lys Phe
1               5                   10                  15

Trp Asp
```

```
<210> SEQ ID NO 529
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 529

Phe Leu Asp Lys Phe Lys Glu Phe Val Lys Asp Tyr Phe Ala Lys Phe
1               5                   10                  15

Trp Asp

<210> SEQ ID NO 530
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 530

Phe Leu Glu Lys Phe Lys Asp Phe Val Lys Asp Tyr Phe Ala Lys Phe
1               5                   10                  15

Trp Asp

<210> SEQ ID NO 531
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 531

Phe Leu Glu Lys Phe Lys Glu Phe Val Lys Glu Tyr Phe Ala Lys Phe
1               5                   10                  15

Trp Asp

<210> SEQ ID NO 532
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 532

Phe Leu Glu Lys Phe Lys Glu Phe Val Lys Asp Tyr Phe Ala Lys Phe
1               5                   10                  15

Trp Glu

<210> SEQ ID NO 533
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 533

Phe Leu Glu Arg Phe Lys Glu Phe Val Lys Asp Tyr Phe Ala Lys Phe
1               5                   10                  15

Trp Asp
```

```
<210> SEQ ID NO 534
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 534

Phe Leu Glu Lys Phe Arg Glu Phe Val Lys Asp Tyr Phe Ala Lys Phe
1               5                   10                  15

Trp Asp

<210> SEQ ID NO 535
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 535

Phe Leu Glu Lys Phe Lys Glu Phe Val Arg Asp Tyr Phe Ala Lys Phe
1               5                   10                  15

Trp Asp

<210> SEQ ID NO 536
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 536

Phe Leu Glu Lys Phe Lys Glu Phe Val Lys Asp Tyr Phe Ala Arg Phe
1               5                   10                  15

Trp Asp

<210> SEQ ID NO 537
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 537

Phe Phe Glu Lys Phe Lys Glu Phe Phe Lys Asp Tyr Phe Ala Lys Leu
1               5                   10                  15

Trp Asp

<210> SEQ ID NO 538
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 538

Phe Phe Glu Lys Phe Lys Glu Phe Phe Lys Glu Tyr Phe Ala Lys Leu
1               5                   10                  15

Trp Glu
```

<210> SEQ ID NO 539
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 539

Phe Phe Asp Lys Phe Lys Asp Phe Phe Lys Asp Tyr Phe Ala Lys Leu
1               5                   10                  15

Trp Asp

<210> SEQ ID NO 540
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 540

Phe Phe Glu Arg Phe Lys Glu Phe Phe Lys Asp Tyr Phe Ala Lys Leu
1               5                   10                  15

Trp Asp

<210> SEQ ID NO 541
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 541

Phe Phe Glu Lys Phe Arg Glu Phe Phe Lys Asp Tyr Phe Ala Lys Leu
1               5                   10                  15

Trp Asp

<210> SEQ ID NO 542
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 542

Phe Phe Glu Lys Phe Lys Glu Phe Phe Arg Asp Tyr Phe Ala Lys Leu
1               5                   10                  15

Trp Asp

<210> SEQ ID NO 543
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 543

Phe Phe Glu Arg Phe Lys Glu Phe Phe Lys Asp Tyr Phe Ala Arg Leu
1               5                   10                  15

Trp Asp

<210> SEQ ID NO 544
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 544

Phe Phe Asp Lys Phe Lys Glu Phe Phe Lys Asp Tyr Phe Ala Lys Leu
1               5                   10                  15

Trp Asp

<210> SEQ ID NO 545
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 545

Phe Phe Glu Lys Phe Lys Asp Phe Phe Lys Asp Tyr Phe Ala Lys Leu
1               5                   10                  15

Trp Asp

<210> SEQ ID NO 546
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 546

Phe Phe Glu Lys Phe Lys Glu Phe Phe Lys Glu Tyr Phe Ala Lys Leu
1               5                   10                  15

Trp Asp

<210> SEQ ID NO 547
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 547

Phe Phe Glu Lys Phe Lys Glu Phe Phe Lys Asp Tyr Phe Ala Lys Leu
1               5                   10                  15

Trp Glu

<210> SEQ ID NO 548
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 548

Phe Ala Glu Lys Phe Lys Glu Ala Val Lys Asp Tyr Phe Ala Lys Phe
1               5                   10                  15

Trp Asp

```
<210> SEQ ID NO 549
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 549

Phe Ala Glu Lys Phe Lys Glu Ala Val Lys Glu Tyr Phe Ala Lys Phe
1               5                   10                  15

Trp Glu

<210> SEQ ID NO 550
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 550

Phe Ala Asp Lys Phe Lys Asp Ala Val Lys Asp Tyr Phe Ala Lys Phe
1               5                   10                  15

Trp Asp

<210> SEQ ID NO 551
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 551

Phe Ala Glu Arg Phe Arg Glu Ala Val Lys Asp Tyr Phe Ala Lys Phe
1               5                   10                  15

Trp Asp

<210> SEQ ID NO 552
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 552

Phe Ala Glu Lys Phe Arg Glu Ala Val Lys Asp Tyr Phe Ala Lys Phe
1               5                   10                  15

Trp Asp

<210> SEQ ID NO 553
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 553

Phe Ala Glu Lys Phe Lys Glu Ala Val Arg Asp Tyr Phe Ala Lys Phe
1               5                   10                  15

Trp Asp
```

```
<210> SEQ ID NO 554
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 554

Phe Ala Glu Lys Phe Lys Glu Ala Val Lys Asp Tyr Phe Ala Arg Phe
1               5                   10                  15

Trp Asp

<210> SEQ ID NO 555
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 555

Asp Lys Trp Lys Ala Val Tyr Asp Lys Phe Ala Glu Ala Phe Lys Glu
1               5                   10                  15

Phe Phe

<210> SEQ ID NO 556
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 556

Glu Lys Trp Lys Ala Val Tyr Glu Lys Phe Ala Glu Ala Phe Lys Glu
1               5                   10                  15

Phe Phe

<210> SEQ ID NO 557
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 557

Asp Lys Trp Lys Ala Val Tyr Asp Lys Phe Ala Asp Ala Phe Lys Asp
1               5                   10                  15

Phe Phe

<210> SEQ ID NO 558
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 558

Asp Arg Trp Lys Ala Val Tyr Asp Lys Phe Ala Glu Ala Phe Lys Glu
1               5                   10                  15

Phe Phe
```

```
<210> SEQ ID NO 559
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 559

Asp Lys Trp Arg Ala Val Tyr Asp Lys Phe Ala Glu Ala Phe Lys Glu
1               5                   10                  15

Phe Phe

<210> SEQ ID NO 560
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 560

Asp Lys Trp Lys Ala Val Tyr Asp Arg Phe Ala Glu Ala Phe Lys Glu
1               5                   10                  15

Phe Phe

<210> SEQ ID NO 561
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 561

Asp Lys Trp Lys Ala Val Tyr Asp Lys Phe Ala Glu Ala Phe Arg Glu
1               5                   10                  15

Phe Phe

<210> SEQ ID NO 562
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 562

Phe Phe Glu Lys Phe Ala Glu Ala Phe Lys Asp Tyr Val Ala Lys Trp
1               5                   10                  15

Lys Asp

<210> SEQ ID NO 563
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 563

Phe Phe Glu Lys Phe Ala Glu Ala Phe Lys Glu Tyr Val Ala Lys Trp
1               5                   10                  15

Lys Glu
```

-continued

```
<210> SEQ ID NO 564
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 564

Phe Phe Asp Lys Phe Ala Asp Ala Phe Lys Asp Tyr Val Ala Lys Trp
1               5                   10                  15

Lys Asp

<210> SEQ ID NO 565
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 565

Phe Phe Glu Arg Phe Ala Glu Ala Phe Lys Asp Tyr Val Ala Lys Trp
1               5                   10                  15

Lys Asp

<210> SEQ ID NO 566
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 566

Phe Phe Glu Arg Phe Ala Glu Ala Phe Arg Asp Tyr Val Ala Lys Trp
1               5                   10                  15

Lys Asp

<210> SEQ ID NO 567
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 567

Phe Phe Glu Lys Phe Ala Glu Ala Phe Lys Asp Tyr Val Ala Arg Trp
1               5                   10                  15

Lys Asp

<210> SEQ ID NO 568
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 568

Phe Phe Glu Arg Phe Ala Glu Ala Phe Lys Asp Tyr Val Ala Lys Trp
1               5                   10                  15

Arg Asp
```

```
<210> SEQ ID NO 569
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 569

Phe Phe Asp Lys Phe Ala Glu Ala Phe Lys Asp Tyr Val Ala Lys Trp
1               5                   10                  15

Lys Asp

<210> SEQ ID NO 570
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 570

Phe Phe Glu Lys Phe Ala Asp Ala Phe Lys Asp Tyr Val Ala Lys Trp
1               5                   10                  15

Lys Asp

<210> SEQ ID NO 571
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 571

Phe Phe Glu Arg Phe Ala Glu Ala Phe Lys Glu Tyr Val Ala Lys Trp
1               5                   10                  15

Lys Asp

<210> SEQ ID NO 572
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 572

Phe Phe Glu Arg Phe Ala Glu Ala Phe Lys Asp Tyr Val Ala Lys Trp
1               5                   10                  15

Lys Glu

<210> SEQ ID NO 573
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 573

Phe Phe Glu Lys Phe Lys Glu Phe Phe Lys Asp Tyr Phe Ala Lys Phe
1               5                   10                  15

Trp Asp
```

<210> SEQ ID NO 574
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 574

Phe Phe Asp Lys Phe Lys Asp Phe Phe Lys Asp Tyr Phe Ala Lys Phe
1               5                   10                  15

Trp Asp

<210> SEQ ID NO 575
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 575

Phe Phe Glu Lys Phe Lys Glu Phe Phe Lys Glu Tyr Phe Ala Lys Phe
1               5                   10                  15

Trp Glu

<210> SEQ ID NO 576
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 576

Phe Phe Glu Arg Phe Lys Glu Phe Phe Lys Asp Tyr Phe Ala Lys Phe
1               5                   10                  15

Trp Asp

<210> SEQ ID NO 577
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 577

Phe Phe Glu Lys Phe Arg Glu Phe Phe Lys Asp Tyr Phe Ala Lys Phe
1               5                   10                  15

Trp Asp

<210> SEQ ID NO 578
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 578

Phe Phe Glu Lys Phe Lys Glu Phe Phe Arg Asp Tyr Phe Ala Lys Phe
1               5                   10                  15

Trp Asp

<210> SEQ ID NO 579
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 579

Phe Phe Glu Lys Phe Lys Glu Phe Phe Lys Asp Tyr Phe Ala Arg Phe
1               5                   10                  15

Trp Asp

<210> SEQ ID NO 580
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 580

Phe Phe Asp Lys Phe Lys Glu Phe Phe Lys Asp Tyr Phe Ala Lys Phe
1               5                   10                  15

Trp Asp

<210> SEQ ID NO 581
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 581

Phe Phe Glu Lys Phe Lys Asp Phe Phe Lys Asp Tyr Phe Ala Lys Phe
1               5                   10                  15

Trp Asp

<210> SEQ ID NO 582
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 582

Phe Phe Glu Lys Phe Lys Glu Phe Phe Lys Glu Tyr Phe Ala Lys Phe
1               5                   10                  15

Trp Asp

<210> SEQ ID NO 583
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 583

Phe Phe Glu Lys Phe Lys Glu Phe Phe Lys Asp Tyr Phe Ala Lys Phe
1               5                   10                  15

Trp Glu

<210> SEQ ID NO 584
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 584

Asp Trp Phe Lys Ala Phe Tyr Asp Lys Val Ala Glu Lys Phe Lys Glu
1               5                   10                  15

Ala Phe

<210> SEQ ID NO 585
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 585

Asp Trp Phe Lys Ala Phe Tyr Asp Lys Val Ala Glu Lys Phe Lys Glu
1               5                   10                  15

Ala Phe

<210> SEQ ID NO 586
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 586

Asp Trp Phe Lys Ala Phe Tyr Asp Lys Val Ala Glu Lys Phe Lys Glu
1               5                   10                  15

Ala Phe

<210> SEQ ID NO 587
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 587

Asp Trp Phe Lys Ala Phe Tyr Asp Lys Val Ala Glu Lys Phe Lys Glu
1               5                   10                  15

Ala Phe

<210> SEQ ID NO 588
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 588

Asp Trp Phe Lys Ala Phe Tyr Asp Lys Val Ala Glu Lys Phe Lys Glu
1               5                   10                  15

Ala Phe

```
<210> SEQ ID NO 589
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 589

Asp Trp Phe Lys Ala Phe Tyr Asp Lys Val Ala Glu Lys Phe Lys Glu
1               5                   10                  15

Ala Phe

<210> SEQ ID NO 590
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 590

Asp Trp Phe Lys Ala Phe Tyr Asp Lys Val Ala Glu Lys Phe Lys Glu
1               5                   10                  15

Ala Phe

<210> SEQ ID NO 591
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 591

Asp Trp Phe Lys Ala Phe Tyr Asp Lys Val Ala Glu Lys Phe Lys Glu
1               5                   10                  15

Ala Phe

<210> SEQ ID NO 592
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 592

Asp Trp Phe Lys Ala Phe Tyr Asp Lys Val Ala Glu Lys Phe Lys Glu
1               5                   10                  15

Ala Phe

<210> SEQ ID NO 593
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 593

Asp Trp Phe Lys Ala Phe Tyr Asp Lys Val Ala Glu Lys Phe Lys Glu
1               5                   10                  15

Ala Phe
```

<210> SEQ ID NO 594
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 594

Asp Trp Phe Lys Ala Phe Tyr Asp Lys Val Ala Glu Lys Phe Lys Glu
1               5                   10                  15

Ala Phe

<210> SEQ ID NO 595
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 595

Asp Trp Phe Lys Ala Phe Tyr Asp Lys Val Ala Glu Lys Phe Lys Glu
1               5                   10                  15

Ala Phe

<210> SEQ ID NO 596
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 596

Asp Trp Phe Lys Ala Phe Tyr Asp Lys Val Ala Glu Lys Phe Lys Glu
1               5                   10                  15

Ala Phe

<210> SEQ ID NO 597
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 597

Asp Trp Phe Lys Ala Phe Tyr Asp Lys Val Ala Glu Lys Phe Lys Glu
1               5                   10                  15

Ala Phe

<210> SEQ ID NO 598
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is homolysine.
<220> FEATURE:
<221> NAME/KEY: misc_feature
<222> LOCATION: (9)..(9)
<223> OTHER INFORMATION: Xaa is homolysine.

```
<220> FEATURE:
<221> NAME/KEY: misc_feature
<222> LOCATION: (13)..(13)
<223> OTHER INFORMATION: Xaa is homolysine.
<220> FEATURE:
<221> NAME/KEY: misc_feature
<222> LOCATION: (15)..(15)
<223> OTHER INFORMATION: Xaa is homolysine.

<400> SEQUENCE: 598

Asp Trp Phe Xaa Ala Phe Tyr Asp Xaa Val Ala Glu Xaa Phe Xaa Glu
1               5                   10                  15

Ala Phe

<210> SEQ ID NO 599
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is homolysine.
<220> FEATURE:
<221> NAME/KEY: misc_feature
<222> LOCATION: (9)..(9)
<223> OTHER INFORMATION: Xaa is homolysine.
<220> FEATURE:
<221> NAME/KEY: misc_feature
<222> LOCATION: (13)..(13)
<223> OTHER INFORMATION: Xaa is homolysine.
<220> FEATURE:
<221> NAME/KEY: misc_feature
<222> LOCATION: (15)..(15)
<223> OTHER INFORMATION: Xaa is homolysine.

<400> SEQUENCE: 599

Asp Trp Phe Xaa Ala Phe Tyr Asp Xaa Val Ala Glu Xaa Phe Xaa Glu
1               5                   10                  15

Ala Phe

<210> SEQ ID NO 600
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is homolysine.
<220> FEATURE:
<221> NAME/KEY: misc_feature
<222> LOCATION: (9)..(9)
<223> OTHER INFORMATION: Xaa is homolysine.
<220> FEATURE:
<221> NAME/KEY: misc_feature
<222> LOCATION: (13)..(13)
<223> OTHER INFORMATION: Xaa is homolysine.
<220> FEATURE:
<221> NAME/KEY: misc_feature
<222> LOCATION: (15)..(15)
<223> OTHER INFORMATION: Xaa is homolysine.

<400> SEQUENCE: 600

Asp Trp Phe Xaa Ala Phe Tyr Asp Xaa Val Ala Glu Xaa Phe Xaa Glu
1               5                   10                  15

Ala Phe
```

```
<210> SEQ ID NO 601
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is homolysine.
<220> FEATURE:
<221> NAME/KEY: misc_feature
<222> LOCATION: (9)..(9)
<223> OTHER INFORMATION: Xaa is homolysine.
<220> FEATURE:
<221> NAME/KEY: misc_feature
<222> LOCATION: (13)..(13)
<223> OTHER INFORMATION: Xaa is homolysine.
<220> FEATURE:
<221> NAME/KEY: misc_feature
<222> LOCATION: (15)..(15)
<223> OTHER INFORMATION: Xaa is homolysine.

<400> SEQUENCE: 601

Asp Trp Phe Xaa Ala Phe Tyr Asp Xaa Val Ala Glu Xaa Phe Xaa Glu
1               5                   10                  15

Ala Phe

<210> SEQ ID NO 602
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is homolysine.
<220> FEATURE:
<221> NAME/KEY: misc_feature
<222> LOCATION: (9)..(9)
<223> OTHER INFORMATION: Xaa is homolysine.
<220> FEATURE:
<221> NAME/KEY: misc_feature
<222> LOCATION: (13)..(13)
<223> OTHER INFORMATION: Xaa is homolysine.
<220> FEATURE:
<221> NAME/KEY: misc_feature
<222> LOCATION: (15)..(15)
<223> OTHER INFORMATION: Xaa is homolysine.

<400> SEQUENCE: 602

Asp Trp Phe Xaa Ala Phe Tyr Asp Xaa Val Ala Glu Xaa Phe Xaa Glu
1               5                   10                  15

Ala Phe

<210> SEQ ID NO 603
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is homolysine.
<220> FEATURE:
<221> NAME/KEY: misc_feature
<222> LOCATION: (9)..(9)
<223> OTHER INFORMATION: Xaa is homolysine.
```

```
<220> FEATURE:
<221> NAME/KEY: misc_feature
<222> LOCATION: (13)..(13)
<223> OTHER INFORMATION: Xaa is homolysine.
<220> FEATURE:
<221> NAME/KEY: misc_feature
<222> LOCATION: (15)..(15)
<223> OTHER INFORMATION: Xaa is homolysine.

<400> SEQUENCE: 603

Asp Trp Phe Xaa Ala Phe Tyr Asp Xaa Val Ala Glu Xaa Phe Xaa Glu
1               5                   10                  15

Ala Phe

<210> SEQ ID NO 604
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is homolysine.
<220> FEATURE:
<221> NAME/KEY: misc_feature
<222> LOCATION: (9)..(9)
<223> OTHER INFORMATION: Xaa is homolysine.
<220> FEATURE:
<221> NAME/KEY: misc_feature
<222> LOCATION: (13)..(13)
<223> OTHER INFORMATION: Xaa is homolysine.
<220> FEATURE:
<221> NAME/KEY: misc_feature
<222> LOCATION: (15)..(15)
<223> OTHER INFORMATION: Xaa is homolysine.

<400> SEQUENCE: 604

Asp Trp Phe Xaa Ala Phe Tyr Asp Xaa Val Ala Glu Xaa Phe Xaa Glu
1               5                   10                  15

Ala Phe

<210> SEQ ID NO 605
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is homolysine.
<220> FEATURE:
<221> NAME/KEY: misc_feature
<222> LOCATION: (9)..(9)
<223> OTHER INFORMATION: Xaa is homolysine.
<220> FEATURE:
<221> NAME/KEY: misc_feature
<222> LOCATION: (13)..(13)
<223> OTHER INFORMATION: Xaa is homolysine.
<220> FEATURE:
<221> NAME/KEY: misc_feature
<222> LOCATION: (15)..(15)
<223> OTHER INFORMATION: Xaa is homolysine.

<400> SEQUENCE: 605

Asp Trp Phe Xaa Ala Phe Tyr Asp Xaa Val Ala Glu Xaa Phe Xaa Glu
1               5                   10                  15

Ala Phe
```

<210> SEQ ID NO 606
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is homolysine.
<220> FEATURE:
<221> NAME/KEY: misc_feature
<222> LOCATION: (9)..(9)
<223> OTHER INFORMATION: Xaa is homolysine.
<220> FEATURE:
<221> NAME/KEY: misc_feature
<222> LOCATION: (13)..(13)
<223> OTHER INFORMATION: Xaa is homolysine.
<220> FEATURE:
<221> NAME/KEY: misc_feature
<222> LOCATION: (15)..(15)
<223> OTHER INFORMATION: Xaa is homolysine.

<400> SEQUENCE: 606

Asp Trp Phe Xaa Ala Phe Tyr Asp Xaa Val Ala Glu Xaa Phe Xaa Glu
1               5                   10                  15

Ala Phe

<210> SEQ ID NO 607
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is homolysine.
<220> FEATURE:
<221> NAME/KEY: misc_feature
<222> LOCATION: (9)..(9)
<223> OTHER INFORMATION: Xaa is homolysine.
<220> FEATURE:
<221> NAME/KEY: misc_feature
<222> LOCATION: (13)..(13)
<223> OTHER INFORMATION: Xaa is homolysine.
<220> FEATURE:
<221> NAME/KEY: misc_feature
<222> LOCATION: (15)..(15)
<223> OTHER INFORMATION: Xaa is homolysine.

<400> SEQUENCE: 607

Asp Trp Phe Xaa Ala Phe Tyr Asp Xaa Val Ala Glu Xaa Phe Xaa Glu
1               5                   10                  15

Ala Phe

<210> SEQ ID NO 608
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is homolysine.
<220> FEATURE:
<221> NAME/KEY: misc_feature
<222> LOCATION: (9)..(9)
<223> OTHER INFORMATION: Xaa is homolysine.

```
<220> FEATURE:
<221> NAME/KEY: misc_feature
<222> LOCATION: (13)..(13)
<223> OTHER INFORMATION: Xaa is homolysine.
<220> FEATURE:
<221> NAME/KEY: misc_feature
<222> LOCATION: (15)..(15)
<223> OTHER INFORMATION: Xaa is homolysine.

<400> SEQUENCE: 608

Asp Trp Phe Xaa Ala Phe Tyr Asp Xaa Val Ala Glu Xaa Phe Xaa Glu
1               5                   10                  15

Ala Phe

<210> SEQ ID NO 609
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is ornithine.
<220> FEATURE:
<221> NAME/KEY: misc_feature
<222> LOCATION: (9)..(9)
<223> OTHER INFORMATION: Xaa is ornithine.
<220> FEATURE:
<221> NAME/KEY: misc_feature
<222> LOCATION: (13)..(13)
<223> OTHER INFORMATION: Xaa is ornithine.
<220> FEATURE:
<221> NAME/KEY: misc_feature
<222> LOCATION: (15)..(15)
<223> OTHER INFORMATION: Xaa is ornithine.

<400> SEQUENCE: 609

Asp Trp Phe Xaa Ala Phe Tyr Asp Xaa Val Ala Glu Xaa Phe Xaa Glu
1               5                   10                  15

Ala Phe

<210> SEQ ID NO 610
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is ornithine.
<220> FEATURE:
<221> NAME/KEY: misc_feature
<222> LOCATION: (9)..(9)
<223> OTHER INFORMATION: Xaa is ornithine.
<220> FEATURE:
<221> NAME/KEY: misc_feature
<222> LOCATION: (13)..(13)
<223> OTHER INFORMATION: Xaa is ornithine.
<220> FEATURE:
<221> NAME/KEY: misc_feature
<222> LOCATION: (15)..(15)
<223> OTHER INFORMATION: Xaa is ornithine.

<400> SEQUENCE: 610

Asp Trp Phe Xaa Ala Phe Tyr Asp Xaa Val Ala Glu Xaa Phe Xaa Glu
1               5                   10                  15

Ala Phe
```

```
<210> SEQ ID NO 611
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is ornithine.
<220> FEATURE:
<221> NAME/KEY: misc_feature
<222> LOCATION: (9)..(9)
<223> OTHER INFORMATION: Xaa is ornithine.
<220> FEATURE:
<221> NAME/KEY: misc_feature
<222> LOCATION: (13)..(13)
<223> OTHER INFORMATION: Xaa is ornithine.
<220> FEATURE:
<221> NAME/KEY: misc_feature
<222> LOCATION: (15)..(15)
<223> OTHER INFORMATION: Xaa is ornithine.

<400> SEQUENCE: 611

Asp Trp Phe Xaa Ala Phe Tyr Asp Xaa Val Ala Glu Xaa Phe Xaa Glu
1               5                   10                  15

Ala Phe

<210> SEQ ID NO 612
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is ornithine.
<220> FEATURE:
<221> NAME/KEY: misc_feature
<222> LOCATION: (9)..(9)
<223> OTHER INFORMATION: Xaa is ornithine.
<220> FEATURE:
<221> NAME/KEY: misc_feature
<222> LOCATION: (13)..(13)
<223> OTHER INFORMATION: Xaa is ornithine.
<220> FEATURE:
<221> NAME/KEY: misc_feature
<222> LOCATION: (15)..(15)
<223> OTHER INFORMATION: Xaa is ornithine.

<400> SEQUENCE: 612

Asp Trp Phe Xaa Ala Phe Tyr Asp Xaa Val Ala Glu Xaa Phe Xaa Glu
1               5                   10                  15

Ala Phe

<210> SEQ ID NO 613
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is ornithine.
<220> FEATURE:
<221> NAME/KEY: misc_feature
<222> LOCATION: (9)..(9)
<223> OTHER INFORMATION: Xaa is ornithine.
```

```
<220> FEATURE:
<221> NAME/KEY: misc_feature
<222> LOCATION: (13)..(13)
<223> OTHER INFORMATION: Xaa is ornithine.
<220> FEATURE:
<221> NAME/KEY: misc_feature
<222> LOCATION: (15)..(15)
<223> OTHER INFORMATION: Xaa is ornithine.

<400> SEQUENCE: 613

Asp Trp Phe Xaa Ala Phe Tyr Asp Xaa Val Ala Glu Xaa Phe Xaa Glu
1               5                   10                  15

Ala Phe

<210> SEQ ID NO 614
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is ornithine.
<220> FEATURE:
<221> NAME/KEY: misc_feature
<222> LOCATION: (9)..(9)
<223> OTHER INFORMATION: Xaa is ornithine.
<220> FEATURE:
<221> NAME/KEY: misc_feature
<222> LOCATION: (13)..(13)
<223> OTHER INFORMATION: Xaa is ornithine.
<220> FEATURE:
<221> NAME/KEY: misc_feature
<222> LOCATION: (15)..(15)
<223> OTHER INFORMATION: Xaa is ornithine.

<400> SEQUENCE: 614

Asp Trp Phe Xaa Ala Phe Tyr Asp Xaa Val Ala Glu Xaa Phe Xaa Glu
1               5                   10                  15

Ala Phe

<210> SEQ ID NO 615
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is ornithine.
<220> FEATURE:
<221> NAME/KEY: misc_feature
<222> LOCATION: (9)..(9)
<223> OTHER INFORMATION: Xaa is ornithine.
<220> FEATURE:
<221> NAME/KEY: misc_feature
<222> LOCATION: (13)..(13)
<223> OTHER INFORMATION: Xaa is ornithine.
<220> FEATURE:
<221> NAME/KEY: misc_feature
<222> LOCATION: (15)..(15)
<223> OTHER INFORMATION: Xaa is ornithine.

<400> SEQUENCE: 615

Asp Trp Phe Xaa Ala Phe Tyr Asp Xaa Val Ala Glu Xaa Phe Xaa Glu
1               5                   10                  15

Ala Phe
```

```
<210> SEQ ID NO 616
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is ornithine.
<220> FEATURE:
<221> NAME/KEY: misc_feature
<222> LOCATION: (9)..(9)
<223> OTHER INFORMATION: Xaa is ornithine.
<220> FEATURE:
<221> NAME/KEY: misc_feature
<222> LOCATION: (13)..(13)
<223> OTHER INFORMATION: Xaa is ornithine.
<220> FEATURE:
<221> NAME/KEY: misc_feature
<222> LOCATION: (15)..(15)
<223> OTHER INFORMATION: Xaa is ornithine.

<400> SEQUENCE: 616

Asp Trp Phe Xaa Ala Phe Tyr Asp Xaa Val Ala Glu Xaa Phe Xaa Glu
1               5                   10                  15

Ala Phe

<210> SEQ ID NO 617
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is ornithine.
<220> FEATURE:
<221> NAME/KEY: misc_feature
<222> LOCATION: (9)..(9)
<223> OTHER INFORMATION: Xaa is ornithine.
<220> FEATURE:
<221> NAME/KEY: misc_feature
<222> LOCATION: (13)..(13)
<223> OTHER INFORMATION: Xaa is ornithine.
<220> FEATURE:
<221> NAME/KEY: misc_feature
<222> LOCATION: (15)..(15)
<223> OTHER INFORMATION: Xaa is ornithine.

<400> SEQUENCE: 617

Asp Trp Phe Xaa Ala Phe Tyr Asp Xaa Val Ala Glu Xaa Phe Xaa Glu
1               5                   10                  15

Ala Phe

<210> SEQ ID NO 618
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is ornithine.
<220> FEATURE:
<221> NAME/KEY: misc_feature
<222> LOCATION: (9)..(9)
<223> OTHER INFORMATION: Xaa is ornithine.
```

```
<220> FEATURE:
<221> NAME/KEY: misc_feature
<222> LOCATION: (13)..(13)
<223> OTHER INFORMATION: Xaa is ornithine.
<220> FEATURE:
<221> NAME/KEY: misc_feature
<222> LOCATION: (15)..(15)
<223> OTHER INFORMATION: Xaa is ornithine.

<400> SEQUENCE: 618

Asp Trp Phe Xaa Ala Phe Tyr Asp Xaa Val Ala Glu Xaa Phe Xaa Glu
1               5                   10                  15

Ala Phe

<210> SEQ ID NO 619
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is ornithine.
<220> FEATURE:
<221> NAME/KEY: misc_feature
<222> LOCATION: (9)..(9)
<223> OTHER INFORMATION: Xaa is ornithine.
<220> FEATURE:
<221> NAME/KEY: misc_feature
<222> LOCATION: (13)..(13)
<223> OTHER INFORMATION: Xaa is ornithine.
<220> FEATURE:
<221> NAME/KEY: misc_feature
<222> LOCATION: (15)..(15)
<223> OTHER INFORMATION: Xaa is ornithine.

<400> SEQUENCE: 619

Asp Trp Phe Xaa Ala Phe Tyr Asp Xaa Val Ala Glu Xaa Phe Xaa Glu
1               5                   10                  15

Ala Phe

<210> SEQ ID NO 620
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 620

Lys Arg Asp Ser
1

<210> SEQ ID NO 621
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 621

Lys Arg Asp Thr
1

<210> SEQ ID NO 622
<211> LENGTH: 4
<212> TYPE: PRT
```

```
<213> ORGANISM: Artificial Sequence
<220> FEATURE:
<223> OTHER INFORMATION: Synthetic D or L peptide with optional
      protecting groups.

<400> SEQUENCE: 622

Trp Arg Asp Ile
1

<210> SEQ ID NO 623
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 623

Trp Arg Asp Leu
1

<210> SEQ ID NO 624
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 624

Phe Arg Asp Leu
1

<210> SEQ ID NO 625
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 625

Phe Arg Asp Ile
1

<210> SEQ ID NO 626
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is norleucine.

<400> SEQUENCE: 626

Phe Arg Asp Xaa
1

<210> SEQ ID NO 627
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
```

```
<222> LOCATION: (4)..(4)
<223> OTHER INFORMATION: Xaa is norleucine.

<400> SEQUENCE: 627

Phe Arg Glu Xaa
1

<210> SEQ ID NO 628
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 628

Phe Arg Glu Ile
1

<210> SEQ ID NO 629
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 629

Phe Asp Arg Ile
1

<210> SEQ ID NO 630
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 630

Phe Glu Arg Ile
1

<210> SEQ ID NO 631
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 631

Phe Asp Arg Leu
1

<210> SEQ ID NO 632
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 632

Phe Arg Glu Leu
1

<210> SEQ ID NO 633
```

```
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 633

Phe Glu Arg Leu
1

<210> SEQ ID NO 634
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is norleucine.

<400> SEQUENCE: 634

Phe Asp Arg Xaa
1

<210> SEQ ID NO 635
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is norleucine.

<400> SEQUENCE: 635

Phe Glu Arg Xaa
1

<210> SEQ ID NO 636
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 636

Lys Glu Arg Ser
1

<210> SEQ ID NO 637
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 637

Lys Glu Arg Thr
1

<210> SEQ ID NO 638
<211> LENGTH: 4
<212> TYPE: PRT
```

```
<213> ORGANISM: Artificial Sequence
<220> FEATURE:
<223> OTHER INFORMATION: Synthetic D or L peptide with optional
      protecting groups.

<400> SEQUENCE: 638

Lys Asp Arg Ser
1

<210> SEQ ID NO 639
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 639

Lys Asp Arg Thr
1

<210> SEQ ID NO 640
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 640

Lys Arg Glu Ser
1

<210> SEQ ID NO 641
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 641

Lys Arg Glu Thr
1

<210> SEQ ID NO 642
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 642

Leu Glu Arg Ser
1

<210> SEQ ID NO 643
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 643

Leu Glu Arg Thr
1
```

<210> SEQ ID NO 644
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 644

Trp Arg Asp Ser
1

<210> SEQ ID NO 645
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 645

Trp Asp Arg Ser
1

<210> SEQ ID NO 646
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 646

Trp Glu Arg Ser
1

<210> SEQ ID NO 647
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 647

Trp Arg Glu Ser
1

<210> SEQ ID NO 648
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 648

Lys Glu Arg Leu
1

<210> SEQ ID NO 649
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 649

Leu Arg Asp Ser
1

<210> SEQ ID NO 650
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 650

Leu Asp Arg Ser
1

<210> SEQ ID NO 651
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 651

Leu Glu Arg Ser
1

<210> SEQ ID NO 652
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 652

Leu Arg Glu Ser
1

<210> SEQ ID NO 653
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 653

Leu Arg Asp Thr
1

<210> SEQ ID NO 654
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 654

Glu Asp Arg Tyr
1

<210> SEQ ID NO 655
<211> LENGTH: 4
<212> TYPE: PRT
<213> ORGANISM: Artificial Sequence
<220> FEATURE:

```
<223> OTHER INFORMATION: Synthetic D or L peptide with optional
      protecting groups.

<400> SEQUENCE: 655

Lys Arg Asp Ser
1

<210> SEQ ID NO 656
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 656

Trp Arg Asp Ile
1

<210> SEQ ID NO 657
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 657

Trp Arg Asp Leu
1

<210> SEQ ID NO 658
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 658

Phe Arg Asp Ile
1

<210> SEQ ID NO 659
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 659

Phe Arg Asp Leu
1

<210> SEQ ID NO 660
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 660

Trp Arg Asp Phe
1

<210> SEQ ID NO 661
```

```
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 661

Trp Arg Asp Tyr
1

<210> SEQ ID NO 662
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 662

Trp Arg Asp Phe
1

<210> SEQ ID NO 663
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 663

Trp Arg Asp Tyr
1

<210> SEQ ID NO 664
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (1)..(1)
<223> OTHER INFORMATION: Xaa is ornithine.

<400> SEQUENCE: 664

Xaa Arg Glu Ser
1

<210> SEQ ID NO 665
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 665

Lys Arg Asp Ser
1

<210> SEQ ID NO 666
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.
```

<400> SEQUENCE: 666

Lys Arg Asp Thr
1

<210> SEQ ID NO 667
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 667

Leu Asp Arg Thr
1

<210> SEQ ID NO 668
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 668

Leu Glu Arg Thr
1

<210> SEQ ID NO 669
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 669

Leu Arg Glu Thr
1

<210> SEQ ID NO 670
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (1)..(1)
<223> OTHER INFORMATION: Xaa is norleucine.

<400> SEQUENCE: 670

Xaa Arg Asp Ser
1

<210> SEQ ID NO 671
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (1)..(1)
<223> OTHER INFORMATION: Xaa is norleucine.

<400> SEQUENCE: 671

```
Xaa Asp Arg Ser
1

<210> SEQ ID NO 672
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (1)..(1)
<223> OTHER INFORMATION: Xaa is norleucine.

<400> SEQUENCE: 672

Xaa Glu Arg Ser
1

<210> SEQ ID NO 673
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (1)..(1)
<223> OTHER INFORMATION: Xaa is norleucine.

<400> SEQUENCE: 673

Xaa Arg Glu Ser
1

<210> SEQ ID NO 674
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 674

Lys Arg Asp Ser
1

<210> SEQ ID NO 675
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 675

Lys Arg Asp Thr
1

<210> SEQ ID NO 676
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 676

Lys Glu Arg Ser
```

<210> SEQ ID NO 677
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 677

Lys Glu Arg Thr
1

<210> SEQ ID NO 678
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 678

Lys Asp Arg Ser
1

<210> SEQ ID NO 679
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 679

Lys Asp Arg Thr
1

<210> SEQ ID NO 680
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 680

Lys Arg Glu Ser
1

<210> SEQ ID NO 681
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 681

Lys Arg Glu Thr
1

<210> SEQ ID NO 682
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

```
<400> SEQUENCE: 682

Lys Glu Arg Leu
1

<210> SEQ ID NO 683
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 683

Lys Arg Glu Leu
1

<210> SEQ ID NO 684
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 684

Lys Arg Asp Thr
1

<210> SEQ ID NO 685
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 685

Lys Glu Arg Ser
1

<210> SEQ ID NO 686
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 686

Lys Glu Arg Thr
1

<210> SEQ ID NO 687
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 687

Lys Asp Arg Ser
1

<210> SEQ ID NO 688
<211> LENGTH: 4
<212> TYPE: PRT
```

```
<213> ORGANISM: Artificial Sequence
<220> FEATURE:
<223> OTHER INFORMATION: Synthetic D or L peptide with optional
      protecting groups.

<400> SEQUENCE: 688

Lys Asp Arg Thr
1

<210> SEQ ID NO 689
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 689

Lys Arg Glu Ser
1

<210> SEQ ID NO 690
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 690

Lys Arg Glu Thr
1

<210> SEQ ID NO 691
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 691

Lys Glu Arg Leu
1

<210> SEQ ID NO 692
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 692

Lys Arg Asp Ser
1

<210> SEQ ID NO 693
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 693

Lys Arg Asp Thr
1
```

```
<210> SEQ ID NO 694
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 694

Lys Glu Arg Ser
1

<210> SEQ ID NO 695
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 695

Lys Glu Arg Thr
1

<210> SEQ ID NO 696
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 696

Lys Asp Arg Ser
1

<210> SEQ ID NO 697
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 697

Lys Asp Arg Thr
1

<210> SEQ ID NO 698
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 698

Lys Arg Glu Ser
1

<210> SEQ ID NO 699
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 699
```

Lys Arg Glu Thr
1

<210> SEQ ID NO 700
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 700

Lys Glu Arg Leu
1

<210> SEQ ID NO 701
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (1)..(1)
<223> OTHER INFORMATION: Xaa is ornithine.

<400> SEQUENCE: 701

Xaa Arg Glu Ser
1

<210> SEQ ID NO 702
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (1)..(1)
<223> OTHER INFORMATION: Xaa is ornithine.

<400> SEQUENCE: 702

Xaa Glu Arg Ser
1

<210> SEQ ID NO 703
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (1)..(1)
<223> OTHER INFORMATION: Xaa is ornithine.

<400> SEQUENCE: 703

Xaa Arg Asp Ser
1

<210> SEQ ID NO 704
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

```
<220> FEATURE:
<221> NAME/KEY: misc_feature
<222> LOCATION: (1)..(1)
<223> OTHER INFORMATION: Xaa is ornithine.

<400> SEQUENCE: 704

Xaa Asp Arg Ser
1

<210> SEQ ID NO 705
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (1)..(1)
<223> OTHER INFORMATION: Xaa is ornithine.

<400> SEQUENCE: 705

Xaa Asp Arg Thr
1

<210> SEQ ID NO 706
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (1)..(1)
<223> OTHER INFORMATION: Xaa is ornithine.

<400> SEQUENCE: 706

Xaa Arg Asp Thr
1

<210> SEQ ID NO 707
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (1)..(1)
<223> OTHER INFORMATION: Xaa is ornithine.

<400> SEQUENCE: 707

Xaa Glu Arg Thr
1

<210> SEQ ID NO 708
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (1)..(1)
<223> OTHER INFORMATION: Xaa is ornithine.

<400> SEQUENCE: 708

Xaa Arg Glu Thr
```

<210> SEQ ID NO 709
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 709

Trp Asp Arg Ile
1

<210> SEQ ID NO 710
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 710

Trp Arg Glu Ile
1

<210> SEQ ID NO 711
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 711

Trp Glu Arg Ile
1

<210> SEQ ID NO 712
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 712

Trp Asp Arg Leu
1

<210> SEQ ID NO 713
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 713

Trp Arg Glu Leu
1

<210> SEQ ID NO 714
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

```
<400> SEQUENCE: 714

Trp Glu Arg Leu
1

<210> SEQ ID NO 715
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 715

Phe Asp Arg Ile
1

<210> SEQ ID NO 716
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 716

Phe Arg Glu Ile
1

<210> SEQ ID NO 717
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 717

Phe Glu Arg Ile
1

<210> SEQ ID NO 718
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 718

Phe Asp Arg Leu
1

<210> SEQ ID NO 719
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 719

Phe Arg Glu Leu
1

<210> SEQ ID NO 720
<211> LENGTH: 4
<212> TYPE: PRT
```

```
<213> ORGANISM: Artificial Sequence
<220> FEATURE:
<223> OTHER INFORMATION: Synthetic D or L peptide with optional
      protecting groups.

<400> SEQUENCE: 720

Phe Glu Arg Leu
1

<210> SEQ ID NO 721
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 721

Trp Arg Asp Phe
1

<210> SEQ ID NO 722
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 722

Trp Arg Glu Phe
1

<210> SEQ ID NO 723
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 723

Trp Glu Arg Phe
1

<210> SEQ ID NO 724
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 724

Trp Asp Arg Tyr
1

<210> SEQ ID NO 725
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 725

Trp Arg Glu Tyr
1
```

```
<210> SEQ ID NO 726
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 726

Trp Glu Arg Tyr
1

<210> SEQ ID NO 727
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 727

Trp Arg Asp Thr
1

<210> SEQ ID NO 728
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 728

Trp Asp Arg Thr
1

<210> SEQ ID NO 729
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 729

Trp Arg Glu Thr
1

<210> SEQ ID NO 730
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 730

Trp Glu Arg Thr
1

<210> SEQ ID NO 731
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
```

```
<222> LOCATION: (4)..(4)
<223> OTHER INFORMATION: Xaa is norleucine.

<400> SEQUENCE: 731

Phe Arg Asp Xaa
1

<210> SEQ ID NO 732
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is norleucine.

<400> SEQUENCE: 732

Phe Arg Glu Xaa
1

<210> SEQ ID NO 733
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 733

Phe Lys Asp Leu
1

<210> SEQ ID NO 734
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 734

Phe Asp Lys Leu
1

<210> SEQ ID NO 735
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 735

Phe Lys Glu Leu
1

<210> SEQ ID NO 736
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 736

Phe Glu Lys Leu
```

<210> SEQ ID NO 737
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 737

Phe Lys Asp Ile
1

<210> SEQ ID NO 738
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 738

Phe Asp Lys Ile
1

<210> SEQ ID NO 739
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 739

Phe Lys Glu Ile
1

<210> SEQ ID NO 740
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 740

Phe Glu Lys Ile
1

<210> SEQ ID NO 741
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is norleucine.

<400> SEQUENCE: 741

Phe Lys Asp Xaa
1

<210> SEQ ID NO 742
<211> LENGTH: 4
<212> TYPE: PRT

```
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is norleucine.

<400> SEQUENCE: 742

Phe Asp Lys Xaa
1

<210> SEQ ID NO 743
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is norleucine.

<400> SEQUENCE: 743

Phe Lys Glu Xaa
1

<210> SEQ ID NO 744
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is norleucine.

<400> SEQUENCE: 744

Phe Glu Lys Xaa
1

<210> SEQ ID NO 745
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 745

Phe His Asp Leu
1

<210> SEQ ID NO 746
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 746

Phe Asp His Leu
1

<210> SEQ ID NO 747
```

```
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 747

Phe His Glu Leu
1

<210> SEQ ID NO 748
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 748

Phe Glu His Leu
1

<210> SEQ ID NO 749
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 749

Phe His Asp Ile
1

<210> SEQ ID NO 750
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 750

Phe Asp His Ile
1

<210> SEQ ID NO 751
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 751

Phe His Glu Ile
1

<210> SEQ ID NO 752
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 752

Phe Glu His Ile
```

```
<210> SEQ ID NO 753
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is norleucine.

<400> SEQUENCE: 753

Phe His Asp Xaa
1

<210> SEQ ID NO 754
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is norleucine.

<400> SEQUENCE: 754

Phe Asp His Xaa
1

<210> SEQ ID NO 755
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is norleucine.

<400> SEQUENCE: 755

Phe His Glu Xaa
1

<210> SEQ ID NO 756
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (4)..(4)
<223> OTHER INFORMATION: Xaa is norleucine.

<400> SEQUENCE: 756

Phe Glu His Xaa
1

<210> SEQ ID NO 757
<211> LENGTH: 4
<212> TYPE: PRT
<213> ORGANISM: Artificial Sequence
<220> FEATURE:
```

<223> OTHER INFORMATION: Synthetic D or L peptide with optional
      protecting groups.

<400> SEQUENCE: 757

Lys Lys Asp Ser
1

<210> SEQ ID NO 758
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 758

Lys Asp Lys Ser
1

<210> SEQ ID NO 759
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 759

Lys Lys Glu Ser
1

<210> SEQ ID NO 760
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 760

Lys Glu Lys Ser
1

<210> SEQ ID NO 761
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 761

Lys His Asp Ser
1

<210> SEQ ID NO 762
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 762

Lys Asp His Ser
1

<210> SEQ ID NO 763

```
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 763

Lys His Glu Ser
1

<210> SEQ ID NO 764
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 764

Lys Glu His Ser
1

<210> SEQ ID NO 765
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 765

Lys Leu Arg Ser
1

<210> SEQ ID NO 766
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 766

Lys Arg Leu Ser
1

<210> SEQ ID NO 767
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 767

Lys Leu Arg Thr
1

<210> SEQ ID NO 768
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 768

Lys Arg Leu Thr
```

```
<210> SEQ ID NO 769
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 769

Lys Glu Leu Ser
1

<210> SEQ ID NO 770
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 770

Lys Leu Glu Ser
1

<210> SEQ ID NO 771
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 771

Lys Glu Leu Thr
1

<210> SEQ ID NO 772
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 772

Lys Leu Arg Ser
1

<210> SEQ ID NO 773
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 773

Lys Leu Arg Thr
1

<210> SEQ ID NO 774
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.
```

```
<400> SEQUENCE: 774

Lys Glu Leu Ser
1

<210> SEQ ID NO 775
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 775

Lys Glu Leu Thr
1

<210> SEQ ID NO 776
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 776

Lys Glu Ile Thr
1

<210> SEQ ID NO 777
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 777

Lys Leu Arg Ser
1

<210> SEQ ID NO 778
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 778

Lys Leu Arg Thr
1

<210> SEQ ID NO 779
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 779

Lys Glu Leu Ser
1

<210> SEQ ID NO 780
<211> LENGTH: 4
<212> TYPE: PRT
```

```
<213> ORGANISM: Artificial Sequence
<220> FEATURE:
<223> OTHER INFORMATION: Synthetic D or L peptide with optional
      protecting groups.

<400> SEQUENCE: 780

Lys Glu Leu Thr
1

<210> SEQ ID NO 781
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 781

Lys Leu Arg Ser
1

<210> SEQ ID NO 782
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 782

Lys Arg Phe Thr
1

<210> SEQ ID NO 783
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 783

Lys Leu Arg Thr
1

<210> SEQ ID NO 784
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 784

Lys Glu Ile Thr
1

<210> SEQ ID NO 785
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 785

Lys Glu Val Thr
1
```

```
<210> SEQ ID NO 786
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 786

Lys Glu Ala Thr
1

<210> SEQ ID NO 787
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 787

Lys Glu Gly Thr
1

<210> SEQ ID NO 788
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 788

Lys Glu Leu Ser
1

<210> SEQ ID NO 789
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 789

Lys Glu Leu Thr
1

<210> SEQ ID NO 790
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 790

Lys Arg Trp Tyr
1

<210> SEQ ID NO 791
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 791
```

Lys Trp Arg Tyr
1

<210> SEQ ID NO 792
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 792

Lys Arg Tyr Trp
1

<210> SEQ ID NO 793
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 793

Lys Tyr Arg Trp
1

<210> SEQ ID NO 794
<211> LENGTH: 5
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 794

Lys Arg Tyr Trp Thr
1               5

<210> SEQ ID NO 795
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 795

Lys Arg Tyr Thr
1

<210> SEQ ID NO 796
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 796

Lys Arg Trp Thr
1

<210> SEQ ID NO 797
<211> LENGTH: 4
<212> TYPE: PRT
<213> ORGANISM: Artificial Sequence
<220> FEATURE:

```
<223> OTHER INFORMATION: Synthetic D or L peptide with optional
      protecting groups.

<400> SEQUENCE: 797

Lys Arg Trp Tyr
1

<210> SEQ ID NO 798
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 798

Lys Arg Tyr Trp
1

<210> SEQ ID NO 799
<211> LENGTH: 5
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 799

Lys Arg Tyr Trp Thr
1               5

<210> SEQ ID NO 800
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 800

Lys Arg Tyr Thr
1

<210> SEQ ID NO 801
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 801

Lys Arg Trp Thr
1

<210> SEQ ID NO 802
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 802

Lys Arg Trp Tyr
1

<210> SEQ ID NO 803
```

```
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 803

Lys Arg Tyr Trp
1

<210> SEQ ID NO 804
<211> LENGTH: 5
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 804

Lys Arg Tyr Trp Thr
1               5

<210> SEQ ID NO 805
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 805

Lys Arg Tyr Thr
1

<210> SEQ ID NO 806
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 806

Lys Arg Trp Thr
1

<210> SEQ ID NO 807
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 807

Glu Lys Arg Tyr
1

<210> SEQ ID NO 808
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 808

Lys Arg Trp Tyr
```

```
<210> SEQ ID NO 809
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 809

Lys Arg Tyr Trp
1

<210> SEQ ID NO 810
<211> LENGTH: 5
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 810

Lys Arg Tyr Trp Thr
1               5

<210> SEQ ID NO 811
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 811

Lys Arg Tyr Thr
1

<210> SEQ ID NO 812
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 812

Lys Arg Phe Thr
1

<210> SEQ ID NO 813
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 813

Lys Arg Trp Thr
1

<210> SEQ ID NO 814
<211> LENGTH: 5
<212> TYPE: PRT
<213> ORGANISM: Artificial Sequence
<220> FEATURE:
<223> OTHER INFORMATION: Synthetic D or L peptide with optional
      protecting groups.
```

```
<400> SEQUENCE: 814

Lys Phe Trp Phe Ser
1               5

<210> SEQ ID NO 815
<211> LENGTH: 5
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 815

Lys Phe Trp Phe Thr
1               5

<210> SEQ ID NO 816
<211> LENGTH: 5
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 816

Lys Phe Tyr Phe Ser
1               5

<210> SEQ ID NO 817
<211> LENGTH: 5
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 817

Lys Phe Tyr Phe Thr
1               5

<210> SEQ ID NO 818
<211> LENGTH: 5
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 818

Lys Phe His Phe Ser
1               5

<210> SEQ ID NO 819
<211> LENGTH: 5
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 819

Lys Phe His Phe Thr
1               5

<210> SEQ ID NO 820
<211> LENGTH: 6
<212> TYPE: PRT
```

```
<213> ORGANISM: Artificial Sequence
<220> FEATURE:
<223> OTHER INFORMATION: Synthetic D or L peptide with optional
      protecting groups.

<400> SEQUENCE: 820

Lys Val Phe Phe Tyr Ser
1               5

<210> SEQ ID NO 821
<211> LENGTH: 5
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 821

Lys Phe Trp Phe Ser
1               5

<210> SEQ ID NO 822
<211> LENGTH: 5
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 822

Lys Phe Trp Phe Thr
1               5

<210> SEQ ID NO 823
<211> LENGTH: 5
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 823

Lys Phe Tyr Phe Ser
1               5

<210> SEQ ID NO 824
<211> LENGTH: 5
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 824

Lys Phe Tyr Phe Thr
1               5

<210> SEQ ID NO 825
<211> LENGTH: 5
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 825

Lys Phe His Phe Ser
1               5
```

```
<210> SEQ ID NO 826
<211> LENGTH: 5
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 826

Lys Phe His Phe Thr
1               5

<210> SEQ ID NO 827
<211> LENGTH: 5
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 827

Leu Phe Trp Phe Thr
1               5

<210> SEQ ID NO 828
<211> LENGTH: 5
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 828

Leu Phe Trp Phe Ser
1               5

<210> SEQ ID NO 829
<211> LENGTH: 22
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 829

Leu Leu Glu Gln Leu Asn Glu Gln Phe Asn Trp Val Ser Arg Leu Ala
1               5                   10                  15

Asn Leu Thr Gln Gly Glu
            20

<210> SEQ ID NO 830
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 830

Leu Leu Glu Gln Leu Asn Glu Gln Phe Asn Trp Val Ser Arg Leu Ala
1               5                   10                  15

Asn Leu

<210> SEQ ID NO 831
<211> LENGTH: 25
<212> TYPE: PRT
<213> ORGANISM: Artificial Sequence
```

```
<220> FEATURE:
<223> OTHER INFORMATION: Synthetic D or L peptide with optional
      protecting groups.

<400> SEQUENCE: 831

Asn Glu Leu Gln Glu Met Ser Asn Gln Gly Ser Lys Tyr Val Asn Lys
1               5                   10                  15

Glu Ile Gln Asn Ala Val Asn Gly Val
            20                  25

<210> SEQ ID NO 832
<211> LENGTH: 21
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 832

Ile Gln Asn Ala Val Asn Gly Val Lys Gln Ile Lys Thr Leu Ile Glu
1               5                   10                  15

Lys Thr Asn Glu Glu
            20

<210> SEQ ID NO 833
<211> LENGTH: 32
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 833

Arg Lys Thr Leu Leu Ser Asn Leu Glu Glu Ala Lys Lys Lys Lys Glu
1               5                   10                  15

Asp Ala Leu Asn Glu Thr Arg Glu Ser Glu Thr Lys Leu Lys Glu Leu
            20                  25                  30

<210> SEQ ID NO 834
<211> LENGTH: 16
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 834

Pro Gly Val Cys Asn Glu Thr Met Met Ala Leu Trp Glu Glu Cys Lys
1               5                   10                  15

<210> SEQ ID NO 835
<211> LENGTH: 16
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 835

Pro Cys Leu Lys Gln Thr Cys Met Lys Phe Tyr Ala Arg Val Cys Arg
1               5                   10                  15

<210> SEQ ID NO 836
<211> LENGTH: 19
<212> TYPE: PRT
<213> ORGANISM: Artificial Sequence
<220> FEATURE:
```

```
<223> OTHER INFORMATION: Synthetic D or L peptide with optional
      protecting groups.

<400> SEQUENCE: 836

Glu Cys Lys Pro Cys Leu Lys Gln Thr Cys Met Lys Phe Tyr Ala Arg
1               5                   10                  15

Val Cys Arg

<210> SEQ ID NO 837
<211> LENGTH: 10
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 837

Leu Val Gly Arg Gln Leu Glu Glu Phe Leu
1               5                   10

<210> SEQ ID NO 838
<211> LENGTH: 12
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 838

Met Asn Gly Asp Arg Ile Asp Ser Leu Leu Glu Asn
1               5                   10

<210> SEQ ID NO 839
<211> LENGTH: 11
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 839

Gln Gln Thr His Met Leu Asp Val Met Gln Asp
1               5                   10

<210> SEQ ID NO 840
<211> LENGTH: 14
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 840

Phe Ser Arg Ala Ser Ser Ile Ile Asp Glu Leu Phe Gln Asp
1               5                   10

<210> SEQ ID NO 841
<211> LENGTH: 15
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 841

Pro Phe Leu Glu Met Ile His Glu Ala Gln Gln Ala Met Asp Ile
1               5                   10                  15
```

<210> SEQ ID NO 842
<211> LENGTH: 11
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 842

Pro Thr Glu Phe Ile Arg Glu Gly Asp Asp Asp
1               5                   10

<210> SEQ ID NO 843
<211> LENGTH: 15
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 843

Arg Met Lys Asp Gln Cys Asp Lys Cys Arg Glu Ile Leu Ser Val
1               5                   10                  15

<210> SEQ ID NO 844
<211> LENGTH: 32
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 844

Pro Ser Gln Ala Lys Leu Arg Arg Glu Leu Asp Glu Ser Leu Gln Val
1               5                   10                  15

Ala Glu Arg Leu Thr Arg Lys Tyr Asn Glu Leu Leu Lys Ser Tyr Gln
            20                  25                  30

<210> SEQ ID NO 845
<211> LENGTH: 22
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 845

Leu Leu Glu Gln Leu Asn Glu Gln Phe Asn Trp Val Ser Arg Leu Ala
1               5                   10                  15

Asn Leu Thr Glu Gly Glu
            20

<210> SEQ ID NO 846
<211> LENGTH: 11
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 846

Asp Gln Tyr Tyr Leu Arg Val Thr Thr Val Ala
1               5                   10

<210> SEQ ID NO 847
<211> LENGTH: 14
<212> TYPE: PRT

```
<213> ORGANISM: Artificial Sequence
<220> FEATURE:
<223> OTHER INFORMATION: Synthetic D or L peptide with optional
      protecting groups.

<400> SEQUENCE: 847

Pro Ser Gly Val Thr Glu Val Val Val Lys Leu Phe Asp Ser
1               5                   10

<210> SEQ ID NO 848
<211> LENGTH: 21
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 848

Pro Lys Phe Met Glu Thr Val Ala Glu Lys Ala Leu Gln Glu Tyr Arg
1               5                   10                  15

Lys Lys His Arg Glu
            20

<210> SEQ ID NO 849
<211> LENGTH: 26
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 849

Trp Asp Arg Val Lys Asp Leu Ala Thr Val Tyr Val Asp Val Leu Lys
1               5                   10                  15

Asp Ser Gly Arg Asp Tyr Val Ser Gln Phe
            20                  25

<210> SEQ ID NO 850
<211> LENGTH: 25
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 850

Val Ala Thr Val Met Trp Asp Tyr Phe Ser Gln Leu Ser Asn Asn Ala
1               5                   10                  15

Lys Glu Ala Val Glu His Leu Gln Lys
            20                  25

<210> SEQ ID NO 851
<211> LENGTH: 27
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 851

Arg Trp Glu Leu Ala Leu Gly Arg Phe Trp Asp Tyr Leu Arg Trp Val
1               5                   10                  15

Gln Thr Leu Ser Glu Gln Val Gln Glu Glu Leu
            20                  25

<210> SEQ ID NO 852
```

```
<211> LENGTH: 35
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 852

Leu Ser Ser Gln Val Thr Gln Glu Leu Arg Ala Leu Met Asp Glu Thr
1               5                   10                  15

Met Lys Glu Leu Lys Glu Leu Lys Ala Tyr Lys Ser Glu Leu Glu Glu
            20                  25                  30

Gln Leu Thr
        35

<210> SEQ ID NO 853
<211> LENGTH: 26
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 853

Ala Arg Leu Ser Lys Glu Leu Gln Ala Ala Gln Ala Arg Leu Gly Ala
1               5                   10                  15

Asp Met Glu Asp Val Cys Gly Arg Leu Val
            20                  25

<210> SEQ ID NO 854
<211> LENGTH: 26
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 854

Val Arg Leu Ala Ser His Leu Arg Lys Leu Arg Lys Arg Leu Leu Arg
1               5                   10                  15

Asp Ala Asp Asp Leu Gln Lys Arg Leu Ala
            20                  25

<210> SEQ ID NO 855
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 855

Pro Leu Val Glu Asp Met Gln Arg Gln Trp Ala Gly Leu Val Glu Lys
1               5                   10                  15

Val Gln Ala

<210> SEQ ID NO 856
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 856

Met Ser Thr Tyr Thr Gly Ile Phe Thr Asp Gln Val Leu Ser Val Leu
```

```
1               5                   10                  15
Lys

<210> SEQ ID NO 857
<211> LENGTH: 22
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 857

Leu Leu Ser Phe Met Gln Gly Tyr Met Lys His Ala Thr Lys Thr Ala
1               5                   10                  15

Lys Asp Ala Leu Ser Ser
            20

<210> SEQ ID NO 858
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 858

Lys Trp Ile Tyr His Leu Thr Glu Gly Ser Thr Asp Leu Arg Thr Glu
1               5                   10                  15

Gly

<210> SEQ ID NO 859
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 859

Lys Trp Phe Tyr His Leu Thr Glu Gly Ser Thr Asp Leu Arg Thr Glu
1               5                   10                  15

Gly

<210> SEQ ID NO 860
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 860

Lys Trp Leu Tyr His Leu Thr Glu Gly Ser Thr Asp Leu Arg Thr Glu
1               5                   10                  15

Gly

<210> SEQ ID NO 861
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 861
```

```
Lys Trp Val Tyr His Leu Thr Glu Gly Ser Thr Asp Leu Arg Thr Glu
1               5                   10                  15

Gly

<210> SEQ ID NO 862
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 862

Lys Tyr Ile Trp His Leu Thr Glu Gly Ser Thr Asp Leu Arg Thr Glu
1               5                   10                  15

Gly

<210> SEQ ID NO 863
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 863

Lys Trp Ile Tyr His Phe Thr Glu Gly Ser Thr Asp Leu Arg Thr Glu
1               5                   10                  15

Gly

<210> SEQ ID NO 864
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 864

Lys Trp Phe Tyr His Ile Thr Glu Gly Ser Thr Asp Leu Arg Thr Glu
1               5                   10                  15

Gly

<210> SEQ ID NO 865
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 865

Lys Trp Leu Tyr His Val Thr Glu Gly Ser Thr Asp Leu Arg Thr Glu
1               5                   10                  15

Gly

<210> SEQ ID NO 866
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 866
```

Lys Trp Val Tyr His Tyr Thr Glu Gly Ser Thr Asp Leu Arg Thr Glu
1               5                   10                  15
Gly

<210> SEQ ID NO 867
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 867

Lys Tyr Ile Trp His Phe Thr Glu Gly Ser Thr Asp Leu Arg Thr Glu
1               5                   10                  15
Gly

<210> SEQ ID NO 868
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 868

Lys Tyr Ile Trp His Ile Thr Glu Gly Ser Thr Asp Leu Arg Thr Glu
1               5                   10                  15
Gly

<210> SEQ ID NO 869
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 869

Lys Tyr Ile Trp His Val Thr Glu Gly Ser Thr Asp Leu Arg Thr Glu
1               5                   10                  15
Gly

<210> SEQ ID NO 870
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 870

Lys Tyr Ile Trp His Tyr Thr Glu Gly Ser Thr Asp Leu Arg Thr Glu
1               5                   10                  15
Gly

<210> SEQ ID NO 871
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 871

```
Lys Phe Ile Trp His Leu Thr Glu Gly Ser Thr Asp Leu Arg Thr Glu
1               5                   10                  15
Gly
```

<210> SEQ ID NO 872
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 872

```
Lys Leu Ile Trp His Leu Thr Glu Gly Ser Thr Asp Leu Arg Thr Glu
1               5                   10                  15
Gly
```

<210> SEQ ID NO 873
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 873

```
Lys Ile Ile Trp His Leu Thr Glu Gly Ser Thr Asp Leu Arg Thr Glu
1               5                   10                  15
Gly
```

<210> SEQ ID NO 874
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 874

```
Lys Tyr Ile Trp Phe Leu Thr Glu Gly Ser Thr Asp Leu Arg Thr Glu
1               5                   10                  15
Gly
```

<210> SEQ ID NO 875
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 875

```
Lys Trp Ile Tyr Phe Leu Thr Glu Gly Ser Thr Asp Leu Arg Thr Glu
1               5                   10                  15
Gly
```

<210> SEQ ID NO 876
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 876

```
Lys Trp Ile Tyr Leu Leu Thr Glu Gly Ser Thr Asp Leu Arg Thr Glu
1               5                   10                  15

Gly

<210> SEQ ID NO 877
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 877

Lys Trp Ile Tyr His Phe Thr Glu Gly Ser Thr Asp Leu Arg Thr Glu
1               5                   10                  15

Gly

<210> SEQ ID NO 878
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 878

Lys Trp Ile Tyr His Tyr Thr Glu Gly Ser Thr Asp Leu Arg Thr Glu
1               5                   10                  15

Gly

<210> SEQ ID NO 879
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 879

Lys Trp Ile Tyr His Ile Thr Glu Gly Ser Thr Asp Leu Arg Thr Glu
1               5                   10                  15

Gly

<210> SEQ ID NO 880
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 880

Lys Trp Ile Tyr His Leu Ser Glu Gly Ser Thr Asp Leu Arg Thr Glu
1               5                   10                  15

Gly

<210> SEQ ID NO 881
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 881
```

Lys Trp Ile Tyr His Leu Thr Asp Gly Ser Thr Asp Leu Arg Thr Glu
1               5                   10                  15
Gly

<210> SEQ ID NO 882
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 882

Lys Trp Ile Tyr His Leu Thr Glu Gly Thr Ser Asp Leu Arg Thr Glu
1               5                   10                  15
Gly

<210> SEQ ID NO 883
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 883

Lys Trp Ile Tyr His Leu Thr Glu Gly Ser Thr Glu Leu Arg Thr Glu
1               5                   10                  15
Gly

<210> SEQ ID NO 884
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 884

Lys Trp Ile Tyr His Leu Thr Glu Gly Ser Thr Asp Phe Arg Thr Glu
1               5                   10                  15
Gly

<210> SEQ ID NO 885
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 885

Lys Trp Ile Tyr His Leu Thr Glu Gly Ser Thr Asp Tyr Arg Thr Glu
1               5                   10                  15
Gly

<210> SEQ ID NO 886
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 886

```
Lys Trp Ile Tyr His Leu Thr Glu Gly Ser Thr Asp Ile Arg Thr Glu
1               5                   10                  15
Gly

<210> SEQ ID NO 887
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 887

Lys Trp Ile Tyr His Leu Thr Glu Gly Ser Thr Asp Val Arg Thr Glu
1               5                   10                  15
Gly

<210> SEQ ID NO 888
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 888

Lys Trp Ile Tyr His Leu Thr Glu Gly Ser Thr Asp Leu Lys Thr Glu
1               5                   10                  15
Gly

<210> SEQ ID NO 889
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 889

Lys Trp Ile Tyr His Leu Thr Glu Gly Ser Thr Asp Leu Arg Ser Glu
1               5                   10                  15
Gly

<210> SEQ ID NO 890
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 890

Lys Trp Ile Tyr His Leu Thr Glu Gly Ser Thr Asp Leu Arg Thr Asp
1               5                   10                  15
Gly

<210> SEQ ID NO 891
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 891
```

Lys Trp Ile Tyr His Leu Thr Glu Gly Ser Thr Asp Ile Lys Thr Glu
1               5                   10                  15

Gly

<210> SEQ ID NO 892
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 892

Lys Trp Ile Tyr His Leu Thr Glu Gly Ser Thr Asp Ile Arg Ser Glu
1               5                   10                  15

Gly

<210> SEQ ID NO 893
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 893

Lys Trp Ile Tyr His Leu Thr Glu Gly Ser Thr Asp Ile Lys Ser Glu
1               5                   10                  15

Gly

<210> SEQ ID NO 894
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 894

Lys Trp Ile Tyr His Leu Thr Glu Gly Ser Thr Asp Ile Lys Ser Asp
1               5                   10                  15

Gly

<210> SEQ ID NO 895
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 895

Arg Trp Ile Tyr His Leu Thr Glu Gly Ser Thr Asp Leu Arg Thr Glu
1               5                   10                  15

Gly

<210> SEQ ID NO 896
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 896

```
Arg Tyr Ile Trp His Leu Thr Glu Gly Ser Thr Asp Ile Arg Thr Glu
1               5                   10                  15

Gly

<210> SEQ ID NO 897
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 897

Arg Trp Ile Tyr His Leu Thr Glu Gly Ser Thr Asp Ile Arg Thr Asp
1               5                   10                  15

Gly

<210> SEQ ID NO 898
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 898

Arg Trp Ile Phe His Leu Thr Glu Gly Ser Thr Asp Ile Arg Thr Glu
1               5                   10                  15

Gly

<210> SEQ ID NO 899
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 899

Arg Trp Ile Tyr His Leu Thr Glu Gly Ser Thr Asp Leu Lys Thr Glu
1               5                   10                  15

Gly

<210> SEQ ID NO 900
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 900

Arg Trp Ile Tyr His Leu Thr Asp Gly Ser Thr Asp Ile Arg Thr Glu
1               5                   10                  15

Gly

<210> SEQ ID NO 901
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 901
```

```
Arg Trp Ile Tyr His Leu Thr Asp Gly Ser Thr Asp Leu Arg Thr Glu
1               5                   10                  15

Gly

<210> SEQ ID NO 902
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 902

Arg Trp Ile Tyr Phe Leu Thr Glu Gly Ser Thr Asp Ile Arg Thr Glu
1               5                   10                  15

Gly

<210> SEQ ID NO 903
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 903

Arg Trp Ile Tyr Phe Leu Thr Glu Gly Ser Thr Asp Leu Arg Thr Glu
1               5                   10                  15

Gly

<210> SEQ ID NO 904
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 904

Lys Trp Phe Tyr His Leu Thr Glu Gly Ser Thr Asp Phe Arg Thr Glu
1               5                   10                  15

Gly

<210> SEQ ID NO 905
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 905

Arg Trp Phe Tyr His Leu Thr Glu Gly Ser Thr Asp Leu Arg Thr Glu
1               5                   10                  15

Gly

<210> SEQ ID NO 906
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 906
```

```
Lys Trp Ile Phe His Leu Thr Glu Gly Ser Thr Asp Ile Arg Thr Asp
1               5                   10                  15

Gly
```

<210> SEQ ID NO 907
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 907

```
Arg Trp Ile Tyr His Leu Thr Glu Gly Ser Thr Asp Ile Arg Thr Asp
1               5                   10                  15

Gly
```

<210> SEQ ID NO 908
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 908

```
Arg Trp Ile Tyr His Leu Thr Glu Gly Ser Thr Asp Leu Arg Thr Asp
1               5                   10                  15

Gly
```

<210> SEQ ID NO 909
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 909

```
Lys Trp Ile Tyr His Leu Thr Glu Gly Ser Thr Asp Ile Lys Thr Glu
1               5                   10                  15

Gly
```

<210> SEQ ID NO 910
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 910

```
Lys Trp Ile Tyr His Leu Thr Glu Gly Ser Thr Asp Ile Lys Thr Asp
1               5                   10                  15

Gly
```

<210> SEQ ID NO 911
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 911

```
Lys Trp Ile Tyr His Leu Thr Glu Gly Ser Thr Asp Phe Lys Thr Glu
1               5                   10                  15

Gly

<210> SEQ ID NO 912
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 912

Lys Trp Ile Tyr His Leu Thr Glu Gly Ser Thr Asp Tyr Lys Thr Glu
1               5                   10                  15

Gly

<210> SEQ ID NO 913
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 913

Lys Trp Ile Tyr His Leu Thr Glu Gly Ser Thr Asp Ile Arg Thr Glu
1               5                   10                  15

Gly

<210> SEQ ID NO 914
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 914

Lys Trp Phe Tyr His Phe Thr Glu Gly Ser Thr Asp Leu Arg Thr Glu
1               5                   10                  15

Gly

<210> SEQ ID NO 915
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 915

Arg Trp Phe Tyr His Phe Thr Glu Gly Ser Thr Asp Leu Arg Thr Glu
1               5                   10                  15

Gly

<210> SEQ ID NO 916
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 916
```

Lys Trp Phe Tyr His Phe Thr Glu Gly Ser Thr Asp Phe Arg Thr Glu
1               5                   10                  15

Gly

<210> SEQ ID NO 917
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 917

Lys Trp Phe Tyr His Phe Thr Asp Gly Ser Thr Asp Ile Arg Thr Glu
1               5                   10                  15

Gly

<210> SEQ ID NO 918
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 918

Arg Trp Phe Tyr His Phe Thr Glu Gly Ser Thr Asp Leu Arg Thr Glu
1               5                   10                  15

Gly

<210> SEQ ID NO 919
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 919

Arg Trp Phe Tyr His Phe Thr Glu Gly Ser Thr Asp Phe Arg Thr Glu
1               5                   10                  15

Gly

<210> SEQ ID NO 920
<211> LENGTH: 17
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 920

Arg Trp Phe Tyr His Phe Thr Glu Gly Ser Thr Asp Phe Arg Thr Asp
1               5                   10                  15

Gly

<210> SEQ ID NO 921
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 921

Glu Lys Cys Val Glu Glu Phe Lys Ser Leu Thr Ser Cys Leu Asp Ser
1               5                   10                  15

Lys Ala Phe

<210> SEQ ID NO 922
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 922

Asp Lys Cys Val Glu Glu Phe Lys Ser Leu Thr Ser Cys Leu Asp Ser
1               5                   10                  15

Lys Ala Phe

<210> SEQ ID NO 923
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 923

Glu Lys Cys Val Asp Glu Phe Lys Ser Leu Thr Ser Cys Leu Asp Ser
1               5                   10                  15

Lys Ala Phe

<210> SEQ ID NO 924
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 924

Glu Lys Cys Val Glu Asp Phe Lys Ser Leu Thr Ser Cys Leu Asp Ser
1               5                   10                  15

Lys Ala Phe

<210> SEQ ID NO 925
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 925

Glu Arg Cys Val Glu Glu Phe Lys Ser Leu Thr Ser Cys Leu Asp Ser
1               5                   10                  15

Lys Ala Phe

<210> SEQ ID NO 926
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 926

Asp Lys Cys Val Asp Asp Phe Lys Ser Leu Thr Ser Cys Leu Asp Ser
1               5                   10                  15

Lys Ala Phe

<210> SEQ ID NO 927
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 927

Asp Arg Cys Val Glu Glu Phe Lys Ser Leu Thr Ser Cys Leu Asp Ser
1               5                   10                  15

Lys Ala Phe

<210> SEQ ID NO 928
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 928

Glu Arg Cys Val Asp Asp Phe Lys Ser Leu Thr Ser Cys Leu Asp Ser
1               5                   10                  15

Lys Ala Phe

<210> SEQ ID NO 929
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 929

Glu Lys Cys Val Glu Glu Phe Lys Ser Phe Thr Ser Cys Leu Asp Ser
1               5                   10                  15

Lys Ala Phe

<210> SEQ ID NO 930
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 930

Glu Lys Cys Val Glu Glu Phe Lys Ser Ile Thr Ser Cys Leu Asp Ser
1               5                   10                  15

Lys Ala Phe

<210> SEQ ID NO 931
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 931

```
Glu Lys Cys Val Glu Glu Phe Lys Ser Val Thr Ser Cys Leu Asp Ser
1               5                   10                  15

Lys Ala Phe

<210> SEQ ID NO 932
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 932

Glu Arg Cys Val Glu Glu Phe Lys Ser Tyr Thr Ser Cys Leu Asp Ser
1               5                   10                  15

Lys Ala Phe

<210> SEQ ID NO 933
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 933

Glu Arg Cys Val Glu Glu Phe Lys Ser Phe Thr Ser Cys Leu Asp Ser
1               5                   10                  15

Lys Ala Phe

<210> SEQ ID NO 934
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 934

Glu Arg Cys Val Glu Glu Phe Lys Ser Ile Thr Ser Cys Leu Asp Ser
1               5                   10                  15

Lys Ala Phe

<210> SEQ ID NO 935
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 935

Glu Arg Cys Val Glu Glu Phe Lys Ser Val Thr Ser Cys Leu Asp Ser
1               5                   10                  15

Lys Ala Phe

<210> SEQ ID NO 936
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 936
```

-continued

Glu Arg Cys Val Glu Glu Phe Lys Ser Tyr Thr Ser Cys Leu Asp Ser
1               5                   10                  15

Lys Ala Phe

<210> SEQ ID NO 937
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 937

Glu Lys Cys Val Glu Glu Phe Lys Ser Phe Thr Thr Cys Leu Asp Ser
1               5                   10                  15

Lys Ala Phe

<210> SEQ ID NO 938
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 938

Glu Lys Cys Val Glu Glu Phe Lys Ser Ile Ser Ser Cys Leu Asp Ser
1               5                   10                  15

Lys Ala Phe

<210> SEQ ID NO 939
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 939

Glu Lys Cys Val Glu Glu Phe Lys Ser Val Ser Thr Cys Leu Asp Ser
1               5                   10                  15

Lys Ala Phe

<210> SEQ ID NO 940
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 940

Glu Lys Cys Val Glu Glu Phe Lys Ser Tyr Thr Ser Cys Leu Asp Ser
1               5                   10                  15

Lys Ala Phe

<210> SEQ ID NO 941
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 941

Glu Lys Cys Val Glu Glu Phe Lys Ser Phe Thr Thr Cys Leu Asp Ser
1               5                   10                  15

Lys Ala Phe

<210> SEQ ID NO 942
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 942

Glu Lys Cys Val Glu Glu Phe Lys Ser Phe Ser Ser Cys Leu Asp Ser
1               5                   10                  15

Lys Ala Phe

<210> SEQ ID NO 943
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 943

Glu Lys Cys Val Glu Glu Phe Lys Ser Phe Thr Ser Cys Leu Asp Ser
1               5                   10                  15

Lys Ala Phe

<210> SEQ ID NO 944
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 944

Glu Lys Cys Val Glu Glu Phe Lys Ser Phe Thr Ser Cys Leu Asp Ser
1               5                   10                  15

Lys Ala Phe

<210> SEQ ID NO 945
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 945

Glu Lys Cys Val Glu Glu Phe Lys Ser Phe Thr Ser Cys Leu Asp Ser
1               5                   10                  15

Lys Ala Phe

<210> SEQ ID NO 946
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 946

Glu Lys Cys Val Glu Glu Phe Lys Ser Phe Thr Ser Cys Phe Asp Ser
1               5                   10                  15

Lys Ala Phe

<210> SEQ ID NO 947
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 947

Glu Lys Cys Val Glu Glu Phe Lys Ser Phe Thr Ser Cys Phe Glu Ser
1               5                   10                  15

Lys Ala Phe

<210> SEQ ID NO 948
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 948

Glu Lys Cys Val Glu Glu Phe Lys Ser Phe Thr Ser Cys Leu Glu Ser
1               5                   10                  15

Lys Ala Phe

<210> SEQ ID NO 949
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 949

Glu Lys Cys Val Glu Glu Phe Lys Ser Phe Thr Ser Cys Ile Asp Ser
1               5                   10                  15

Lys Ala Phe

<210> SEQ ID NO 950
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 950

Glu Lys Cys Val Glu Glu Leu Lys Ser Phe Thr Ser Cys Phe Asp Ser
1               5                   10                  15

Lys Ala Phe

<210> SEQ ID NO 951
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 951

Asp Lys Cys Val Glu Glu Phe Lys Ser Phe Thr Ser Cys Phe Asp Ser
1               5                   10                  15

Lys Ala Phe

<210> SEQ ID NO 952
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 952

Asp Lys Cys Val Glu Glu Phe Lys Ser Phe Thr Ser Cys Phe Glu Ser
1               5                   10                  15

Lys Ala Phe

<210> SEQ ID NO 953
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 953

Glu Arg Cys Val Glu Glu Phe Lys Ser Phe Thr Ser Cys Phe Asp Ser
1               5                   10                  15

Lys Ala Phe

<210> SEQ ID NO 954
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 954

Glu Lys Cys Phe Glu Glu Phe Lys Ser Phe Thr Ser Cys Phe Asp Ser
1               5                   10                  15

Lys Ala Phe

<210> SEQ ID NO 955
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 955

Glu Lys Cys Phe Glu Glu Phe Lys Ser Phe Thr Ser Cys Phe Glu Ser
1               5                   10                  15

Lys Ala Phe

<210> SEQ ID NO 956
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 956

Glu Lys Cys Val Glu Glu Phe Lys Ser Phe Ser Ser Cys Phe Glu Ser
1               5                   10                  15

Lys Ala Phe

<210> SEQ ID NO 957
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 957

Glu Lys Cys Val Glu Glu Phe Lys Ser Phe Gln Ser Cys Phe Asp Ser
1               5                   10                  15

Lys Ala Phe

<210> SEQ ID NO 958
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 958

Glu Lys Cys Phe Glu Glu Phe Lys Ser Phe Gln Ser Cys Phe Asp Ser
1               5                   10                  15

Lys Ala Phe

<210> SEQ ID NO 959
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 959

Glu Lys Cys Val Glu Glu Phe Lys Gln Phe Thr Ser Cys Phe Asp Ser
1               5                   10                  15

Lys Ala Phe

<210> SEQ ID NO 960
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 960

Glu Lys Cys Val Glu Glu Phe Lys Gln Leu Thr Ser Cys Leu Asp Ser
1               5                   10                  15

Lys Ala Phe

<210> SEQ ID NO 961
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 961

Glu Lys Cys Phe Glu Glu Phe Lys Ser Phe Gln Ser Cys Leu Asp Ser
1               5                   10                  15

Lys Ala Phe

<210> SEQ ID NO 962
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 962

Glu Lys Cys Val Glu Glu Phe Lys Gln Phe Thr Ser Cys Phe Asp Ser
1               5                   10                  15

Lys Ala Phe

<210> SEQ ID NO 963
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 963

Glu Lys Cys Val Glu Glu Phe Lys Ser Phe Thr Ser Cys Phe Glu Ser
1               5                   10                  15

Lys Ala Phe

<210> SEQ ID NO 964
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 964

Glu Arg Cys Phe Glu Glu Phe Lys Ser Phe Thr Ser Cys Phe Asp Ser
1               5                   10                  15

Lys Ala Phe

<210> SEQ ID NO 965
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 965

Asp Lys Cys Phe Glu Glu Phe Lys Ser Phe Thr Ser Cys Phe Asp Ser
1               5                   10                  15

Lys Ala Phe

<210> SEQ ID NO 966
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 966

```
Glu Arg Cys Val Glu Glu Phe Lys Ser Leu Thr Ser Cys Leu Glu Ser
1               5                   10                  15

Lys Ala Phe

<210> SEQ ID NO 967
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 967

Glu Lys Cys Val Glu Glu Phe Lys Ser Leu Thr Ser Cys Leu Asp Ser
1               5                   10                  15

Lys Phe Phe

<210> SEQ ID NO 968
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 968

Glu Lys Cys Phe Glu Glu Phe Lys Ser Phe Thr Ser Cys Phe Asp Ser
1               5                   10                  15

Lys Phe Phe

<210> SEQ ID NO 969
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 969

Asp Lys Cys Phe Glu Glu Phe Lys Ser Phe Thr Ser Cys Leu Asp Ser
1               5                   10                  15

Lys Phe Phe

<210> SEQ ID NO 970
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 970

Asp Lys Cys Phe Glu Glu Phe Lys Ser Phe Thr Ser Cys Leu Glu Ser
1               5                   10                  15

Lys Phe Phe

<210> SEQ ID NO 971
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 971
```

Asp Lys Cys Phe Glu Glu Leu Lys Ser Phe Thr Ser Cys Leu Asp Ser
1               5                   10                  15

Lys Phe Phe

<210> SEQ ID NO 972
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 972

Glu Arg Cys Phe Glu Glu Phe Lys Ser Phe Thr Ser Cys Leu Asp Ser
1               5                   10                  15

Lys Phe Phe

<210> SEQ ID NO 973
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 973

Glu Lys Ala Val Glu Glu Phe Lys Ser Phe Thr Ser Cys Leu Asp Ser
1               5                   10                  15

Lys Ala Phe

<210> SEQ ID NO 974
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 974

Asp Lys Ala Val Glu Glu Phe Lys Ser Phe Thr Ser Cys Leu Asp Ser
1               5                   10                  15

Lys Phe Phe

<210> SEQ ID NO 975
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 975

Glu Lys Ala Val Glu Glu Phe Lys Ser Phe Thr Ser Ala Leu Asp Ser
1               5                   10                  15

Lys Ala Phe

<210> SEQ ID NO 976
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 976

```
Asp Lys Ala Val Glu Glu Phe Lys Ser Phe Thr Ser Ala Leu Asp Ser
1               5                   10                  15

Lys Ala Phe

<210> SEQ ID NO 977
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 977

Asp Arg Ala Phe Glu Glu Phe Lys Ser Phe Thr Ser Cys Leu Asp Ser
1               5                   10                  15

Lys Phe Phe

<210> SEQ ID NO 978
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 978

Asp Arg Ala Phe Glu Glu Phe Lys Ser Phe Thr Ser Ala Leu Asp Ser
1               5                   10                  15

Lys Phe Phe

<210> SEQ ID NO 979
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 979

Asp Lys Cys Phe Glu Glu Phe Lys Ser Phe Thr Ser Cys Phe Glu Ser
1               5                   10                  15

Lys Phe Phe

<210> SEQ ID NO 980
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 980

Glu Lys Cys Tyr Glu Glu Phe Lys Ser Phe Thr Ser Cys Leu Asp Ser
1               5                   10                  15

Lys Phe Phe

<210> SEQ ID NO 981
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 981
```

```
Asp Lys Cys Trp Glu Glu Phe Lys Ser Phe Thr Ser Cys Leu Asp Ser
1               5                   10                  15

Lys Phe Phe

<210> SEQ ID NO 982
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 982

Glu Lys Cys Phe Glu Glu Phe Lys Ser Tyr Thr Ser Cys Leu Asp Ser
1               5                   10                  15

Lys Phe Phe

<210> SEQ ID NO 983
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 983

Glu Lys Cys Phe Glu Glu Phe Lys Ser Trp Thr Ser Cys Leu Asp Ser
1               5                   10                  15

Lys Phe Phe

<210> SEQ ID NO 984
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 984

Glu Lys Cys Val Glu Glu Phe Lys Ser Trp Thr Ser Cys Leu Asp Ser
1               5                   10                  15

Lys Ala Phe

<210> SEQ ID NO 985
<211> LENGTH: 19
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 985

Asp Lys Cys Phe Glu Glu Phe Lys Ser Trp Thr Ser Cys Leu Asp Ser
1               5                   10                  15

Lys Ala Phe

<210> SEQ ID NO 986
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 986
```

```
Asp Val Trp Lys Ala Ala Tyr Asp Lys Phe Ala Glu Lys Phe Lys Glu
1               5                   10                  15

Phe Phe

<210> SEQ ID NO 987
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 987

Asp Val Trp Lys Ala Phe Tyr Asp Lys Phe Ala Glu Lys Phe Lys Glu
1               5                   10                  15

Ala Phe

<210> SEQ ID NO 988
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 988

Asp Phe Trp Lys Ala Phe Tyr Asp Lys Val Ala Glu Lys Phe Lys Glu
1               5                   10                  15

Ala Phe

<210> SEQ ID NO 989
<211> LENGTH: 5
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (1)..(1)
<223> OTHER INFORMATION: Xaa is dimethyltyrosine.

<400> SEQUENCE: 989

Xaa Asp Arg Phe Lys
1               5

<210> SEQ ID NO 990
<211> LENGTH: 4
<212> TYPE: PRT
<213> ORGANISM: Artificial Sequence
<220> FEATURE:
<223> OTHER INFORMATION: Synthetic D or L peptide with optional
      protecting groups.
<220> FEATURE:
<221> NAME/KEY: misc_feature
<222> LOCATION: (1)..(1)
<223> OTHER INFORMATION: Xaa is dimethyltyrosine.

<400> SEQUENCE: 990

Xaa Arg Glu Leu
1

<210> SEQ ID NO 991
<211> LENGTH: 7
<212> TYPE: PRT
<213> ORGANISM: Artificial Sequence
<220> FEATURE:
<223> OTHER INFORMATION: Synthetic D or L peptide with optional
``` protecting groups.

<400> SEQUENCE: 991

Leu Ala Glu Tyr His Ala Lys
1               5

<210> SEQ ID NO 992
<211> LENGTH: 8
<212> TYPE: PRT
<213> ORGANISM: Artificial Sequence
<220> FEATURE:
<223> OTHER INFORMATION: Synthetic D or L peptide linker.

<400> SEQUENCE: 992

Gly Gly Gly Gly Ser Ser Ser Ser
1               5

<210> SEQ ID NO 993
<211> LENGTH: 45
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 993

Leu Leu Glu Gln Leu Asn Glu Gln Phe Asn Trp Val Ser Arg Leu Ala
1               5                   10                  15

Asn Leu Thr Gln Gly Glu Pro Leu Leu Glu Gln Leu Asn Glu Gln Phe
            20                  25                  30

Asn Trp Val Ser Arg Leu Ala Asn Leu Thr Gln Gly Glu
        35                  40                  45

<210> SEQ ID NO 994
<211> LENGTH: 41
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 994

Leu Leu Glu Gln Leu Asn Glu Gln Phe Asn Trp Val Ser Arg Leu Ala
1               5                   10                  15

Asn Leu Thr Gln Gly Glu Pro Asp Trp Phe Lys Ala Phe Tyr Asp Lys
            20                  25                  30

Val Ala Glu Lys Phe Lys Glu Ala Phe
            35                  40

<210> SEQ ID NO 995
<211> LENGTH: 18
<212> TYPE: PRT
<213> ORGANISM: Artificial Sequence
<220> FEATURE:
<223> OTHER INFORMATION: Synthetic D or L peptide with optional
      protecting groups.

<400> SEQUENCE: 995

Asp Arg Leu Lys Ala Phe Tyr Asp Lys Val Ala Trp Lys Leu Lys Glu
1               5                   10                  15

Ala Phe